United States Patent
Lashinski et al.

(10) Patent No.: US 8,632,454 B2
(45) Date of Patent: Jan. 21, 2014

(54) MINIMALLY INVASIVE TISSUE SUPPORT SYSTEM AND METHOD WITH A SUPERIOR TISSUE SUPPORT AND AN INFERIOR ANCHOR

(75) Inventors: Randall Lashinski, Santa Rosa, CA (US); Michael J. Lee, Santa Rosa, CA (US); Gordon Bishop, Santa Rosa, CA (US); Anthony Beatty, Encinitas, CA (US); Jasper Benke, San Diego, CA (US); Alexe Calarasu, FPO, AP (US); Jeremy Kinkade, Santa Rosa, CA (US); Sean Saint, San Diego, CA (US); Heather Saladin, Carlsbad, CA (US)

(73) Assignee: Refine, LLC, Santa Rosa, CA (US)

( * ) Notice: Subject to any disclaimer, the term of this patent is extended or adjusted under 35 U.S.C. 154(b) by 896 days.

(21) Appl. No.: 12/611,038

(22) Filed: Nov. 2, 2009

(65) Prior Publication Data

US 2010/0331612 A1 Dec. 30, 2010

Related U.S. Application Data

(63) Continuation-in-part of application No. PCT/US2009/062879, filed on Oct. 30, 2009.

(60) Provisional application No. 61/110,409, filed on Oct. 31, 2008.

(51) Int. Cl.
*A61F 2/02* (2006.01)

(52) U.S. Cl.
USPC .............................. 600/37; 128/897; 606/151

(58) Field of Classification Search
USPC ............. 600/37; 128/897–899; 606/151, 192, 606/232; 623/7, 8
See application file for complete search history.

(56) References Cited

U.S. PATENT DOCUMENTS

| | | | |
|---|---|---|---|
| 4,372,293 | A | 2/1983 | Vijil-Rosales |
| 4,840,629 | A | 6/1989 | Bustos |
| 5,584,884 | A | 12/1996 | Pignataro |
| 5,676,161 | A | 10/1997 | Breiner |
| 5,910,124 | A | 6/1999 | Rubin |
| 6,110,101 | A | 8/2000 | Tihon et al. |
| 6,203,570 | B1 | 3/2001 | Baeke |
| 6,210,439 | B1 | 4/2001 | Firmin et al. |

(Continued)

OTHER PUBLICATIONS

U.S. Appl. No. 13/609,069, filed Sep. 10, 2012, Bishop et al.

(Continued)

*Primary Examiner* — Christine Matthews
*Assistant Examiner* — Joshua D Lannu
(74) *Attorney, Agent, or Firm* — Knobbe, Martens, Olson & Bear LLP

(57) ABSTRACT

Described are methods and apparatus for use in supporting tissue in a patient's body. In some embodiments, the patient's breast or another tissue is supported. One method involves introducing a superior soft tissue anchor into a patient, the anchor having an inferiorly facing total surface area; and introducing at least one inferior soft tissue anchor into the patient, such that the at least one inferior soft tissue anchor is suspended from the superior soft tissue anchor, the sum of all of the at least one inferior soft tissue anchors having a superiorly facing total surface area. The inferiorly facing total surface area of the superior anchor can be greater, such as at least two times greater than the superiorly facing total surface area of the at least one inferior anchor.

15 Claims, 130 Drawing Sheets

(56) References Cited

U.S. PATENT DOCUMENTS

| | | |
|---|---|---|
| 6,402,585 B1 | 6/2002 | Gatto et al. |
| 6,464,726 B1 | 10/2002 | Heljenek |
| 6,595,911 B2 | 7/2003 | LoVuolo |
| 6,695,855 B1 | 2/2004 | Gaston |
| 6,908,473 B2 | 6/2005 | Skiba et al. |
| 6,960,160 B2 | 11/2005 | Browning |
| 7,081,129 B2 | 7/2006 | Chobotov |
| 7,081,135 B2 | 7/2006 | Smith et al. |
| 7,326,213 B2 | 2/2008 | Benderev et al. |
| 7,410,460 B2 | 8/2008 | Benderev |
| 7,476,249 B2 | 1/2009 | Frank |
| 7,601,164 B2 | 10/2009 | Wu |
| 7,837,613 B2 | 11/2010 | Lashinski et al. |
| 2002/0029011 A1 | 3/2002 | Dyer |
| 2004/0106847 A1* | 6/2004 | Benderev ................ 600/37 |
| 2005/0090827 A1 | 4/2005 | Gedebou |
| 2006/0036333 A1 | 2/2006 | Smith et al. |
| 2006/0041185 A1 | 2/2006 | Browning |
| 2006/0069403 A1 | 3/2006 | Shalon |
| 2006/0074314 A1 | 4/2006 | Slayton et al. |
| 2006/0089525 A1 | 4/2006 | Mamo et al. |
| 2006/0167338 A1 | 7/2006 | Shfaram |
| 2006/0201519 A1 | 9/2006 | Frazier et al. |
| 2007/0055095 A1* | 3/2007 | Chu et al. ................ 600/37 |
| 2007/0156175 A1* | 7/2007 | Weadock et al. ............ 606/216 |
| 2008/0027273 A1* | 1/2008 | Gutterman ................ 600/37 |
| 2008/0027486 A1 | 1/2008 | Jones et al. |
| 2008/0082113 A1* | 4/2008 | Bishop et al. ............... 606/151 |
| 2008/0097526 A1 | 4/2008 | Accardo |
| 2009/0248071 A1 | 10/2009 | Saint et al. |
| 2012/0232653 A1 | 9/2012 | Saint et al. |

OTHER PUBLICATIONS

International Search Report mailed Feb. 3, 2010 for PCT App. No. PCT/US2009/062879 in 10 pages.

* cited by examiner

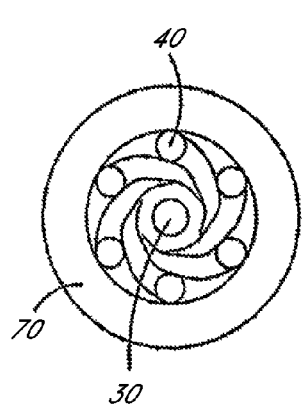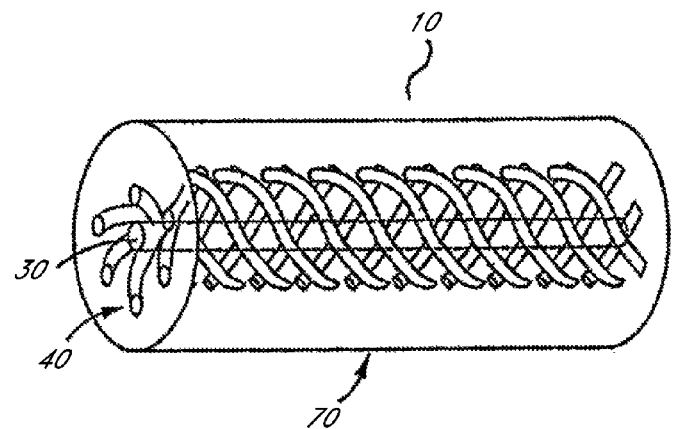
FIG. 7A  FIG. 7B
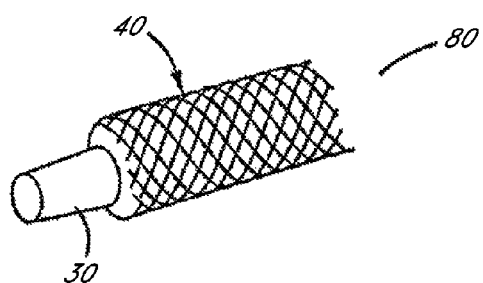
FIG. 8A
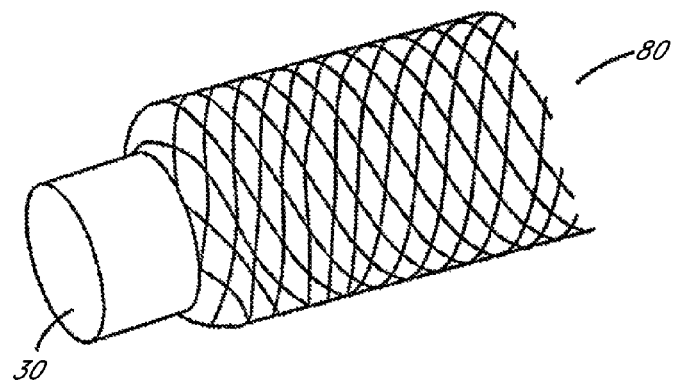
FIG. 8B

 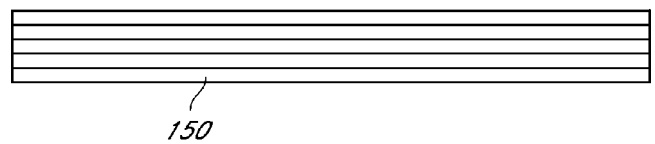
FIG. 14A    FIG. 14B
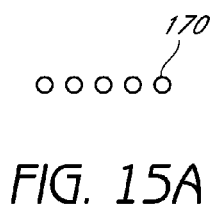 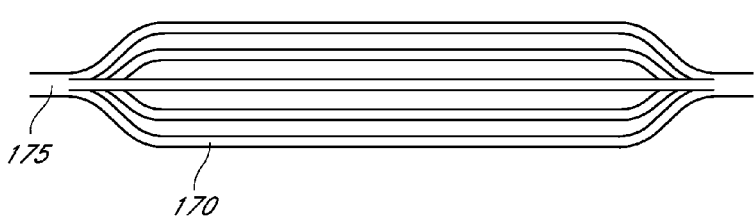
FIG. 15A
FIG. 15B

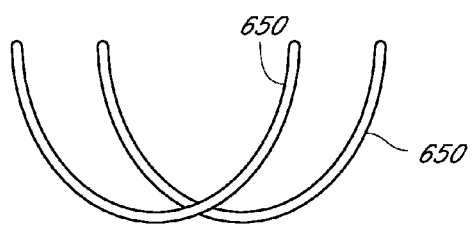
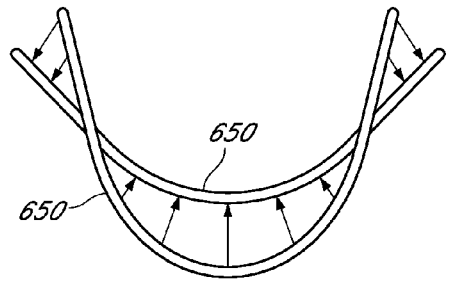
FIG. 38A  FIG. 38B
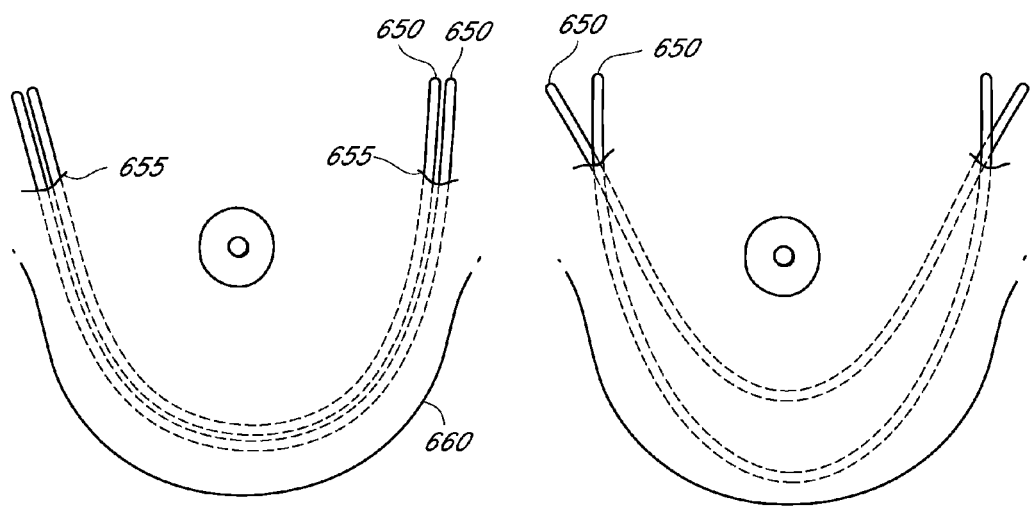
FIG. 38C  FIG. 38D

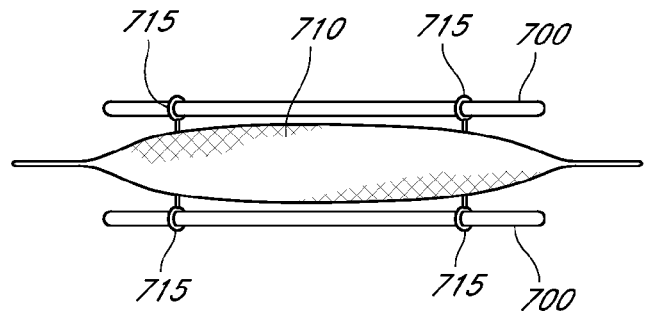
FIG. 39A
FIG. 39B
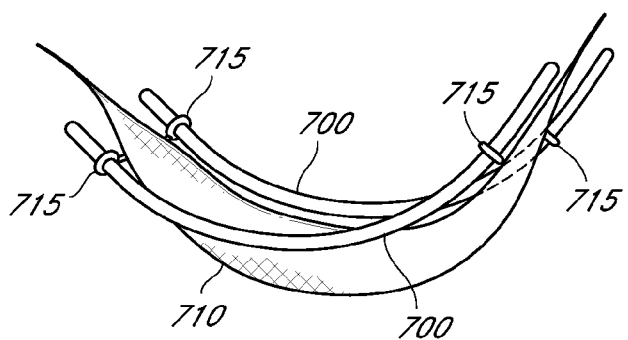
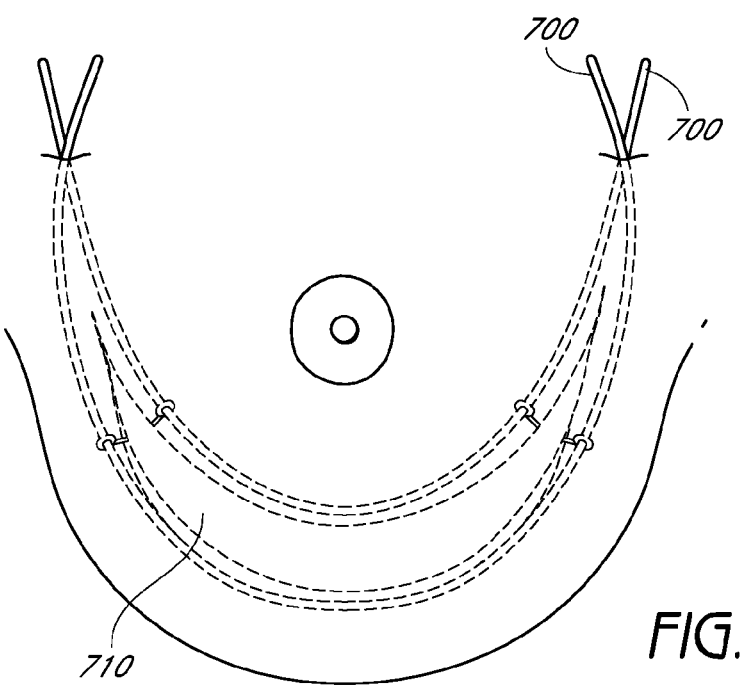
FIG. 39C

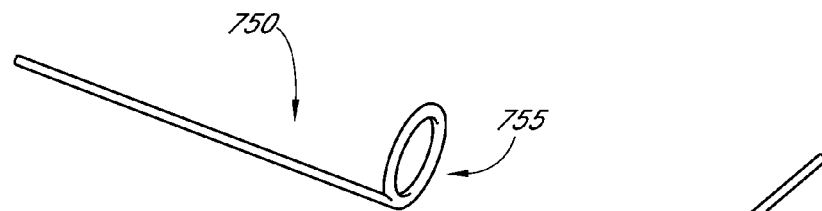
FIG. 40A
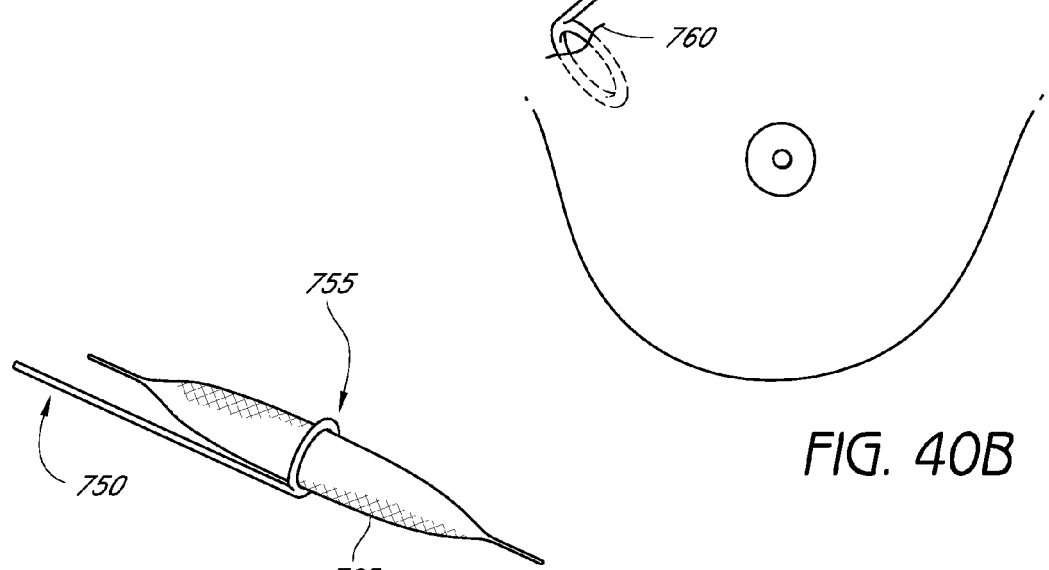
FIG. 40B
FIG. 40C
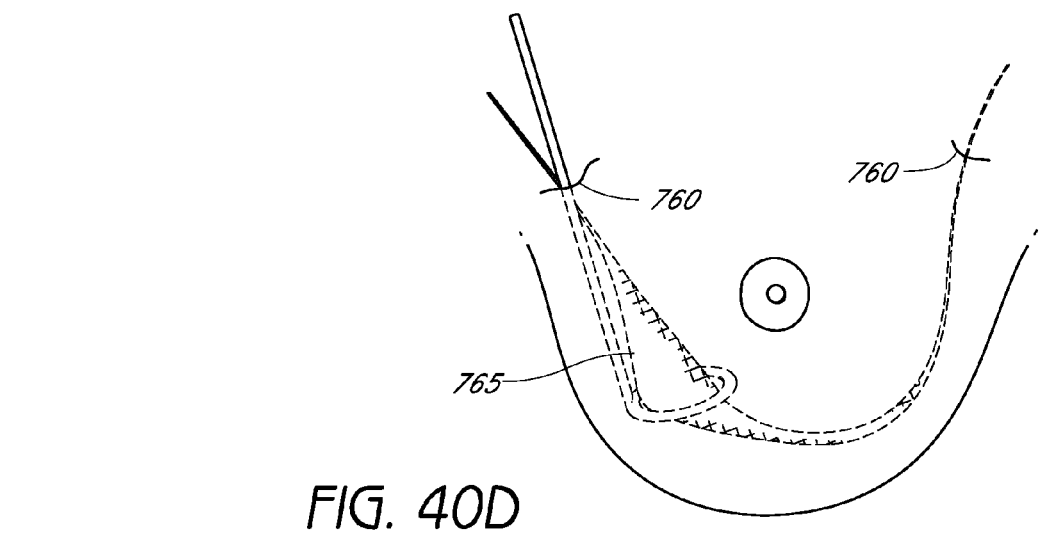
FIG. 40D

| | | |
|---|---|---|
| Points 1-4 | Points 1-5 | Points 1-6 |
| Points 2-4 | Points 2-5 | Points 2-6 |
| Points 3-4 | Points 3-5 | Points 3-6 |

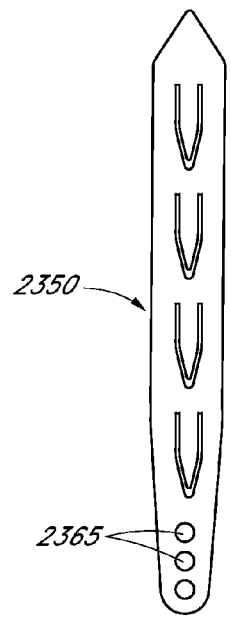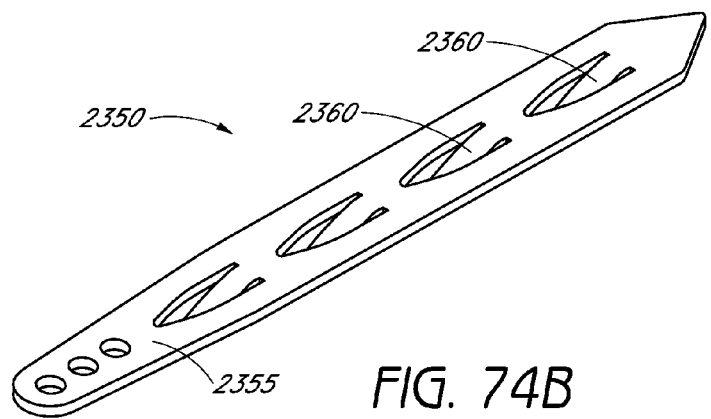
FIG. 74A
FIG. 74B
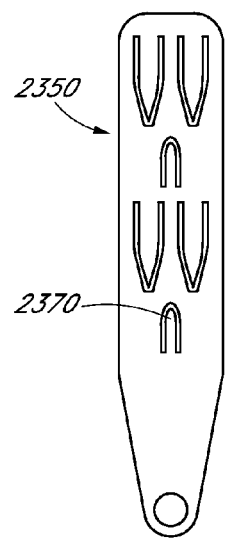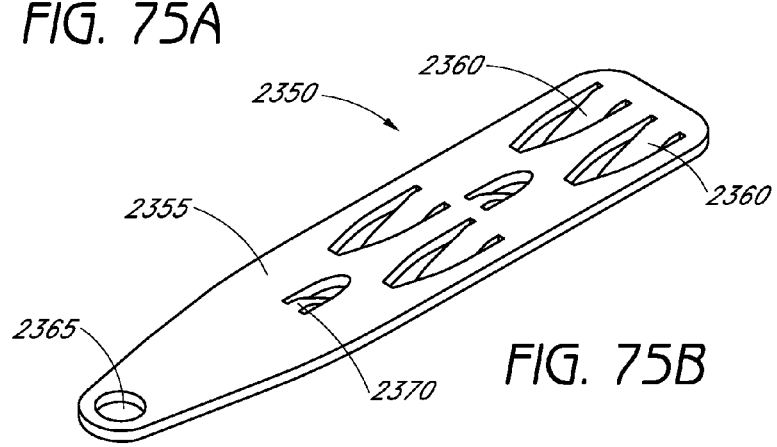
FIG. 75A
FIG. 75B

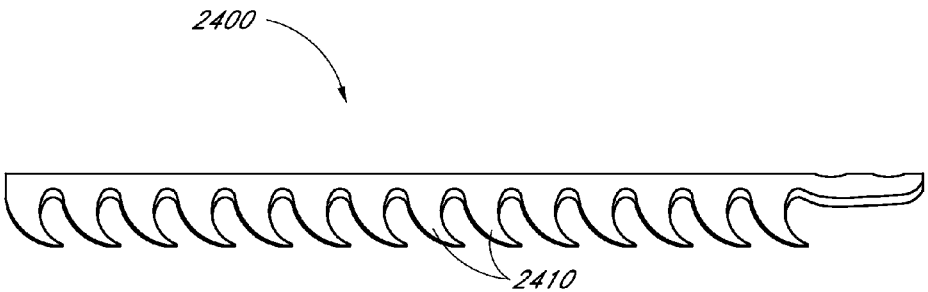
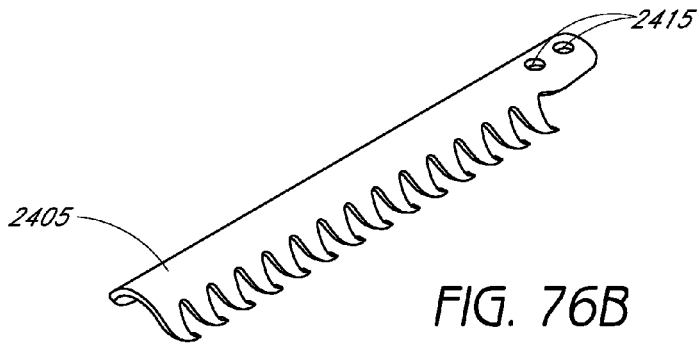
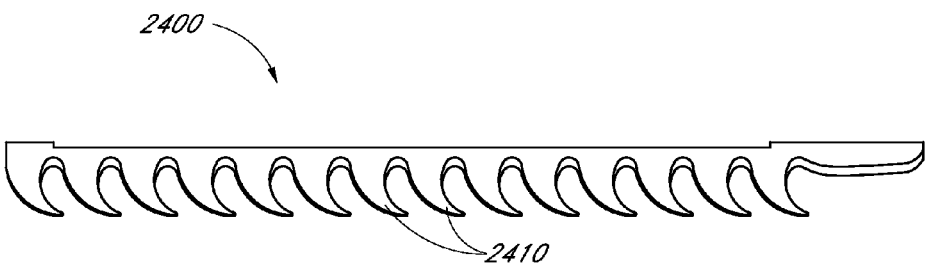
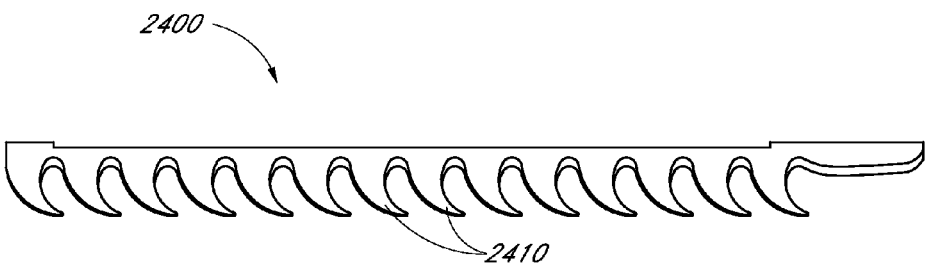
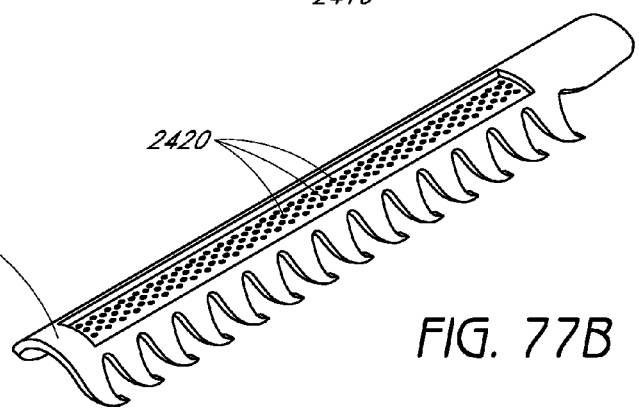

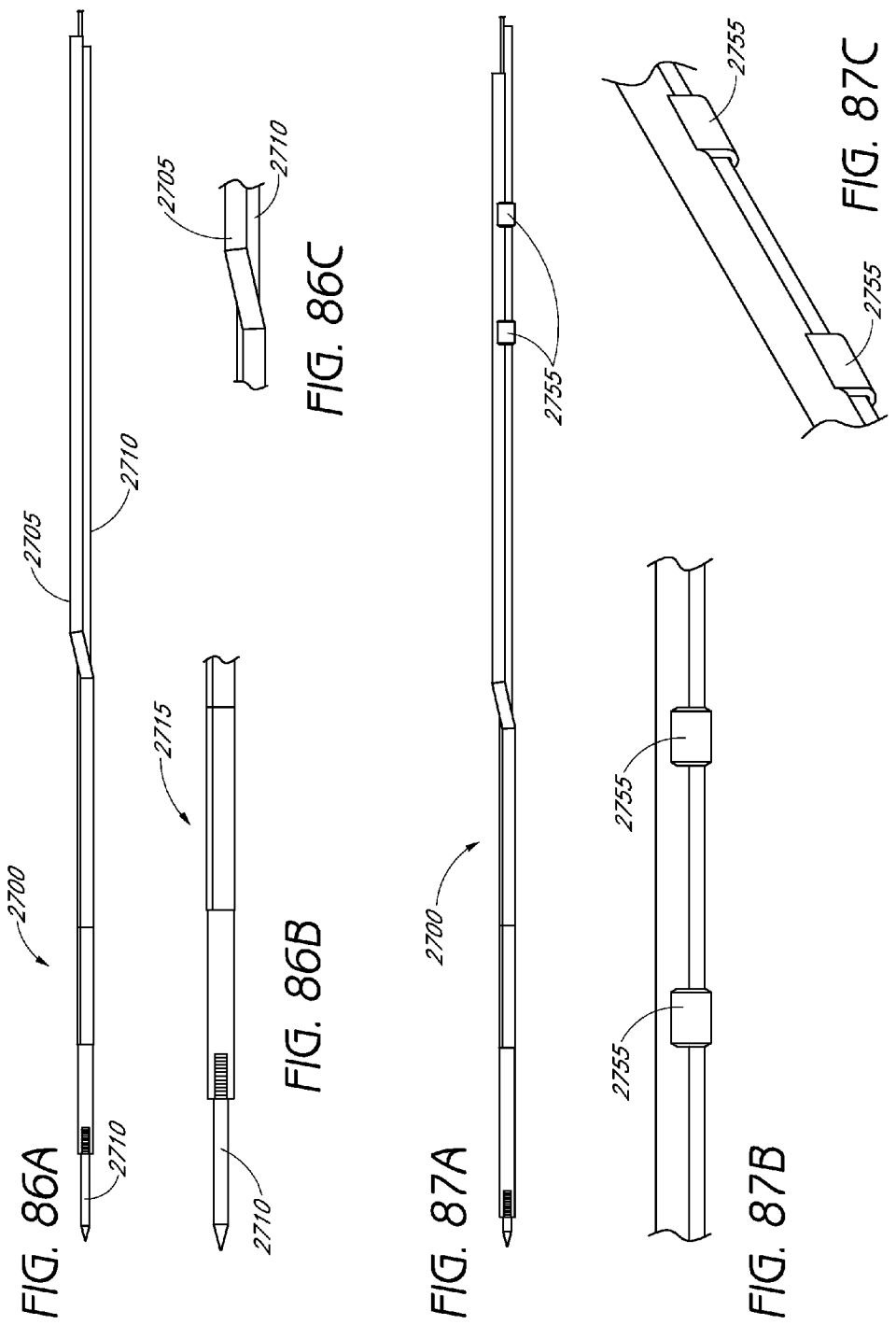

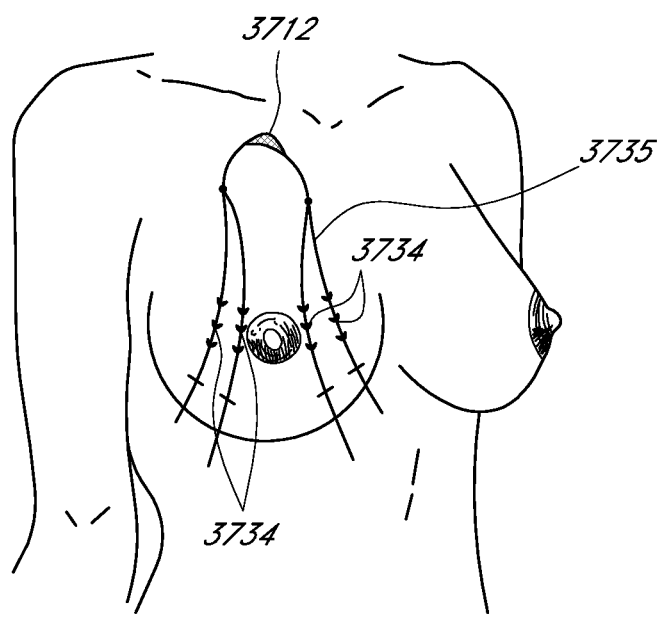
FIG. 1035

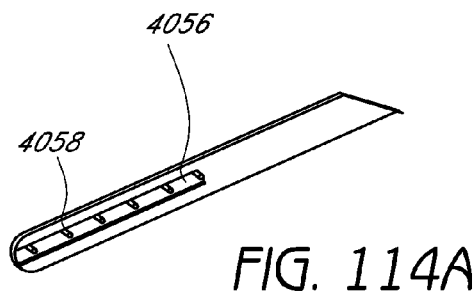
FIG. 114A
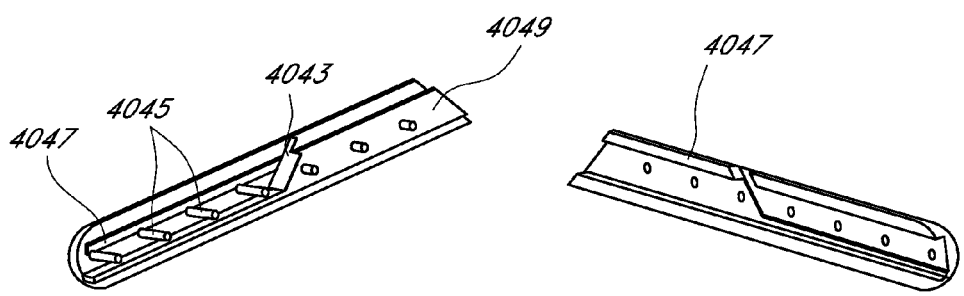
FIG. 114B
FIG. 114C
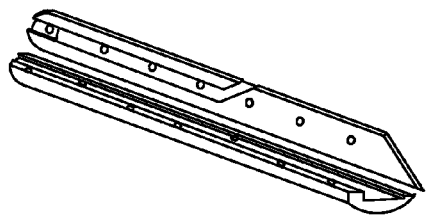
FIG. 114D
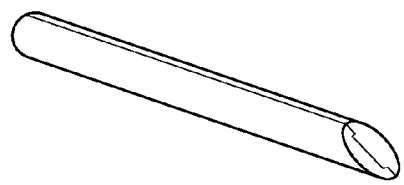
FIG. 114E

SCISSOR TYPE

SCREW TYPE

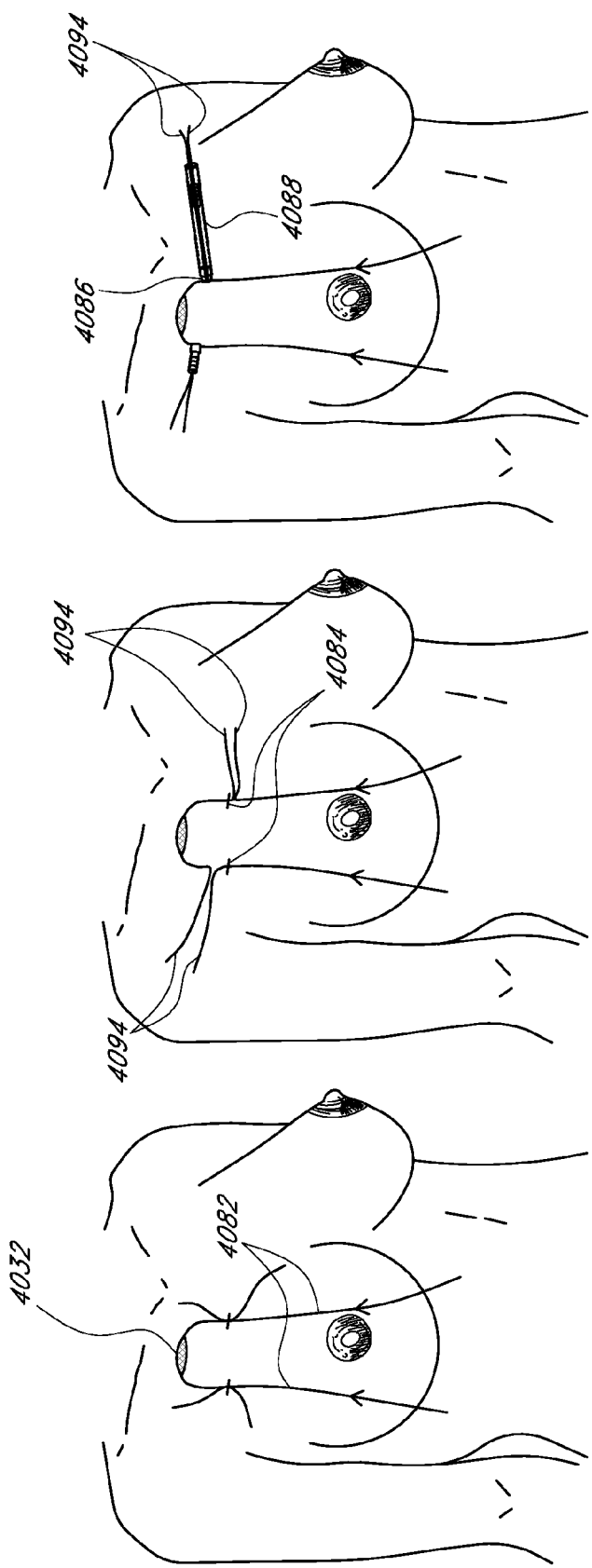

MINIMALLY INVASIVE TISSUE SUPPORT SYSTEM AND METHOD WITH A SUPERIOR TISSUE SUPPORT AND AN INFERIOR ANCHOR

CROSS-REFERENCE TO RELATED APPLICATIONS

This application claims priority under 35 U.S.C. §119(e) to U.S. Provisional Application No. 61/110,409 filed Oct. 31, 2008, which is hereby incorporated by reference in its entirety. This application also claims priority as a continuation-in-part application to PCT Application No. PCT/US2009/062879 filed on Oct. 30, 2009, which is also incorporated by reference in its entirety.

BACKGROUND

1. Field of the Invention

Embodiments of the invention are useful in the field of minimally invasive surgical devices and methods, and in particular, devices and methods for use in mastopexy.

2. Description of the Related Art

Ptosis is a condition in a tissue or organ of the body in which the tissue or organ sags, or falls, with respect to its previous position in the body. A variety of surgical and non-surgical procedures and devices have been developed to restore tissues and organs to a previous position. In particular, cosmetic surgery is frequently directed at restoring tissues to a pre-sag position.

For example, in mastopexy, mammary ptosis is corrected using a surgical procedure, without altering breast volume. In augmentation, breast volume is increased, while in reduction surgery, breast volume is decreased. Procedures can include combinations of mastopexy and augmentation or reduction procedures as well.

SUMMARY OF THE INVENTION

Disclosed herein is a system for performing a tissue lift. The system can include an elongate, flexible sling having a first end and a second end and configured to be subcutaneously introduced along a generally medial-lateral axis; a first suspension line carrying a first inferior soft tissue anchor and having a first superior free end; and a second suspension line carrying a second inferior soft tissue anchor and having a second superior free end. The first superior free end can be configured to be connected to the first end of the sling, and the second superior free end is configured to be connected to the second end of the sling. The sling can be made of any appropriate material, such as a mesh, e.g., polypropylene. A suspension line could include a suture that could be bioabsorbable or non-bioabsorbable. The anchor could have a first reduced configuration during delivery and an enlarged configuration when implanted in tissue. The anchor could, in some embodiments, include a threaded element, such as a corkscrew. The system could also include a needle for introducing a sling subcutaneously. The needle could have an arc of at about 180 or 270 degrees, or between about 180-360 degrees in some embodiments. The sling and first inferior soft tissue anchor could be configured such that when implanted in tissue, a force in an inferior direction required to pull out the sling exceeds by at least 2× the force in the superior direction to pull out the inferior anchor. In some embodiments, the sling could have a first surface area that is defined as an inferiorly facing surface area, and wherein the first and second inferior anchors collectively comprise a second surface area defined as the sum of the superiorly facing surface areas of the first and the second inferior anchors, wherein the first surface area exceeds the second surface area by at least about 1.5×, 2×, 3×, 4×, 5×, 6×, 7×, 8×, 9×, 10×, or more. In some embodiments, either the superior anchor, inferior anchor, or both could be free-floating in tissue, that is, suspended in soft tissue as opposed to bone or cartilage. In some embodiments, the sling can be configured to distribute a load from the first and second inferior anchors over an area of at least about 1 cm$^2$, 2 cm$^2$, 3 cm$^2$, 4 cm$^2$, 6 cm$^2$, 8 cm$^2$, 10 cm$^2$, or more of the sling.

One embodiment of the invention includes a system or kit for performing minimally invasive mastopexy (also known as a tissue lift). Unlike conventional mastopexy, some embodiments of the invention do not involve or substantially do not involve removal of the patient's skin in order to create the tissue lift. The system could include an elongate flexible sling having a first end and a second end; a first suspension line carrying a first soft tissue anchor and a first superior free end; a second suspension line carrying a second soft tissue anchor and a second superior free end; a curved needle for creating a tissue pathway for the elongate flexible sling; an inferior anchor insertion tool for creating a tissue pathway for an anchor along a generally superior-inferior axis; a trocar for creating a tissue pathway for a superior port; and a superior port. The system or kit could also include other components, such as, for example, a feeder rod having a proximal end and a distal end, the rod having a loop on the proximal end. The system or kit could also include an adjustment mechanism, such as a spool tensioner, for adjusting tension of at least one of the first suspension line and the second suspension line.

Also disclosed herein is a method of performing a tissue lift, that can include the steps of: introducing an elongate, flexible sling, having a first end and a second end, subcutaneously along a generally medial-lateral axis above a breast; introducing a first suspension line along a first generally inferior-superior axis, the first suspension line carrying a first inferior soft tissue anchor and having a first superior free end; introducing a second suspension line along a second generally inferior-superior axis, the second suspension line carrying a second inferior soft tissue anchor and having a second superior free end; connecting the first superior free end to the first end of the sling; and connecting the second free end to the second end of the sling. Connecting the sling to the suspension line can involve knotting the two together.

Also disclosed herein is a method of treating ptosis of a body tissue. The method could include the steps of introducing an elongate, flexible sling, having a first end and a second end, subcutaneously along a generally medial-lateral axis above a tissue to be treated; introducing a first suspension line along a first generally inferior-superior axis, the first suspension line carrying a first inferior soft tissue anchor and having a first superior free end; introducing a second suspension line along a second generally inferior-superior axis, the second suspension line carrying a second inferior soft tissue anchor and having a second superior free end; connecting the first superior free end to the first end of the sling; and connecting the second free end to the second end of the sling.

In another embodiment, disclosed is a method of tissue suspension in a patient, that includes the steps of introducing a tissue suspension system into a patient, such that the system comprises an elongate, flexible sling having a lateral aspect and a medial aspect, at least a first suspension line extending inferiorly from the lateral aspect of the sling and carrying at least a first inferior soft tissue anchor, and at least a second suspension line extending inferiorly from the medial aspect of the sling and carrying at least a second inferior soft tissue anchor, wherein downward movement of tissue supported by the first and second inferior soft tissue anchors causes the lateral aspect and the medial aspect of the sling to move inferiorly with respect to a midpoint on the sling, and causes a linear distance between at least one of the first and second inferior anchors and the midpoint to at least momentarily lengthen. The introducing step could include introducing the sling and introducing the first and second suspension lines separately.

Also disclosed herein is a method of performing a tissue lift, including the steps of introducing a superior, soft tissue anchor into a patient, the anchor having an inferiorly facing total surface area; and introducing at least one inferior soft tissue anchor into the patient, such that the at least one inferior soft tissue anchor is suspended from the superior soft tissue anchor, the sum of all of the at least one inferior soft tissue anchors having a superiorly facing total surface area. The inferiorly facing total surface area of the superior anchor can be at least 2, 3, 4, 5, 6, 7, 8, 9, 10, or more times greater than the superiorly facing total surface area of the at least one inferior anchor.

Embodiments disclosed herein are directed to minimally invasive methods and apparatus of tissue support. In some embodiments, there is provided a device, for use in supporting a tissue in a patient's body, comprising: a support member, adapted to engage at least a portion of a tissue, the support member comprising a first end and a second end, the support member further comprising a plurality of support elements; and first and second suspension members, the first suspension member being coupled to the first end of the support member, the second suspension member being coupled to the second end of the support member; wherein at least one of the first and second suspension members is configured to be secured to a location in the patient's body; wherein the plurality of support elements is configured to distribute a load, from the tissue engaged by the support member, imposed on the support member; and wherein at least one of the first and second suspension members is configured to transmit a force through the support member, the force effective to move the engaged portion of the tissue from a first position to a second position.

In some embodiments, the first suspension member is coupled to each support element at a first end of each support element, and the second suspension member is coupled to each support element at a second end of each support element.

In some embodiments, the second position is superior to the first position. In some embodiments, the second position is at least one of posterior, medial, and lateral, relative to the first position. In some embodiments, the second position is posterior to the first position.

In some embodiments, each of the plurality of support elements is elongate and has a length extending along an arc, or line, that extends between the first end of the support member and the second end of the support member; wherein a first of the plurality of support elements is spaced apart from a second of the plurality of support elements along at least about 10% of a length of the first of the plurality of support elements; and wherein the length of the plurality of support elements extends from the first end of the support member to the second end of the support member.

In some embodiments, a first of the plurality of support elements is spaced apart from a second of the plurality of support elements along at least about 30% of a length of the first of the plurality of support elements; and wherein the length of the plurality of support elements extends from the first end of the support member to the second end of the support member.

In some embodiments, at least one of the support elements is fusiform shaped.

In some embodiments, at least one suspension member is configured to be secured to at least one of muscle, fascia, bone, ligament, tendon, and skin. In some embodiments, the portion of the tissue being engaged comprises at least one of breast tissue, buttock tissue, facial tissue, arm tissue, abdominal tissue, and leg tissue.

In some embodiments, each support element comprises at least one of an elongate member and a mesh.

In some embodiments, each of the plurality of support elements is coupled to a separator, effective to maintain spacing between adjacent support elements.

In some embodiments, the support member comprises an engagement member, effective to limit movement of the support member relative to the engaged portion of the tissue. In some embodiments, the engagement member comprises at least one of a barb, a hook, and a suture.

In some embodiments, at least a portion of the device comprises a biodegradable material. In some embodiments, the device further comprises a coating effective to enhance at least one of biocompatibility and healing. Further, the device could be used as a wound closure device or trauma device, in which some applications would warrant a full biodegradable device. Other instances would warrant partial biodegradable devices. And yet other instances, a durable device would be desirable.

In some embodiments, there is provided a device, for use in supporting a tissue in a patient's body, comprising: a support member, adapted to engage at least a portion of a tissue, the support member comprising a first end, a second end, and an inflatable portion therebetween; wherein, upon inflation, the inflatable portion is effective to increase an apparent volume of the tissue; first and second suspension members, the first suspension member being coupled to the first end of the support member, and the second suspension member being coupled to the second end of the support member; wherein at least one of the first and second suspension members is configured to be secured to a location in the patient's body; wherein the support member is configured to distribute a load imposed on the support member from the tissue engaged by the support member; and wherein at least one of the first and second suspension members is configured to transmit a force through the support member, the force effective to move the engaged portion of the tissue from a first position to a second position.

In some embodiments, the second position is superior to the first position. In some embodiments, the second position is at least one of posterior, medial, and lateral, relative to the first position. In some embodiments, the second position is inferior to the first position, and in some embodiments, the second position is at least one of posterior, medial, and lateral, relative to the first position.

In some embodiments, the tissue being supported comprises at least one of breast tissue, buttock tissue, facial tissue, arm tissue, abdominal tissue, and leg tissue.

In some embodiments, the inflatable portion comprises pleats. In some embodiments, the device further comprises a port for inflating the inflatable portion. In some embodiments, the port is in or on at least one of the suspension members.

In some embodiments, there is provided a device, for use in supporting tissue, comprising: a support member, adapted to engage at least a portion of a tissue, the support member comprising a first end and a second end; wherein the support member is configured to distribute a load imposed on the support member from the tissue engaged by the support member; and first and second suspension members, the first suspension member being coupled to the first end of the support member and the second suspension member being coupled to the second end of the support member; wherein at least one suspension member is configured to be secured to a location at least about 5 cm away from the engaged portion of the tissue; wherein at least one of the first suspension member, the second suspension member, and the support member comprises an elastic element; wherein at least one of the first and second suspension members is configured to transmit a force through the support member, the force effective to move the engaged portion of the tissue from a first position to a second position; and wherein the elastic element is configured to permit movement of the engaged portion of the tissue from the second position toward the first position.

In some embodiments, the second position is superior to the first position. In some embodiments, the second position is at least one of posterior, medial, and lateral, relative to the first position.

In some embodiments, the portion of the tissue being engaged comprises at least one of breast tissue, buttock tissue, facial tissue, arm tissue, abdominal tissue, and leg tissue.

In some embodiments, the elastic element comprises at least one of an elastomeric core and an elastomeric cover. In some embodiments, the elastic element comprises a spring.

In some embodiments, the at least one suspension member comprises a braided portion. In some embodiments, at least a portion of the elastic element has a nonlinear elastic constant.

In some embodiments, the device further comprises a channel member through which at least a portion of a suspension member passes, when the device is implanted in the body; wherein the channel member is configured to limit contact of surrounding tissue by the portion of the suspension member. In some embodiments, the channel member is tubular.

In some embodiments, there is provided a device, for use in supporting a tissue in a patient's body, comprising: a support member, adapted to engage at least a portion of a tissue, the support member comprising a first end and a second end; wherein the support member is configured to distribute a load imposed on the support member from the tissue engaged by the support member; first and second suspension members, the first suspension member being coupled to the first end of the support member, and the second suspension member being coupled to the second end of the support member; and a disconnect member, configured to release tension in the suspension member when a load on the device exceeds a threshold load; wherein at least one of the suspension members is configured to be secured to a location in the patient's body; and wherein at least one of the suspension members is configured to transmit a force through the support member, the force effective to move an engaged portion of the tissue of the patient from a first position to a second position.

In some embodiments, the second position is superior to the first position. In some embodiments, the second position is at least one of posterior, medial, and lateral, relative to the first position. In some embodiments, the portion of the tissue being engaged comprises at least one of breast tissue, buttock tissue, facial tissue, arm tissue, abdominal tissue, and leg tissue.

In some embodiments, the disconnect member is configured to separate a first portion of at least one of the suspension members from a second portion of the at least one of the suspension members in response to the load that exceeds the threshold. In some embodiments, the disconnect member is configured to separate at least one of the suspension members from the support member in response to the load that exceeds the threshold.

In some embodiments, there is provided a device, for use in supporting a tissue in a patient's body, comprising: an elongate suspension member, having a first end and a second end, and a length extending therebetween; wherein the suspension member is configured to engage, and exert traction on, a tissue, resulting in the tissue moving from a first position to a second position; wherein at least a portion of suspension member is configured to shorten along the length of the suspension member in response to delivery of an energy to the suspension member; wherein the suspension member further comprises at least one engagement member, configured to engage at least a portion of the tissue; an elongate energy delivery member, coupled to at least a portion of the suspension member; wherein at least a portion of the elongate energy delivery member extends alongside at least a portion of the length of the suspension member; and wherein the elongate energy delivery member is configured to deliver the energy to the suspension member.

In some embodiments, the energy comprises at least one of electromagnetic energy, acoustic energy, and thermal energy. In some embodiments, the at least a portion of the elongate suspension member comprises collagen. In some embodiments, the at least a portion of the elongate suspension member comprises at least one of a shape memory alloy and a shape memory polymer. In some embodiments, the at least a portion of the elongate suspension member comprises a swellable material. In some embodiments, the swellable material comprises a hydrogel. In some embodiments, the at least a portion of the elongate suspension member comprises a braid.

In some embodiments, there is provided a method, for supporting a breast in a body of a patient, comprising: providing a supporting device having a first end, a second end, and a support member positioned between the first end and second end; advancing the first end of the supporting device into a breast, through a first incision that is located on one of a medial and a lateral side of the breast; withdrawing the first end of the supporting device from the breast through a second incision, located on the other of the medial and the lateral side of the breast, until the support member is positioned within breast tissue between the first incision and second incision; advancing the first end of the supporting device, from a position within the breast adjacent the second incision, to a first location, and the second end of the supporting device, from a position within the breast adjacent the first incision, to a second location; wherein both of the first and second locations are superior to the first and second incisions; drawing the breast tissue toward the first and second locations; and anchoring the first and second ends of the supporting device at the first and second locations, respectively.

In some embodiments, the first and second locations are substantially the same location.

In some embodiments, the method further comprises coupling a portion of the first end to a portion of the second end, inside the body. In some embodiments, anchoring comprises coupling the first and second ends to at least one of bone, muscle, fascia, tendon, ligament, and skin.

In some embodiments, there is provided a method, for supporting a tissue in a body of a patient, comprising: placing a supporting device into the body, the supporting device comprising: a support member, adapted to engage at least a portion of a tissue, the support member comprising a first end and a second end; wherein the support member is configured to distribute a load imposed on the support member from the tissue engaged by the support member; at least one suspension member coupled to the support member; engaging the at least a portion of the tissue with the support member; applying tension to the at least one suspension member, thereby moving the engaged portion of the tissue from a first position to a second position; securing the at least one suspension member to a location in the body, such that the engaged portion of the tissue is effectively maintained in the second position; and inflating at least a portion of the supporting device to increase an apparent volume of the tissue.

In some embodiments, the portion of the tissue being engaged comprises at least one of breast tissue, buttock tissue, facial tissue, arm tissue, abdominal tissue, and leg tissue.

In some embodiments, there is provided a method, for supporting a tissue in a body of a patient, comprising: placing a supporting device into the body, the supporting device comprising: a support member, adapted to engage at least portion of a tissue, the support member comprising a first end and a second end; wherein the support member is configured to distribute a load imposed on the support member from the tissue engaged by the support member; and at least one suspension member coupled to the support member; placing the support member so as to effectively engage at least a portion of the tissue; applying tension to the at least one suspension member, thereby moving the engaged portion of the tissue from a first position to a second position; securing the at least one suspension member to a location in the body, such that the engaged portion of the tissue is effectively maintained substantially in the second position; and wherein the supporting device is configured, in response to a load that exceeds a threshold, to release tension in the at least one suspension member.

In some embodiments, the supporting device is configured to uncouple a first portion of at least one of the suspension members from a second portion of the at least one of the suspension members in response to the load that exceeds the threshold. In some embodiments, the supporting device is configured to uncouple at least one of the suspension members from the support member in response to the load that exceeds the threshold. In some embodiments, the at least one suspension member increases in length when the load exceeds the threshold.

In some embodiments, there is provided a method for use in supporting breast tissue in a patient's body, comprising: providing a support member, adapted to engage breast tissue, the support member comprising a first end and a second end; wherein the support member is configured to distribute a load imposed on the support member from the breast tissue engaged by the support member; and providing first and second suspension members, the first suspension member being coupled to the first end of the support member and the second suspension member being coupled to the second end of the support member; wherein, when implanted, the first suspension member, extends superiorly from the first end of the support member, and the second suspension member, extends superiorly from the second end of the support member; anchoring the first suspension member at a first location, and the second suspension member at a second location; wherein the first and second locations are located superiorly to the engaged breast tissue; wherein a distance between the first and second locations is greater than a greatest distance between the first and second ends of the support member.

In some embodiments, there is provided a method, for use in supporting a tissue in a patient's body, comprising: providing an elongate suspension member, having a first end and a second end, and a length extending therebetween; wherein the suspension member is configured to engage, and exert traction on, a tissue, resulting in the tissue moving from a first position to a second position; wherein at least a portion of suspension member is configured to shorten along the length of the suspension member in response to delivery of an energy to the suspension member; wherein the suspension member further comprises at least one engagement member, configured to engage at least a portion of the tissue; providing an elongate energy delivery member, coupled to at least a portion of the suspension member; wherein at least a portion of the energy delivery member extends alongside at least a portion of the length of the suspension member; and wherein the energy delivery member is configured to deliver the energy to the suspension member; delivering the energy to the energy delivery member, thereby shortening the suspension member. In some embodiments, delivering energy comprises delivering at least one of electromagnetic energy, acoustic energy, and thermal energy.

Some embodiments describe a device including an elongate member and a plurality of side members, each of which has a first end and a second end. In some embodiments, each of the plurality of side members being coupled to, or integral with, the elongate member at the first end. In some embodiments, each of the plurality of side members subtending an acute angle with respect to the elongate member when the device is in an expanded state. Some embodiments provide that advancement of the device in a first direction results in a securing of the device in a tissue. In certain embodiments, after the securing, advancement of the device in a second direction, opposite the first direction, through the tissue results in the device changing from the expanded state to a collapsed state as the second end of each of the plurality of side members moves closer to the elongate member, permitting passage of the device through the tissue in the second direction.

In some embodiments, the device includes an elongate member having a lumen passing therethrough, the elongate member configured to hold the device when the device is in the collapsed state, for delivery of the device into the tissue.

Some embodiments describe a device, for use in supporting a tissue in a patient's body, including a support member, adapted to engage at least a portion of a tissue, the support member comprising a first portion and a second portion; and first and second suspension members, the first suspension member coupled to, and movable with respect to, the first portion of the support member, the second suspension member coupled to, and movable with respect to, the second portion of the support member. In some embodiments, at least one of the first and second suspension members is configured to be secured to a location in the patient's body. In some embodiments, at least one of the first and second suspension members is configured to transmit a force through the support member, the force effective to move the engaged portion of the tissue from a first position to a second position.

In some embodiments, the first suspension member is slidable with respect to the first portion of the support member, and the second suspension member is slidable with respect to the second portion of the support member. In some embodiments, the device further includes an anchor member coupled to, or integral with, at least one of the first and second suspension members.

In some embodiments, the anchor member includes an elongate member and a plurality of side members, each of which has a first end and a second end; each of the plurality of side members being coupled to, or integral with, the elongate member at the first end; and each of the plurality of side members subtending an acute angle with respect to the elongate member when the anchor member is in an expanded state. In some embodiments, advancement of the anchor member in a first direction results in a securing of the anchor member in a tissue. In some embodiments, after the securing, advancement of the anchor member in a second direction, opposite the first direction, through the tissue results in the anchor member changing from the expanded state to a collapsed state as the second end of each of the plurality of side members moves closer to the elongate member, permitting passage of the anchor member through the tissue in the second direction. In some embodiments, the anchor member comprises at least one of a hook, a dart, a barb, and a clasp.

Some embodiments provide minimally invasive methods, for elevating soft tissue in a body, that include providing a supporting device, comprising a first portion, a second portion, and a support member positioned between the first portion and second portion; advancing the first portion of the supporting device into the body, through a single incision, to a first location in the body; advancing the second portion of the supporting device into the body, through the incision, to a second location in the body; securing the first portion of the supporting device at the first location; and shifting soft tissue in the body with the support member.

In some embodiments, the shifting comprises elevating the soft tissue superiorly. In some embodiments, both of the first and second locations are located superior to the incision. In some embodiments, at least one of the first and second locations is located superior to the incision. In some embodiments, the method further includes drawing the soft tissue toward at least one of the first and second locations.

Some embodiments provide that the soft tissue comprises breast tissue. In some embodiments, the first and second locations are substantially the same location. In some embodiments, at least one of the first and second locations is at a fascia. In some embodiments, at least one of the first and second locations is at a muscle. In some embodiments, at least one of the first and second locations is at a clavicle. In some embodiments, at least one of the first and second locations is at a rib. In some embodiments, the securing comprises suturing the first portion. In some embodiments, the securing comprises positioning an anchoring member at the first location. In some embodiments, the anchoring member comprises at least one of a hook, a dart, a barb, and a clasp. In some embodiments, securing the second portion of the supporting device at the second location.

In some embodiments, the incision is made during a first time period, and the first and second portions are secured during a second time period, and no additional incision is made in the body between the first and second time periods, and no additional incision is made in the body during the second time period. In some embodiments, a distance between the first and second locations is greater than a longest dimension of the support member. In some embodiments, the first and second portions comprise suspension elements. In some embodiments, the incision is no greater than about 1.0 centimeter in length. In some embodiments, the incision is no greater than about 0.5 centimeters in length. In some embodiments, the incision is substantially parasagittal in orientation. In some embodiments, the incision is transverse to a long axis of the body.

Some embodiments provide methods, of dissecting breast tissue, including inserting a distal end of an elongate member into one of a medial and a lateral aspect of a breast; after the inserting, advancing the distal end inferiorly within the breast; and after the advancing the distal end inferiorly, advancing the distal end superiorly within the breast to the other of the medial and lateral aspect, and then out of the breast, such that the distal end and a proximal end of the elongate member are outside the breast and a central portion of the elongate member, between the distal end and the proximal end, is within the breast.

In some embodiments, the advancing the distal end inferiorly comprises advancing the distal end to a point inferior to the areola of the breast. In some embodiments, the advancing the distal end inferiorly comprises dissecting breast tissue. In some embodiments, the elongate member comprises a needle. In some embodiments, the elongate member is arcuate. In some embodiments, the elongate member comprises a sheath. In some embodiments, the distal end is sharp. In some embodiments, the method further includes advancing a support member along the elongate member. In some embodiments, the method further includes shifting breast tissue with the support member. In some embodiments, the method further includes creating a channel in the breast tissue that extends from a point at which the elongate member is inserted into the breast; and expanding a cross-sectional dimension of the channel. In some embodiments, the expanding the cross-sectional dimension of the channel comprises expanding an expandable member within the channel. In some embodiments, the expandable member comprises distal end having a polygonal structure. In some embodiments, the polygonal structure comprises a quadrilateral.

Some embodiments describe methods, for elevating soft tissue in a body, including advancing a supporting device into an incision in the body at a first location superior to the soft tissue; advancing a plurality of anchor members inferiorly, from the first location, to a second location within the soft tissue; and with at least one of the plurality of anchor members, elevating the soft tissue superiorly toward the supporting device, thereby decreasing a length between the first location and the second location.

In some embodiments, the soft tissue comprises a breast. In some embodiments, the first location is superior to an areola of the breast. Some embodiments further include securing the plurality of anchor members with the supporting device after the plurality of anchor members are advanced to the second location. Some embodiments further include advancing a distal portion of one or more of the plurality of anchor members through one or more openings in the soft tissue inferior to the first location. Some embodiments further include advancing one or more of the plurality of anchor members entirely through the one or more openings and out of the body.

In some embodiments, advancing the plurality of anchor members comprises advancing an anchor within a sheath inferiorly from the first location. Some embodiments further include engaging the soft tissue with an anchor member by removing the sheath. In certain embodiments, advancing the plurality of anchor members comprises advancing a sheath inferiorly from the first location. Some embodiments further include advancing an anchor inferiorly through the sheath and engaging the tissue with the anchor by removing the sheath.

In certain embodiments, advancing the plurality of anchors members includes advancing an anchor inferiorly into the soft tissue to a third location; removing the anchor from the soft tissue; and after removing the anchor from the soft tissue, advancing the anchor inferiorly into the soft tissue to the second location. Some embodiments include securing the support device to one of fascia, clavicle, rib, and muscle.

Some methods described herein, for elevating a patient's breast, include inserting into the breast a supporting device at a first location superior to the areola of the breast; and drawing breast tissue, inferior to the first location, superiorly toward the supporting device by decreasing a length of one or more anchoring members extending inferiorly from the supporting device.

Some embodiments further include securing the one or more anchoring members with the supporting device after the drawing breast tissue. Some embodiments further include advancing a distal portion of the one or more anchoring members through one or more openings inferior to the areola. Some embodiments further include advancing the one or more anchoring members entirely through the one or more openings. Some embodiments further include advancing the one or more anchoring members within a sheath inferiorly from the first location. Some embodiments further include engaging breast tissue with an anchor by removing the sheath and retaining the anchor within the breast tissue.

Some embodiments also include advancing an anchor member inferiorly to a second location within breast tissue; removing the anchor member from the breast tissue; and after removing the anchor member from the breast tissue, advancing the anchor member inferiorly to a third location within breast tissue.

Some embodiments described herein related to a device, for adjusting soft tissue in a body, having a supporting member that is configured to be implanted in the body at a location superior to the soft tissue, the supporting member having a first portion and a second portion; a plurality of anchor members coupled to the supporting member and configured to be implanted in the body at respective locations inferior to the supporting member; wherein, when the device is implanted within the body, elevation of at least one of the plurality of anchor members elevates the soft tissue, thereby bringing one or more of the plurality of anchor members closer to the supporting member.

For purposes of summarizing the disclosure, certain aspects, advantages, and novel features of the disclosure have been described herein. It is to be understood that not necessarily all such advantages may be achieved in accordance with any particular embodiment of the disclosure. Thus, the disclosure may be embodied or carried out in a manner that achieves or optimizes one advantage or group of advantages as taught herein without necessarily achieving other advantages as may be taught or suggested herein.

BRIEF DESCRIPTION OF THE DRAWINGS

A general architecture that implements various features of the disclosure will now be described with reference to the drawings. The drawings and the associated descriptions are provided to illustrate embodiments of the disclosure and not to limit the scope of the disclosure. Throughout the drawings, reference numbers are re-used to indicate correspondence between referenced elements.

FIG. 7A is a cross-sectional view of an embodiment of a braided suture impregnated with an elastomeric coating.

FIG. 7B is a perspective view of the suture illustrated in FIG. 7A.

FIG. 8A illustrates an embodiment of a braided suture with a hydrogel core in a pre-activation (elongated) configuration.

FIG. 8B illustrates an embodiment of a braided suture with a hydrogel core in a post-activation (shortened) configuration.

FIG. 14A is a cross-sectional view of a suture with a flat support region rolled into a circular cross-section for easy placement in the patient.

FIG. 14B is a side view of the suture shown in FIG. 14A.

FIG. 15A is a cross-sectional view of a suture with a support region comprising multiple strands that provide tissue support.

FIG. 15B is a side view of the suture shown in FIG. 15A.

FIGS. 38A-38D depict embodiments of needles that can be used to create a dissecting plane.

FIGS. 39A-39C depict embodiments of dissecting needles that are used in conjunction with an implantable sling.

FIGS. 40A-40D depict embodiments for dissecting tissue or creating a dissecting plane.

FIGS. 74A-74B depict embodiments of a barbed plate.

FIGS. 75A-75B depict embodiments of a barbed plate.

FIGS. 76A-76B depict embodiments of a staple anchor.

FIGS. 77A-77B depict embodiments of a staple anchor.

FIGS. 86A-86C depict embodiments of an interrupted lumen.

FIGS. 87A-87C depict embodiments of an attached lumen delivery system.

FIGS. 94A-94B depict embodiments of a hanger anchor.

FIG. 95 depicts embodiments of a braid overlay corkscrew.

FIG. 96 depicts embodiments of a leaf anchor.

FIG. 97 depicts embodiments of an umbrella anchor.

FIGS. 98A-98B depict embodiments of a washer anchor.

FIG. 99 depicts embodiments of a T-bar anchor support.

FIG. 100 depicts embodiments of a fascia puncture deployment system.

Figure 101:
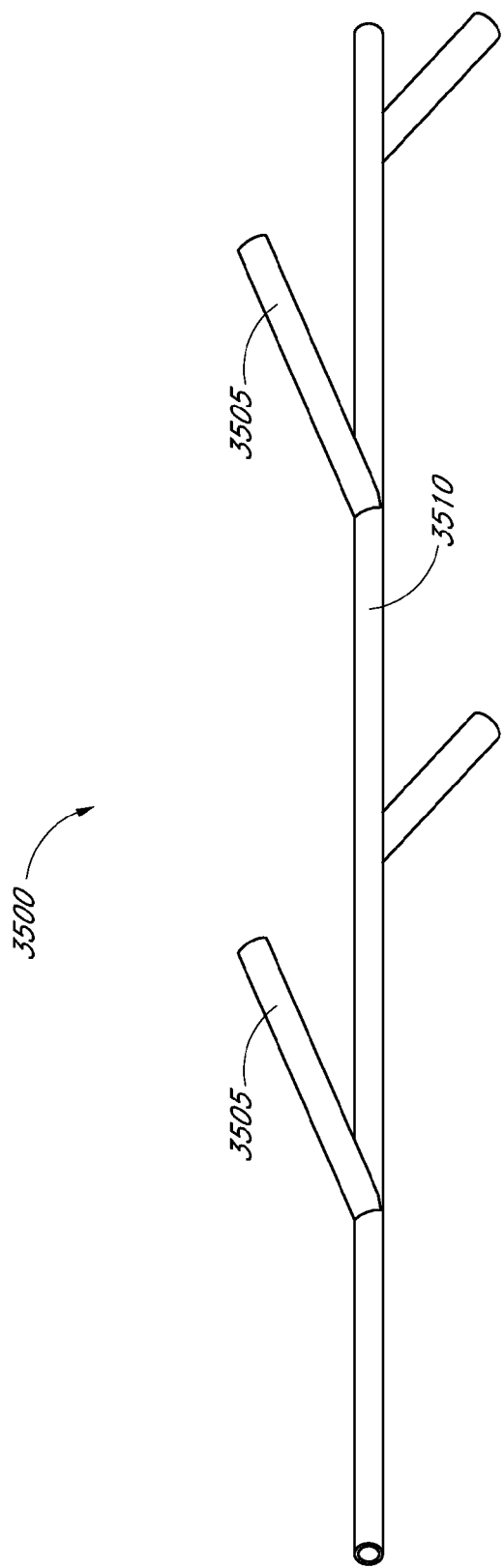

FIG. 101 schematically depicts an embodiment of a tissue anchor.

FIGS. 102A-102D depict embodiments of a tissue anchor described herein.

Figure 103A:
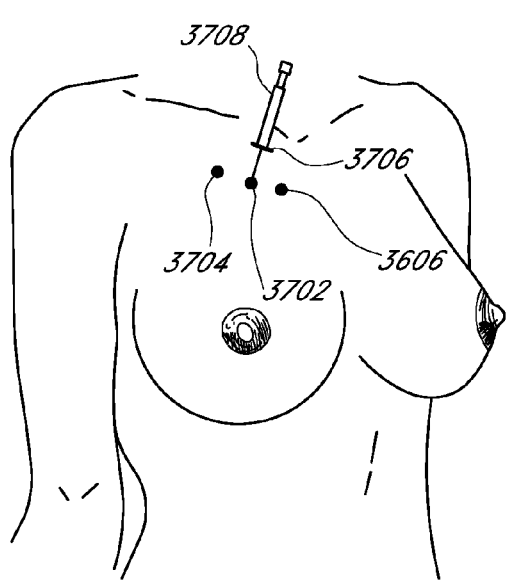

FIGS. 103A-103S depict embodiments of introducing tissue supports into a patient.

FIGS. 104A-104H depict embodiments of introducing tissue supports into a patient.

FIGS. 105A-105J depict embodiments of introducing tissue supports into a patient.

Figure 106:
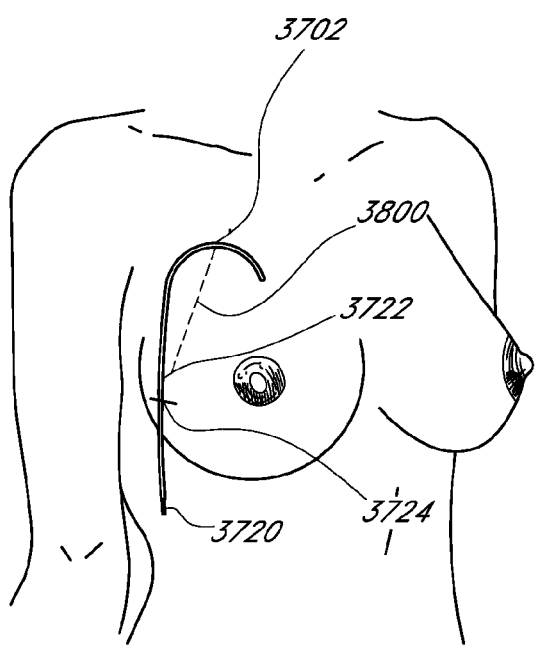
Figure 107:
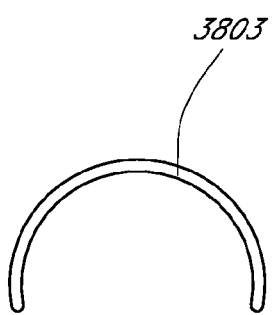

FIGS. 106 and 107 schematically illustrate components of one embodiment of a mastopexy installation system.

Figure 108:
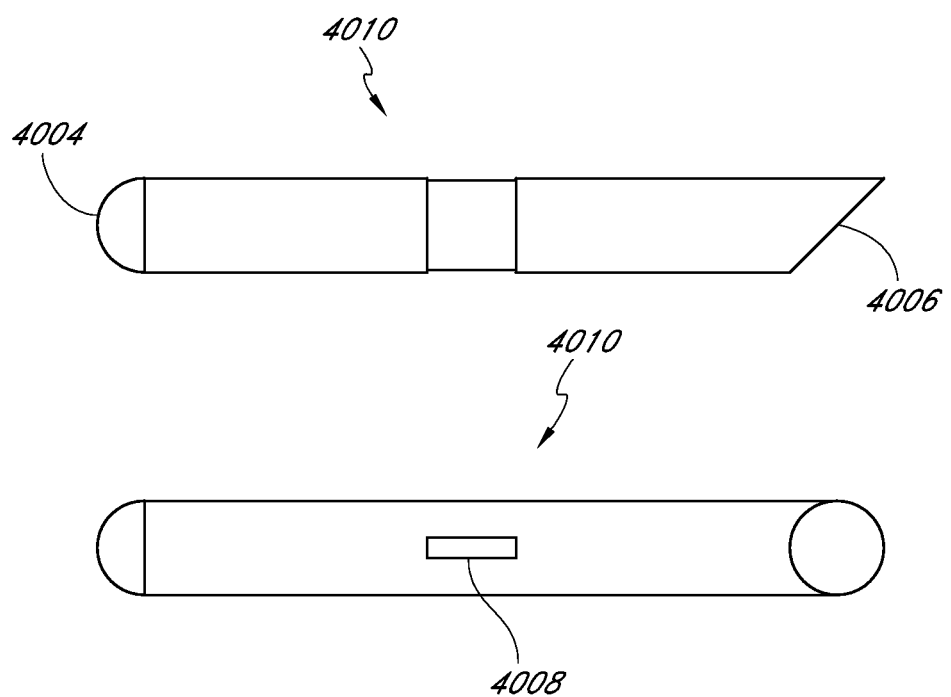

FIG. 108 illustrates manufacturing steps for making a tissue anchor, according to one embodiment of the invention.

FIG. 109A-G illustrate embodiments of tissue anchors with various apertures and/or reinforcing elements, according to some embodiments.

FIGS. 110A-110C and FIG. 111 illustrate a process of attaching an anchor to a suture line, according to some embodiments of the invention.

Figure 112:
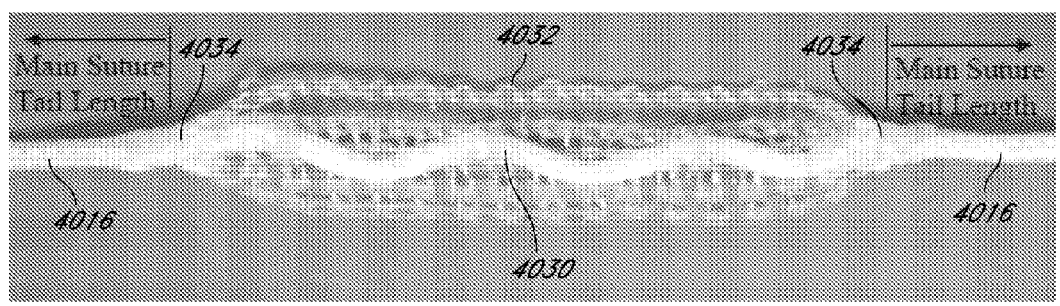

FIG. 112 illustrates a process of attaching the support sling to a suture line, according to one embodiment of the invention.

Figure 113A:
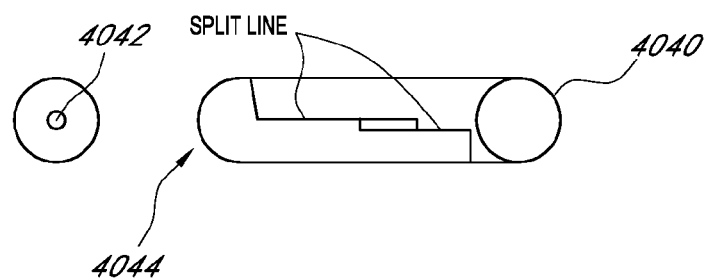
Figure 113B:
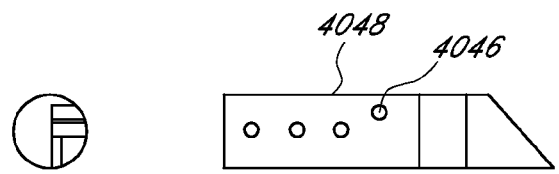
Figure 113C:
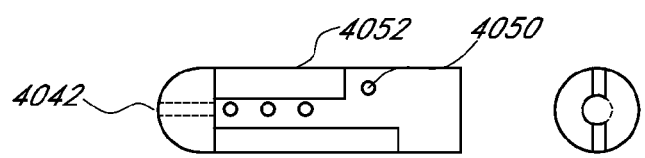

FIGS. 113A-C illustrate additional anchor configurations, according to some embodiments of the invention.

FIGS. 114A-E illustrate various views of complementary elements of an anchor, according to some embodiments of the invention.

Figure 115:
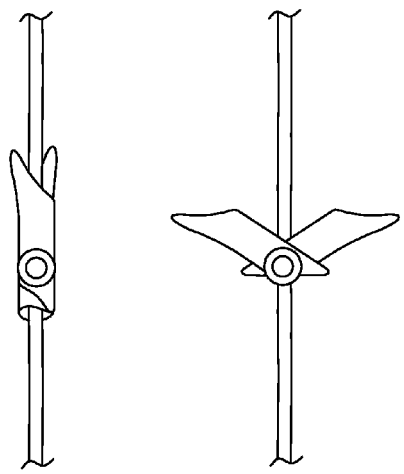

FIG. 115 illustrates a radially expandable anchor, according to one embodiment of the invention.

Figure 116:
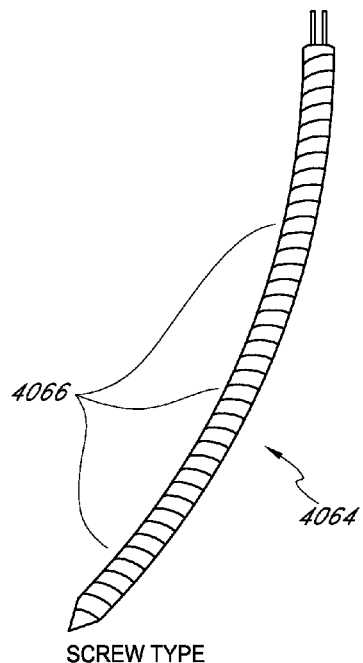

FIG. 116 illustrates a threadable anchor, according to one embodiment of the invention.

Figure 117:
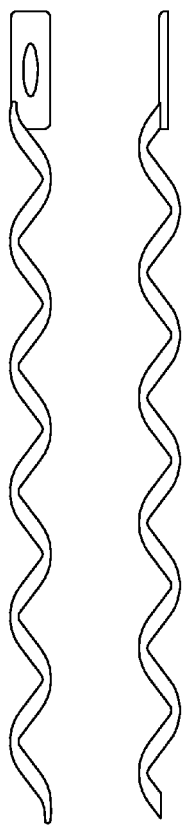

FIG. 117 illustrates a corkscrew-type anchor, according to one embodiment of the invention.

Figure 118:
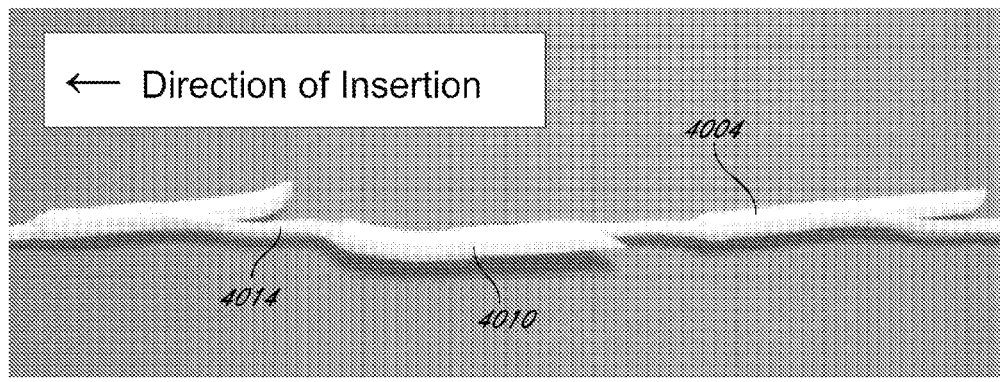
Figure 119:
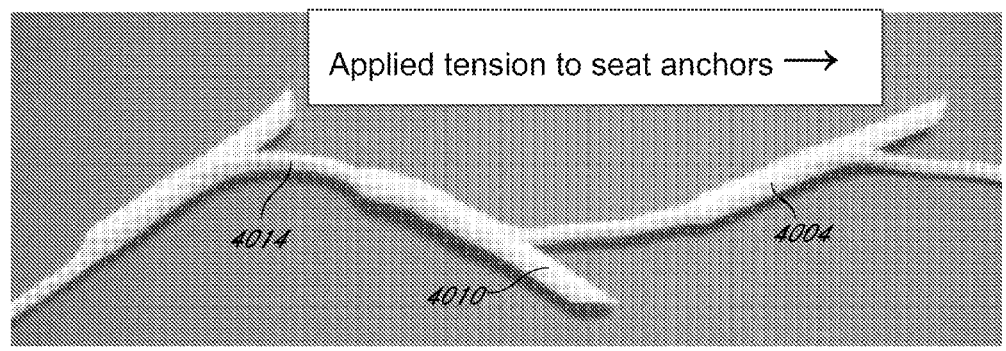

FIGS. 118-119 illustrate an interrelationship between an anchor and a suture line as tension is applied.

Figure 120:
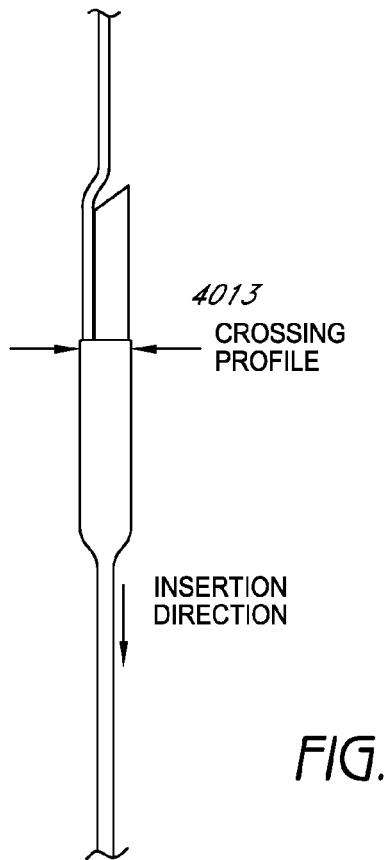
Figure 121:
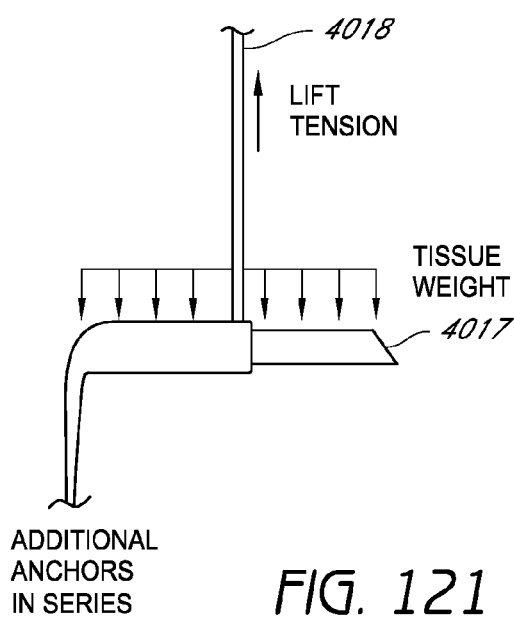
Figure 122:
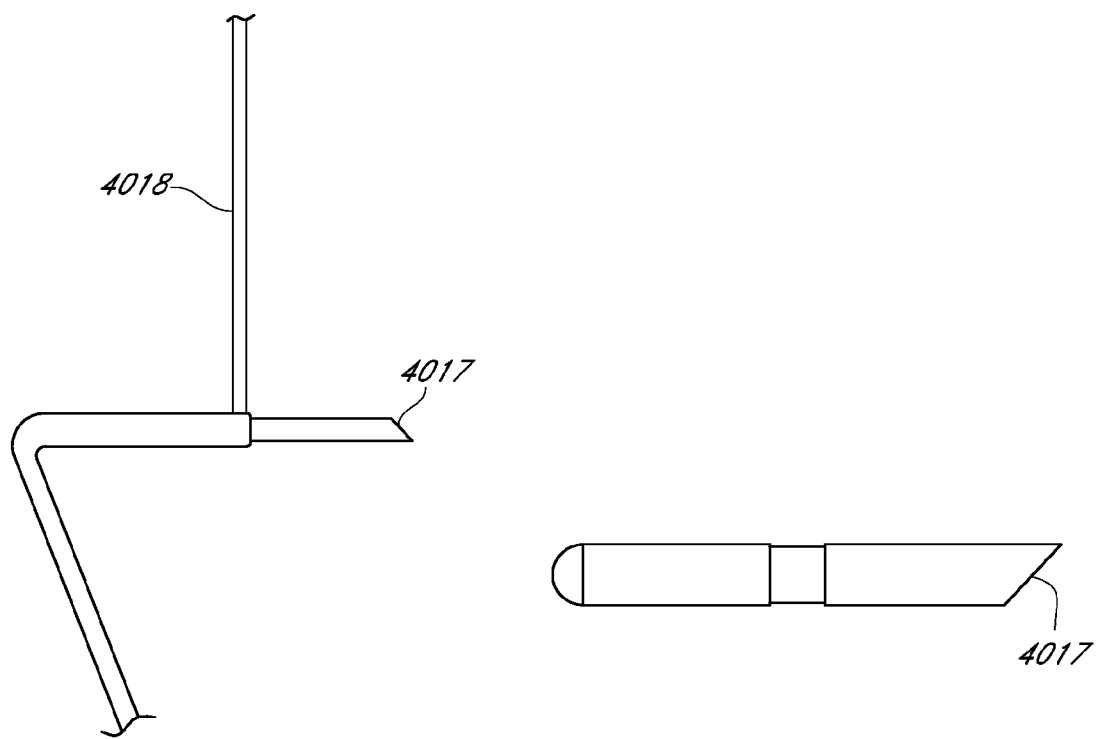

FIGS. 120-122 illustrate reduced and enlarged configurations of anchors, according to some embodiments of the invention.

Figure 123:
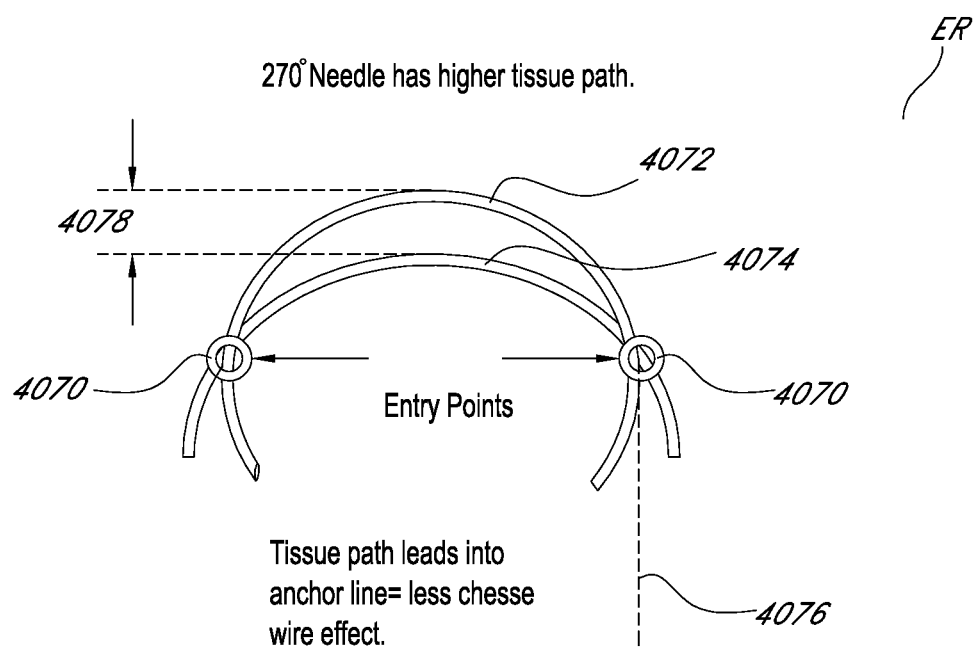

FIG. 123 illustrate various arc configurations for a sling insertion needle, according to one embodiment of the invention.

FIGS. 124A-J illustrate steps and components of a mastopexy procedure for tensioning, securement, and adjustment, according to one embodiment of the invention.

FIGS. 125A-E illustrate a spool tensioning system for tensioning a suture line in situ, according to one embodiment of the invention.

FIGS. 126A-D illustrate a hook tool for capturing a suture line for retensioning, according to some embodiments of the invention.

FIGS. 127A-D illustrate a tension adjustment procedure following installation of a mastopexy system, according to one embodiment of the invention.

FIGS. 128A-D illustrate an alternative tension adjustment procedure.

FIGS. 129A-D illustrate various embodiments of implants with one or more positioning tabs.

DETAILED DESCRIPTION OF THE PREFERRED EMBODIMENT

As used herein, the term "suture" is to be construed broadly. In general, the term "suture" refers to suspension members, while "support system" generally refers to complex, multi-component devices that can include, without limitation, at least one support member, and associated components such as suspension members, elastic elements, safety mechanisms, and anchoring portions. A support member can comprise, in some embodiments, a plurality of support elements.

Figure 1:
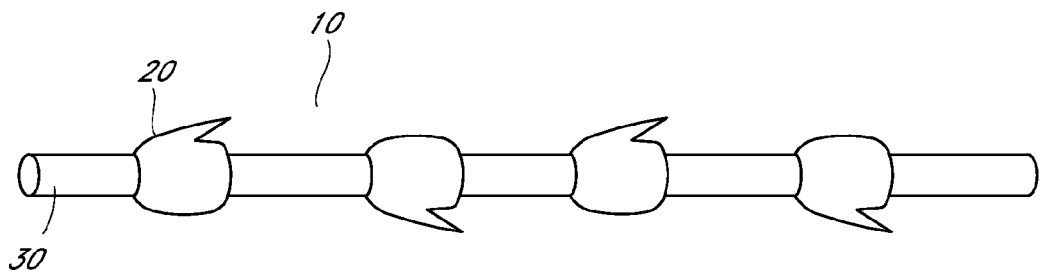
FIG. 1 illustrates an embodiment of a suture with molded barbs.

In some embodiments, a suture 10 comprising barbs 20 is provided, as shown in FIG. 1. In some embodiments, the core 30 has a relatively high tensile strength. High tensile strength can be achieved by using a polymeric material in a manufacturing process that results in a structure where the polymer chains are substantially oriented parallel to the longitudinal axis of the suture.

The core 30 of the suture 10 can be partially or completely surrounded by a like, or different material, forming the barbs 20. The properties of the suture materials can be selected on the basis of desired absorption rates, tissue in-growth, as well as a consideration of mechanical needs.

In some embodiments, the suture 10 is formed by extruding the core material to form a filament. The core 30 can then be placed in a mold that provides the barb shapes, and the mold cavity filled with material that when solid forms the outer layer of the suture, and the barbs 20.

Figure 2A:
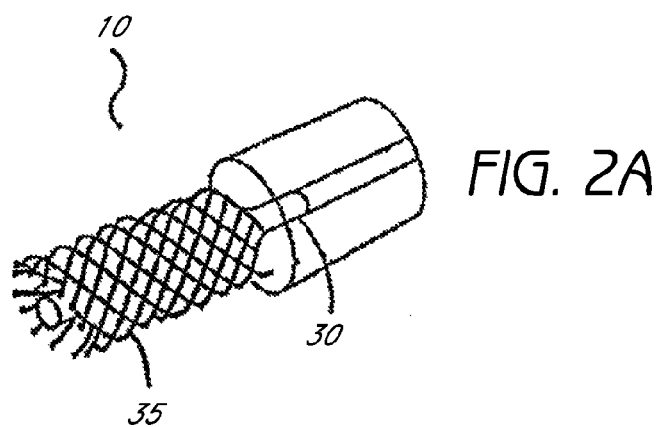
FIG. 2A illustrates an embodiment of a suture with a filamentous core and a braided portion.
Figure 2B:
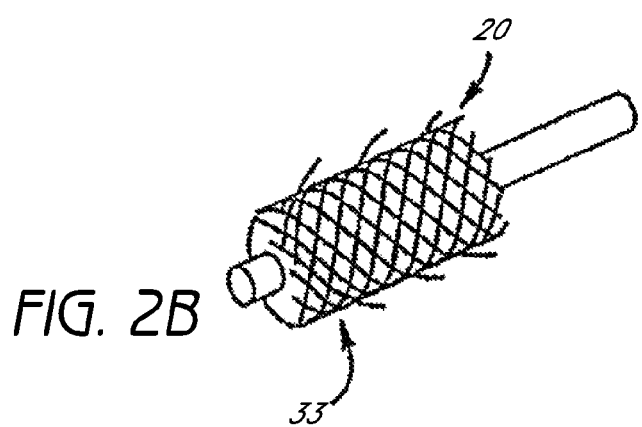
FIG. 2B illustrates an embodiment of a suture like that shown in FIG. 2A, where filaments extend outward to form barbs.

In some embodiments, the core 30 can comprise multiple filaments 33, as shown in FIG. 2A. A multiple filament design allows the suture 10 to attain a higher ratio of axial tensile strength compared to bending stiffness (i.e., resistance to bending). A portion of the filaments 33 can protrude, as shown in FIG. 2B. These protruding filaments can extend a pre-determined distance, for example between about 0.2 and 2 mm. In some embodiments, the ends of the protruding filaments are configured in the shape of barbs 20. The suture can be coated with another material or can be left uncoated.

Figure 3:
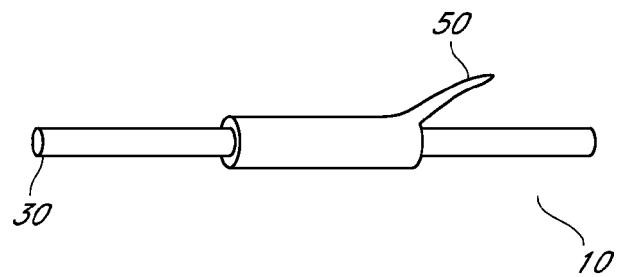
FIG. 3 illustrates an embodiment of a suture with a separately attached barb element.

In some embodiments of a suture 10, like that shown in FIG. 3, barbs 50 can be attached to the core 30 as separate members. These attached barbs 50 can be secured by bonding, gluing, or welding of the barb 50 to the outer surface of the suture core 30.

Elastic Properties

In conventional suture designs, an elastic suture typically displays only modest extensibility. Ideally, an elastic suture used in securing a healing wound should have sufficient elasticity to accommodate the swelling of tissue that occurs as part of the normal inflammatory response at the onset of healing. Additionally, the suture should continue to provide support to the tissue or wound, once inflammation and swelling have substantially subsided.

When sutures are used to support tissue, as in plastic surgery procedures, different elastic properties may be desirable. For example, during the first part of the healing process, it is possible for the sutures to pull out from the tissue in response to a modest amount of longitudinally applied force. Thus, a more elastic suture can yield enough to prevent pull-out, yet recover to its initial length, thus providing a gradual and more effective remodeling of tissue over time.

Figure 4:
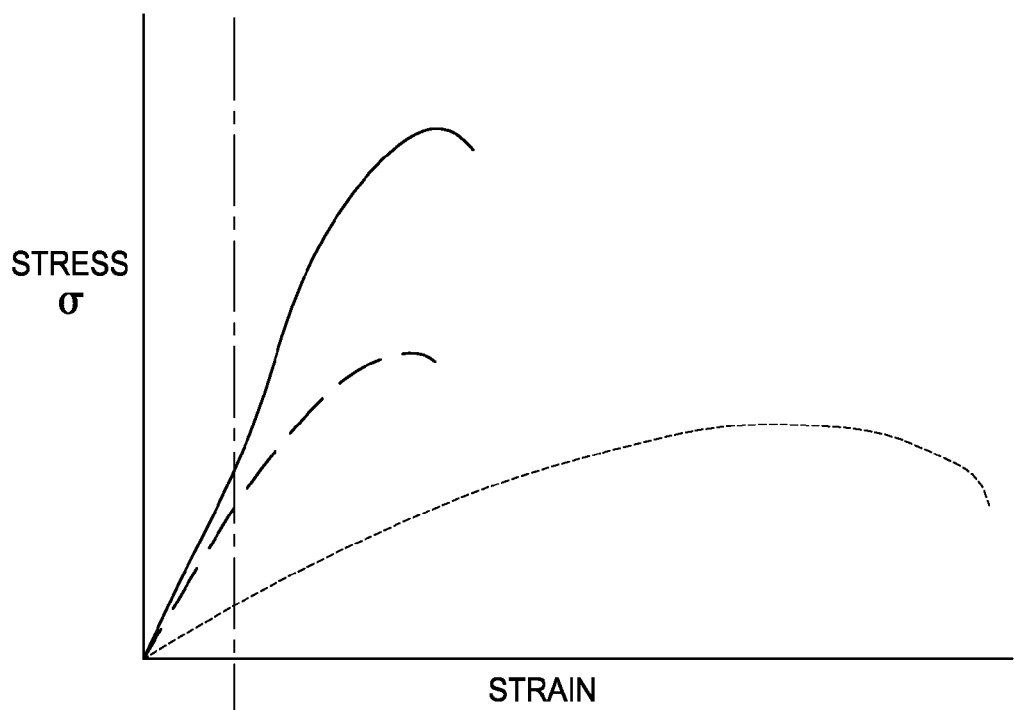
FIG. 4 illustrates the stress strain relationship among various suture types.

In some embodiments, a suture designed for use in plastic surgery procedures, for example in a facelift procedure, is capable of extending in length to 10-25%, while retaining the ability to fully recover to substantially its initial length. An example of the stress-strain curves for various types of sutures is provided in FIG. 4. Embodiments of the present disclosure (FIG. 4, dotted line), sutures are able to accommodate significant strain while displaying less stress than traditional high tensile strength sutures (FIG. 4, solid line), or even traditional elastic sutures (FIG. 4, dashed line). Thus, examples of the disclosed suture are capable of acting like a constant force spring, where force (i.e., strain) is relatively constant over a wide range of deflections.

In some embodiments, where a large mass of relatively immobile tissue is to be supported, for example in a breast lift application, it can be advantageous to provide a suture with a more progressive spring rate. In these embodiments, the stress-strain properties of the suture or support system can be optimized to simulate the natural biomechanical properties of the tissue. For example, in the case of a system for supporting the breast, the force/deflection characteristics of the support system can be designed to simulate that of Cooper's ligaments, or the combination of Cooper's ligaments and tissue that make up the outer structure of the breast.

Commonly used suture materials do not normally exhibit the properties of high elongation that are desirable in plastic surgery procedures. Natural materials, such as collagen, do however provide a highly extensible matrix that is useful in embodiments of the present disclosure. Collagen based sutures are often referred to as "gut" sutures. The source of collagen is varied and can include, without limitation, intestinal submucosa, pericardium, and tendon, from animals including humans, cow, pig, horse, donkey, kangaroo, and ostriches, etc.

Where the source of collagen is a native tissue, the tissue can be fixed in order to cross-link the collagen. Common fixatives include glutaraldehyde. Where greater extensibility is desired, chromic acid can be used as the fixative. Still other fixatives can be used, and the choice of fixative is not considered to be limiting to the scope of the present disclosure. For example, tissues can be fixed using radiation, dehydration, or heat.

In some embodiments, the suture can comprise a core made from a highly elastic synthetic polymer. Some suture materials can be made from formulations that are elastic in compression but have low strength in tension, for example hydrogel polymers. In some embodiments, the biocompatible gelling material is a solution containing water-insoluble polymers, for example non-cross-linked acrylonitrile polymers or their co-polymers, polyvinyl acetate, a linear or low-branched polymer or copolymer of 2-hydroxyethyl-acrylate and methyl acrylate, poly-n-vinyliminocarbonile and dimethylsulfoxide or other polar or readily water miscible solvents, for example as disclosed in U.S. Pat. No. 4,631,188 to Stoy et al., the contents of which are herein incorporated by reference in their entirety. These exemplary polymers solidify when placed in contact with living tissue as a result of absorption of water from the tissue and gradual release of the solvent into the surrounding tissue.

In obtaining copolymers, use can be made of additional monomers, such as acrylamide (including N-substituted), acryl hydrazide (including N-substituted), acrylic acid and acrylates, glutarimide and vinyl sulfone. Solvents can include glycerol and its mono- or diacetates, methanol, ethanol, propanol and iso-propanol, dimethylformamide, glycols, and other suitable solvents.

Figure 5A:
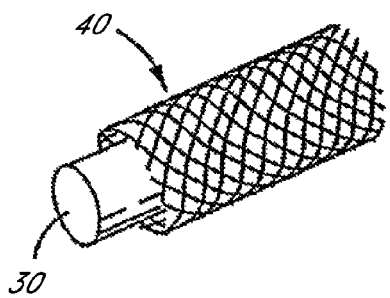
FIG. 5A illustrates an embodiment of a braided suture.
Figure 5B:
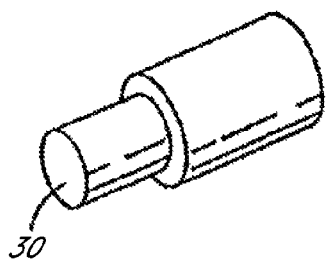
FIG. 5B illustrates an embodiment of the suture shown in FIG. 5A, with the braided portion removed to reveal the core.

In some embodiments, the core 30 can be covered with a braided portion 40 as shown in FIG. 5A. The braid can be made from traditional high tensile strength suture materials. Here, the angle of the braid can be selected such that the braided structure can elongate from its free state. Elongating the braid results in a decrease in the diameter of the lumen of the braid, and in turn results in compression of the core 30, which in turn resists further deformation of the braid. An embodiment of a suture core with the braid 40 relaxed is shown in FIG. 5B. As indicted above, in embodiments employing a hydrogel polymer core, the core material will be weak in tension, but will effectively resist compression.

Figure 6A:
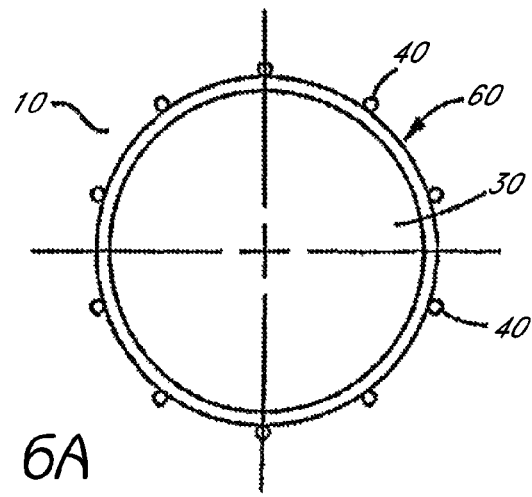
FIG. 6A is a cross-sectional view of an embodiment of a braided suture that includes a membrane lying between the braid and the suture core.
Figure 6B:
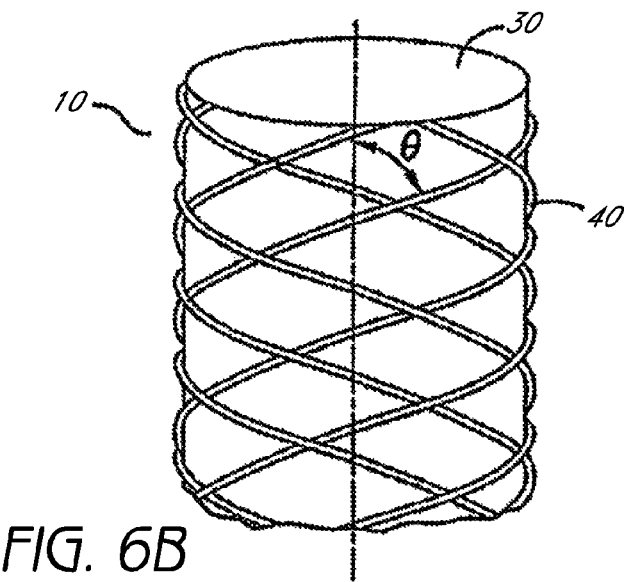
FIG. 6B is a side view of the suture illustrated in FIG. 6A.

In some embodiments, the core 30 can be separated from the braided portion 40 by a membrane 60 that prevents the individual braid filaments from cutting into the core material, as shown in FIGS. 6A and B. Again the angle of the braids, relative to the longitudinal axis of the core (0 in FIG. 6B), can be selected such that the braid can be elongated.

In some embodiments of a highly elastic suture, the suture includes a core 30, a braided portion, 40, all of which is impregnated with an elastomer 70. In some embodiments the elastomeric portion can comprise a "core" of one or more components the device. In some embodiments, an elastomeric material can be used to cover device components. In some embodiments, an elastomeric material can cover other portions of the device, providing an "elastomeric cover." For example, during manufacture, the suture can be forced into a foreshortened configuration and then impregnated with an elastomeric coating. The elastomer 70 can substantially impregnate the weave of the braid 40 and is effective to behave mechanically like an additional "core." The elastomer is also effective to provide resistance to elongation. Neither the composition of the elastomer, nor methods of coupling or applying it to other components of the suture are limiting. Conveniently, in some embodiments, the elastomer can comprise without limitation, silicone, thermoset polyurethane, glycolide-co-caprolactone, copolymers of lactic acid and sebacic acid, and the like, as well as combinations of more than one elastomeric material.

Shrinkable Sutures

In some surgical applications, an advantage is provided by embodiments that are able to gradually shrink in length over time, or which can be made to shrink at a later time, in response to an activation provided by a physician.

In some embodiments, a shrinkable suture 80 comprises a core 30 surrounded with a filamentous braid, as shown in FIG. 8A. Here the angle of the braid is such that as the core is allowed to expand in diameter it applies a force to the braid which shortens in length as a result, as shown in FIG. 8B. Shortening of the braided portion results in an overall shortening of the entire suture. The core material can comprise a hydrogel or other suitable swellable material.

In some embodiments, a shrinkable suture comprises a bioabsorbable core, surrounded by a shape memory or other form of bias member. When placed in the patient, the bioabsorbable core 35 is absorbed over time. As the bioabsorbable core is absorbed it will weaken, with the result being that the force generated by the bias member, will dominate the biomechanical property of the suture.

Figure 9:
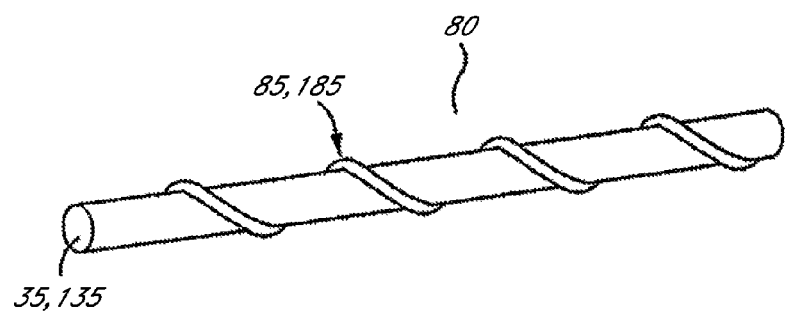
FIG. 9 illustrates an embodiment of a suture in which shortening of the suture is provided by a shape memory material.

In some embodiments, an example of which is shown in FIG. 9, the shrinkable suture 80 is configured to shrink in response to an activation energy or signal. In one case, a shrinkable suture comprises a shrinkable core 35 that heals into the tissue into which the suture is placed. In some embodiments, the shrinkable core 35 comprises collagen. The shrinkable suture 80 further comprises an energy transfer member 85 for delivering energy to the shrinkable core 35. In some embodiments, the energy transfer member 85 comprises a wire that can be heated by RF energy, or via a directly applied electrical current. Upon heating, the wire transfers energy to the shrinkable core 35, which in turn results in heating of the shrinkable core 35. In response to the thermal energy, the shrinkable core 35 in turn shrinks, creating tension in the tissue into which the shrinkable suture 80 is embedded. In the case of a shrinkable core comprised of an unfixed tissue, a temperature of 42° C. can be effective to result in shrinkage. In some applications it can also be desirable to cool the tissue immediately after the heat shrinkage step in order to minimize damage to surrounding tissue.

In some embodiments of a shrinkable suture, the suture comprises a first material 185 having a relaxed length and a deformed length, where the deformed length is longer that the relaxed length. In some cases the deformed length is 10-30% greater than the relaxed length. In some embodiments, the suture is extended to its deformed length, and that configuration held by a second material 135 that resists relaxation. Conveniently, the second material 135 can be biodegradable, such that when the suture is placed in the body, the second material is absorbed over time. Once enough of the second material has been absorbed, the first material 185 assumes its relaxed length, and the suture shortens.

In some embodiments, the first material can comprise Nitinol or any other suitably elastic material, as shown in FIG. 9. In some embodiments the first material 185 can comprise a shape memory material, that can be activated after a period of time to assume a memorized length that results in shortening of the suture, or an increase in tension imparted by the suture on the surrounding tissue. Activation can be performed after a period of time sufficient for the second material 135 to be absorbed by the body.

Tissue Ingrowth

Healing typically occurs in three stages: inflammation, tissue formation, and matrix formation and remodeling. Matrix formation and remodeling can persist for as long as 6-12 months after wounding. Sutures used for temporarily holding tissues together are generally designed to minimize inflammation. Sutures designed to support tissue, such as those used in plastic surgery lift procedures, should also encourage tissue ingrowth, so that eventually the suture is further supported by a column of native collagen-containing scar tissue.

A variety of methods can be used to promote tissue ingrowth. When sutures made from naturally occurring material are used, this can include, methods of fixation of the suture material(s). For example, glutaraldehyde, EDC or epoxy fixatives result in sutures with more tissue ingrowth potential than do other fixatives. Where synthetic suture materials are used, braiding can be used to enhance tissue ingrowth. In some cases, synthetic materials can be manufactured such that they are porous. Implants with porosity greater than about 50 to 75 gm will generally permit tissue infiltration and vascularization. Porosity can be varied the construction of the suture, for example by providing a multifilament suture with a loose braid, or with twisted filaments.

Absorbability

All embodiments described herein can be fashioned from bioabsorbable materials. Materials can include those from natural sources such as gut, and other like materials, or synthetic materials. A variety of polymers can be used to produce bioabsorbable sutures including, without limitation, poly(glycolic acid), poly(glactin), poly(para-dioxanone), poly(trimethylenecarbonate), or poly(caprolactone). Different combinations of materials can be used to produce sutures that display different rates of absorption in vivo. In some embodiments, sutures can comprise both absorbable and non-absorbable materials.

Preventing "Cheese-Wire" Effect

For supporting tissues, especially larger masses of tissue, such as the breast or buttocks, some embodiments can be designed to prevent what is known as the "cheese-wire" effect; i.e., cutting through tissue by the suture or support member due to movement of the suture or support relative to the adjacent tissue. Cheese-wiring is particularly evident when using very thin sutures, or ones with abrasive surfaces. In some embodiments, using a suture made from a natural material can be effective to reduce the cheese-wire effect, due to their relatively large cross section and smooth surface, and because they better heal into the surrounding tissue.

Figures 10A, 10B:
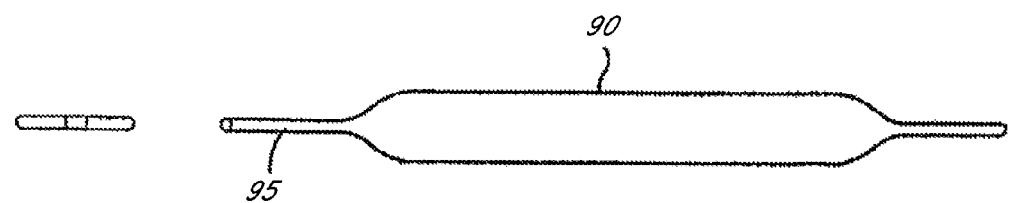
FIG. 10A is a cross-sectional view of an embodiment of a suture having a widened portion to spread out loading and limit cheese wiring of the suture through tissue.
FIG. 10B is a side view of the suture shown in FIG. 10A.

In some embodiments, a suture or a support system can comprise a region with a wide cross section 90 in at least one direction, as shown in FIGS. 10A and B. Thinner ends 95 can be provided to improve ease of securing the suture in place in the patient. In some embodiments, the suture can be configured as a thin-walled tube, analogous to an angioplasty balloon.

Figure 11A:
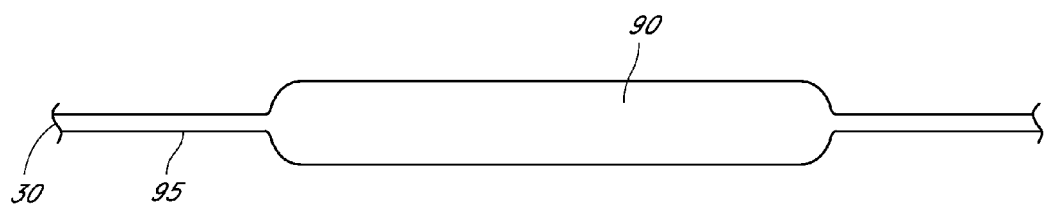
FIG. 11A illustrates side view of an embodiment of a suture having a widened portion to spread out loading in an extended conformation, where the widened portion is expandable.
Figure 11B:
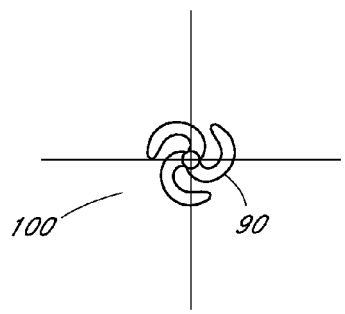
FIG. 11B illustrates a suture like that shown in FIG. 11A that has been rolled up for delivery.
Figure 11C:
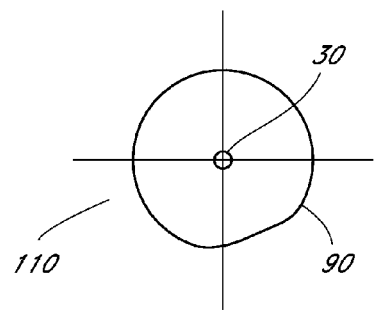
FIG. 11C illustrates an end view of suture like that shown in FIG. 11A that has been expanded.
Figure 11D:
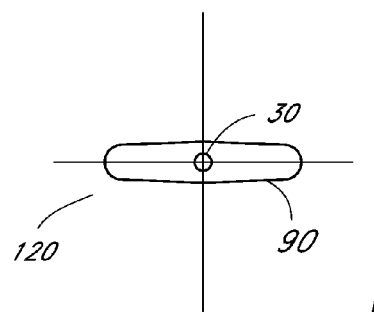
FIG. 11D illustrates an end view of a suture like that shown in FIG. 11A that has been expanded and then flattened.

The suture can be folded down into other configurations. For example, a folded suture 100 can be produced by drawing the unfolded suture, shown in FIG. 11A, through a folding die, as in FIG. 11B. Once the suture is placed in a desired position, it can be configured to assume a shape that provides a wider support area effective to support tissue, while limiting the extent to which the suture will cut into the tissue. In one method, the folded suture 100 shown in FIG. 11B is expanded to form an inflated or expanded suture 110, shown in FIG. 11C, which is then deflated in order to provide a flattened suture 120, shown in FIG. 11D.

Figure 12A:
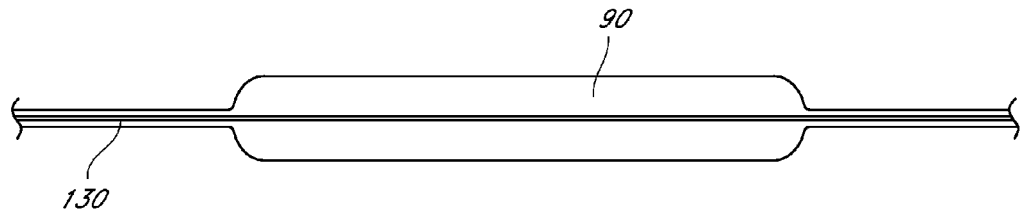
FIG. 12A illustrates side view of an embodiment of a suture having a widened portion, and further comprising support members.

The suture can optionally include supports 130 running either internally or externally, to provide additional tensile strength, as shown in FIG. 12A. In some embodiments, the supports comprises wires running along the longitudinal axis of the suture. Other supporting elements other than wires can also be used.

Figure 12B:
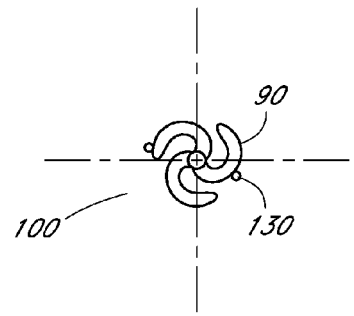
FIG. 12B illustrates a suture like that shown in FIG. 12 that has been rolled up for delivery.
Figure 12C:
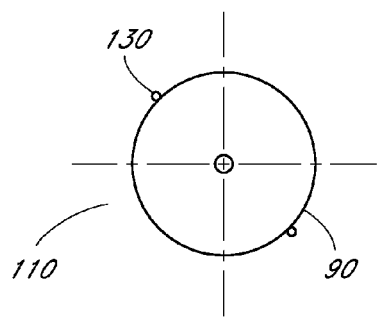
FIG. 12C illustrates a cross-sectional view of a suture like that shown in FIG. 12 that has been expanded.
Figure 12D:
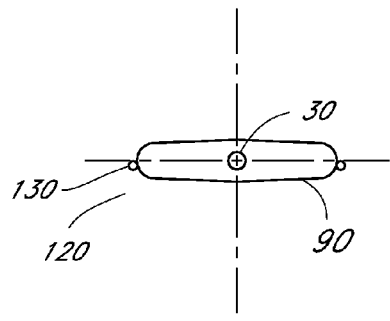
FIG. 12D illustrates an end view suture like that shown in FIG. 11A that has been expanded and then flattened.

A suture with supports 130 can be reconfigured as described above. For example, as with the suture shown in FIG. 11, a portion of a supported suture can comprise an inflatable region. As above, the suture 90 can be folded 100, by drawing through a folding die, as in FIG. 12B. The folded suture can be expanded 110, as in FIG. 12C, and then flattened 120, as in FIG. 12D.

In some embodiments, the device can be inflated with an inflation media. In some embodiments, the inflation media can be removed and the device deflated, or the inflation media can remain, in which case the device remains inflated. In some embodiments, the device can be inflated with a fluid (i.e., gas or liquid) that later changes viscosity, converts to a gel, or solidifies. In some embodiments, the device can be expanded mechanically by use of a dilation tool. The dilation tool, in some embodiments, comprises a wire or plurality of wires that can also be used to form the device into the flattened configuration 120.

Figure 13A:
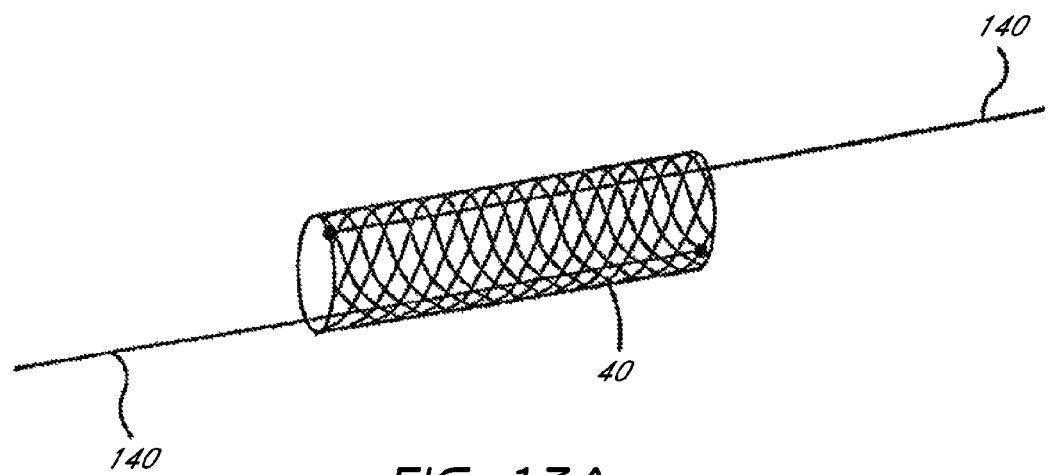
FIG. 13A illustrates a perspective view of a suture with a braided region that shortens and widens when attached sutures are placed under tension, in an extended conformation.
Figure 13B:
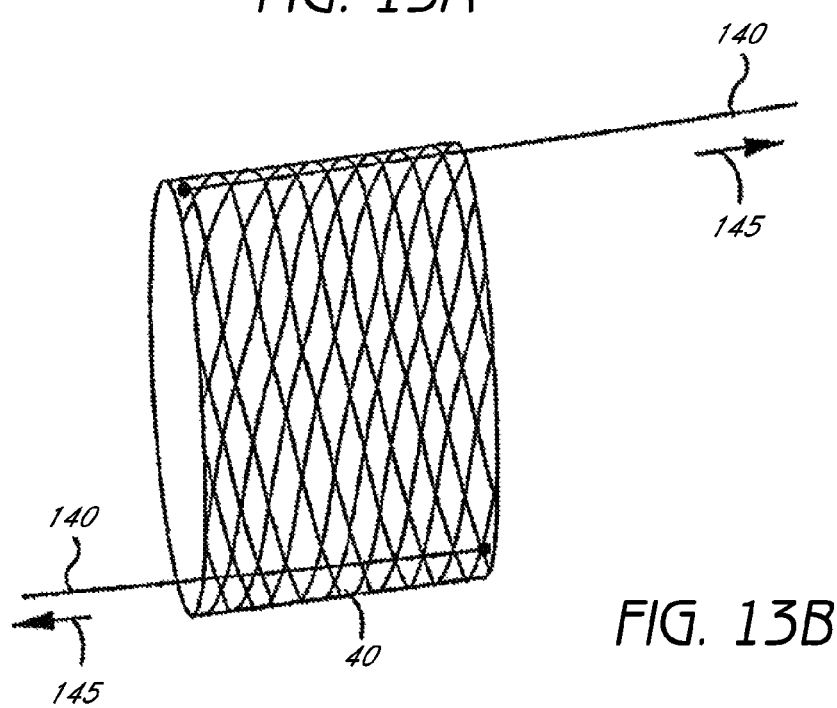
FIG. 13B illustrates a perspective view of a suture like that shown in FIG. 13A in the shortened conformation

In some embodiments, wires 140 are connected to opposite ends, of a braided section 40, as shown in FIG. 13. Tensioning 145 of the wires will result in shortening and widening of the braided region, resulting in a wider support area.

In some embodiments, an expandable suture can be fashioned from a small diameter, expandable tube. In some embodiments, a second suture passes through the lumen of the tubular suture, and is attached to a plug having a significantly larger diameter than the inner diameter of the tubular suture. Once the tubular suture is in place in the patient, the plug is drawn through the tubular suture, resulting in expansion of the tubular suture diameter. In some embodiments, the tubular suture diameter can be expanded by 500%. By optimizing the wall thickness of the tubular suture, the suture once expanded, will tend to assume a flattened configuration.

In some embodiments, a suture can be expanded with a heated fluid. Increasing the temperature of the suture can provide several advantages, including, and without limitation, allowing easier expansion of the suture, accelerating tissue-ingrowth, and inducing shrinkage of collagen in the region surrounding the suture.

In some embodiments, a suture 150 is provided as a flat strip of material, which can then be rolled up into a smaller diameter for easier insertion into the patient, as shown in FIGS. 14A and B. After insertion, the suture can be unrolled back to the flattened configuration to provide more effective tissue support. In some embodiments, at least the flat portion of the suture comprises a shape memory material, such that it spontaneously assumes a flattened configuration upon release from a delivery device, for example a sheath, specialized needle, or trocar.

In some embodiments, a suture can comprise a plurality of wires 170 coupled to either an anchor point, or a gathering point 175 short of an anchor point, as shown in FIG. 15. Providing a multiplicity of wires effectively spread out the weight of the tissue being support, thereby reducing the tendency for a single wire to cut into tissue.

Figure 16A:
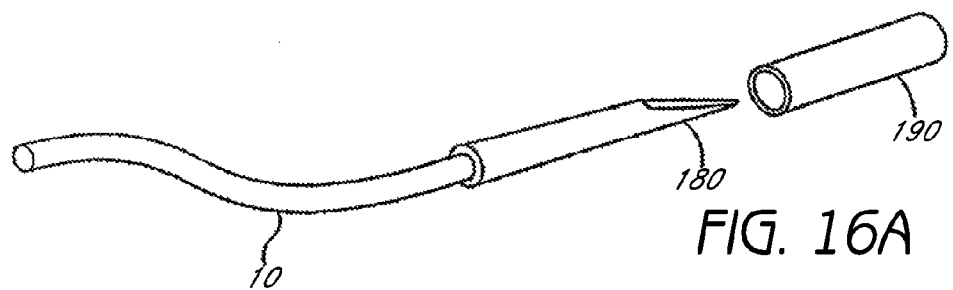
FIG. 16A illustrates a needle and sheath arrangement for use in delivering a suture.
Figure 16B:
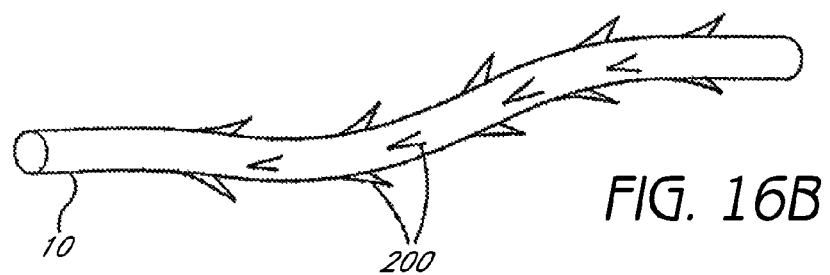
FIG. 16B illustrates a suture having bidirectionally oriented barbs.

In delivering embodiments of a suture as described herein, the suture 10 can be provided attached to a needle 180, or inserted inside a protective delivery sheath 190, as shown in FIG. 16A. Delivery of a barbed suture inside a trocar, sheath, or catheter, for example, allows efficient delivery of the suture regardless of the orientation of barbs. In some designs, delivery of barbed sutures by needle required that the barbs be oriented such that the suture can glide into the tissue into which it is inserted (i.e., the barbs face away from the direction of insertion). These designs also require that the skin be punctured a second time in order to access the implanted needle, so that it can be trimmed from the suture and removed following suture placement.

In embodiments of the present disclosure where the suture can be delivered within a trocar or sheath, some techniques permit delivery of the suture with only a single skin puncture. This can reduce the risk of complications due to infection, reduce the amount of pain involved in a procedure, and allow for more rapid recovery of the patient. In addition, use of a the delivery sheath can prevent engagement of the tissue by the barbs until the sheath is removed, as so sutures with bidirectionally oriented barbs 200 can be easily delivered.

For example, with current sutures, performing a facelift procedure requires sutures enter near the hair line and exit through the cheek near the nasolabial fold. After the procedure, the patient is left with sutures that protrude from the face, which is aesthetically unappealing. In response, the suture ends are trimmed such that they lie just below the surface of the skin. In some case, however, the ends can erode through and reappear on above the surface of the skin. Trocar or sheath delivery avoids these problems.

Figure 16C:
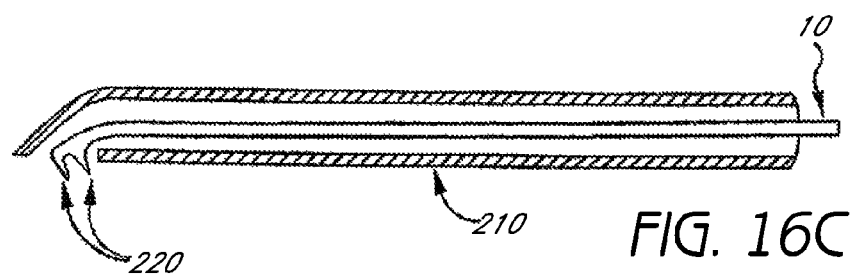
FIG. 16C illustrates a sheathed suture with barbs to engage tissue to assist in deployment.
Figure 16D:
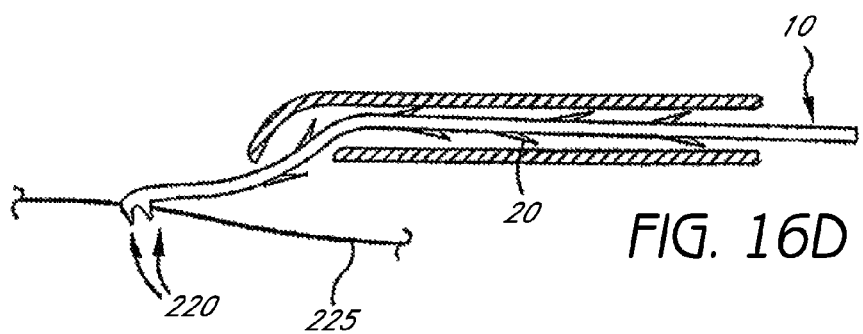
FIG. 16D illustrates the suture of FIG. 16C with an end extended from the sheath as during deployment.

In some embodiments, one of which is shown in FIG. 16C, a delivery sheath 210 for a suture 10 includes a small opening through which a portion of the suture can protrude. A region at or near the tip of the suture can comprise a barbed end 220. During placement of the suture, the suture can be substantially fully enclosed within the sheath, such that the barbs do not grasp tissue while the sheath and suture are being advanced, as shown in FIG. 16C. After the suture end is in a desired location, the barbed end 220 of the suture 10 can be advanced out of the sheath 210, allowing the barbs to engage adjacent tissue 225. Once engaged, the barbs will effectively anchor the end of the suture substantially in place, while the sheath is withdrawn, exposing the remainder of the suture, as shown in FIG. 16D. The suture can include additional barbs 20 in addition to those located at or near the end, to further anchor the suture in place once the delivery sheath has been removed.

Figure 16E:
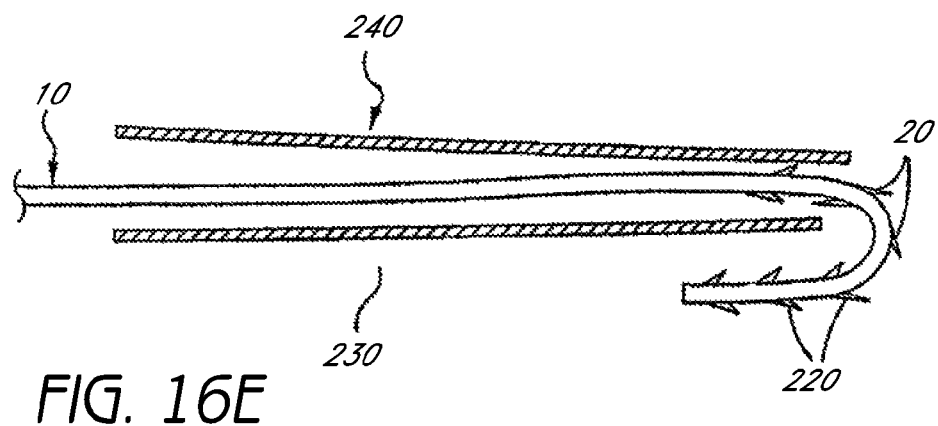
FIG. 16E illustrates an embodiment of a sheathed suture and deployment sheath where the end of the suture can be bent backwards as part of the method of deployment.

In some embodiments, a trocar 240 that is open at both ends 240 can be provided to deliver the suture 10. A barbed suture can be passed through the trocar, the barbs oriented so that the suture, once exposed to adjacent tissue, resists movement relative to the trocar. In some embodiments, a length of the barbed suture extends out from the end of the trocar, as shown in FIG. 16E. The length of suture extending from the suture can be from about 0.5 cm to about 5 cm, although this is not considered limiting. Pushing on the trocar results in the exposed portion of the suture doubling back on itself, such that the barbs will engage the adjacent tissue, as shown in FIG. 16E. Once the end of the suture is set in place, the trocar can be withdrawn, leaving the suture in place. Tensioning can be performed in a similar manner as that used with other barbed suture embodiments described herein.

The distal end of the trocar can be cut at an angle or ground such that the end of the trocar forms a point, while providing room for bending of the suture. In an exemplary embodiment, a trocar has a 0.5 mm OD and a 0.3 mm ID, and is about 225 mm long. A suture of slightly less than 0.3 mm diameter fits easily within the trocar.

Figure 16F:
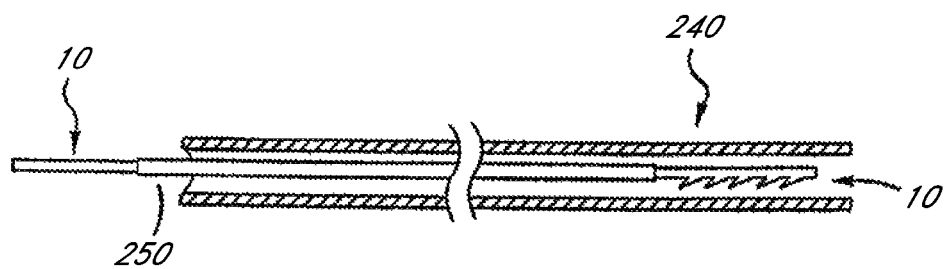
FIG. 16F illustrates an embodiment of a sheathed suture where deployment is aided by a pushable tube.

In some embodiments, coaxial arrangement of a support material surrounding the suture can be used to improve pushability of the suture, as shown in FIG. 16F. The support member 250 can be coupled to the proximal end of the suture to aid in delivering the suture with a pushing force. After delivery, cutting the end of the suture distal of the coupling would release the support from the suture, and allow withdrawal of the support and trocar, leaving the suture in place. The support member can be made from a variety of materials including, without limitation, Nitinol, surgical steel, or polymers such as PEEK, polyimide, polyethylene, polypropylene, or composite material suitable for use in medical devices such as catheters.

In some embodiments, the delivery system includes a multi-part needle, as shown in FIG. 17A-D. In some embodiments, the needle has two components, a needle 260 having a first radius of curvature, and a hypodermic tube 270 having a second radius of curvature. The first radius will be greater than the second radius. For example, the first radius of curvature of the needle can be 5 cm, while the radius of curvature of the tube can be 15 cm. The needle and tube are coaxially arranged such that the needle is slidably held within the tube.

Figure 17A:
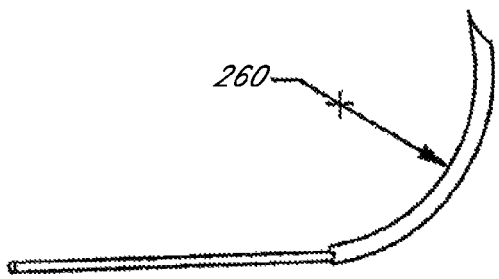
FIG. 17A illustrates an embodiment of a curved needle for use in deploying a suture along a curved path.
Figure 17B:
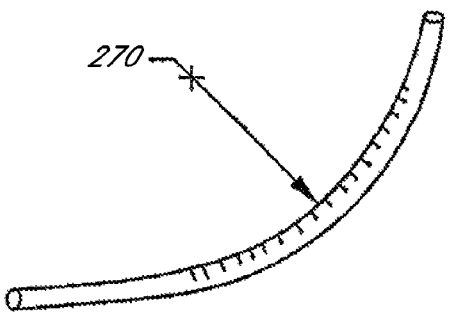
FIG. 17B illustrates a tube configured to hold a needle, and which has a larger radius of curvature than the needle of FIG. 17A.
Figure 17C:
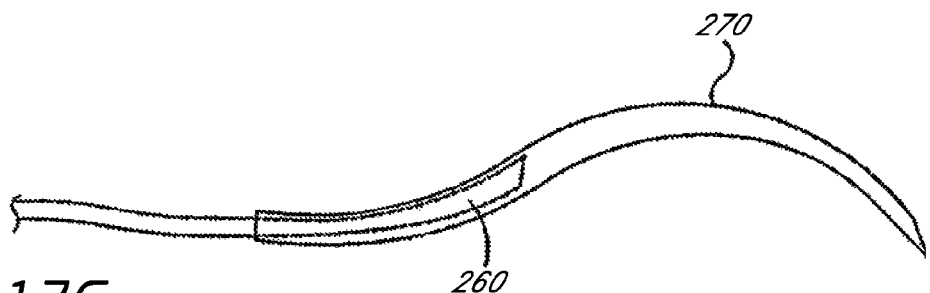
FIG. 17C illustrates a coaxial needle combination where the tip of the inner needle is pulled back from the end of the outer needle.
Figure 17D:
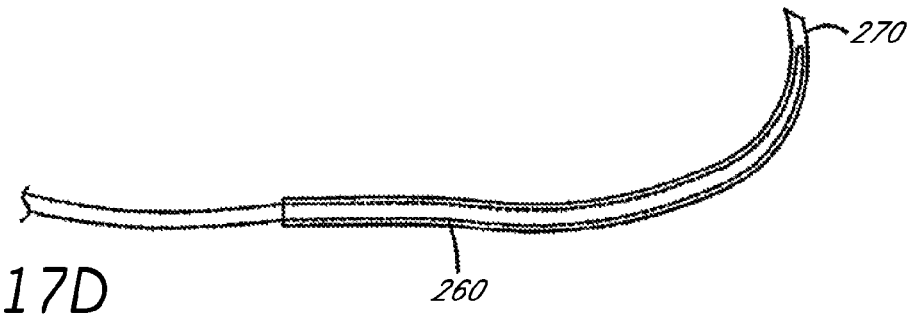
FIG. 17D illustrates a coaxial needle combination where the tip of the inner needle is inserted nearly to the end of the outer needle.

In using this system, the surgeon can continually alter the path of the suture by simply regulating how much of the needle 260 is held within the hypodermic tube 270. Where less of the needle is within the tube, the radius of curvature will be dominated by the shape of the tube and have, in this example a radius of 15 cm. Where more of the needle is within the tube, the needle will force the tube to take on a shape with a smaller radius, and thus follow a track of smaller radius, for example a radius of 5 cm. Thus, the surgeon can advance a suture over a more or less curved path, as shown in FIGS. 17C and D.

It will be readily understood that the radii recited above are provided only as examples, and various combinations of needles and tubes with varying radii can be used. In addition, the system can include a needle and a plurality of tubes, such that the device could be telescoped in order to provide even finer control of the suture path through tissue.

Coaxial, multiaxial, steerable designs can also be applied to the trocars and catheters as described above. In addition, the systems can also include guide wires that the trocar or catheter passes over. Guide wires can include a needle tip and be steerable, providing an even smaller radius pathway through tissue.

To aid the physician in placing sutures, the suture can include identifiers to mark barbed regions, or the length of the suture contained within a trocar, for example. In one embodiment, the suture is color coded with a particular color indicating a barbed region, while a different color can be used to indicate a non-barbed region. In some embodiments, other colors or marking can be used to indicate regions with distinctive mechanical properties. For example, and without being limiting, a third color can be used to indicate a region of increased elasticity.

During the surgical procedure, visualization can be accomplished by direct or indirect methods, including ultrasound, MRI, CT, or using an endoscopic tool and camera combination, among other imaging modalities. Sutures, needles, and trocars, can include markers as are known in the art for visualization when using radiographic imaging modalities. Such markers can be made, without limitation, from metals such as gold, platinum, stainless steel, and other suitable metallic alloys or even non-metallic materials. Such markers can be included during the manufacturing process.

An advantage provided by some suture embodiments, as described herein, is the ability to adjust or re-tension the suture after placement. Adjustment permits the surgeon to maintain a particular tissue configuration and appearance over time. In some cases, such as where the suture does not include barbs, or where the suture does not protrude through the skin and is therefore relatively inaccessible, an additional adjustment mechanism can be included with the suture, in order to provide a way in which to vary tension of the suture during the course of the healing process, and even afterward.

In some embodiments, the adjustment mechanism comprises a knot and a ratchet mechanism. In some embodiments, the adjustment mechanism can comprise a tang in a groove, analogous to a zip tie device. Where possible, embodiments comprising a knot are designed to be low-profile, such that the adjuster does not produce a bump, or erode through the skin.

Figure 18:
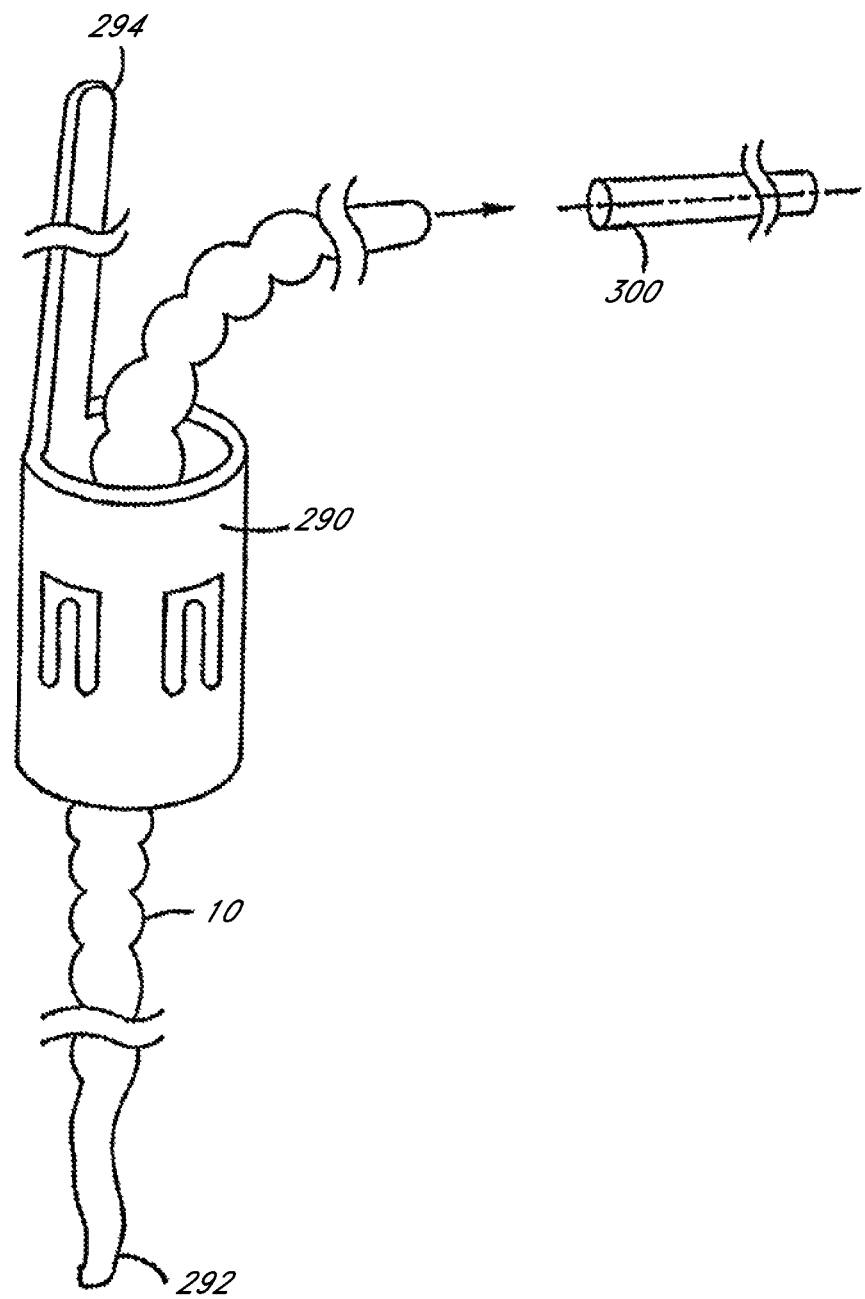
FIG. 18 illustrates an embodiment of a device for deploying and tensioning a suture, as well as for connecting suture ends.

In some embodiments, the ends of a single suture, or the ends of two separate sutures, can be joined by a linking device, where a first end is a tube 290, and a second end has a substantially round cross-section 300, as shown in FIG. 18. The second end is inserted into the tubular section of the first end. A skived area near the first end allows the second end to protrude.

A variety of methods of securing the first and second ends can be used. In some embodiments the ends can be secured by an adhesive that is cured in response to heat, pressure, moisture, or a chemical catalyst. In some embodiments, the tubular section can be made to be shrinkable, or alternatively be made from a shape memory material. In some embodiments, the second ends includes barbs that engage the first end, or a feature on the first end such as a pocket. In some embodiments the barbs can be on the first end, in the lumen of the tubular portion, and engage the second end which can be barbed or not. The second end can further comprise a textured surface, or multiple regions of varying diameter to better engage the first end. In some embodiments, a tubular section engages two separate sutures having substantially round cross sections. In some embodiments, the tubular connector section can be deformable, and will adapt to the cross-sectional shapes of the sutures to be joined. Conveniently, the tubular member 290 can include an anchor 294, for securing the joining device in place in the patient. A suture end can also include an anchor 292.

A number of embodiments of the present disclosure are compatible for use in performing breast lift procedures. In some embodiments, the support member can be composed of Proline, a non-elastic polymer line. The support member can be placed underneath the breast tissue, and secured by means of a knot or a fastener to a body landmark such as a tendon, bone, or the like. As described above, the system can include suspension members that are either elastic or non-elastic. The system can further include a safety disconnect, permitting the suspension members to release when under an increased load, in order to prevent damage to the breast tissue by the support system.

Use in Breast Procedures

Figure 19:
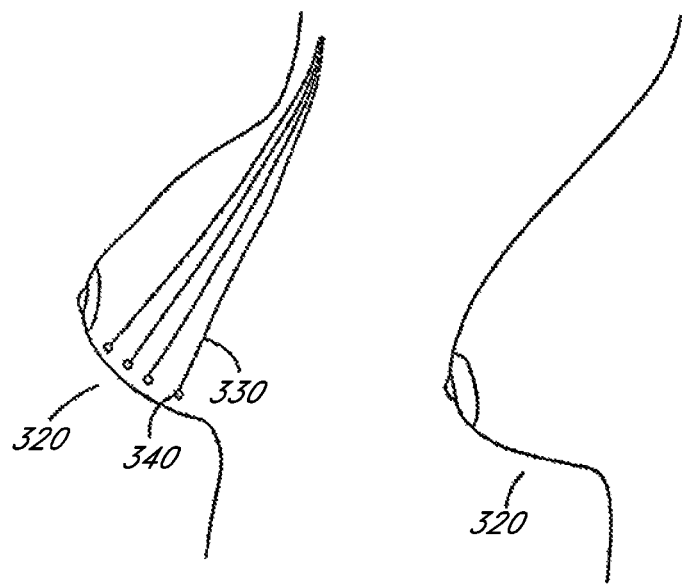
FIG. 19 is a side view illustrating a placement of sutures to perform a breast lifting procedure.
Figure 20:
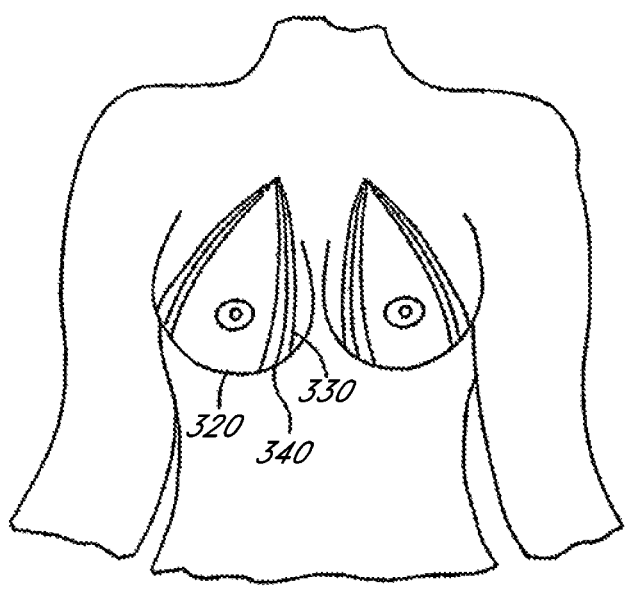
FIG. 20 is a front view illustrating a placement of sutures to perform a breast lift procedure.

In some embodiments, sutures of the present disclosure are used to perform a minimally invasive breast lift, as shown in FIG. 19. In one method, suspension members 330 are inserted through the skin and advanced at a depth of between about 2.5 and 25 mm under the skin surface. The suture is passed through the Cooper's ligaments and fatty tissue. One or more loops of suture material are looped under the breast 320, and suture ends are attached to an area in the chest 342, serving as anchor points for the suspension members 330. The sutures are tensioned in order to simulate support provided by natural, healthy Cooper's ligaments, as shown in FIGS. 19 and 20, and are effective to lift the breast 320 (compare left and right panels in FIG. 19).

In some embodiments, the attachment to the chest areas comprises a loop of suture material threaded around a portion of the pectoral muscle, fascia, sternum, a rib, or a ligament, or combinations thereof. The loop is inserted through the skin with a small caliber needle, and positioned below the top edge of the breast, so that the suture support is not visible through the skin. A curved needle attached to the suture can be used to insert the suture material. In some embodiments, the needle comprises two parts that are axially movable relative to each other, and which have different curvatures, such that the surgeon can adjust the curvature of the needle is it is being inserted. In some embodiments, the suture is delivered within a sheath.

In some embodiments, the anchor can comprise a bone screw, attached to bone or cartilage in the sternum or rib cage.

In some embodiments, a suture 330 can run from the anchor point 342, along one side of the breast 320, under the breast, and up the other side back to the anchor point 342. A number of sutures 330 placed in this way will be effective to cradle and lift the breast from below. In some embodiments the sutures 330 could run down either side of the breast and attach at support points 340 either under or to one side of the breast. A number of possible ways of placing and orienting sutures will be possible in achieving lifting of the breast while maintaining breast symmetry and aesthetic appearance. These various arrangements and combinations will be apparent to those of skill in the art.

In some embodiments, the suture lines can be extended transcutaneously around the nipple area to preferentially reposition this portion of the breast. This corrects the situation where the nipple turns downwards in response to age or as a result of breastfeeding. Looping a suture line around the nipple provides for support of the nipple, without having to support the entire weight of the breast. Where a nipple repositioning technique is used, the suture can be anchored using the methods as described above.

In some embodiments, lifting of the pectoral muscle is used to adjust the physical appearance of the breast. A method to modify the muscle tissue by shortening it can comprise cutting the muscle and drawing it together, or drawing it together using a series of threads similar to a corset. Lacing the tissue together results in lifting of the breast tissue resulting in a more youthful appearance, and a reduction in breast ptosis.

In some embodiments, shortening of the muscle fibers is accomplished by internal anchors deployed into the muscle fibers. Drawing the anchors together in turn draws the muscle tissue together. The anchors can be connected by suspension members comprising elastic or inelastic materials. Elastic material can be used to allow for normal loading conditions such as physical movement and activity. Additionally, elastic materials can result in further lifting of the breast tissue.

Elastic material examples can include, without limitation, silicone core braided materials similar to a "shock cord" construction, polypropylene mesh as used in hernia mesh, NiTi alloy wires or braids, coiled type springs, and similar materials and combinations known in the art. In some embodiments the materials distribute the entire load throughout the length of the suspension line limiting longitudinal movement. In some embodiments, the suture lines comprise relatively inelastic materials including, without limitation, polypropylene suture, NiTi wire, stainless steel wire, polypropylene mesh and the like. These materials can be attached to anchors such as barbs, hooks, flared materials such as NiTi elements and the like.

This system can be foreshortened during initial implantation or post implantation with mechanisms such as, and without limitation, screws, loops, cams and rotary pulleys, or any other means effective to shorten thread or wire-like elements. The muscle can be additionally suspended by hernia mesh material and tied to land marks such as, without limitation, bone, fascia, tendon, and other areas that would bear the loading conditions. In some embodiments an exemplary diameter of a suspension line can range from about 0.005 inches to about 0.090 inches. In some embodiments the diameter of a suspension line would be about 0.030 inches.

In some embodiments the material permits tissue ingrowth, and thus moves with the native tissue, reducing irritation and cutting of the tissue. The material can be coated with a therapeutic agent to enhance tissue ingrowth, and in some embodiments the suture material is manufactured to include the therapeutic agent. In some embodiments, the therapeutic agent is added just prior to implantation, either by impregnation, by coating, or by a combination of the two processes.

In some embodiments, coatings or treatments can include an inhibitory agent to limit or prevent tissue ingrowth such that the material will not adhere to the surrounding tissue. In some embodiments a suspension line runs through a cylinder of fluid that allows movement between the suspension line and the tissue.

Figure 21:
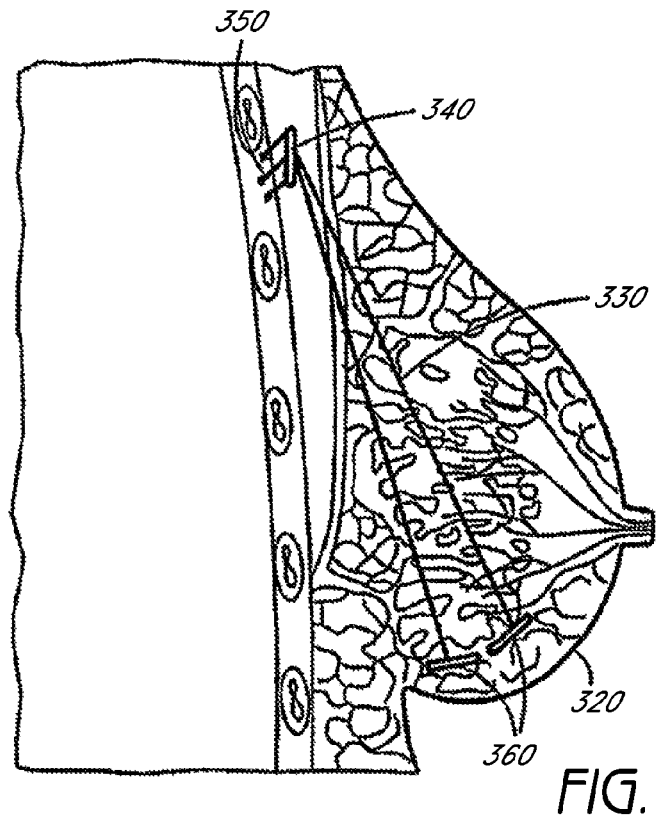
FIG. 21 is a side view of a breast and an embodiment of a support system comprising a support member and vertically oriented suspension members.
Figure 22:
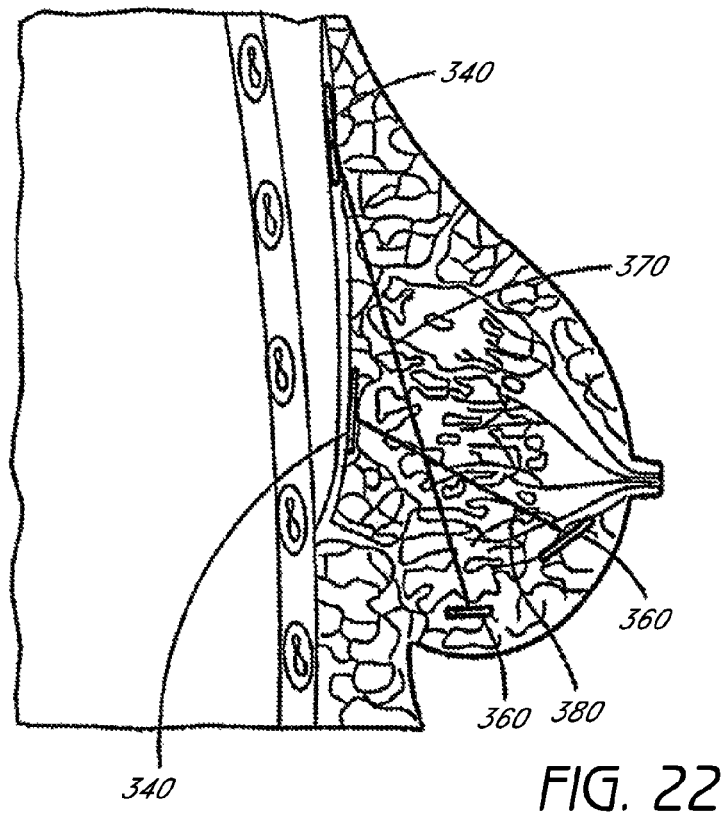
FIG. 22 is a side view of a breast and an embodiment of a support system comprising a support member and suspension members oriented vertically and non-vertically.

In some embodiments the support system comprises suspension members 330 are provided that are oriented in a substantially vertical orientation, as shown in FIG. 21, and attach to an anchor point 340 above the breast. The support members 360 are coupled to the suture lines 330. In some embodiments, angles for suspension members other than vertical are used to customize the shape of the breast or where the procedure is used to correct breast asymmetries. As shown in FIG. 22, angled suture lines 380 can provide lifting or additional lateral adjustment, in addition to what can be provided using vertically oriented suspension members. For example, by placing the support lines angled either to the right or left of vertical, the nipple and/or breast may be adjusted medially or laterally as desired by the surgeon, in addition to vertical repositioning. In some embodiments, a vertical support line and secondary tensioning line can be used, and the vertical lines can thus be pulled laterally, redirecting the force vector supporting the breast tissue. In some embodiments, it can be useful to provide laterally oriented suspension members alone, such as where lateral repositioning is required, but lifting is not desired or otherwise indicated.

Figure 23:
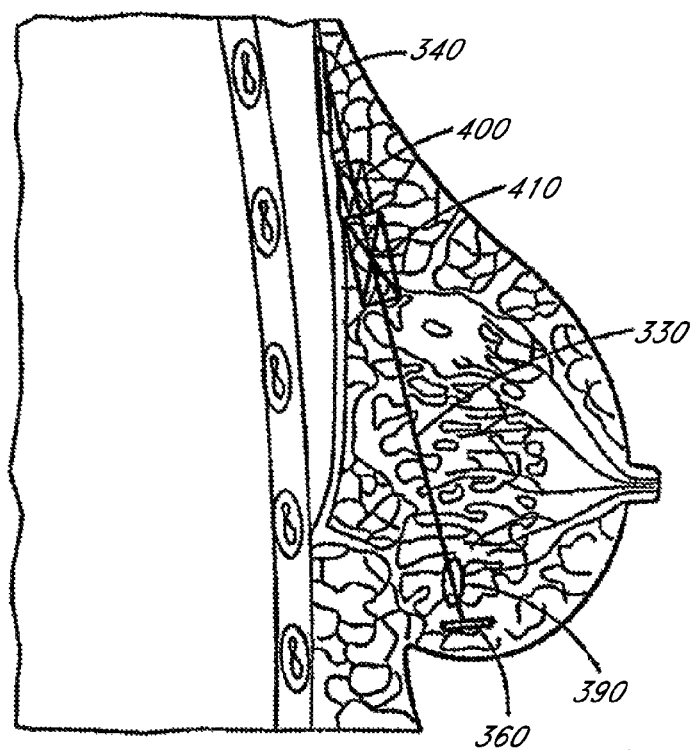
FIG. 23 is a side view of a breast and an embodiment of a support system comprising two types of elastomeric components, and a safety mechanism to prevent overloading of the tissue.

In some embodiments, the support system comprises components with non-linear elastic constants (e.g., a secondary elastomer to increase the load bearing at the bottom of the stroke). This allows for normal support while standing, and provides additional load bearing capacity during activities such as walking, running, and jumping. In some embodiments, components that allow for complex loading are designed using larger cross sectional areas or by providing components fashioned from more than one material, where the individual materials have distinct elongation characteristics. In some embodiments first 400 and/or second 410 elastic components can be used to provide more complex mechanical behavior, as shown in FIG. 23. In some embodiments, the first and/or second elastic components can comprise springs. In some embodiments, the first and second elastic components can have the same or different elastic constants. In some embodiments, the first and/or second elastic components can be positioned anywhere along the length of a suspension member.

Safety Disconnect

In some embodiments, a safety release 390, shown in FIG. 23, provides a mechanism to protect the attachment area or the supported tissue from damage caused by support system components when large loads are imposed on the tissue and/or the support system. For example, excessive load can occur during excessive motion or concurrent with a trauma. The safety release 390 is designed to separate the support member 360 from the suspension members upon exceeding a defined loading.

In some embodiments, the safety release 390 comprises a region engineered to fail at a predetermined limit. In some embodiments the mechanism comprises a necked section to allow for yielding. In some embodiments, a slip disconnection that decouples, or a joint that unlatches can be examples of effective safety releases. In some cases the safety release mechanism can be designed such that it can be reconnected or repaired following release. The loading limit effective to result in release of the suspension members from the support member can range, for example, from about 0.5 kg to about 8 kg, and in particular from about 1 kg to about 3 kg of force.

Figure 24:
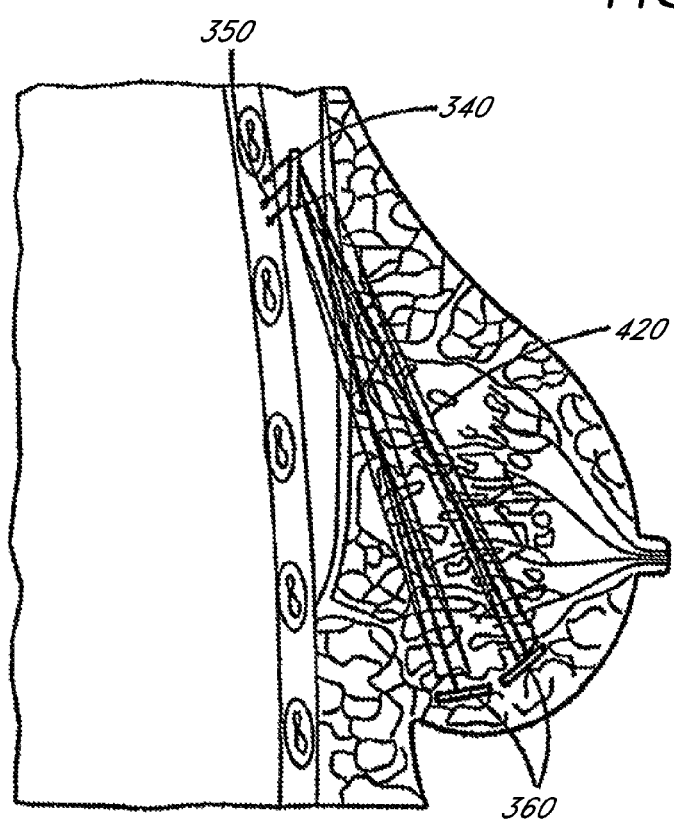
FIG. 24 is a side view of a breast and an embodiment of a support system comprising continuous length suspension members, and a length adjustment mechanism.

In some embodiments, selecting the elastic characteristics of the support member to carry partial or complete loading can allow for a least amount of tissue movement relative to the suspension element. In some embodiments, the entire length of the support system can assume the stress where the least amount of movement is shared throughout the entire system. Continuous length elastic elements 420 can be used to support the loading to lessen the stress concentrations in one area of the implant, as shown in FIG. 24. In some embodiments, the system can also include an adjustment mechanism 350, useful to vary the tension exerted on the tissue by the support system either at the time of implantation, or later once the healing process is complete or near complete. Adjustments could also be made over extended times in order to maintain the supported tissue in a desired position.

Support Member with Inflation Pleats

In some embodiments, the support member can include additional load carrying or shock absorption capability. For example, hydraulic (gas or liquid) elements can provide a resilient cushion in order to compensate for various loading conditions, such as jogging and other sporting activities, or to absorb some of the effects of trauma. In some embodiments, shock absorption is provided by a support member comprising inflation chambers 430. The chambers can be configured to compress during heavy loading, with compression providing the resiliency to return the device to a pre-loading configuration once the activity or other source of loading has ended. Similarly, the system can include a charged system, analogous to an automotive shock absorber, to dampen loading, and where the charge would allow for recoil loading.

The chambers can have a wall thickness in a range, for example, from about 5 μm to about 250 μm, depending upon the material, the inflation pressure to be used, and the degree of resiliency desired. There can be a single chamber or multiple chambers. Material choice, chamber wall thickness, and/or inflation pressure can provide customized mechanical properties to support members. In some embodiments, the length of the chambers ranges from about 5 cm to about 15 cm, and width ranges from 0.5 cm to about 4.0 cm. In some embodiments, the length of the inflation chamber is about 10 cm, and the width is about 3 cm. Precise shapes and dimension can be varied depending on the particular anatomical makeup of the patient, or on the kind of support or aesthetic results desired.

In some embodiments, the chamber(s) can be filled with a media that solidifies or gels. In some cases, the media remains in a liquid form. Composition of the media can include, without limitation, silicone, saline, epoxy, and any other safe implantable fluids, solids, or gases that will be substantially retained within the chamber(s).

Figure 25:
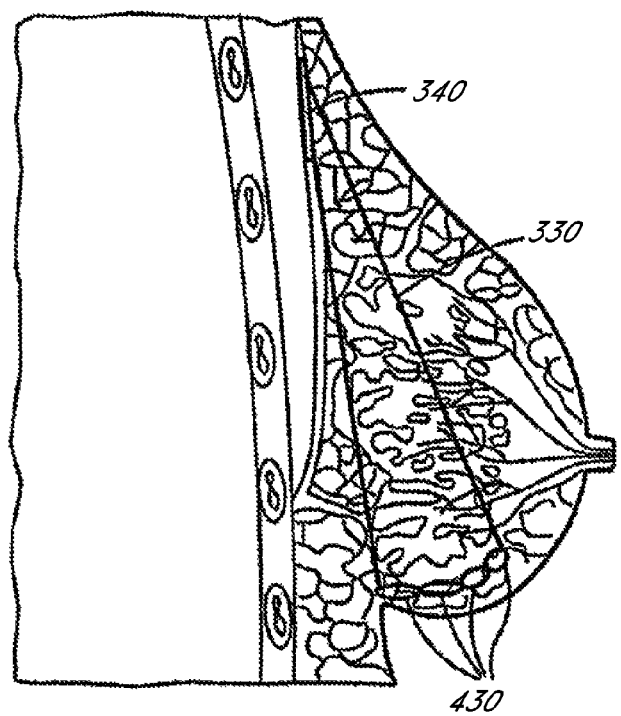
FIG. 25 is a side view of a breast and an embodiment of a support system where the support member comprises inflation chambers.

In some embodiments, addition of one or more volume elements supported by suspension elements can be used to augment low volume breast tissue and enhance the final outcome with respect to a patient's fullness. The volume element can comprise a prior art augmentation device such as a silicone or saline implant or it can use a dermal filler to soften the look of the breast. In some embodiments, support members comprising chambers 430, an example of which is illustrated in FIG. 25, can be adapted to provide volume enhancement. Fillers can include, without limitation, commercially available materials such as Radiance, Juvederm or other suitable filler materials. Additionally, the patient's own cells or other tissue could be used to offset the decrease or need for additional filling. These cells could be harvested and replaced or harvested and processed by centrifuging or filtering to collect cells suitable for implantation.

In some embodiments, different connection points for suspension and support members can be used to adjust the position of each breast separately, or to allow shape changes that improve the cosmetic appearance of the breasts, for example to provide symmetry.

Folded Support Member for Easier Insertion

As described above, in some embodiments the support system is folded prior to delivery. Folding reduces the device profile, such that a smaller incision can be used to provide an entry point when introducing a support suture or system into the body. The smaller incision in turn limits the size of the scar resulting from the implant procedure. A number of manipulations well known in the art including, without limitation, rolling, folding and twisting of the support member, can be used to reduce the device profile prior to delivery.

Figure 26:
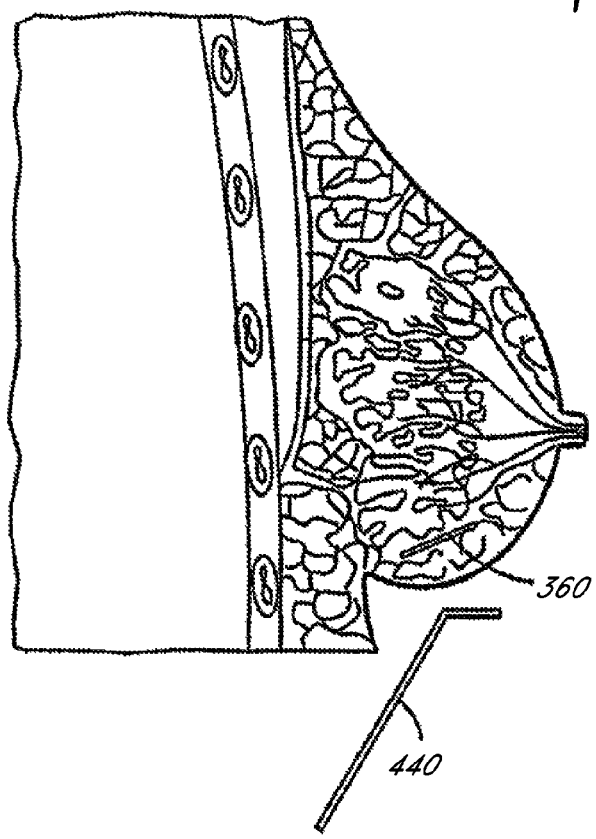
FIG. 26 is a side view of a breast and an embodiment of a tool for inserting and spreading or flattening a support member in the tissue.

Post-insertion, the mesh support member can be opened and flattened for final placement. In some embodiments, the unfolding process is performed using specialized instruments, such as a small tool 440 in similar in shape to a "hockey stick" as shown in FIG. 26. Spoon shaped tools are also effectively used to unfold and place the device in the desired location.

Support System Including Barbed Elements

Figure 27:
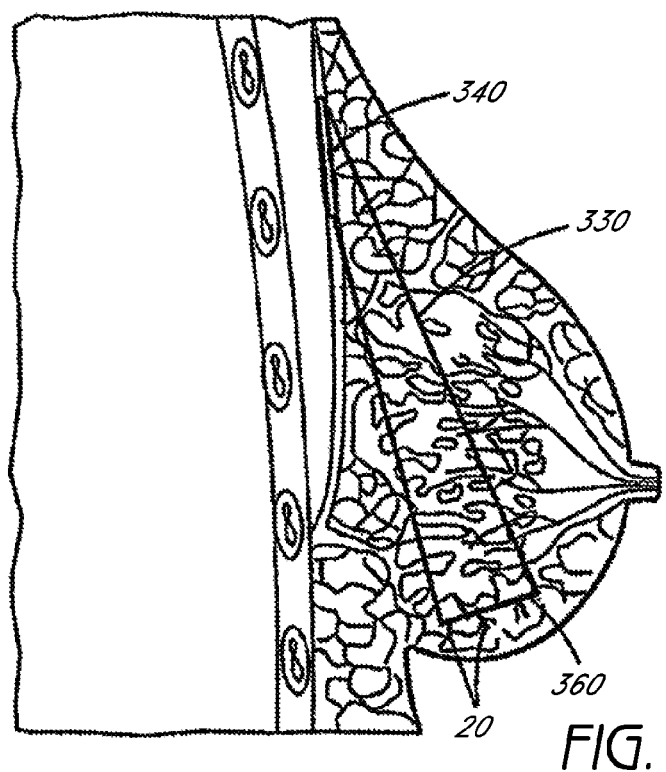
FIG. 27 is a side view of a breast and an embodiment of a support member comprising barbs.

In some embodiments, the support member 360, the suspension members, or both, can comprise engagement members, for example, barbs 20, as shown in FIG. 27. Barbs are effective to improve engagement of the adjacent tissue and reduce movement of the support system relative to the tissue. Barbs can be fashioned from materials similar to those used to construct the support member or suspension members, including, without limitation, stainless steel, Nitinol and any other biocompatible materials.

In some embodiments, the barbs can be from about 0.25 mm to about 2 mm in diameter, and from about 0.25 mm to about 5 mm in length. In some embodiments the barbs are 0.5 mm in diameter, and about 2.5 mm in length. These are examples of barb dimensions and other dimension of barbs can be used without limitation. Barbs can be oriented all in the same direction or they can be oriented in alternate directions in order to provide resistance to both proximal and distal movement.

Other Suspension Elements

Figure 28:
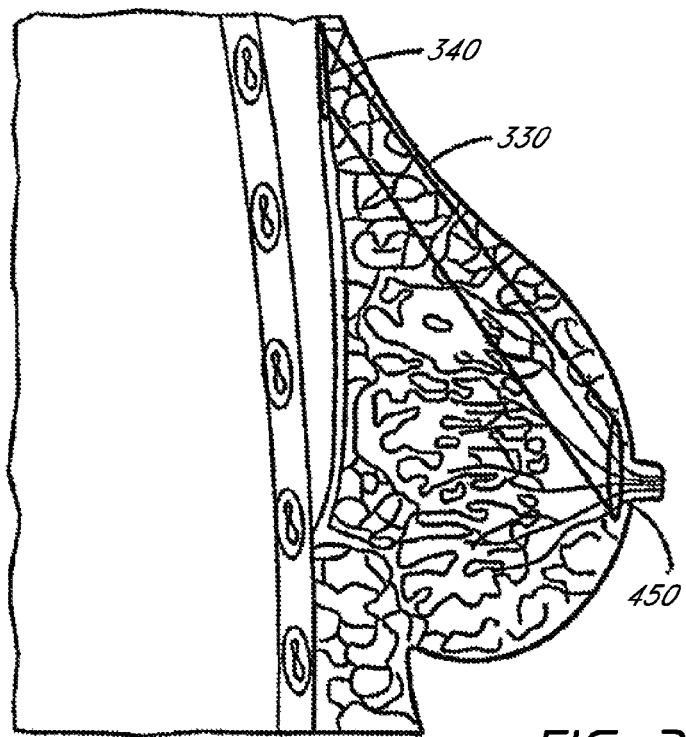
FIG. 28 is a side view of a breast and an embodiment of a support system comprising a nipple repositioning element.

In some embodiments, the device can comprise a nipple suspension element 450 to raise the nipple and/or reposition it with respect to the support members, as shown in FIG. 28. Positioning the nipple using a separate element allows for separate positioning of the breast relative to the nipple. Including addition suspension or tensioning elements provides the ability to make vertical and/or horizontal adjustments to the nipple.

Additional Support System Components

Figure 29A:
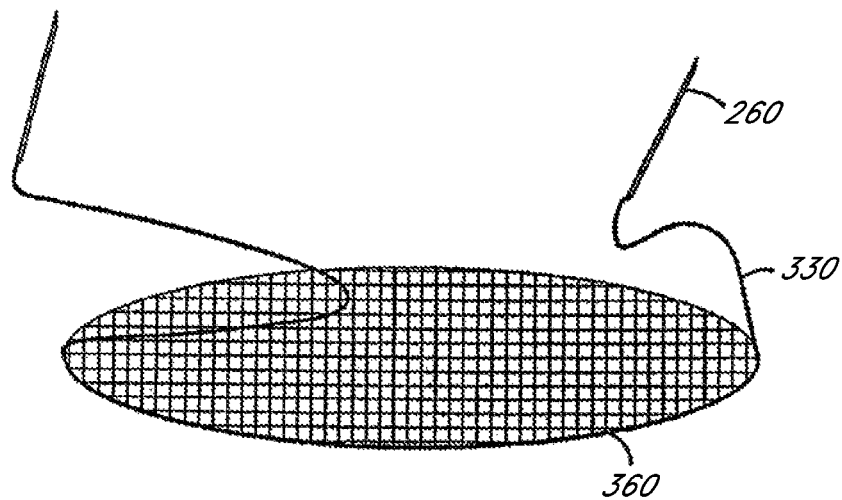
FIG. 29A is an embodiment of a support member, associated suspension members, and needles for insertion.

In some embodiments, the support system can comprise a webbed, or mesh, support member 360, suspension members 330, and attached needles 260 for insertion into the patient, as shown in FIGS. 29A and B. In some embodiments, the suspension members and support members can comprise a contiguous structure. In some embodiments, the suspension members and support member can comprise separate pieces that are assembled prior to use.

Figure 29B:
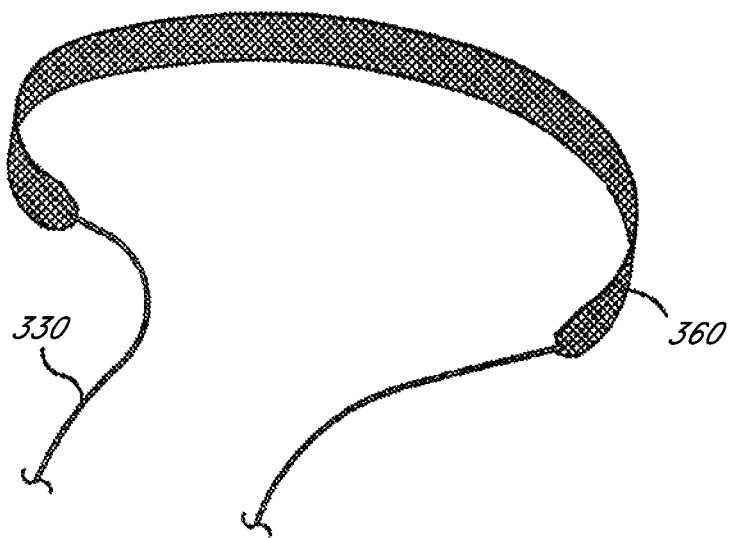
FIG. 29B is a photograph of an embodiment of a support member and attached suspension member.

Conveniently, in some embodiments, the support member can be fashioned in the shape of a sling or hammock, an example of which is shown in FIG. 29B. As used herein, the term "sling" or "hammock" is intended to include, without limitation, a wide variety of shapes and sizes, materials and treatments. A sling (or hammock) can be rectangular, other shapes are also contemplated included oval, circular, elliptical, and tear drop shaped. In some embodiments, the sling can be made of a mesh material. The mesh material can comprise one or more woven or inter-linked filaments or fibers that form multiple fiber junctions throughout the mesh. The fiber junctions can be formed via weaving, bonding, ultrasonic welding or other junction forming techniques, and combinations thereof.

Figure 30:
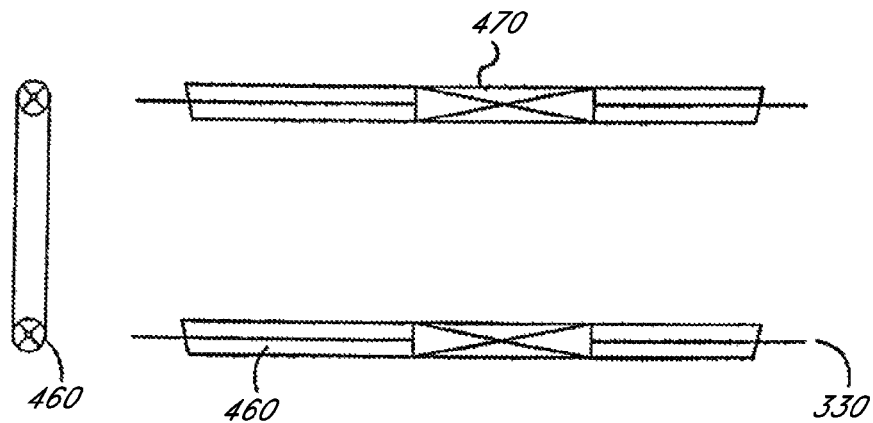
FIG. 30 illustrates an embodiment of a support system including channels for the suspension members, and spring elements.
Figure 31:
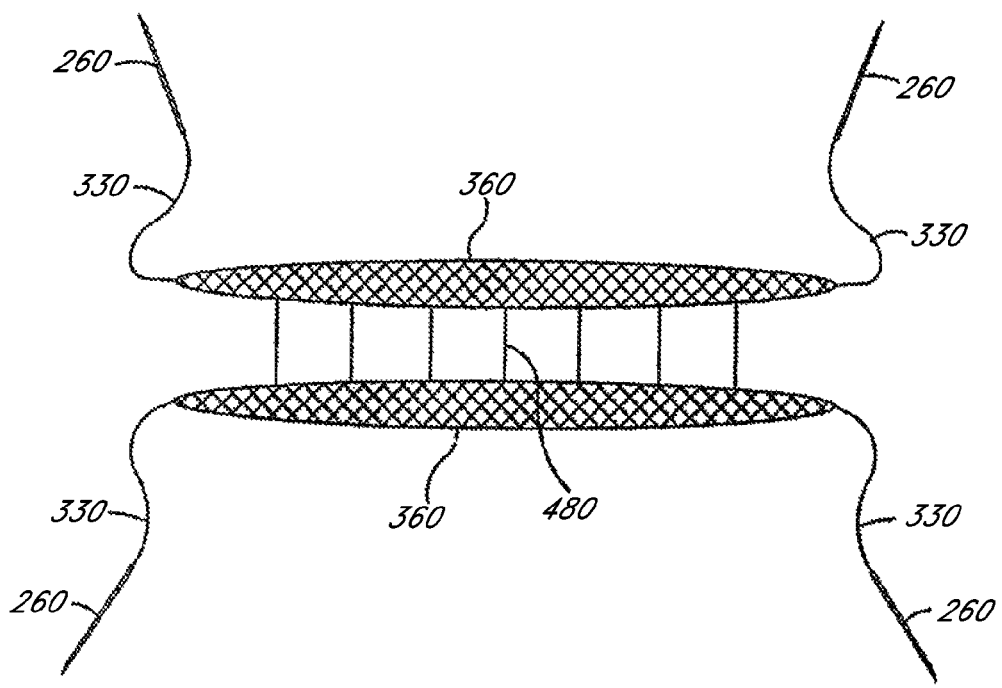
FIG. 31 illustrates an embodiment of a support system comprising separators to maintain spacing between adjacent support members.

In addition to suspension members and a support member, a support system can comprise additional components. For example, channels 460 can be used to hide the wire or springs 470, which can be effective to eliminate irritation to the surrounding tissue, as shown in FIG. 30. These channels may be open or closed to either allow or limit contact with body fluids. In some embodiments, the channel may utilize a perforated channel to allow fluid to flow or move within or around a wire or spring. In some embodiments, fluids in channels can serve as a lubricant for suspension members within channels.

Where multiple support members are used, separation of the elements can be provided, as shown in FIG. 31, by separators 480. One or more separators 480 between support members 360 can be effective to limit motion of support members relative to each other. Separators can resist movement of elements toward or away from each other by geometric column strength or tensile stress, respectively. In some embodiments, separators 480 can be measure about 0.25 mm to about 2.5 mm in diameter with a length of 0.5 mm to about 8 mm. It will be understood that these dimensions are exemplary only, and other dimensions of separators can be successfully used. A variety of materials can be used to make separators, including without limitation, plastics, polymers, metals, and these materials can be permanent or absorbable.

Maintaining a defined separation of support members during or post implantation provides for more even suspension of tissue with loading distributed across the effective area encompassed by the support member(s). Embodiments of support members can be provided as a mesh material with different patterns depending on the loading or stress expected. Additionally, support members can be fashioned with a preset shape effective to resist collapse when the ends are tensioned as during loading.

A wire mesh work made from NiTi or stainless steel can allow for a flatter looking implant during loading, whereas a limp thread element may provide little support on the sides of the breast when loaded. This allows for a rounder shape definition rather than squeezing at each side of the breast during loading. The wire elements can be pre-shaped and memory set to allow for normal motion and tissue manipulation.

Figure 32A:
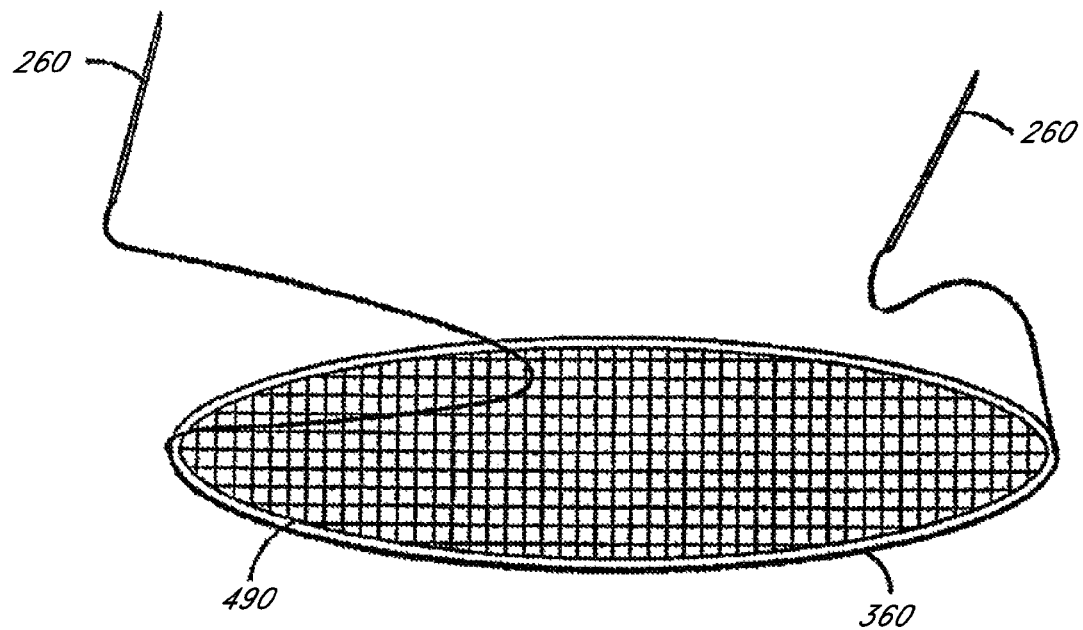
FIG. 32A-B illustrate an embodiment of a support system including an additional structural support member.
Figure 32B:

For example, as shown in FIG. 32A, a wire support 490 included in the support member 360 mesh can increase strength and provide means for coupling the support member to other components of the system. By adding additional components to the support member, properties of strength or elasticity can be imparted, depending on the choice of materials, for example, and without being limiting, elastomers, pre-shaped shape memory elements, springs and the like. These additional elements can be located above or below the mesh or embedded into the mesh for motion encapsulation. FIG. 32B illustrates an embodiment of a wire support 490, separated from the support member 360.

Insertion Method

Figure 33A:
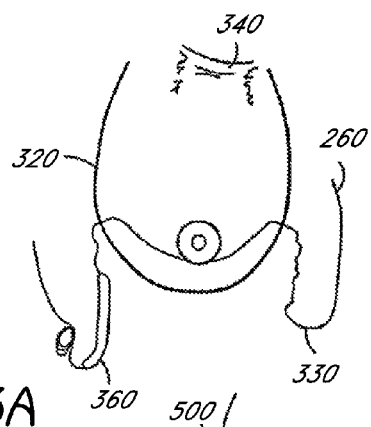
FIGS. 33A-33F illustrates a method of surgical placement of an embodiment in a breast lift procedure.
Figure 33D:
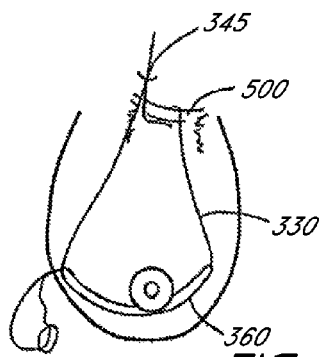
Figure 33B:
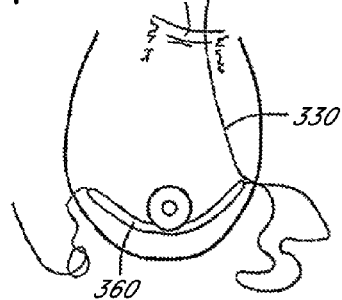
Figure 33E:
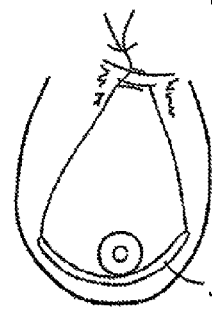
Figure 33C:
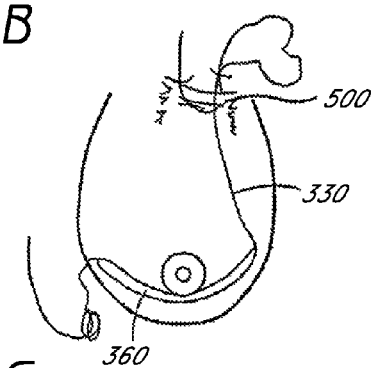
Figure 33F:
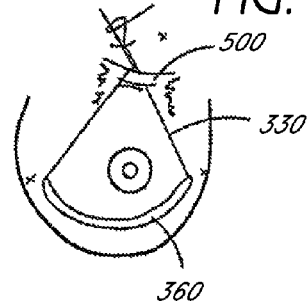

In some embodiments, there is also provided a method of insertion of the device, as shown in FIG. 33A-F. In one embodiment, insertion is performed by a needle 260 inserted at the base of the breast 320, exiting the other side of the base, and pulling the support member 360 through the tissue between the glandular structure and the subcutaneous fat (FIG. 33A). Once the support member 360 is positioned correctly, the needle 260 can be passed back into the same needle hole and vertically to the anchoring position (FIG. 33B). As the needle is passed back into the fascia of the pectoral muscle, the piercing of the fascia is captured and the needle is once again pulled out of the transcutaneous needle hole (FIG. 33C). In the same fashion the other support line can be passed and the fascia again can be captured and tied to the other support member where a knot pusher can be used to slide the knot 345 deep beneath the skin where it can be hidden to avoid producing a bump that might otherwise show on the surface of the skin (FIG. 33D). Anchoring of the support system can be achieved by looping or otherwise tying the ends of the suspension members to a suitable anatomical feature, such as a bone 500, for example (FIG. 33 E & F).

Some embodiments of a method of insertion of support system include an initial pathway being introduced under the skin with a guidewire system, and providing a tubular sheath for guidance, along with the ability to exchange wires. A tubular sheath allows the surgeon to maintain access to a common pathway for device installation and manipulation. The guidewire can be introduced under the skin through a small trocar or needle where the softer tubular sheath is exchanged out, and other elements can be passed through such as thread, suspension elements, and the like. A larger incision at the lower portion of the breast can be used to introduce a wider support member, for example a sling or hammock as has been described herein. This can include an incision to introduce the wide sling at one or both sides of the breast. Additionally, these techniques could be all completed in an open procedure as normally seen in a mastopexy operation.

Additional Exemplary Procedures

Embodiments of sutures as presently disclosed can be used to resuspend loose tissue in the neck region. A suture can be inserted using a similar technique as that used for a breast lift. The suture can also be configured to spread out support over multiple lines, or using slings or other types of configurations as described above, so as to prevent the cheese wiring effect that can occur when using a single thin-lined sutures. Designs applicable for use in breast lift procedures, are thus equally applicable for use in a neck lift procedure.

Figures 34A, 34B:
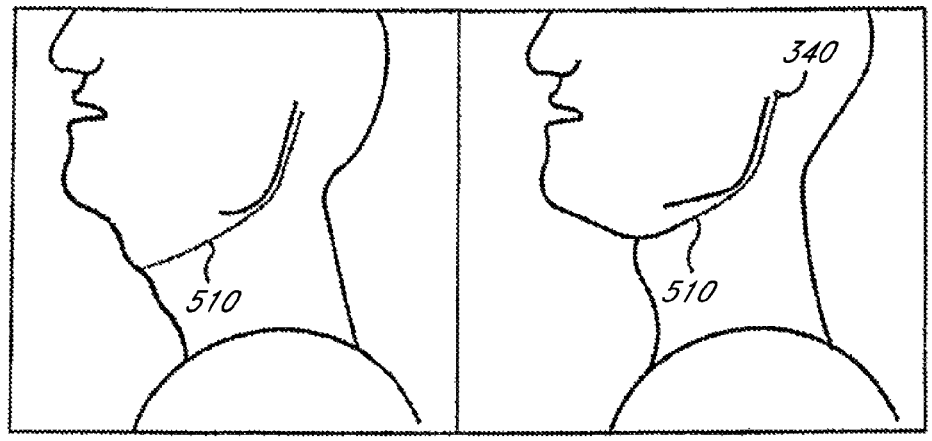
FIG. 34A-34B illustrates the use of an embodiment of a suture to perform a neck lift procedure.

As shown in FIG. 34, in one method, the suture 510 is inserted under the skin surface and advanced below the surface following a line extending along the crease in the skin where the underside of the jaw area meets the neck. In some embodiments of a neck lift method, the upper portion of the suture 510 is turned upward and extended posteriorly to the jaw bone. The suture can be anchored 340 with a loop of suture material to the connective tissue located behind the jaw bone and just below the ear.

Embodiments of barbed sutures can be used effectively to lift tissue in the lower thigh area that has sagged down above the knee, as can occur during aging. Sutures with barbs at either end can be inserted from above the skirt line and used to pull the skin from the lower thigh up towards the tissue in the upper thigh area. The barbs located in the part of the suture located in the upper thigh region can be anchored to the dermis, or to tendons, ligaments, bone, or muscle, further below the surface. The portion of the suture located in the lower thigh area can engage the dermis or fascia, or other tissue, typically at a depth of 0.2 to 20 mm below the skin surface. A method similar to that used to lift thigh tissue can be used in the region of the upper arm.

Figure 35:
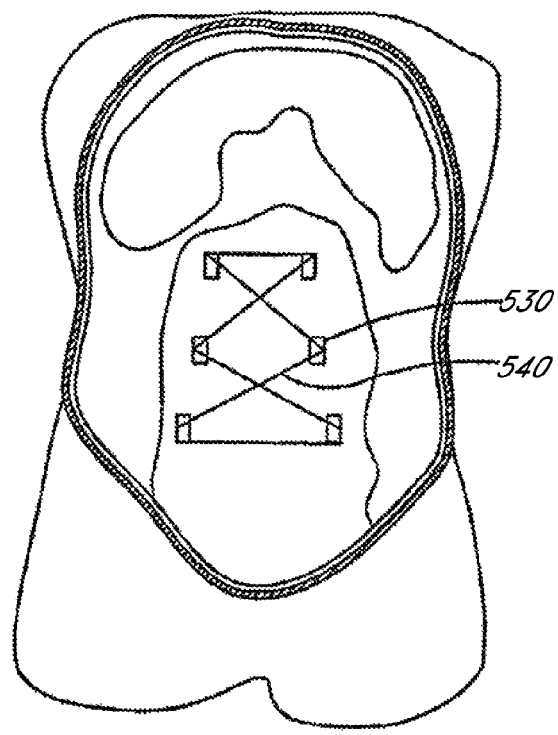
FIG. 35 illustrates the use of an embodiment of a suture to perform an abdominal wall tightening procedure.

Embodiments comprising barbed sutures can also be used to engage muscle. For example, in some embodiments, sutures can be placed in the abdominal region, and then tensioned to pull the abdominal muscles back into position. In some embodiments, the method can further providing a support system comprising a series of tabs 530 and sutures 540. In these embodiments, additional tension canto be applied to the sutures, while at the same time avoiding pulling the suture through or otherwise tearing the tissue to which they are attached, or through which they have been threaded. By weaving a series of line from one tab to the other, the muscles can be further supported, for example as illustrated in FIG. 35. The tabs can be inserted by a small incision, and placed under the skin. Suture material can be pre-loaded into each tab, and sutures connected to each other by a transcutaneous knot or series of knots.

Figures 36A, 36B:
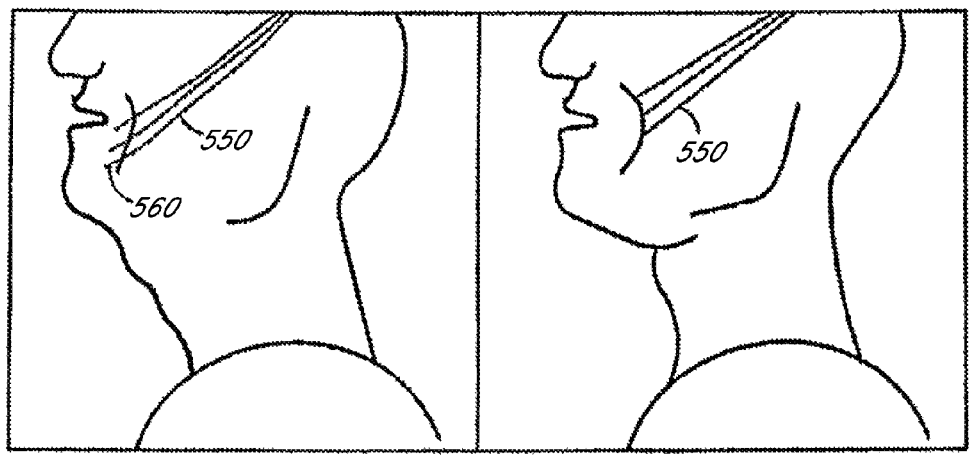
FIG. 36A-36B illustrates the use of an embodiment of a suture to perform a facelift procedure.

As shown in FIG. 36, embodiments comprising barbed sutures can also be used to improve upon prior art methods of performing facelift procedures. In the prior art methods, shown in FIG. 36A, sutures 550 are inserted under the skin near the front of the cheek, pass up towards the hairline, where they exit out of the skin. This method leaves exposed suture ends 560 near the front of the face, which are unsightly. Although these ends can be trimmed such that the ends lie under the surface of the skin, over time it is possible for these ends to erode through the skin and reappear.

In contrast, in some embodiments of the present disclosure, the suture 550 is fashioned to have barbs at a first end of the suture. The barbs are effective to engage the tissue and resist movement (or to create tension) once in place. The first end can be delivered into the facial area through a trocar. In some methods, the insertion point of the trocar can be above the hairline. Once the first end is in the desired position the trocar can be removed wherein the barbs are exposed to, and ultimately engage, the surrounding tissue. Tension can be applied to better secure the barbed end of the suture within the tissue. The suture can optionally include markings that inform the surgeon how deeply the suture has been placed. If placement is unsatisfactory, the same trocar, or a second trocar, can be inserted over the suture to facilitate removal and/or relocation. The method obviates the need for an insertion point near the front of the face, and further avoids having suture ends exposed in the facial region, as occurs with the prior art method.

Once the first end is in place, the second end of the suture can be anchored in the scalp, or other suitable region. The second end can also include barbs to improve anchoring. To place the second end, the end can connected to a long needle. The needle can be inserted through the same hole where the trocar was inserted and then advanced up the scalp. In some embodiments, the distance is from about 3 inches to about 7 inches, although this is not limiting. The suture can be exited through the skin, and satisfactory tension on the suture can be achieved by pulling on the exposed end. In some embodiments, the free end near the hairline can be trimmed to below the surface of the skin. In some embodiments it can be useful to re-tension the sutures after the barbed portions have healed into the tissue. In these cases, a short portion of the second end of the suture can be left protruding from the scalp to enable the surgeon to access it more easily at a later date. The end can be covered with a small adhesive bandage, or with a liquid bandage in order to protect the end.

Use of the above described techniques can be useful if providing lifting for this buttocks region. In the buttocks, single or multiple support systems can be used. The system can designed to provide for additional load bearing, while preventing cutting or tearing of supported tissue during movement associated with normal activity. One end of the support system can be attached to the outer hip, while the opposite end can be attached to the upper hip bone. Anchoring in this way provides that the support can function effectively under either static or dynamic loading conditions. In some embodiments, the use of crescent shaped support straps can be used to accommodate the majority of the tissue to be supported. Additional branch suspension members can be included to allow for further lifting and shaping of the tissue. Barbed sutures can be used to improve anchoring within tissues.

Extended Needle

Figure 37A:
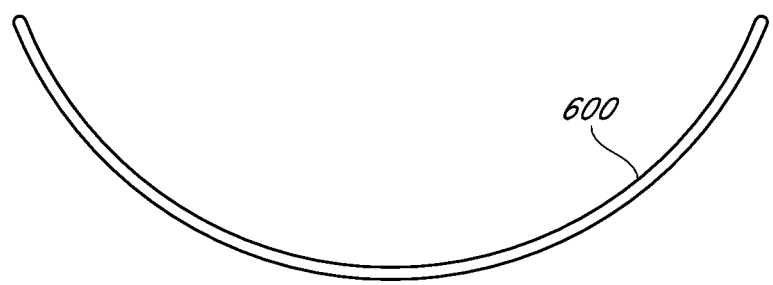
FIGS. 37A-37B depict embodiments of an needle that can be used as a guide.
Figure 37B:
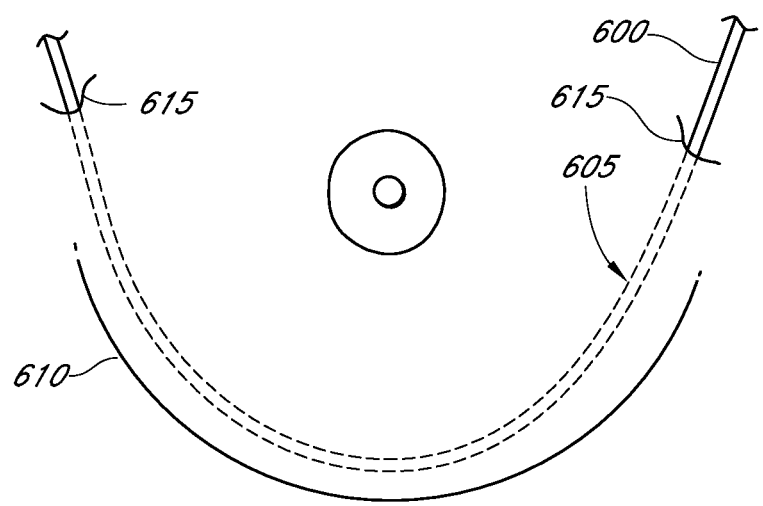

FIGS. 37A-37B depict embodiments of an needle 600 that can be used as a guide, as well as to control tools and implants, over, along, and/or through a dissecting path 605. The extended needle will be a full size needle 600 that extends out both exit points on the breast for manipulation by the hand FIG. 37A depicts a bent needle 600, and FIG. 37B depicts a bent needle 600 in the breast 610, showing exit points 615 in the medial and lateral aspects of the breast. The exit points are depicted as positioned slightly above the areola, but the exit points 615 could also be below, level with, or above the areola, depending on the desired modification of the soft tissue of the breast.

Double Extended Needle

FIGS. 38A-38D depict embodiments of needles 650 that can be used to create a dissecting plane. The purpose of the double extended needle is to create a dissecting plane within the breast. The device consists of two extended length needles. In application, the two needles extend out of both exit points 655 of the breast 660 along the same plane. The two needles 650 will cross at either exit points, creating an expandable area between the two needles 650. The area can be manipulated via a 'scissor' action at either exit point. FIG. 38B depicts relative motion between the two needles to create a dissecting plane. In some embodiments, the motion of the two needles 650 is substantially radial with respect to a longitudinal axis of one or both of the needles.

Double Extended Needle with Sling Guide

FIGS. 39A-39C depict embodiments of dissecting needles 700 that are used in conjunction with an implantable sling 710. The double extended needle with sling guide includes two extended needles 700 and a sling 710, which has four loops 715 for attachment, used to guide the sling 710 along the dissecting plane. The four loops 715 will be at either corner of the sling. The two left loops, along the long length of the sling, will be inserted on one needle 700, and the two opposite side loops on the sling will be inserted onto the second needle 700. Before insertion there will be two needles with a collapsed sling. Once inserted, the needles can be manipulated at the exit points in a "scissor" cut to create a distinct area plane. Once the needles are expanded, the sling will also be expanded. The needles can then be removed, leaving the extended sling of proper orientation within the created dissecting plane.

Some embodiments include an internal sheath that is configured to allow the items (e.g., tools, implants, etc.) to be positioned before extending the needles to create the dissecting plane area. The insertion assembly consists of the double extended needle with sling guide having an external sheath. The sheath may be removed once assembly is installed and before any manipulation of the items within the breast.

"Hockey Stick" Dissector

FIGS. 40A-40D depict embodiments for dissecting tissue or creating a dissecting plane. The purpose of the "Hockey Stick" dissector 750 is to create a dissecting plane with back and forth motion for sling insertion. The dissector will be straight with an "L" Shaped end 755. The end will be looped and used to feed the sling through.

As illustrated in FIGS. 40A-40D, the dissector 750 can be inserted into an exit point 760 in the breast and advanced into the breast to create a dissecting plane. In some embodiments, this can be accomplished with a sling 765 inserted through the looped end 755 of the dissector, as illustrated in FIG. 40C. With the dissector 750 within the breast tissue, the sling 765 can be advanced to a second exit point 760.

Figure 41A:
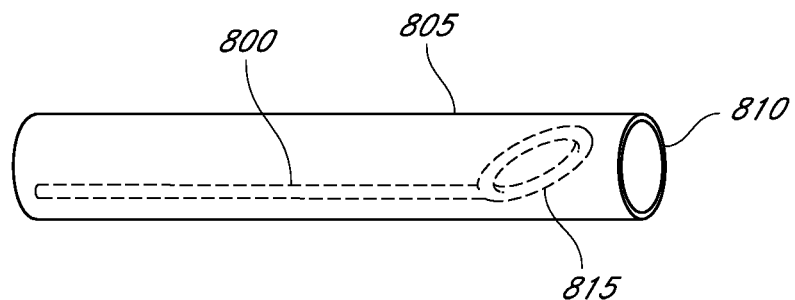
FIGS. 41A-41B depict embodiments of a retractable dissector.
Figure 41B:
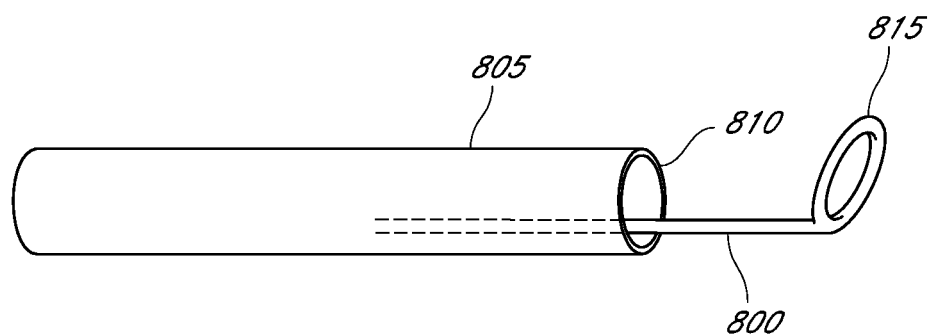
Figure 42A:
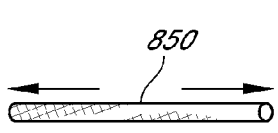
FIGS. 42A-42F depict embodiments of a conforming sheath that is configured to create a dissecting plane.
Figure 42B:
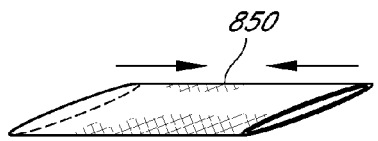
Figure 42C:
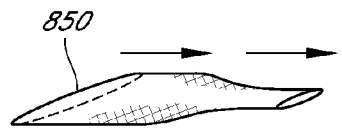
Figure 42D:
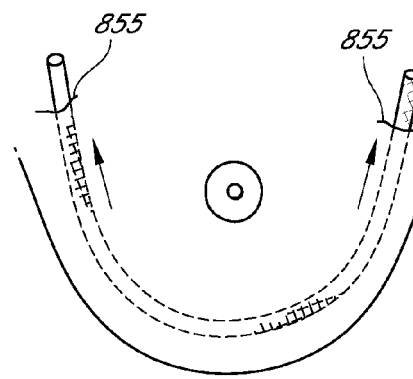
Figure 42E:
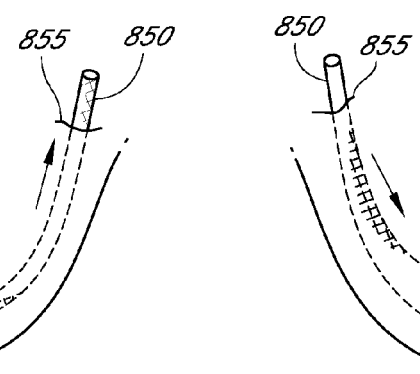
Figure 42F:
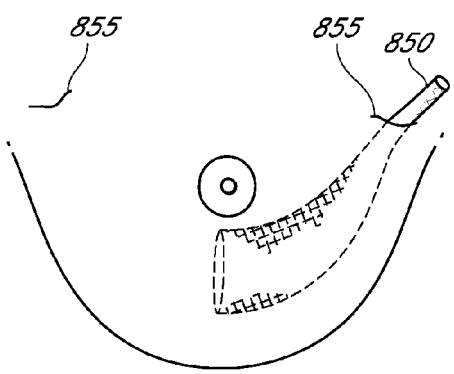

FIGS. 41A-41B depict embodiments of a retractable dissector 800. The purpose of the retractable "Hockey Stick"

dissector 800 is to create a dissecting plane for the sling without interfering with the sling-suture connection. The dissector 800 will be retracted into a sheath 805. Once the sheath 805 is removed, the end 815 of the dissector 800 will open enough to slide over the sling-suture connection for removal. In some embodiments, the dissector comprises a material having shape-memory material and is oriented, when unrestrained, in the open configuration illustrated in FIG. 41B. FIG. 41A depicts a dissector 800 retracted into a delivery sheath 805, and FIG. 41B depicts the dissector 800 extended from a distal end 810 of the delivery sheath 805.

Conforming Sheath

FIGS. 42A-42F depict embodiments of a conforming sheath 850 that is configured to create a dissecting plane for the sling to be maneuvered within. The conforming sheath, when pulled at both ends (FIGS. 42A, 42D), maintains a circular shape with a small diameter. Once inserted in the breast, extending out both exit holes, can be pushed at both ends (FIGS. 42B, 42E) to conform to a varying shape. The varying shape, in some embodiments, will be oval, having a much wider base than height. Expansion of the sheath creates a plane through which a sling can be inserted and advanced. Once the sling is in position within the breast, the conforming sheath may be removed. By pulling at only one end (FIGS. 42C, 42F), the sheath will maintain its extended shape over the sling and only contract at exit point 855.

Safety Suture Loop Installer

Figure 43A:
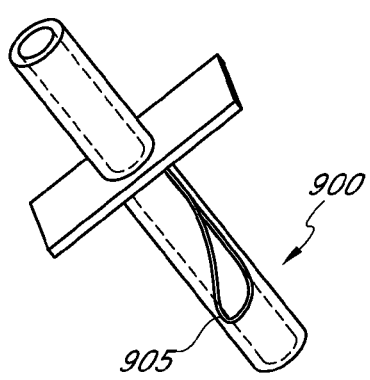
FIGS. 43A-43C depict embodiments of a safety suture loop installer.
Figure 43B:
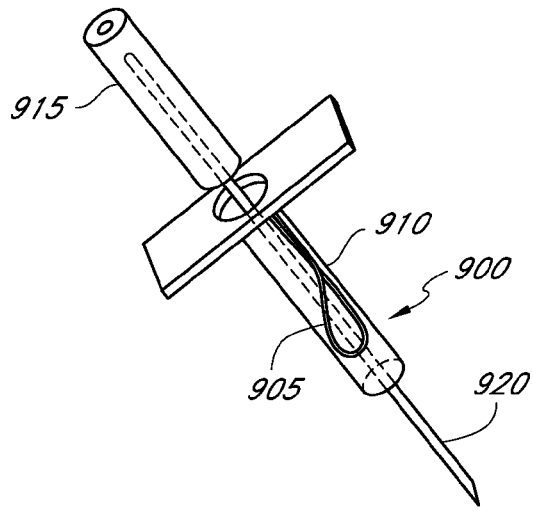
Figure 43C:
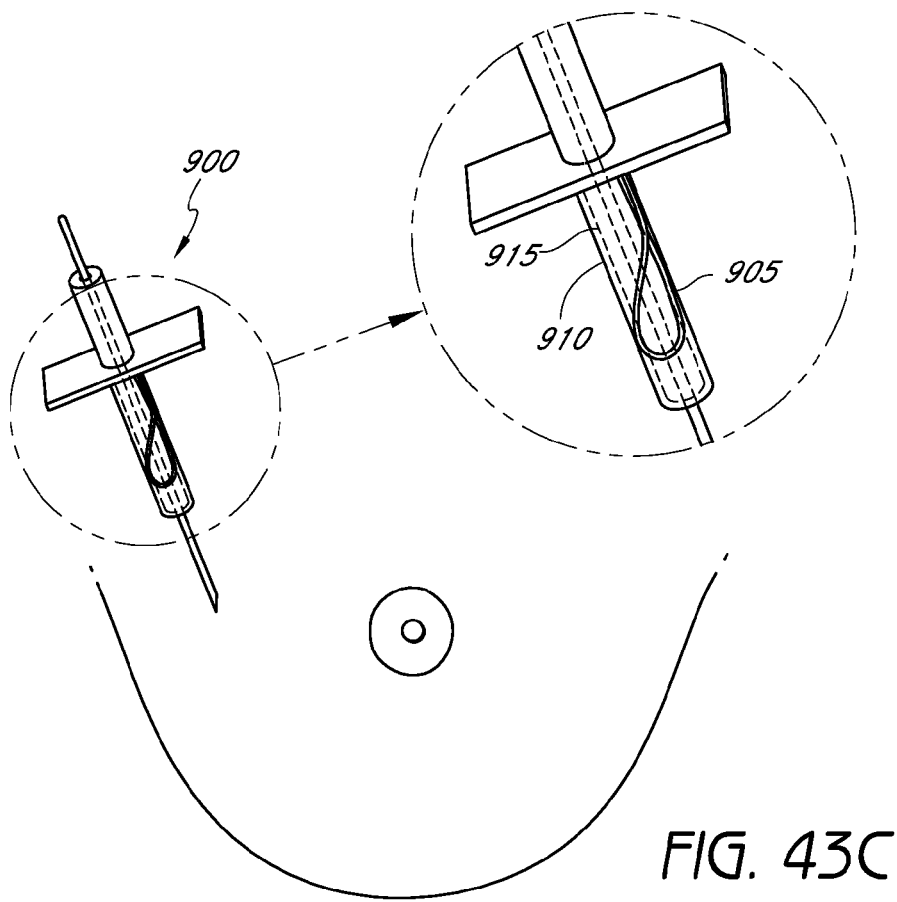

FIGS. 43A-43C depict embodiments of a safety suture loop installer 900. The purpose of the safety suture loop installer is to automatically install a safety suture loop 905 around an exit braid to maintain controllability once the braid is reinserted. The installer is a double layer introducer. The safety suture loop 905 is fed through the first layer between the outer layer 910 and inner layer 915. The needle 920 with a braid is then fed through the center layer. Once the braid is installed, the center layer is removed, leaving the needle 920 within the outer layer 910. The introducer is then removed and the safety suture loop 905 is installed around the braid.

Depth Gauge Introducer

Figure 44A:
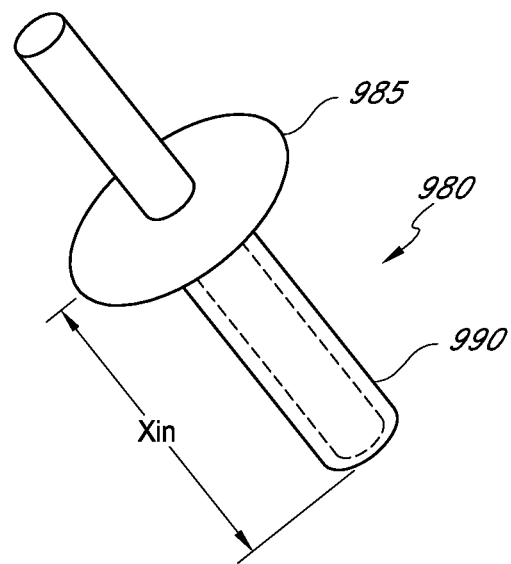
FIGS. 44A-44B depict embodiments of a depth gauge introducer.
Figure 44B:
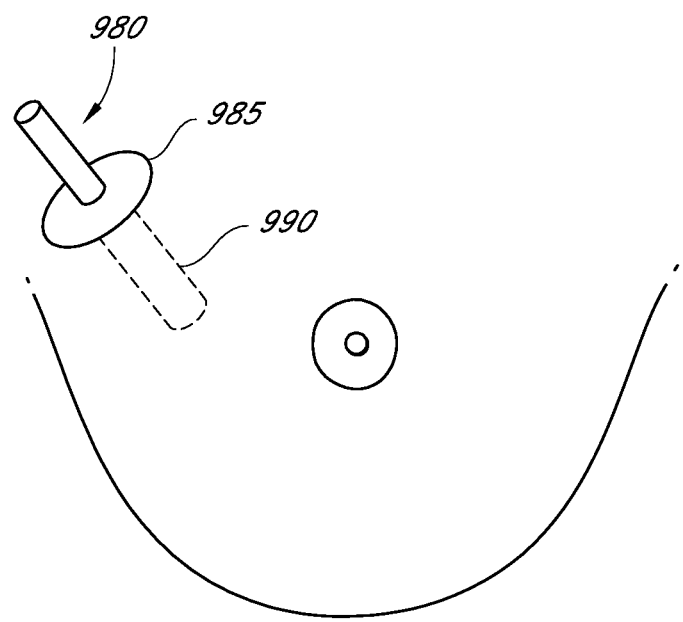

FIGS. 44A-44B depict embodiments of a depth gauge introducer 980. The purpose of the depth gauge introducer 980 is to create a method of knowing the depth of the introducer. The device will be an introducer 980 having a disk 985 at specified height around the trunk 990 of the introducer 980. The introducer 980 will be inserted into the skin and further insertion will be stopped at the disk 985. During surgery, the user can use to depth gauge introducer to maintain the entrance port into the breast (or other soft) tissue at the specified height, or depth within the tissue, Xin.

Sling Guide

Figure 45A:
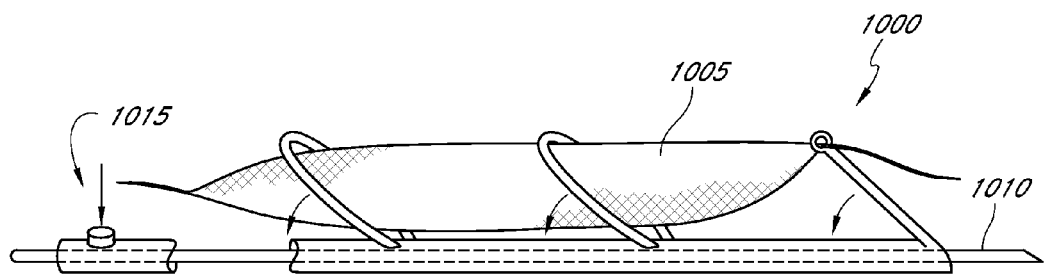
FIGS. 45A-45C depict embodiments of an expandable sling guide.
Figure 45B:
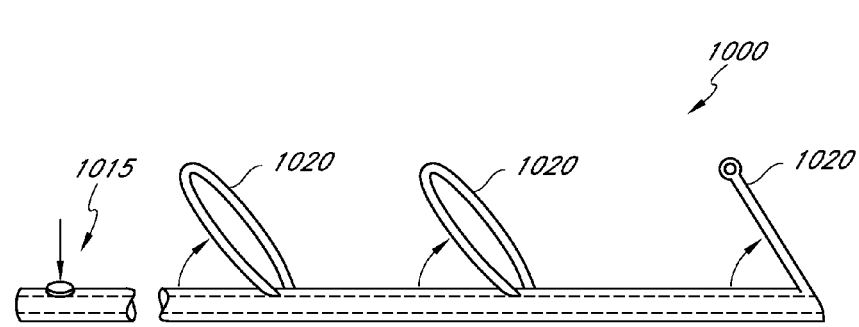
Figure 45C:
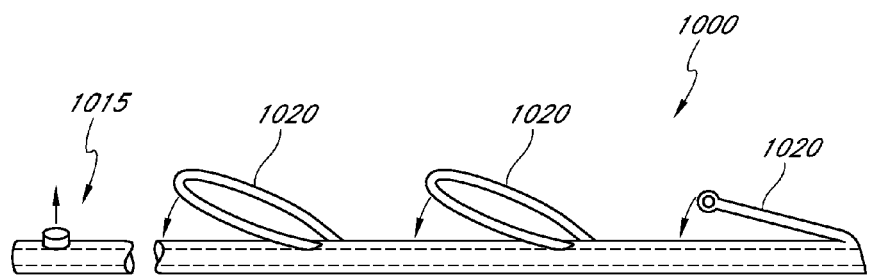

FIGS. 45A-45C depict embodiments of an expandable sling guide 1000. The purpose of the sling guide 1000 is to guide the sling 1005 over the pre-inserted extended needle 1010. The guide 1000 can have an exit control 1015 used to contract a series of loops 1020 on the guide 1000. The loops 1020 can be contracted for insertion at the exit hole and can extend up once inserted (FIG. 45B). The contracting portion will also be used, once inside the breast, to create a dissecting plane. Once the sling 1005 is in place, the sling guide 1000 can be removed, leaving the specified form for the sling 1005.

Retracting "Diamond" Dissector

Figure 46A:
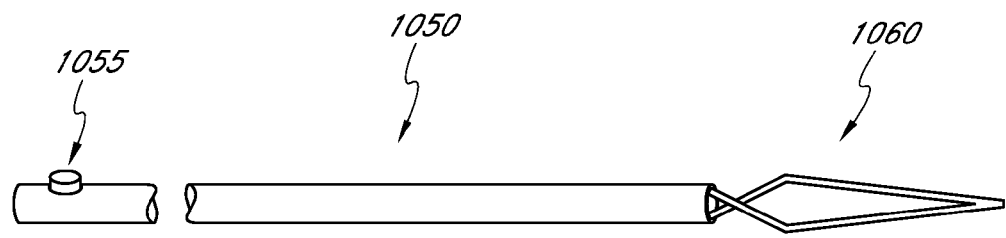
FIGS. 46A-46B depict embodiments of a retracting "diamond" dissector.
Figure 46B:
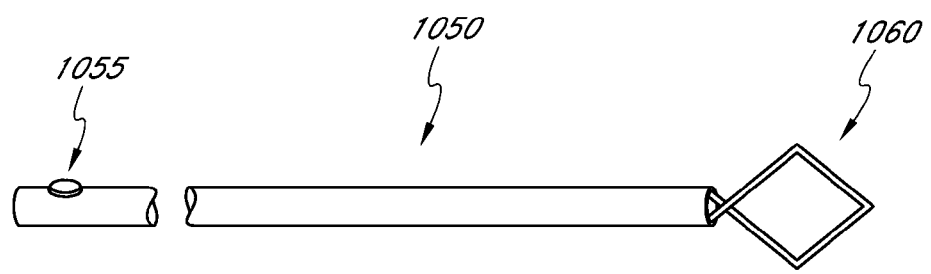

FIGS. 46A-46B depict embodiments of a retracting "diamond" dissector 1050. The purpose of the retracting dissector 1050 is to easily create a dissecting plane within the breast. The retracting dissector 1050 will, in some embodiments, have a button 1055 at one end 1060, outside of the breast. The button 1055 can be pressed to extend the retracting dissector 1050 into a narrow and sleek shape (FIG. 46A). Once the button 1055 is released, the dissector 1050 is extended out to a flat and wide shape (FIG. 46B) having an increased cross-sectional measurement or dimension. Depression of the button 1055 can be used to create a back and forth "cutting" action.

Retracting 'Diamond' Dissector with Sling Mount

Figure 47A:
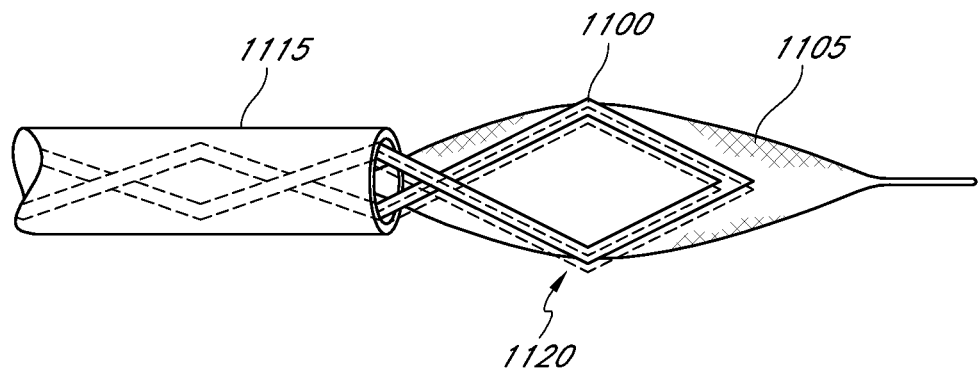
FIGS. 47A-47B depict embodiments of a retracting "diamond" dissector with sling mount.
Figure 47B:
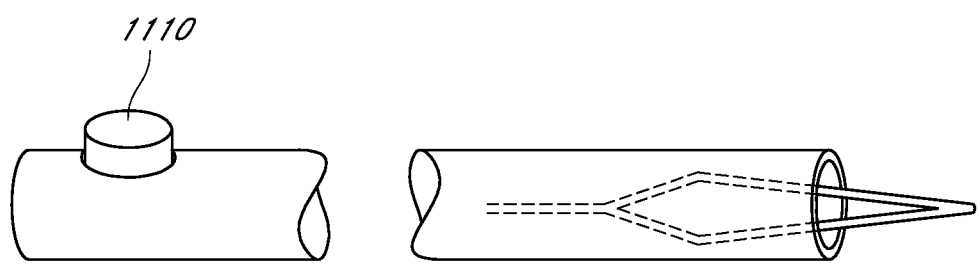

FIGS. 47A-47B depict embodiments of a retracting "diamond" dissector 1100 with sling mount. The purpose of this device 1100 is to create a dissecting plane while installing the sling 1105. The device 1100 will have a control button 1110 at exit point that will extend a flat and wide portion 1120 to create a dissecting plane. The button 1110 can be depressed to create a back and forth action to "cut" the plane. The portion will have a sling 1105 attached to it that will contract and expand with the "diamond" portion of the device.

In operation, the device can be advanced from the distal end of an elongate body 1115 that is inserted into the tissue of the patient. As the button 1110 is depressed, the flat and wide portion 1120 can change between a compressed configuration and an expanded configuration. This change can permit advancement through the tissue in the compressed configuration and expansion of a channel (or dissecting plane) in the tissue by expanding the device 1100. In some embodiments, the device 1100 can be retractable into the elongate body 1115 (FIG. 47B). In some embodiments, the device 1100 can have a plurality of flat and wide portions 1120, as depicted in FIG. 47A, that cooperate to secure the sling 1105. In some embodiments, the plurality of portions 1120 can hold or secure the sling 1105 therebetween, for example by pinching the sling between the plurality of portions 1120, during operation and/or advancement through tissue.

Retracting Dissector with Sheath Control

Figure 48A:
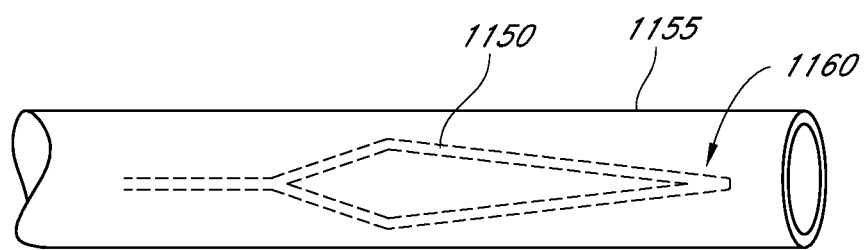
FIGS. 48A-48B depict embodiments of a retracting dissector with sheath control.
Figure 48B:
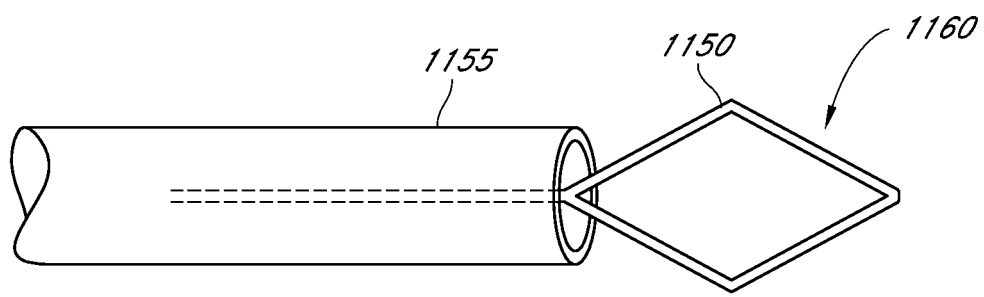

FIGS. 48A-48B depict embodiments of a retracting dissector 1150 with sheath control. The purpose of this device 1150 is to create a dissecting plane that can be done via sheath 1155 control. The dissector 1150 includes a "diamond" shaped point 1160 that changes from a compressed configuration, having a first cross-sectional dimension, to an expanded configuration, having a second cross-sectional dimension that is greater than the first cross-sectional dimension, when unrestrained.

The sheath 1155 can be introduced into a plane within tissue and by selectively advancing the dissector 1150 relative to the sheath 1155, the dissecting plane can be advanced and expanded. As the dissector 1150 is advanced out of the sheath 1155, the dissector 1150 preferably separates tissue in an axial and lateral direction, as shown in FIG. 48B. After the dissector 1150 is expanded, the sheath 1155 can be advanced over the dissector 1150 to compress and substantially contain the dissector within the sheath 1155 (for example, within a lumen of the sheath 1155). The user is then able to feed the sheath 1155 back and forth over the dissector 1150 as the dissector 1150 moves through the tissue, expanding and advancing the dissecting plane.

Self-Dissecting Sling

Figure 49A:
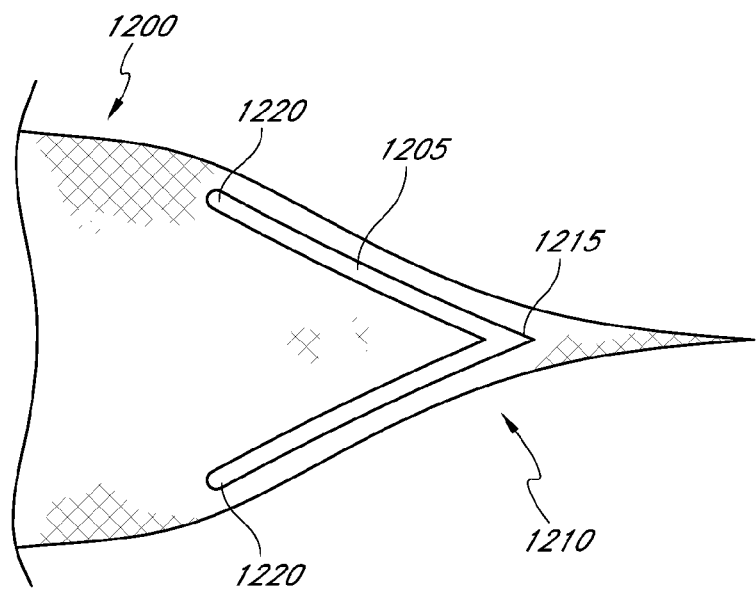
FIGS. 49A-49B depict embodiments of a self-dissecting sling.
Figure 49B:
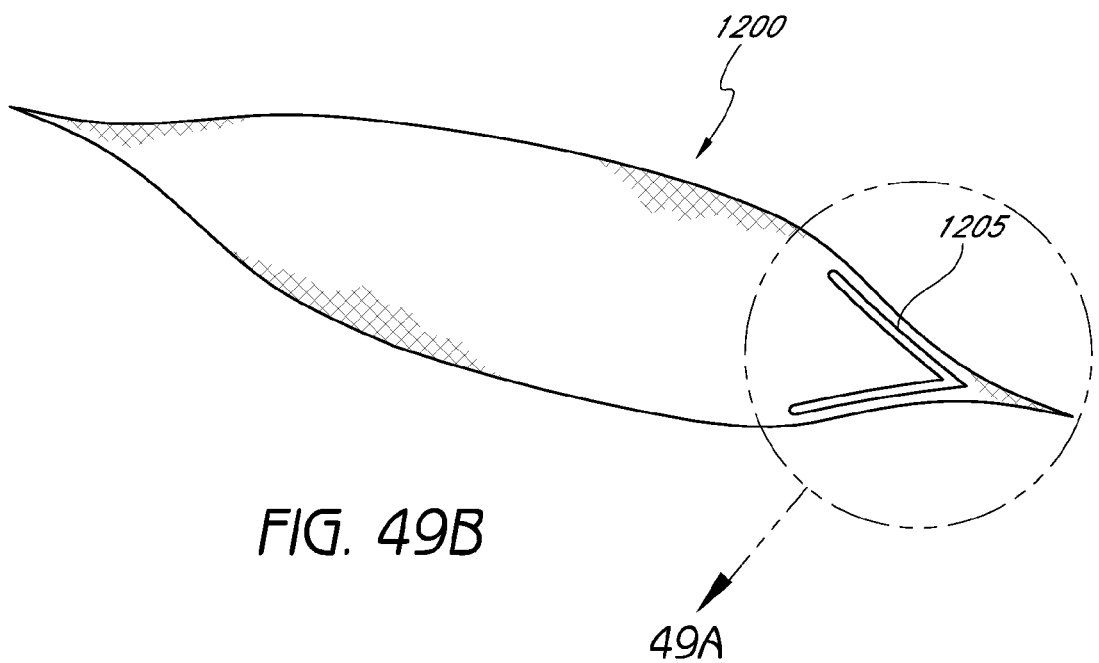

FIGS. 49A-49B depict embodiments of a self-dissecting sling 1200. The purpose of the self-dissecting sling 1200 is to have one apparatus which can be placed but also has the ability to be maneuvered. The sling 1200 will have a rigid implant 1205 woven into the sling at the sling-suture connection 1210. As the sling 1200 is advanced through a channel in tissue, the rigid implant 1205 can be used to increase a cross-sectional dimension of the channel by separating tissue.

In some embodiments, the rigid portion 1205 will have a "V" shape. Some embodiments provide that the rigid portion 1205 can be contracted for introduction into the tissue channel. For example, the point 1215 of the rigid portion 1205 can act as a dissecting tool, and the two tail ends 1220 of the "V" can be brought together and narrowed for insertion in the exit points of the tissue. After the rigid portion 1205 is introduced with in the tissue, it can assume its expanded configuration to increase a cross-sectional dimension of the channel by separating tissue by allowing the two tail ends 1220 of the "V" to expand outward away from each other. In some embodiments, the sling 1200 can be drawn through the tissue by pulling, and in some embodiments, the sling 1200 can be advanced by pushing the sling through the tissue.

"Railroad Tracks"

Figure 50A:
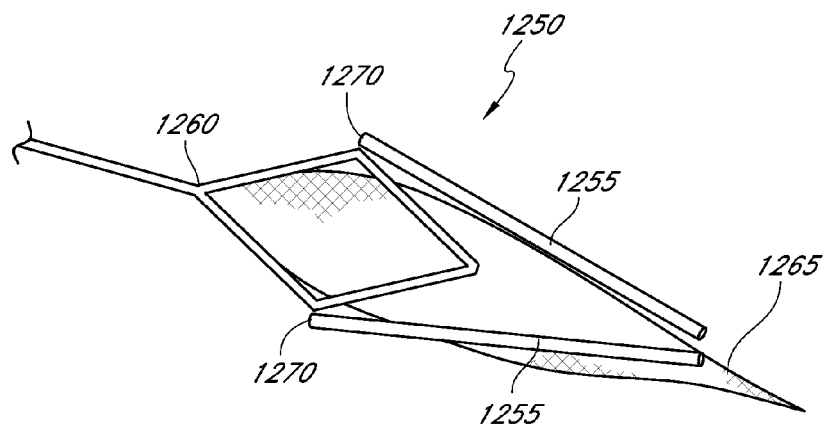
FIGS. 50A-50B depict embodiments of needles that are used in conjunction with a dissecting tool and a sling.
Figure 50B:
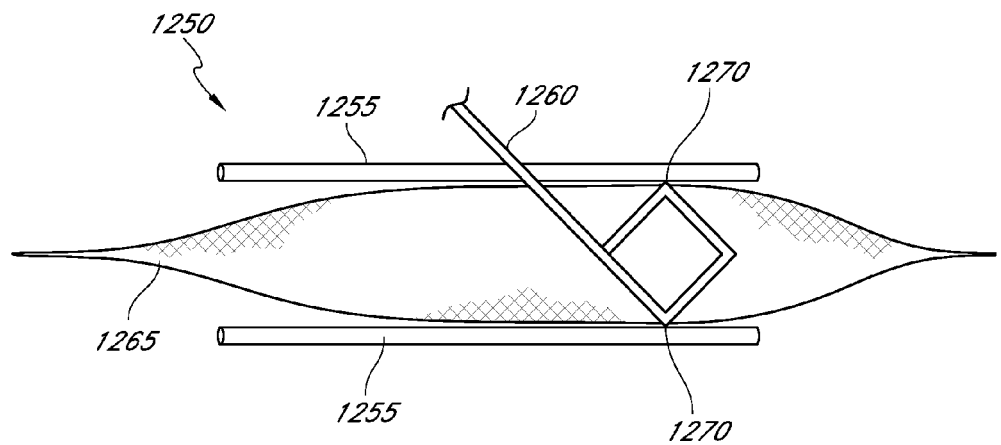

FIGS. 50A-50B depict embodiments of a "railroad track" dissecting device 1250 that includes a plurality (for example, two) needles 1255, or elongate members, that are used in conjunction with a dissecting tool 1260 and a sling 1265. The purpose of the device 1250 is to create a dissecting plane and to install the sling 1265 at the same time. The sling 1265 can be connected or coupled to two needles 1255 that will be inserted into the breast. After the needles are introduced, or inserted, in the tissue, the "Railroad Tracks" operation is created by sliding a dissector 1260 along each of the needles 1255. The dissector 1260 preferably has a substantially rigid configuration that will separate the needles 1255 from each other as it is advanced along the needles.

In some embodiments, the dissector 1260 is connected or coupled to the needles 1255 (for example, by eyelets 1270 that extend around each needle 1255). As the dissector 1260 separates the needles 1255, the needles 1255 expand the channel of tissue to increase a cross-sectional dimension of the channel In some embodiments, as the needles 1255 are separated, the needles, which can be coupled to the sling 1265, spreads the sling 1265 within the channel to increase the cross-sectional dimension, or width, of the sling 1265 within the tissue. In some embodiments, the dissector 1260 is expandable at least to a cross-sectional dimension of a width of the sling 1265, such that the dissector 1260 separates the needles 1255, when advanced along the needles 1255, by substantially the width of the sling 1265. Following creation and/or expansion of the plane within the tissue by the device 1250, the dissector 1260 can then be removed.

"Wrist Slap" Needle

Figure 51A:
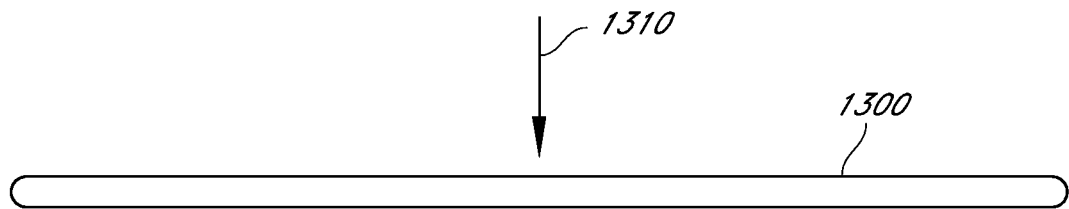
FIGS. 51A-51B depict embodiments of a needle having bistable configurations.
Figure 51B:
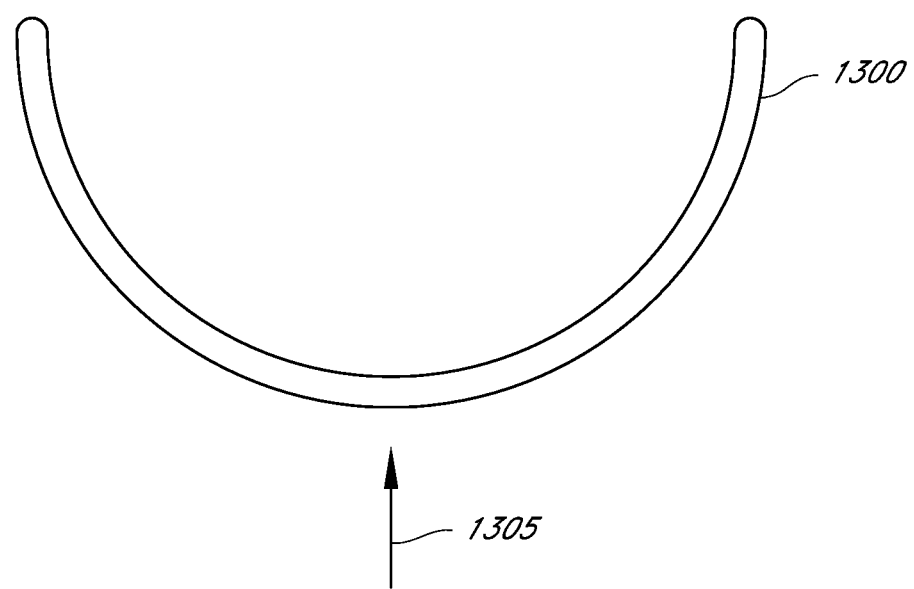

FIGS. 51A-51B depict embodiments of a needle 1300 having bistable configurations. The wrist slap needle has multi-purpose use. The needle 1300 will have a natural bent curvature, as illustrated in FIG. 51B. When a force is applied in the upward direction 1305, the needle 1300 will then flatten to a straight needle, shown in FIG. 51A. Pressure, or force, can then be applied in the opposite, or downward, direction 1310 to change to needle 1300 to having a bent curvature. Ideally, this tool can be used as a curved needle during sling application, or introduction, and then flattened to a straight needle for use with an anchor (e.g., a fascia anchor).

Detectable Sling-Suture Connectors

Figure 52:
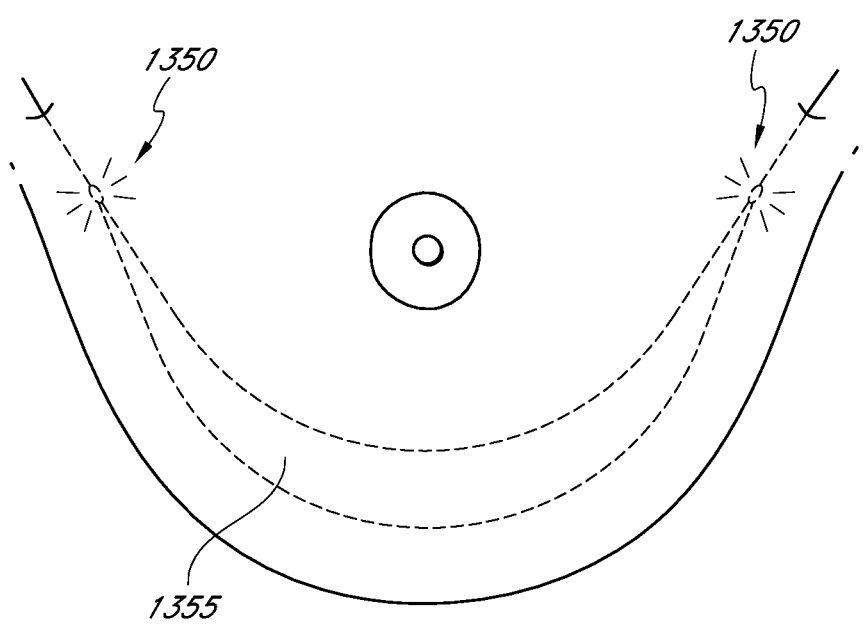
FIG. 52 depicts embodiments of a detectable sling-suture connector.

FIG. 52 depicts embodiments of a detectable sling-suture connector 1350. The purpose of this concept is to have manageability over the location of the sling 1355 within the breast. By applying sling-suture connectors 1350 that can be detected from outside of the breast, those points can then be determined externally for position modification of the sling 1355. In some embodiments, the points of the connectors 1350 can be palpable externally. In certain embodiments, the points can be echogenic. In some embodiments, the points emit light, and are visible to the eye.

Sling Exit Points

Figures 53A, 53B:
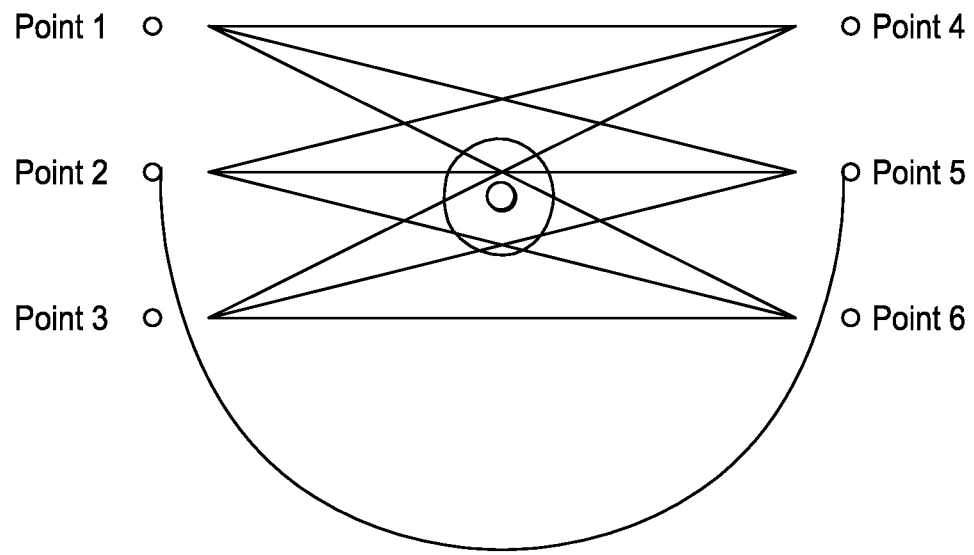
FIGS. 53A-53B depict embodiments of sling exit points for procedures as described herein.

FIGS. 53A-53B depict embodiments of sling exit points for procedures as described herein. Having predefined sling exit points will ensure proper positioning of the sling and breast lift and direction. There are a possible of 6 exit holes for the breast; three on the outer breast and three on the inner breast. The three on either side will lie above, across, or below the nipple. The direction of the needle will be a combination of one point on the outer breast to one point on the inner breast, varying the three points on either side. FIG. 53B depicts a table of possible connectors between the six points.

One Exit Hole Breast Lift

Depicted herein are several embodiments relating to systems, devices, and methods for performing a breast lift through one incision. While the disclosure below refers specifically, by way of example, to breast lifts, the disclosure can be applicable to lifts, shifting, or moving any soft tissue. Additionally, the embodiments described below can be used in conjunction with other embodiments described in this disclosure.

The one exit hole breast lift consists of an insertion point located at the bottom of the breast, approximately halfway from the inframammary fold to the bottom of the areola. This one exit point allows each of the two or more breast needles, or other tools, to be directed up to the anchor point, one up medially and the other laterally. The location of the hole is dependent of the required trajectory of lift. For most vertical lifts, the hole would be located at about the halfway point of the breast diameter, however, if the lift required is one which the breast and nipple should be pulled together toward the sternal notch then the hole may be located along the line connecting the nipple to the sternal notch or mid-clavicle, or positioned slightly laterally. With the assistance of a sling port, the same hole may be used for both breast needles. For the procedure including an anchor knot located at the second or third rib, the medial breast needle is directed first and comes out at the medial anchor point. The anchor needle is then inserted to grab a bite of fascia. The lateral breast needle may then be inserted in the exit hole using a sling port, exiting out the lateral anchor hole. The sling may then be pulled inside the breast, and adjusted appropriately from the two sutures exiting the lateral anchor hole.

The one exit hole breast lift may also be used in conjunction with a distal anchor, which may be deployed from the one exit hole. Once the anchors are secure at either side of the top of the breast, the sling may be inserted and lifted in order to lift the breast. The suture would then be secured leaving a single closure point at the bottom of the breast.

In some embodiments, the length of the device used in connection with the One Exit Hole Breast Lift embodiments is long enough to simultaneously insert both anchors and still have maneuverable access to the sling. This length may vary dependent on the site of application and the tissue being lifted. In addition, a diameter of the access port should be wide enough, in some embodiments, to encompass two springs at the same time and also the sling doubled over with two suture stands. In some embodiments, the diameter of the port accommodates the larger of the two.

Variable Length Port

Figure 54A:
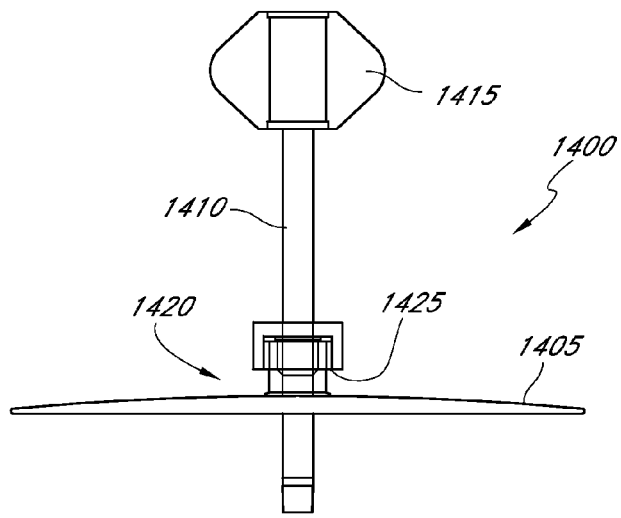
FIGS. 54A-54C depict embodiments of a variable length port.
Figure 54B:
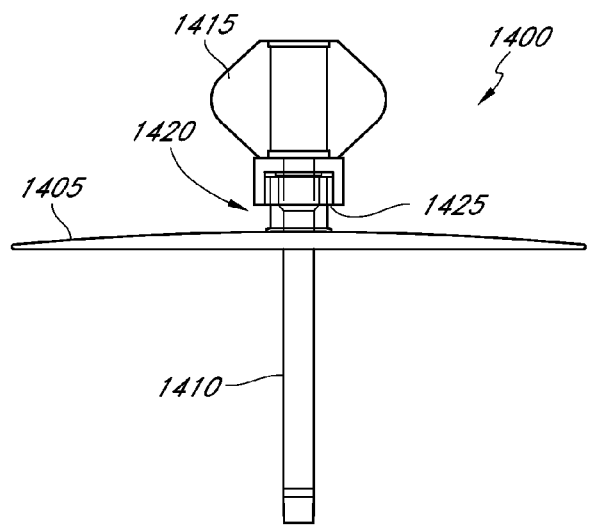
Figure 54C:
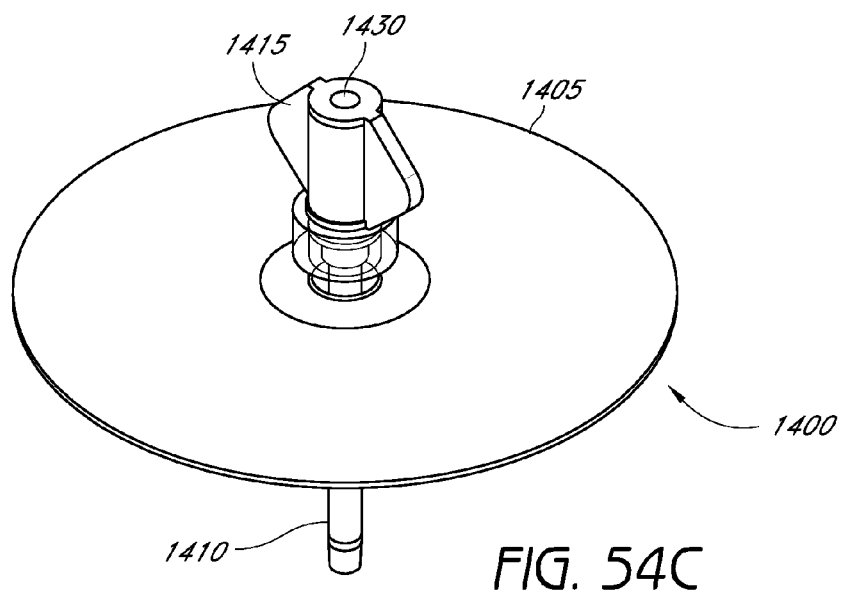

FIGS. 54A-54C depict embodiments of a variable length port 1400. The variable length port is designed to change length in order to better assist with implantation of the device, primarily to accommodate different breast sizes. There is a round disk 1405 that will sit against the skin. Also, there is a fixed length sheath 1410 with a handle 1415 that the needle can slide into. The port 1400 contains a component 1420 similar to a tuohy borst adapter, in which there is a screw lock 1425 allowing the sheath 1410 to move up and down then lock into the desired depth.

Some embodiments provide that the material of the port would be made of an implantable grade resorbable or non-resorbable polymer and/or metal material, including but not limited to, Polypropylene, Polyester, Nylon, PEEK, Polyurethane, Polycarbonate, Titanium, and Stainless Steel. The sheath 1410 preferably includes an internal lumen 1430 that has a diameter preferably large enough, in some embodiments, to allow for anchor delivery system and sling component. This diameter may be dependent on the implant location and specification, but it should range, in most embodiments, from about 5 French to about 24 French. The length of the device may also be dependent on the implant location, but it should be limited, in most embodiments, to range from about 0.25 inches to about 4 inches. In some embodiments, the length may be less than about 0.25 inches or greater than about 4 inches. The diameter of the sheath 1410, in some embodiments, will be less than about 2 inches on its largest dimension, dependent on the shape of the disk 1405, whether circular or oval, but wide enough to place the sheath 1410, for example, in the center.

Suture Clamp

Figure 55A:
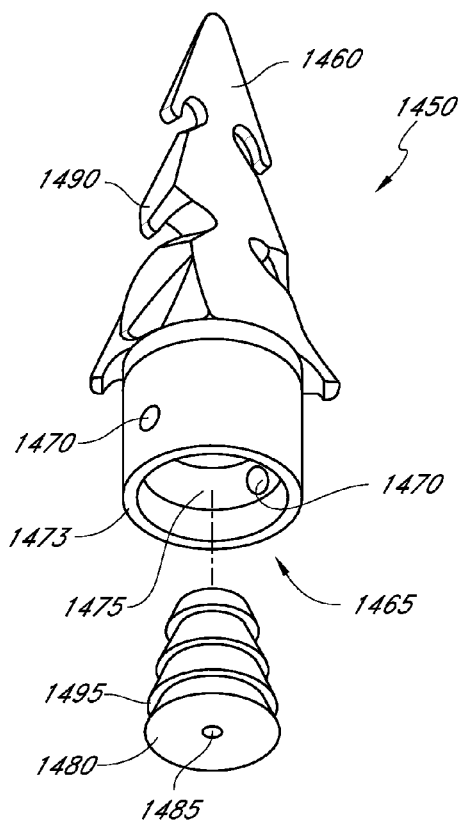
FIGS. 55A-55C depict embodiments of a suture clamp.
Figure 55B:
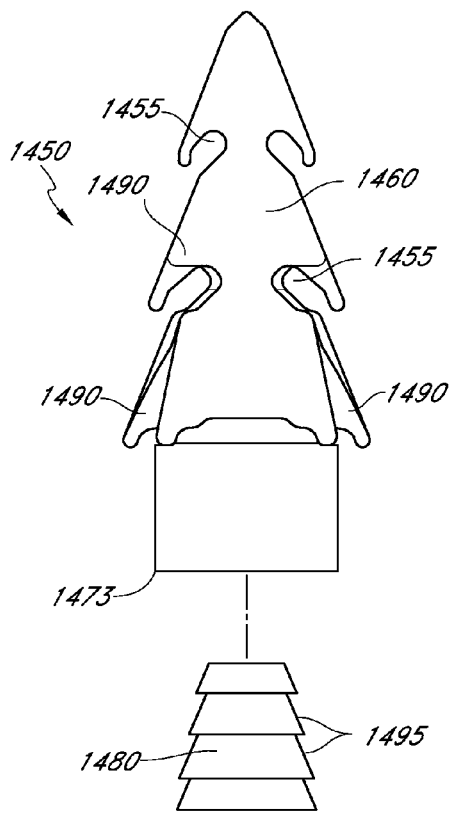
Figure 55C:
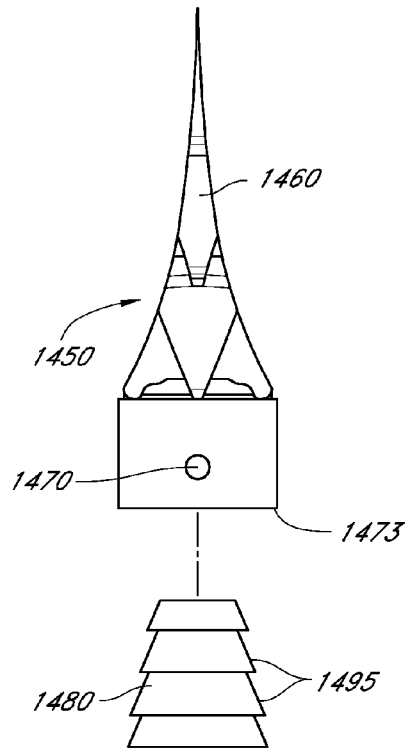

FIGS. 55A-55C depict embodiments of a suture clamp 1450. The suture clamp 1450 is preferably a non-resorbable, two component anchoring system with small holes 1455 for tissue ingrowth. The top component 1460 contains the anchoring device which will secure into the fascia or adipose. The device top component 1460 will have a line of suture feeding through a bottom opening 1465 coming out of, for example, two holes 1470 on either side. The two suture pieces will meet together at a bottom portion 1473 of the top component 1460 and feed into the center 1475 of the bottom component 1480 of the device 1450 which has a hole 1485 down the center 1475. A sheath with a diameter of the bottom portion 1473 of the top component 1460 may be used to drive the top component 1460 of the device 1450. Once in desired location, the suture may be pulled on to allow for the locking grooves 1490 of the device to secure into the tissue. Using a smaller diameter tube, the bottom component 1480 of the device may be pushed up into the bottom portion 1473 of the already installed anchor. The bottom component 1480 preferably includes grooves 1495 that secure the bottom component 1480 within the top component 1460 and clamp down of the suture. After connection of the top component 1460 and bottom component 1480 of the Anchor clamp 1450, the sheaths may be removed.

The material of the clamp 1450 would be made, in some embodiments, of an implantable grade resorbable or non-resorbable polymer and/or metal material, including but not limited to, Polypropylene, Polyester, Nylon, PEEK, Polyurethane, Polycarbonate, Titanium, and Stainless Steel. The overall length of the device, is some embodiments, will be between about 0.125 inches and about 2 inches dependent on the location of implantation. In some embodiments, the length may be less than about 0.125 inches or more than about 2 inches. In some embodiments, the device will be less than or equal to about 0.75 inches in diameter. The bottom portion 1473 will preferably be wide enough to accommodate the bottom component 1480 of the clamp 1450 and two layers of suture material. This range will be, for example, between about 0.1875 inches and about 0.75 inches.

Hooked Slide

Figure 56A:
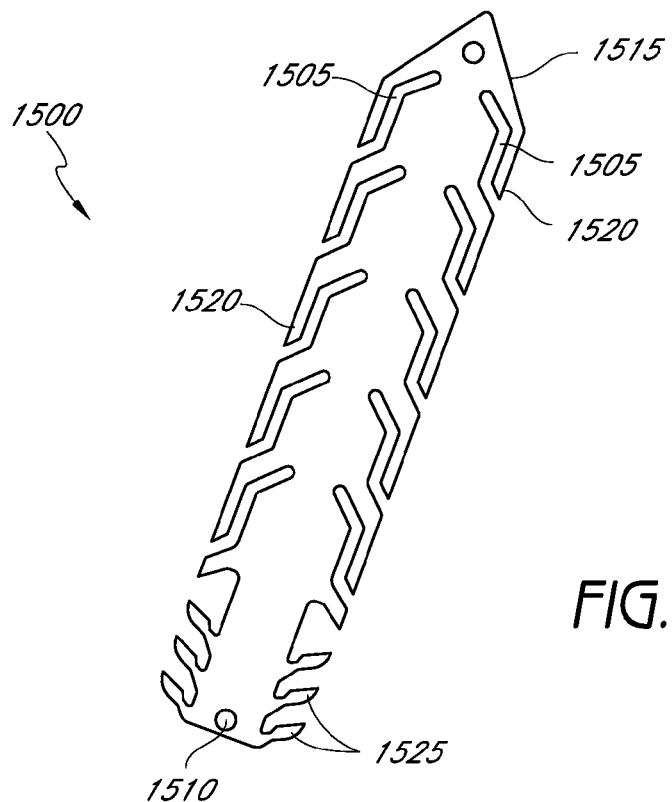
FIGS. 56A-56B depict embodiments of a hooked slide.
Figure 56B:
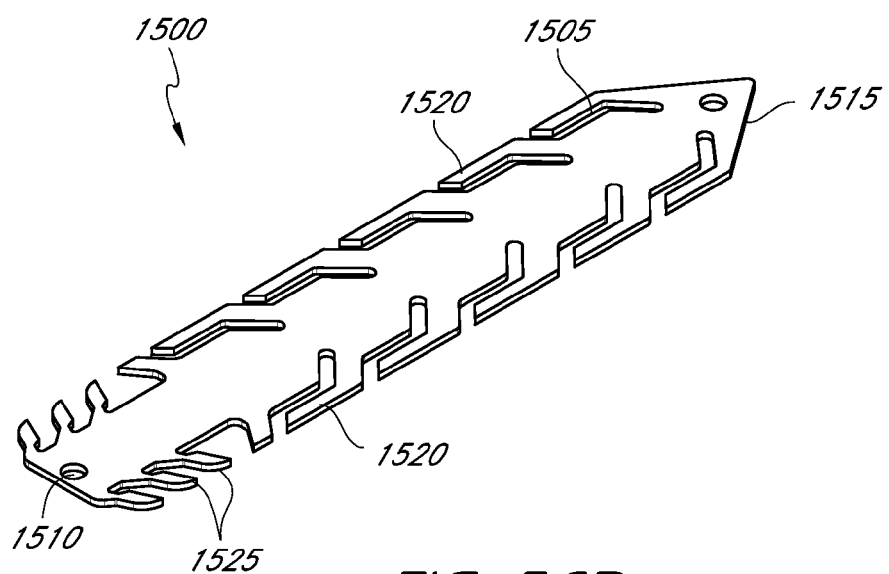

FIGS. 56A-56B depict embodiments of a hooked slide 1500. The hooked slide 1500 is a non-resorbable device with small holes 1505 for tissue ingrowth connected to the suture used as an anchoring tool. The slide 1500 would preferably be covered by a sheath and fed up to anchor point in fascia by a hook. Once at the desired location, the sheath and hook can be removed, leaving the hooked slide 1500 in place. A lower hole 1510 is provided for a suture connection. The hooked slide 1500 contains a pointed top portion 1515 to facilitate advancing the slide 1500 through the tissue. Downward directing hooks 1520 are on either slide, therefore, allowing ease of insertion. Once at correct location, the downward hooks 1520 will increase stabilization of the slide 1500 within the tissue. In addition, some embodiments provide that there are upward facing hooks 1525 to secure the device 1500, allowing the entire device to be restrained from both directions.

The material of the hooked slide 1500 would preferably be of an implantable grade resorbable or non-resorbable polymer and/or metal material, including but not limited to, Polypropylene, Polyester, Nylon, PEEK, Polyurethane, Polycarbonate, Titanium, and Stainless Steel. The overall length of the hooked slide 1500 will preferably be between about 0.125 inches and about 2 inches with a thickness between about 1/32 inches and about 0.1875 inches. In some embodiments, the thickness can be less than about 1/32 inches or greater than about 0.1875 inches. In some embodiments, the device will be between about 0.0625 inches and about 0.75 inches wide.

Multiple Dart Suture

Figure 57:
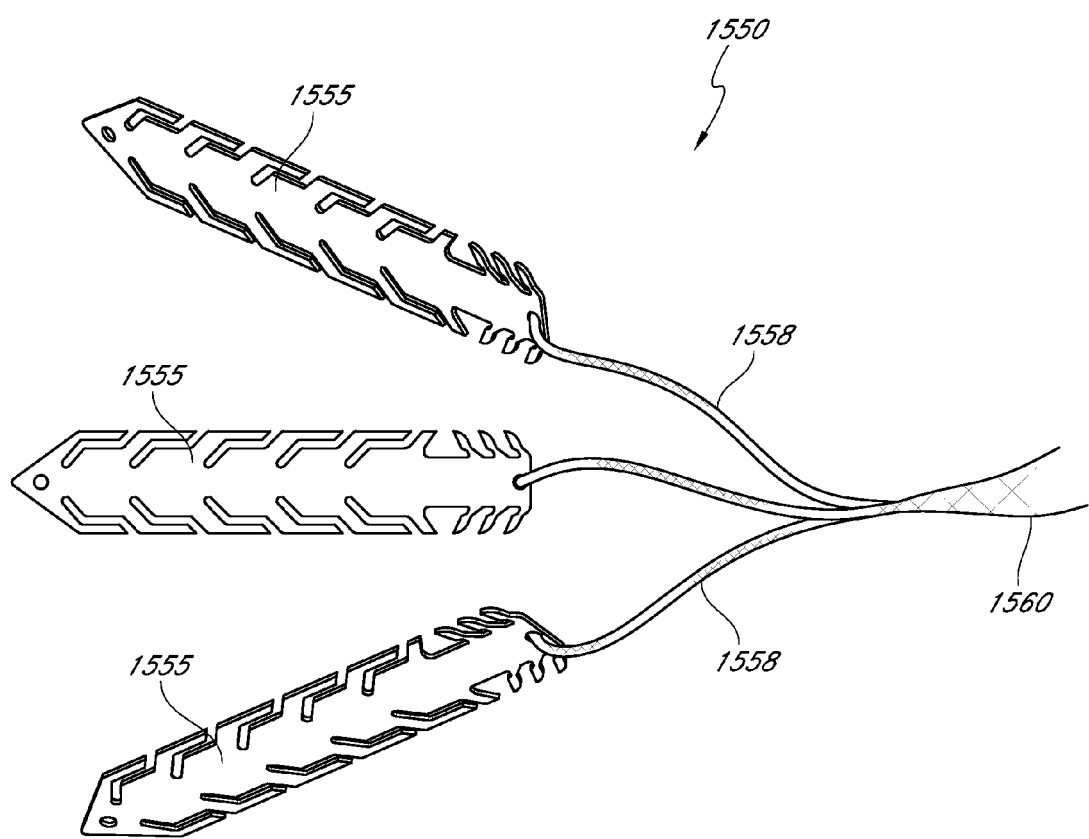
FIG. 57 depicts embodiments of a multiple dart suture.
Figure 58A:
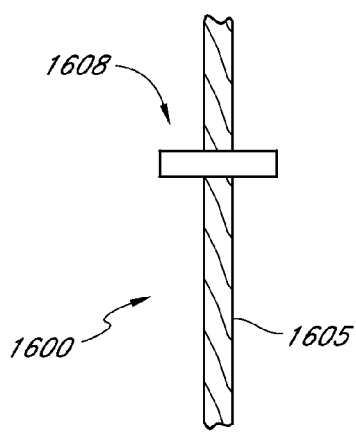
FIGS. 58A-58D depict embodiments of an anchor clasp.
Figure 58B:
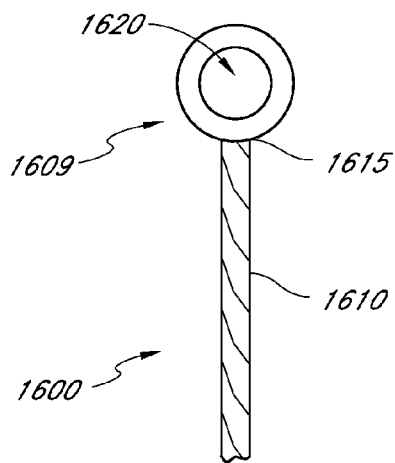
Figure 58C:
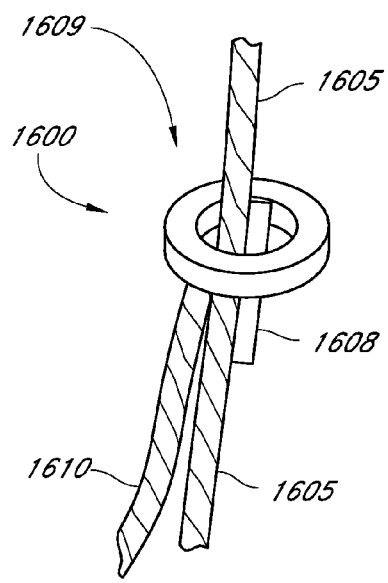
Figure 58D:
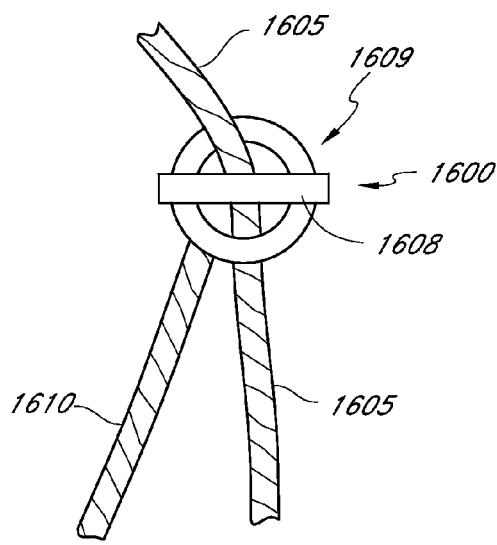

FIG. 57 depicts embodiments of a multiple dart suture 1550. The multiple dart suture 1550 is one that has multiple barbed ends 1555 connected, for example via a suture 1558, at each side of the sling 1560. These would be inserted up through the sling exit ports. Using a sheath each individual suture will be fed up to the anchor point and released. The sheath may be moved for each portion to allow for a range of securing sites.

The anchor material and size can be dependent of anchor that is attached. The overall length of the dart sutures 1550 is preferably enough to allow for individual insertion of each device component while having access to the other components out of the exit hole.

Anchor Clasp

FIGS. 58A-58D depict embodiments of an anchor clasp 1600. This device would be used as a method of securing two sutures at the anchoring site. The device 1600 preferably allows reversible securing of the sutures, allowing for later adjustments, if needed. One suture 1605 would have a perpendicular rod 1608 (polymer based). The second 1610 would have a ring 1609 attached to the end 1615 of the suture 1610. Once the two components are to be secured together, the rod 1608 would be substantially aligned with an axis passing through a center 1620 of the ring 1609 and inserted through the ring center 1620. Once through the ring 1609, the rod 1608 would be repositioned to be substantially perpendicular to the axis of the ring, ensuring, when properly sized, the inability to release through the ring 1620.

The material of the suture could be made of an implantable grade resorbable or non-resorbable polymer material, including but not limited to, Polypropylene, Polyester, Nylon, PEEK, Polyurethane, and Polycarbonate. An additional component of the perpendicular rod 1608 and ring 1609 may be made of an implantable grade resorbable or non-resorbable polymer and/or metal material, including but not limited to, Polypropylene, Polyester, Nylon, PEEK, Polyurethane, Polycarbonate, Titanium, and Stainless Steel.

The length of the rod 1608 would be, in some embodiments, larger than the internal dimension (ID) of the ring 1609 by about 1/32 inch up to about 0.0625 inch over the outer dimension (OD) of the ring 1609 dependent of the application and location of implantation. The ring 1609 may have an ID ranging from about 0.0625 inch to about 0.5 inch and an OD from about 1/32 inch to about 0.0625 inch. In some embodiments, the ID can be less than about 0.0625 inch or greater than about 0.5 inch, and in some embodiments, the ring OD can be less than about 1/32 inch or greater than about 0.0625 inch. The ring 1609 is preferably large enough to pass the suture 1605 and the rod 1608 simultaneously.

Zip Tie Sling Closure

Figure 59A:
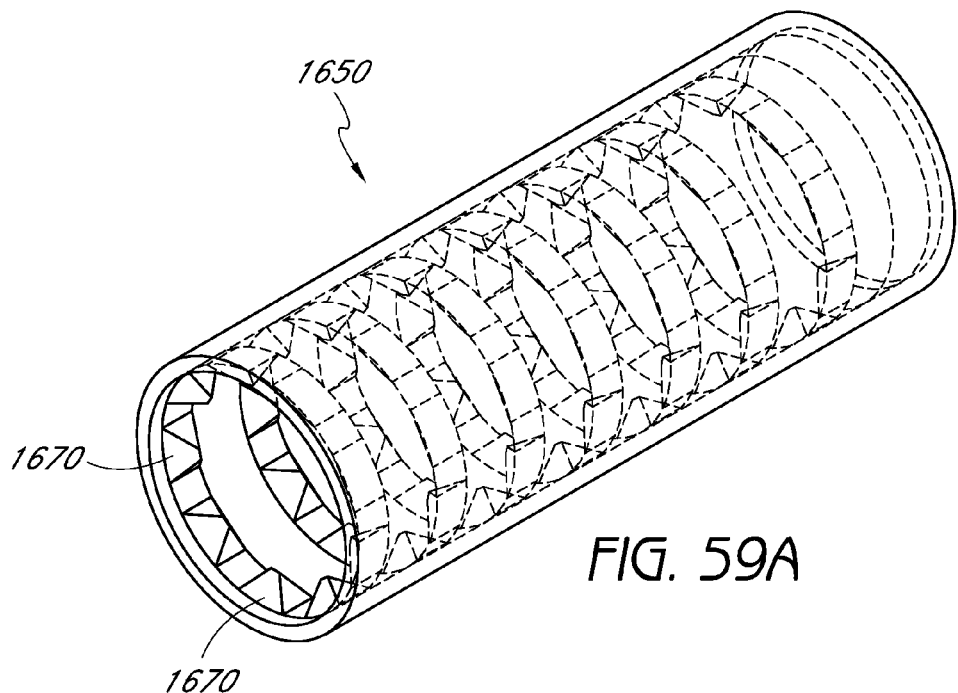
FIGS. 59A-59B depict embodiments of zip tie sling closures.
Figure 59B:
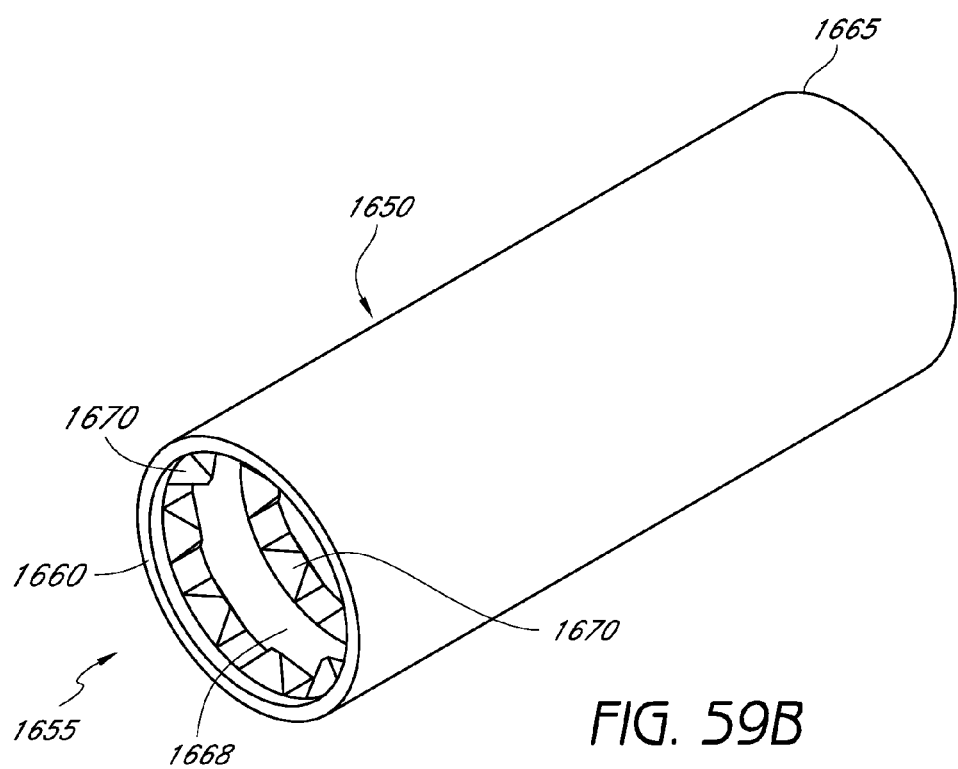
Figure 60A:
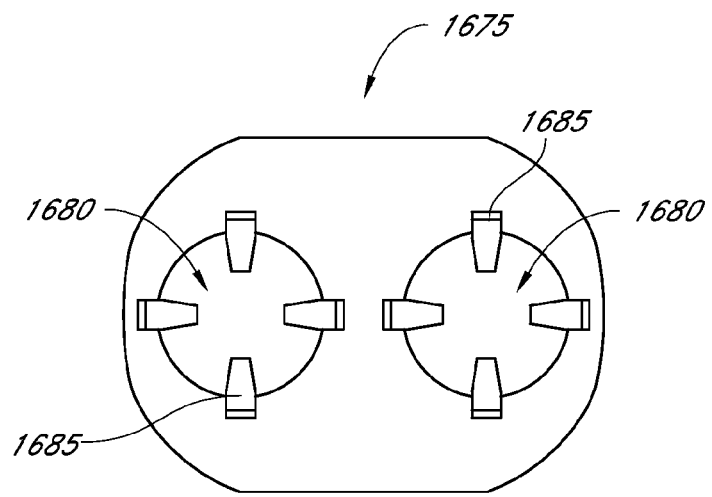
FIGS. 60A-60C depict embodiments of zip tie sling closures.
Figure 60B:
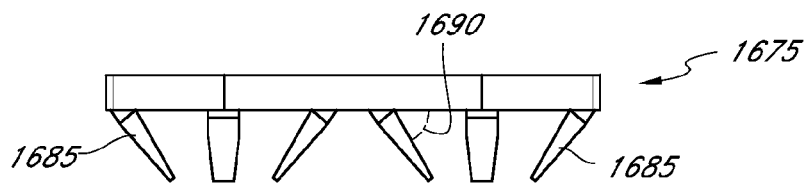
Figure 60C:
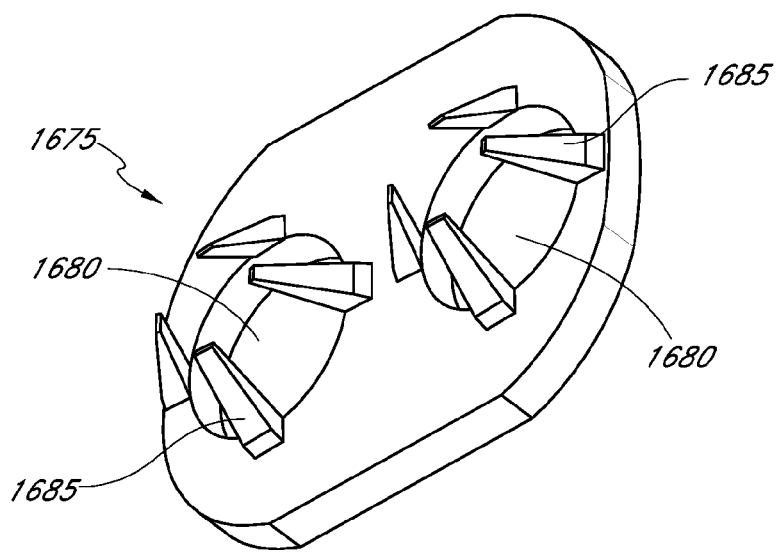

FIGS. 59A-59B and 60A-60C depict embodiments of a zip tie sling closures. The purpose of the non-resorbable zip tie closure is to assist in the securing of the sling rather than using a knot with small holes throughout for tissue ingrowth. FIGS. 59A-59B illustrates a first version of a closure 1650 that is preferably optimally used for braid-in-braid securing, where there is only one strand of suture to lock. Version one 1650 of the closure is preferably a substantially cylindrical member having a lumen 1655 extending between ends 1660, 1665 of the closure. The interior wall 1668 of the lumen preferably includes a plurality of inwardly projecting members 1670 for securing and/or engaging a suture that is extended through the lumen. The second version of the closure 1675, FIGS. 60A-60C, is preferably a small button-like device that has two holes 1680 for either suture on the sling within the device suture would only be able to enter one way. Once inside, the suture would not release but only be able to pull through the direction it entered because of inwardly projecting members 1685 around each hole that engage the suture extending through the hole. This feature would also allow for future adjustment lifts. In some embodiments, the closures can be combined, where version one 1650 sits on top of version two 1675 as a single piece, to provide addition securing.

The material of the closure is preferably made of an implantable grade resorbable or non-resorbable polymer and/or metal material, including but not limited to, Polypropylene, Polyester, Nylon, PEEK, Polyurethane, Polycarbonate, Titanium, and Stainless Steel. For the first version 1650, the length of the device 1650 will preferably be within about 0.125 inch to about 0.375 inch. The ID of the tube or cylinder, without the inner teeth or inwardly projecting members 1670, can be that of double the diameter (or cross-sectional dimension) of the suture under compression. The teeth or members 1670 can be small enough to allow two strands of suture to pass through but large enough to induce significant friction if pulled in the opposite side of entry.

For the second version 1675, the diameter of each suture hole 1680 is preferably equal to or less than the suture diameter (or cross-sectional dimension) not under compression, so as to allow the suture to pass through easily but allow the teeth or members 1685 to grab. A stationary angle 1690 of the teeth 1685 is less than about 90° but flexible enough to expand to about 90° to allow for suture passage.

Friction Fit Anchor

Figure 61A:
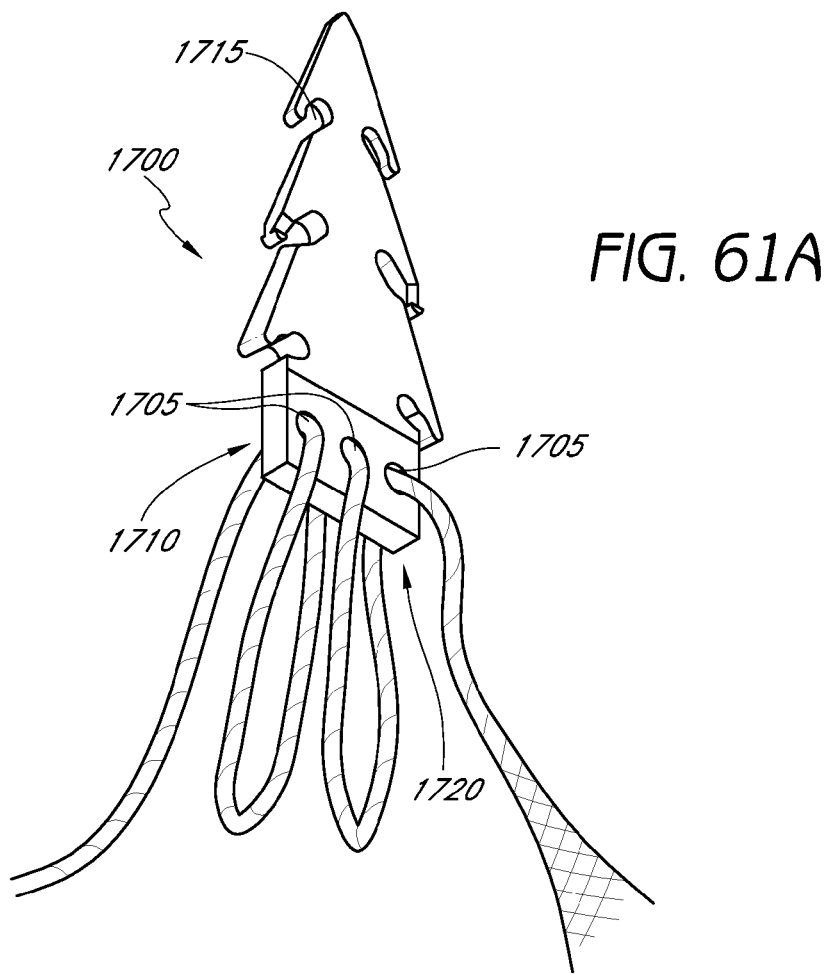
FIGS. 61A-61B depict embodiments of friction fit anchor.
Figure 61B:
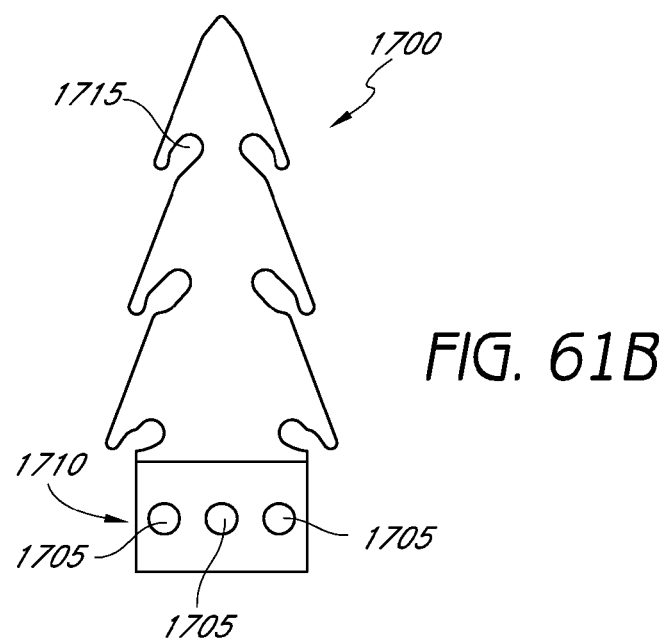

FIGS. 61A-61B depict embodiments of a friction fit anchor 1700. The non-resorbable anchor 1700 contains three holes 1705 at a bottom 1710 of anchor 1700 and with small holes 1715 throughout for tissue ingrowth. The suture is weaved between these three holes 1705 loosely, allowing access for three loops at the exit point. The last suture loop 1720 leads directly to the sling. The anchor 1700 is driven into place and once at the optimal location, suture tightening begins. In order to tighten the suture, each loop is pulled until all obtain a friction fit within the holes 1705. This will allow the suture to maintain in place without movement.

The material of the anchor 1700 is preferably made of an implantable grade resorbable or non-resorbable polymer and/or metal material, including but not limited to, Polypropylene, Polyester, Nylon, PEEK, Polyurethane, Polycarbonate, Titanium, and Stainless Steel. The overall length of the anchor 1700 is preferably between about 0.125" and about 2" with a thickness between about 1/32" and about 0.1875". The device is preferably between about 0.0625" and about 0.75" wide. The diameter of the suture holes 1705 can approximate the diameter of the suture used.

Anchor Spring

Figure 62:
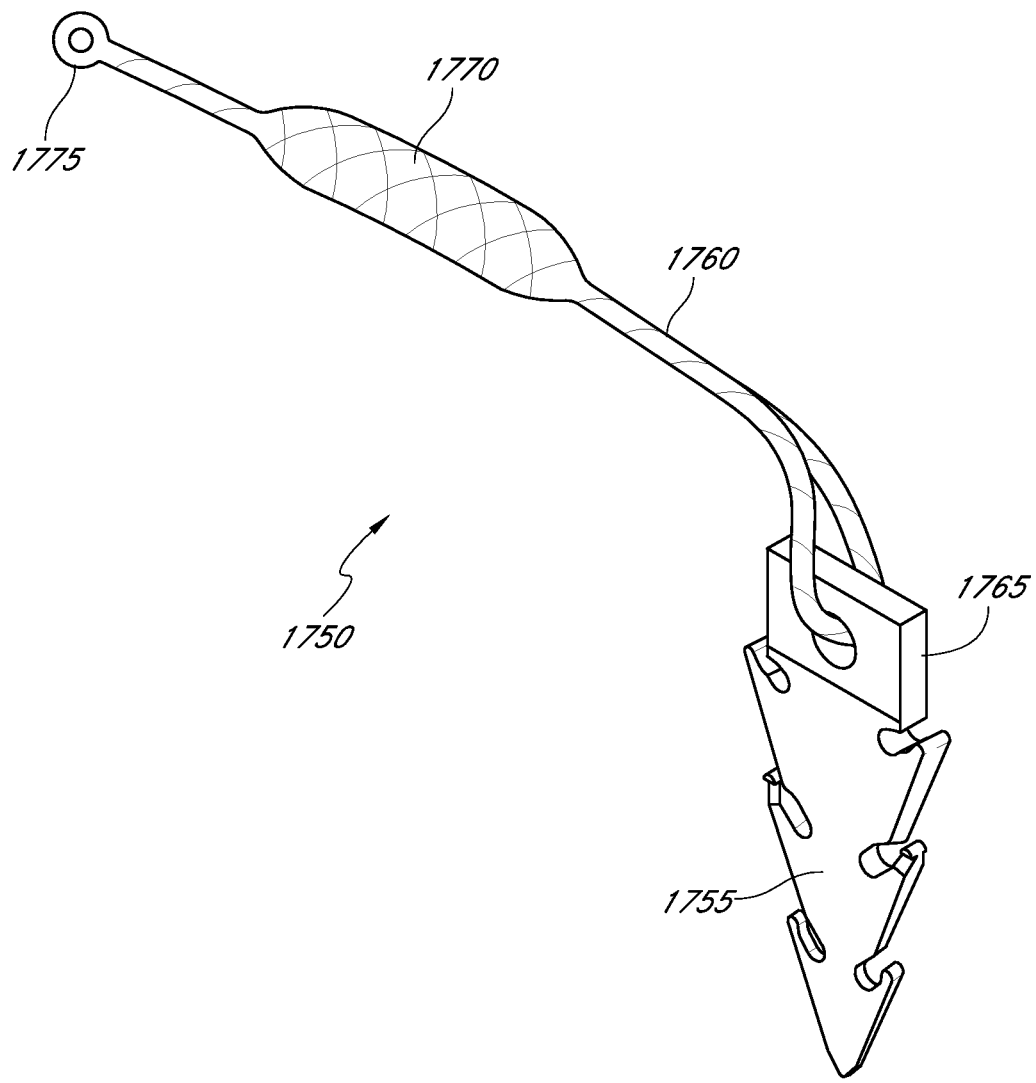
FIG. 62 depicts embodiments of an anchor spring.

FIG. 62 depicts embodiments of an anchor spring 1750. The non-resorbable anchor spring 1750 is an anchor 1755 with a line of suture 1760 coming from the end 1765 of the anchor 1755. The suture will preferably be a specified length and preferably contains a spring 1770. At the opposite end of the anchor 1755 and spring 1770, there will be a loop 1775 to allow for another line of suture to feed through. The anchor 1750 will be deployed independent of the sling, allowing for multiple anchors to be used and more variations in lift.

In some embodiments, the anchor spring 1750 without suture would be one with the silicone spring directly overmolded onto the anchor 1755. This would eliminate the need to connect the suture to the anchor 1755, feed the spring 1770 inside, and then loop at the end 1765.

In some embodiments, the material of the anchor spring 1750 may be made of an implantable grade resorbable or non-resorbable polymer and/or metal material, including but not limited to, Polypropylene, Polyester, Nylon, PEEK, Polyurethane, Polycarbonate, Titanium, and Stainless Steel. The overall length of the anchor will preferably be between about 0.125" and about 2" with a thickness, in some embodiments, of between about 1/32" and about 0.1875". The device will preferably be between about 0.0625" and about 0.75" wide. The diameter of the suture hole approximates, in some embodiments, the diameter of the suture used.

The length of the suture extension that contains the spring 1770 will preferably be between about 0.25" and about 6" depending on the location of implantation. The loop and the bottom may be created from overlapping the suture within itself or by applying a separate component that will be made of the same previously list materials. The ring or loop may have an ID of about 0.015" up to about 0.25" and a diameter from about 1/32" to about 0.0625". The spring will preferably be made of an implantable grade flexible polymer including, but not limited to, silicone that can be shorter than the overall length of the suture attachment portion but, in some embodiments, greater than about 0.0625".

Anchor Spring Device

Figure 63A:
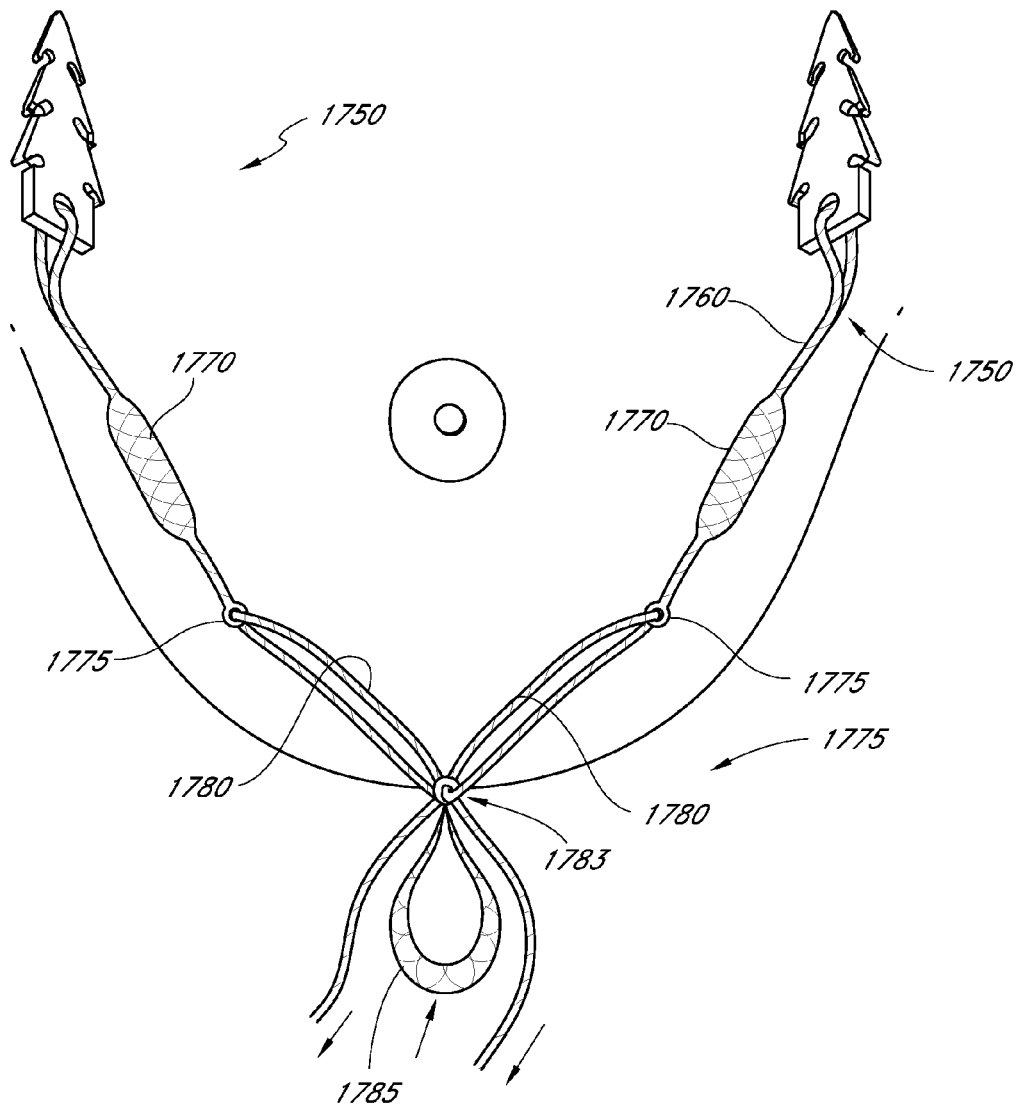
FIGS. 63A-63C depict embodiments of an anchor spring device.
Figure 63B:
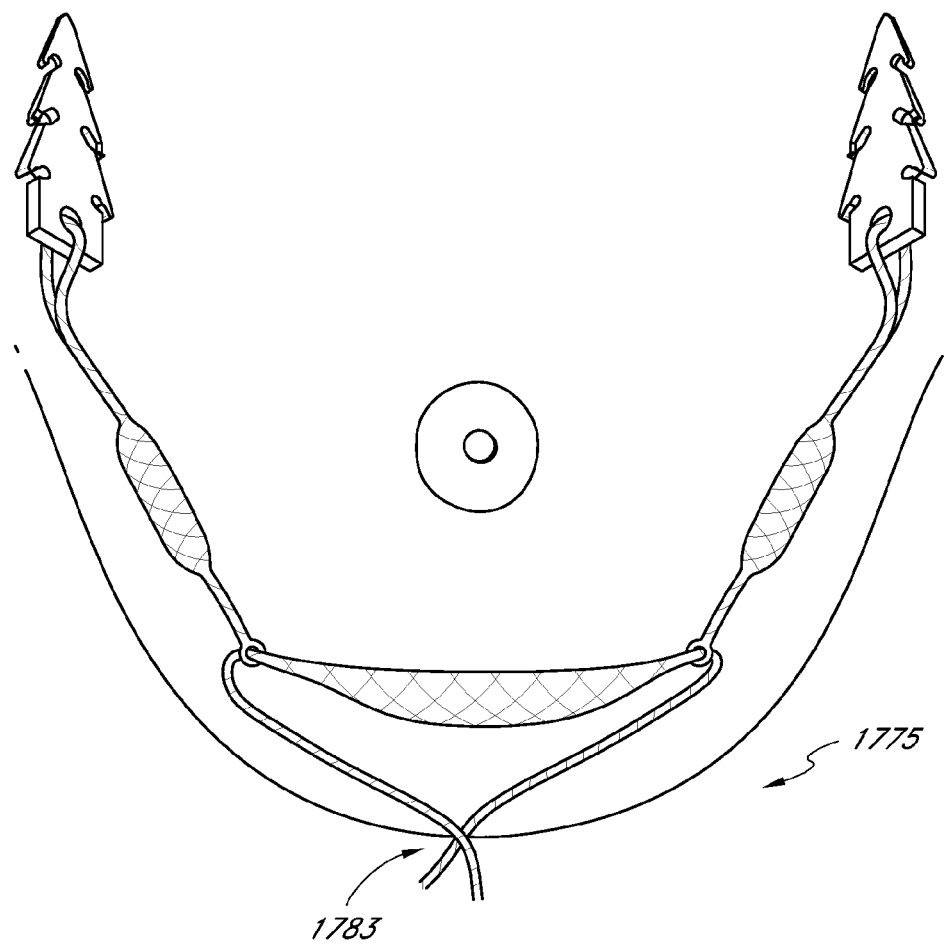
Figure 63C:
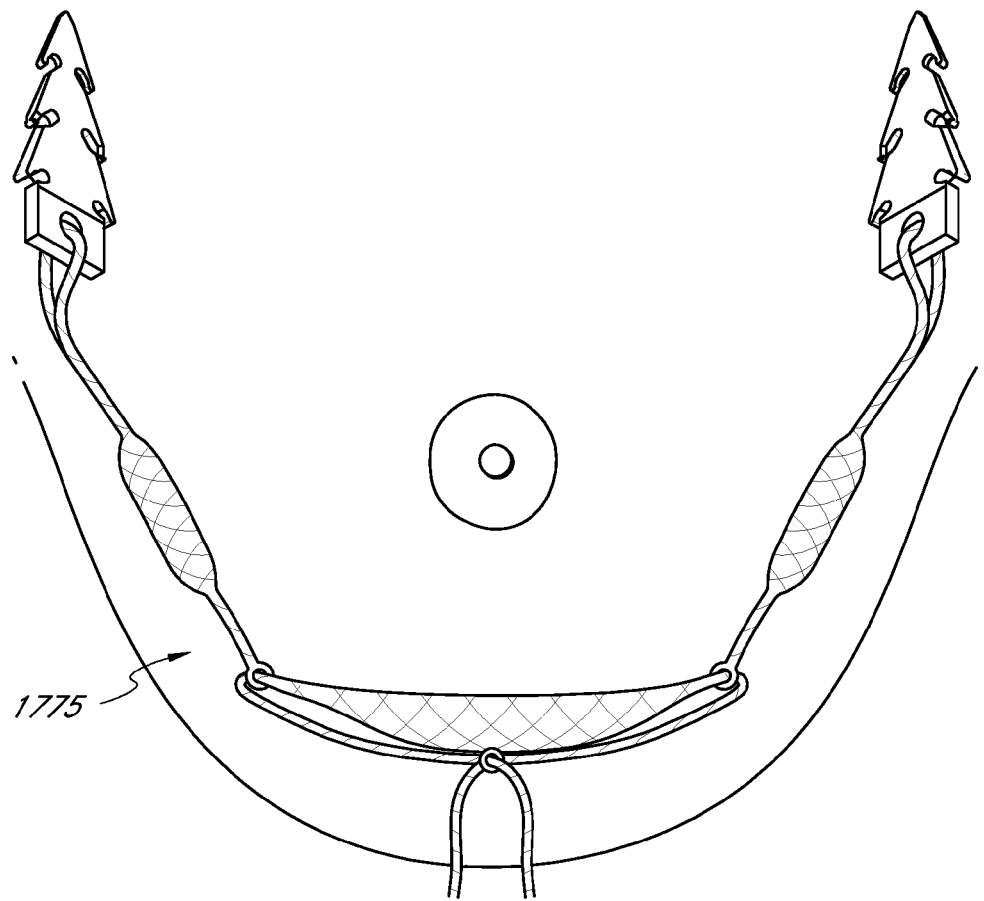

FIGS. 63A-63C depict embodiments of an anchor spring device. The anchor spring device consists of two or even four anchor springs 1750. Each of the springs 1750 has the suture 1780 looped through hole 1775 at the end of the anchor spring 1750. The anchor 1755 is, in some embodiments, deployed up one side of the breast through the bottom anchor hole 1783, such that the two suture ends are protruding, one of the ends being a suture connected to one end of the sling 1785. A second anchor 1755 is then fed up to the opposing side of the breast and secured into place. For this anchor, there are also two strings protruding, one of which is the opposite of end of the sling. Now both anchors will be in place and there should be a sling and two suture ends coming out of the exit hole 1783. By pulling the two suture ends, the sling will retract into the breast through the exit hole 1783 (FIG. 63B). The breast will lift and once at optimal location, the suture ends may be tied together (FIG. 63C) to secure the sling 1785 in place, as shown in FIGS. 63B-63C.

Figure 63D:
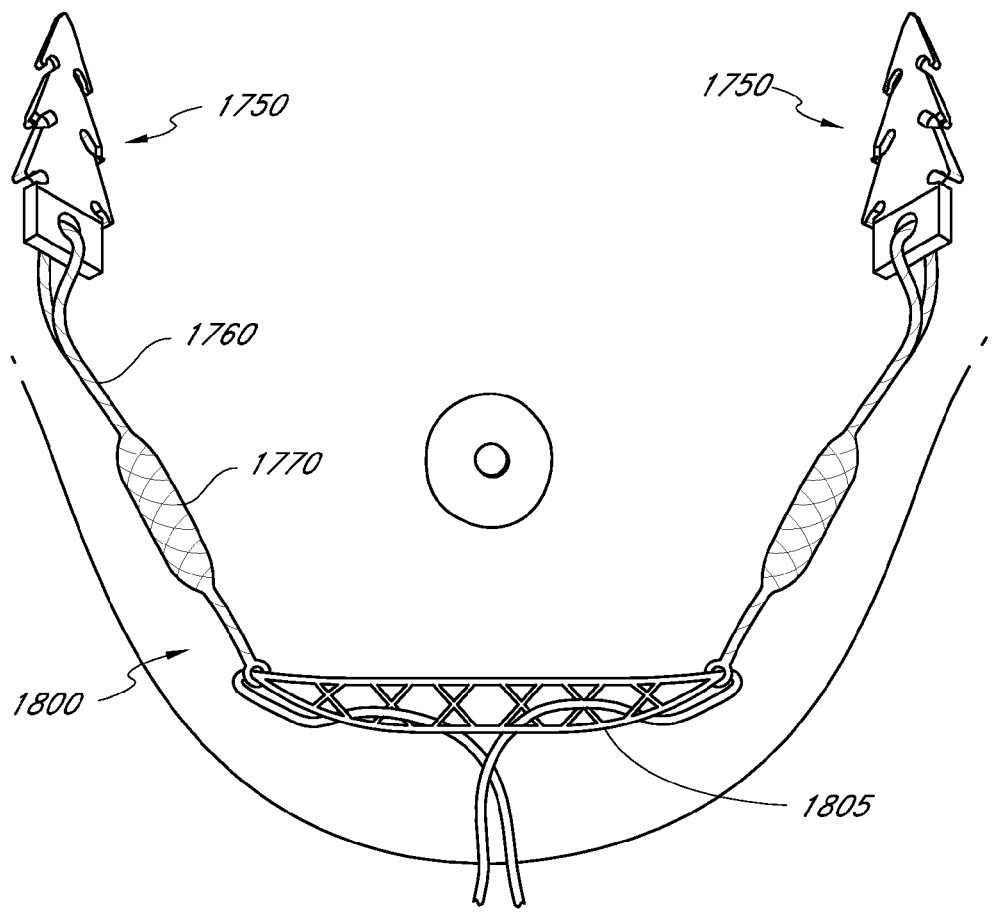
FIG. 63D depicts embodiments of a sling weave anchor spring device.

FIG. 63D depicts embodiments of a sling weave anchor spring device 1800. Similar to the sling loop anchor spring device, depicted in FIGS. 63A-63C, the two suture ends would be oriented to the exit hole at the bottom of the breast. However, with the sling weave 1800, the two suture ends would be weaved within the sling 1805 to its center and then down to the exit hole. This would allow a knot to be tied at the center of the sling. Two main advantages include there being no cheese wiring of the suture and the inability for the sling to rotate. Once the anchors are deployed and at the desired location, the sling may then be pushed up into the breast, by pulling on the suture ends. Once the lift is obtained, a knot may be tied to secure the device.

The material of the anchor 1750 of the device 1800 may include an implantable grade resorbable or non-resorbable polymer and/or metal material, including but not limited to, Polypropylene, Polyester, Nylon, PEEK, Polyurethane, Polycarbonate, Titanium, and Stainless Steel. The overall length of the anchor will be between about 0.125" and about 2" with a thickness between about 1/32" and about 0.1875". The device will be between about 0.0625" and about 0.75" wide. The diameter of the suture hole can approximate the diameter of the suture used. The spring will preferably be made of an implantable grade flexible polymer including but not limited to silicone. The length of the spring extension will be between about 0.25" and about 6".

The length of the device 1800 is preferably long enough to simultaneously insert both anchors 1750 and still have maneuverable access to the sling 1805. This length could vary dependent on the site of application. In addition, the diameter (or cross-sectional measurement) of the access port (that can be used in connection with this and other embodiments) should, in some embodiments, be wide enough to encompass two springs 1770 at the same time and also the sling 1805 doubled over with two suture stands. The diameter of the port could accommodate the larger of the two. The spring may be implantable non-resorbable grade flexible polymer including but not limited to silicone.

Double Anchor Spring

Figure 64:
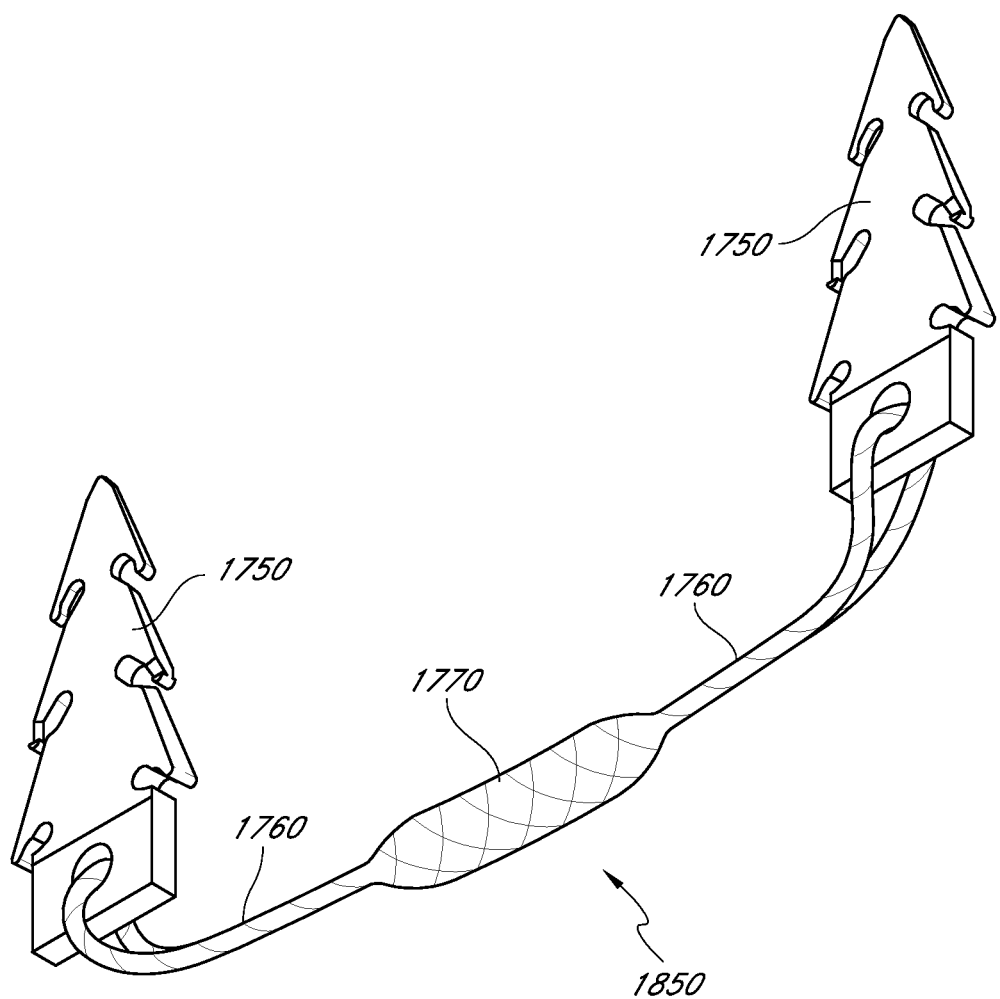
FIG. 64 depicts embodiments of a double anchor spring.

FIG. 64 depicts embodiments of a double anchor spring 1850. The non-resorbable double anchor spring 1850 is a spring 1770 with two anchors 1750 on opposite ends facing in opposing directions. Each anchor 1750 has a hole that is connected to a suture 1760, so as to allow for controllability of the anchor 1750. Once one anchor 1750 is in place, the second anchor 1750 may be placed to allow tissue to be drawn together. This can be used for supraareolar lift, as well as for other lifts.

In some embodiments, the anchor material and dimensions are dependent on the anchor used. The length of the connecting suture, depending on the location of implantation, may be between about 0.025" and about 6" long. The suture material may be resorbable or non-resorbable monofilament or multifilament polymer material. The spring may be implantable non-resorbable grade flexible polymer including but not limited to silicone.

Barbed Anchor Release Device

Figure 65A:
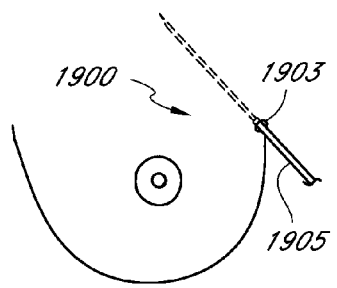
FIGS. 65A-65E depict embodiments of a barbed anchor release device.
Figure 65B:
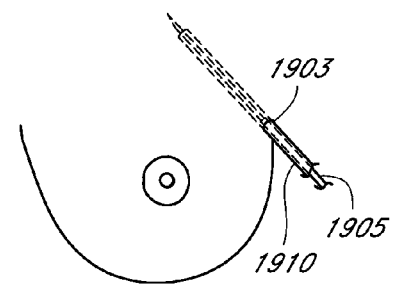
Figure 65C:
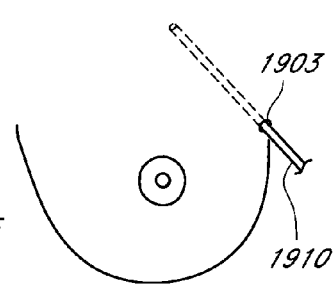
Figure 65D:
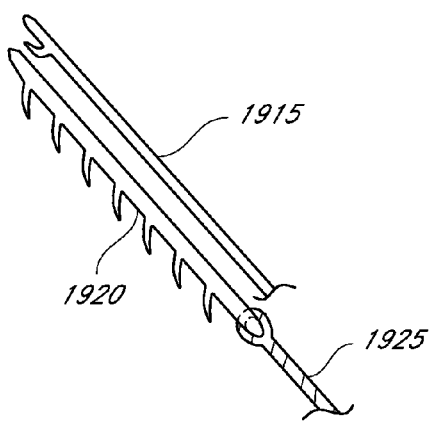
Figure 65E:
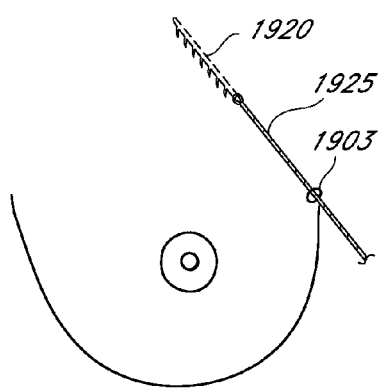

FIGS. 65A-65E depict embodiments of a barbed anchor release device 1900. Starting from a side breast exit point 1903, a needle 1905, or elongate member, is inserted up to an anchor point in the tissue, without puncturing skin at the anchor point. Once at the correct location, a sheath tube 1910 is slid over the needle 1905 up to the anchor point. The needle 1905 is removed, and, a hooked rod 1915 is used to advance a barbed plate 1920, connected or coupled to a suture 1925, through the sheath 1910. Once the barbed plate 1920 is at a desired anchor point, the sheath 1910 is withdrawn, and the hooked rod 1915 releases the barbed plate 1920, leaving suture 1925 with barbed plate 1920 at the anchor point. The same process can be repeated on the opposite side of the breast or tissue. In some embodiments, multiple device 1900 can be inserted through each exit point 1903. Following advancement of the barbed plate 1920 to the desired anchor point, a sling can be inserted into the tissue, and a knot can be tied with the suture 1925 on each side of the sling connecting to anchoring suture 1925. In FIG. 65A, a needle 1905 is inserted at sling exit hole 1903. A dilator with a sheath 1910 is inserted over the needle, as shown in FIG. 65B. In FIG. 65C, the needle 1905 and dilator are then removed, leaving the sheath 1910 and the anchor. A hooked rod 1915 slides through the sheath 1910, advancing the barbed plate 1920, attached to suture 1925, as shown in FIG. 65D. In FIG. 65E, the sheath 1910 is removed, and the barbed plate 1920 is left in place.

The delivery system is preferably wide enough to encompass the anchor, and in some embodiments, is between about 0.0625" and about 0.75". The length of the delivery system is preferably long enough to obtain desired delivery location, and in some embodiments, is equal to or greater than about 0.25"

Key Hole Anchor

Figure 66A:
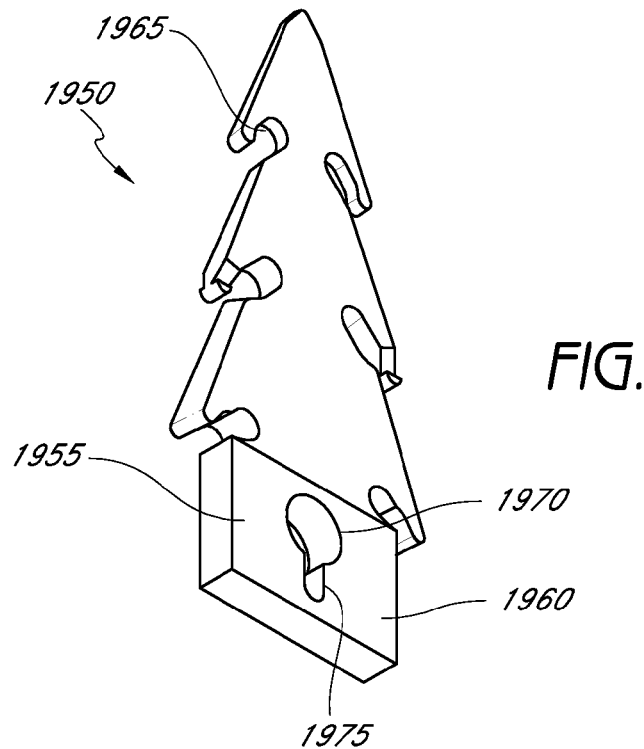
FIGS. 66A-66B depict embodiments of a key hole anchor.
Figure 66B:
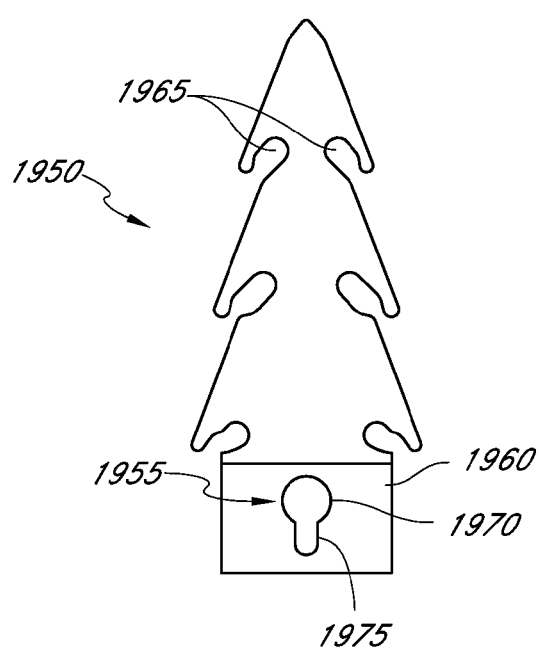

FIGS. 66A-66B depict embodiments of a key hole anchor 1950. The non-resorbable key-hole anchor 1950 is one with a key-hole shaped hole 1955 (with a key-shaped slot) at the bottom 1960 with small holes 1965 throughout for tissue ingrowth. Once the anchor 1950 has been placed properly within the tissue, the suture may be pulled through the larger portion 1970 of the hole 1955, and once sufficient lift is obtained by pulling on the suture, the suture may be pulled into the smaller portion 1975 of the key-hole 1955, locking it into place.

The material of the anchor 1950 is preferably made of an implantable grade resorbable or non-resorbable polymer and/or metal material, including but not limited to, Polypropylene, Polyester, Nylon, PEEK, Polyurethane, Polycarbonate, Titanium, and Stainless Steel. The overall length of the anchor 1950 is preferably between about 0.125" and about 2" with a thickness of between about 1/32" and about 0.1875". The device will preferably be between about 0.0625" and about 0.75" wide. The larger portion 1970 of the hole 1955 will be, in some embodiments, equal to the diameter of the suture used. The smaller portion 1975 of the hole will be the diameter of the suture at maximum compression.

"V" Anchor

Figure 67A:
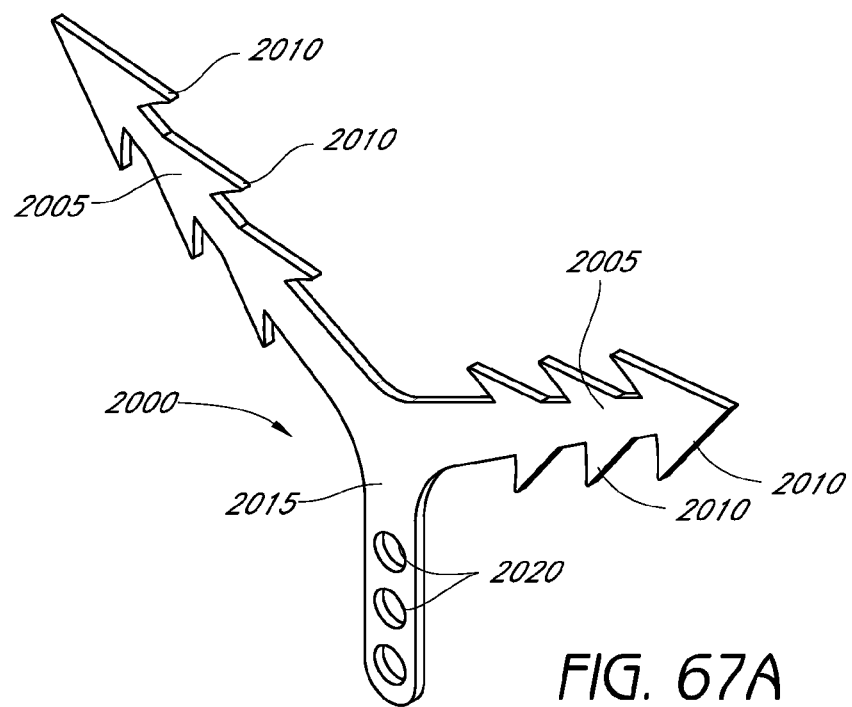
FIGS. 67A-67B depict embodiments of a "V"-shaped anchor.
Figure 67B:
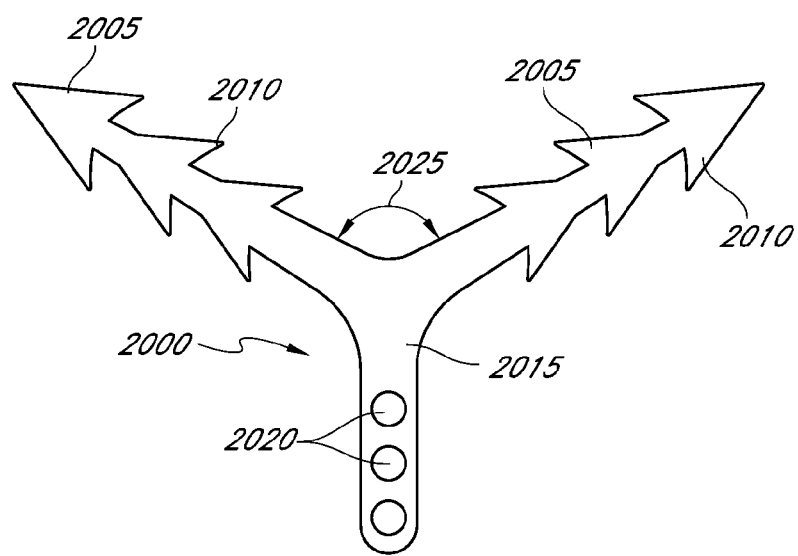

FIGS. 67A-67B depict embodiments of a "V"-shaped anchor 2000. The non-resorbable anchor 2000 is shaped like a "V" with small holes throughout for tissue ingrowth. The device will be deployed and the "V" shape will allow more area of tissue to be grabbed. Each leg 2005 of the "V" includes smaller barbs 2010 attached allowing for further securing. Each leg 2005 of the "V" will be able to be rotated inward, into a compressed configuration, in order to deliver to the anchoring site. The anchor 2000 preferably includes a bottom portion 2015 that includes one or more holes 2020 for securing to a suture.

The material of the anchor 2000 is preferably made of an implantable grade resorbable or non-resorbable polymer and/or metal material, including but not limited to, Polypropylene, Polyester, Nylon, PEEK, Polyurethane, Polycarbonate, Titanium, and Stainless Steel. The overall length of the anchor 2000 is preferably between about 0.125" and about 2" with a thickness between about 1/32" and about 0.1875". The device 2000 will be between about 0.0625" and about 0.75" wide. The hole will be equal to the diameter of the suture used. An angle 2025 of separation between the two legs 2005 can be between about 10° and about 160°, and in some embodiments, the angle between the two legs can be between about 10° and about 45°.

Tongue Depressor Anchor

Figure 68A:
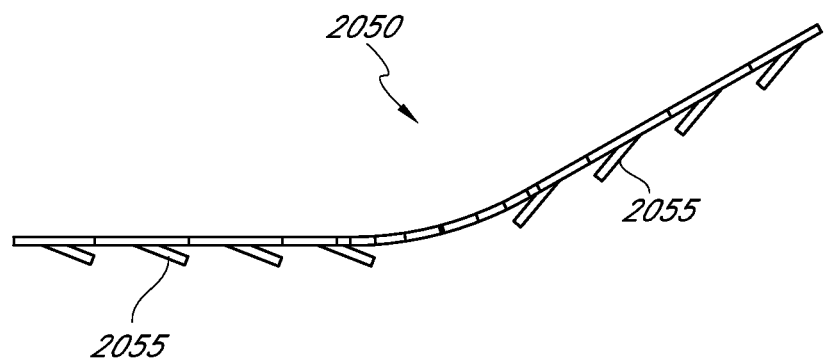
FIGS. 68A-68B depict embodiments of a tongue depressor anchor.
Figure 68B:
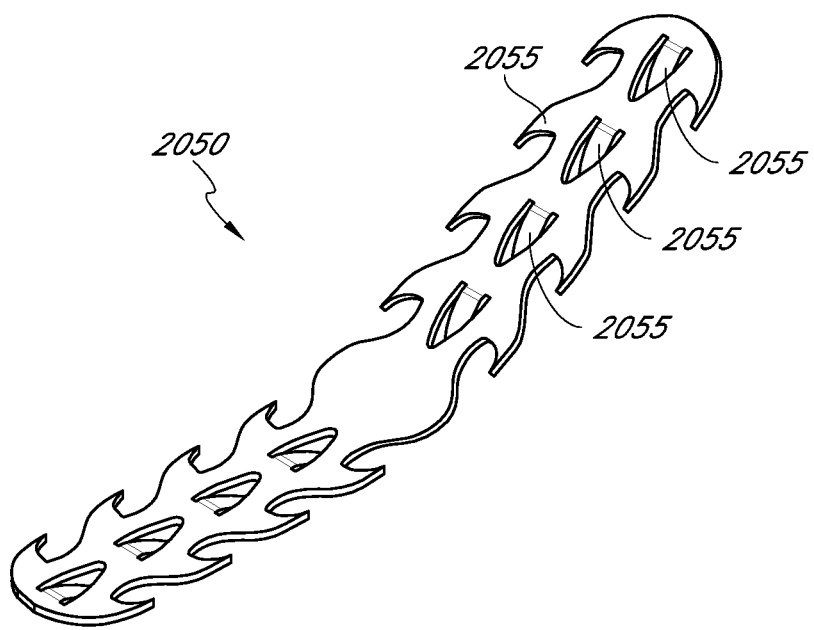

FIGS. 68A-68B depict embodiments of a tongue depressor anchor 2050. This non-resorbable anchor 2050 is one that is shaped like a tongue depressor, but is bent slightly with small holes throughout for tissue ingrowth. Each side preferably contains small barbs 2055. The device will preferably be deployed to a desired anchor location within the tissue, and once at the anchor location, the device may be moved back and forth slightly in order to secure into the tissue. This device 2050 may be used for supraareolar lift, as well as for other lifts.

The material of the port is preferably made of an implantable grade resorbable or non-resorbable polymer and/or metal material, including but not limited to, Polypropylene, Polyester, Nylon, PEEK, Polyurethane, Polycarbonate, Titanium, and Stainless Steel. The overall length of the anchor will preferably be between about 0.125" and about 4" with a thickness between about $1/32$" and about 0.1875". The device 2050 will preferably be between about 0.0625" and about 0.75" wide. The angle of bend in the device 2050 is preferably less than about 180°. The plate barbs 2055 will be bent, in some embodiments, in an direction substantially different (or opposite in some embodiments) than the bending of the device 2050.

Wall Anchor

Figure 69A:
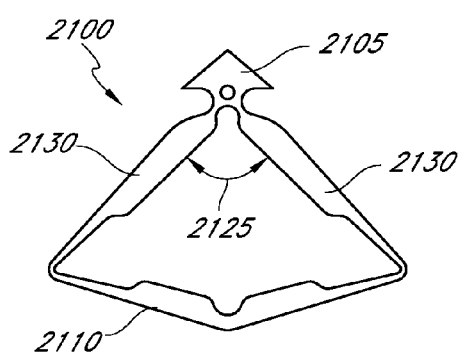
FIGS. 69A-69F depict embodiments of a wall anchor used in connection with the systems and methods described herein.
Figure 69B:
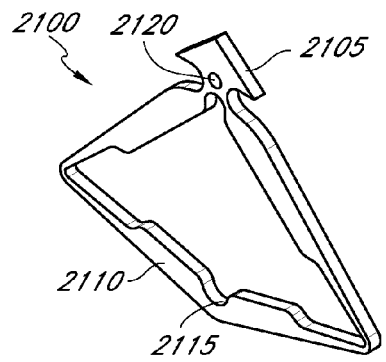
Figure 69C:
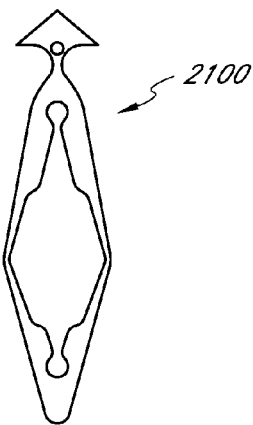
Figure 69D:
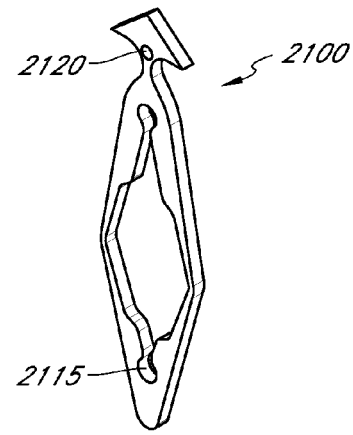
Figure 69E:
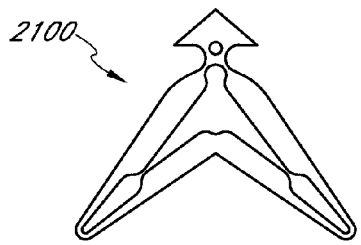
Figure 69F:
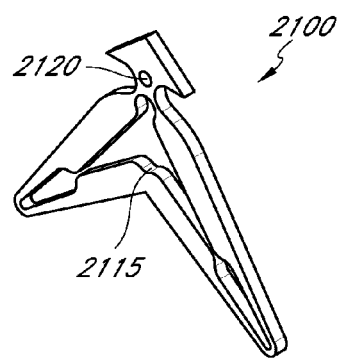

FIGS. 69A-69F depict embodiments of a wall anchor 2100 used in connection with the systems and methods described herein. This non-resorbable anchor 2100 is diamond shaped when relaxed or unrestrained (FIGS. 69A-69B), and has a pointed head 2105 for driving or advancing the anchor 2100 through tissue. At a bottom 2110 of the anchor 2100, there is preferably a hole 2115 for attaching a suture. The suture is then fed up to a hole 2120 at the top head 2105 and then back down through the bottom hole 2115. When directing the device into place, it straightens out to be long and thin (FIGS. 69C-69D). Once at a desired location, the suture coming from the bottom 2110 of the anchor 2100 can be pulled, pulling the top head 2105 and bottom 2110 of the device 2100 together, changing the shape to increase a cross-sectional dimension of the anchor 2100. The device 2100 will change from the long and thin shape to the diamond shape, and further pulling will allow the device 2100 to change from a vertical-oriented shape to a horizontal oriented shape, further engaging tissue substantially perpendicular to direction that the suture is pulled (FIGS. 69E-69F).

The material of the anchor 2100 is preferably made of an implantable grade resorbable or non-resorbable polymer and/or metal material, including but not limited to, Polypropylene, Polyester, Nylon, PEEK, Polyurethane, Polycarbonate, Titanium, and Stainless Steel. The device 2100 will preferably be between about 0.0625" and about 0.75" wide and long at deployment. An angle 2125 between two legs 2130 extending toward the bottom 2110 from the top head 2105 will preferably be less than about 90° in relation to each other at deployment. The thickness of the device 2100 will preferably be between about $1/32$" and about 0.1875".

Suture In-Weave Anchor

Figure 70:
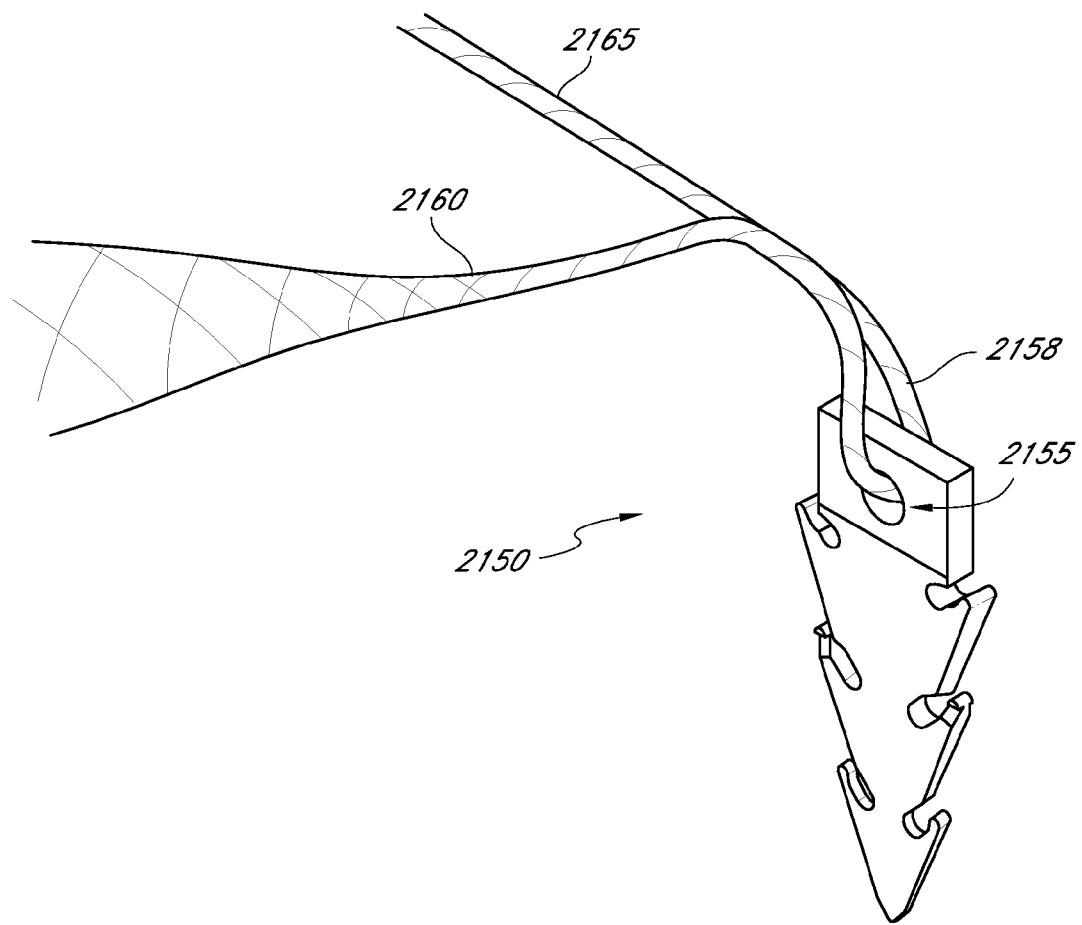
FIG. 70 depicts embodiments of a suture in-weave anchor.

FIG. 70 depicts embodiments of a suture in-weave anchor 2150. This non-resorbable anchor 2150 is one with a suture hole 2155 at the bottom. Passing through the suture hole 2155 is preferably a suture loop 2158 of braid that is about 0.25". One suture tail 2160 is attached to the sling, and the other suture tail 2165 is used for securing. The anchor 2150 may be directed into a desired location, and once at the locations, the securing suture 2165 end is pulled until desired lift is obtained. The suture may then be secured.

The material of the anchor 2150 is preferably made of an implantable grade resorbable or non-resorbable polymer and/or metal material, including but not limited to, Polypropylene, Polyester, Nylon, PEEK, Polyurethane, Polycarbonate, Titanium, and Stainless Steel. The overall length of the anchor will preferably be between about 0.125" and about 2" with a thickness between about $1/32$" and about 0.1875". The device 2150 will be between about 0.0625" and about 0.75" wide. The diameter of the suture hole approximates, in some embodiments, the diameter of the suture used. The length of the suture extension will preferably be between about 0.25" and about 6", depending on the location of implantation and sufficient to loop within itself in a portion greater or equal to the diameter of the suture itself. The suture material may be resorbable or non-resorbable multifilament polymer material.

Hybrid Anchor

Figure 71:
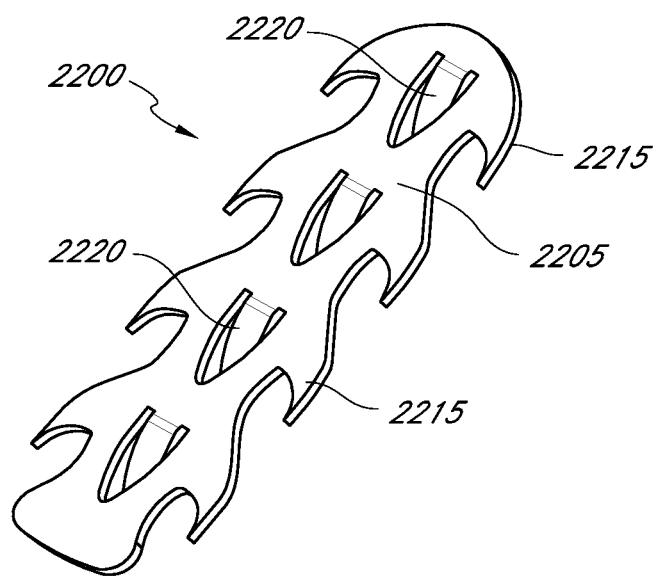
FIG. 71 depicts embodiments of a hybrid anchor.

FIG. 71 depicts embodiments of a hybrid anchor 2200. The non-resorbable hybrid anchor 2200 is a plate 2205 with barbs, (for example, for adipose and fascia securing) with small holes throughout the anchor 2200 for tissue ingrowth. In some embodiments, adipose barbs 2215 are directed outwardly in a plane that is substantially parallel to the plate 2205, and in certain embodiments, fascia barbs 2220 extend in a plane that is transverse to the plane of the plate. Some embodiments include both barbs 2220, 2215, allowing for securing in both tissues.

The material of the anchor 2200 is preferably made of an implantable grade resorbable or non-resorbable polymer and/or metal material, including but not limited to, Polypropylene, Polyester, Nylon, PEEK, Polyurethane, Polycarbonate, Titanium, and Stainless Steel. The overall length of the anchor 2200 will, in some embodiments, be between about 0.125" and about 2" with a thickness between about $1/32$" and about 0.1875". The device will preferably be between about 0.0625" and about 0.75" wide.

Trap Anchor

Figure 72A:
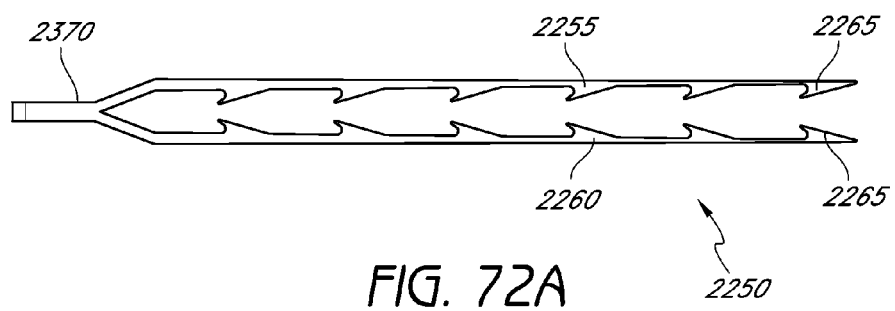
FIGS. 72A-72B depict embodiments of a trap anchor.
Figure 72B:
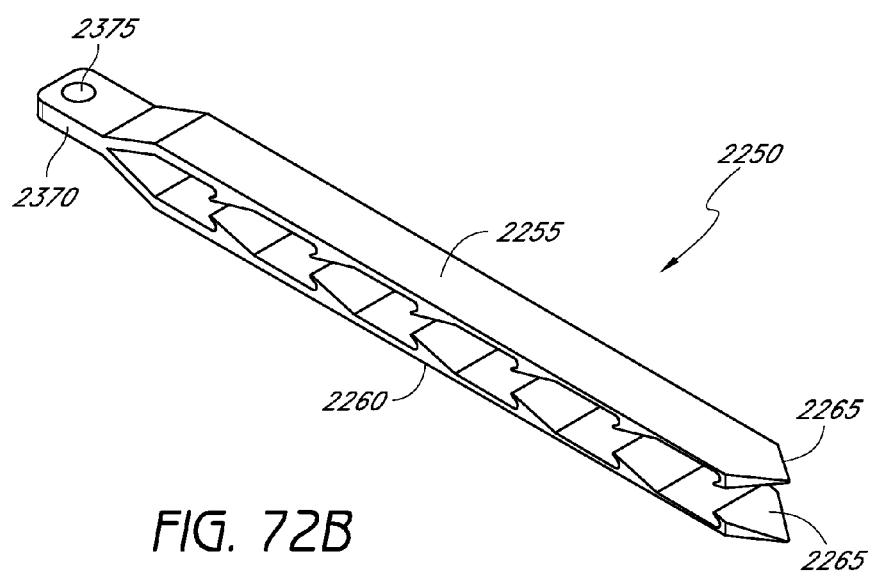

FIGS. 72A-72B depict embodiments of a trap anchor 2250. The non-resorbable trap anchor 2250 is one with two plates, a first plate 2255 on top of a second plate 2260 in a substantially parallel orientation, with small holes throughout for tissue ingrowth. Each plate 2255, 2260 with have a pointed head 2265 for separating tissue while the plate is being advanced through tissue, and each plate is attached at a base 2370, that has a hole 2375 for securing to a suture. As the parallel plates are driven into the tissue, the tissue becomes trapped within the two plates by small divots, which allow the tissue to enter but not exit.

The material of the anchor 2250 is preferably made of an implantable grade resorbable or non-resorbable polymer and/or metal material, including but not limited to, Polypropylene, Polyester, Nylon, PEEK, Polyurethane, Polycarbonate, Titanium, and Stainless Steel. The overall length of the anchor will preferably be between about 0.125" and about 2" with a thickness between about $1/32$" and about 0.1875". The device will be between about 0.0625" and about 0.75" wide. The jaw width is preferably between about 0.15" and about 0.5" depending on the location of insertion.

Bent Barbed Anchor

Figure 73A:
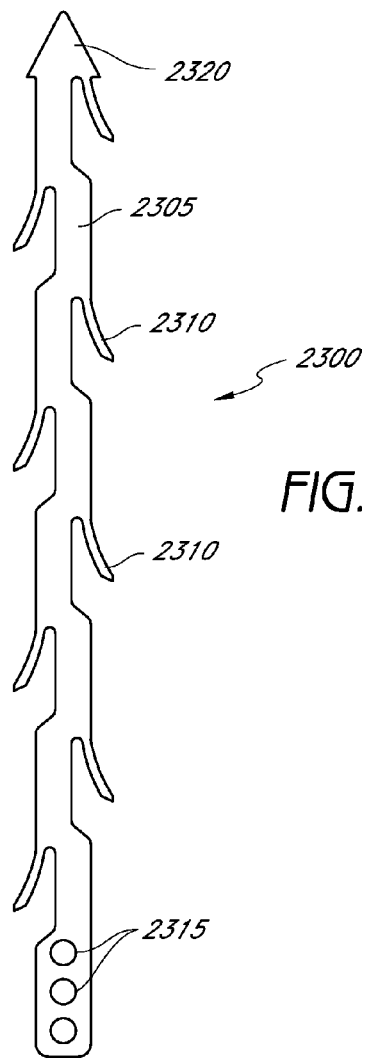
FIGS. 73A-73B depict embodiments of a bent barbed anchor.
Figure 73B:
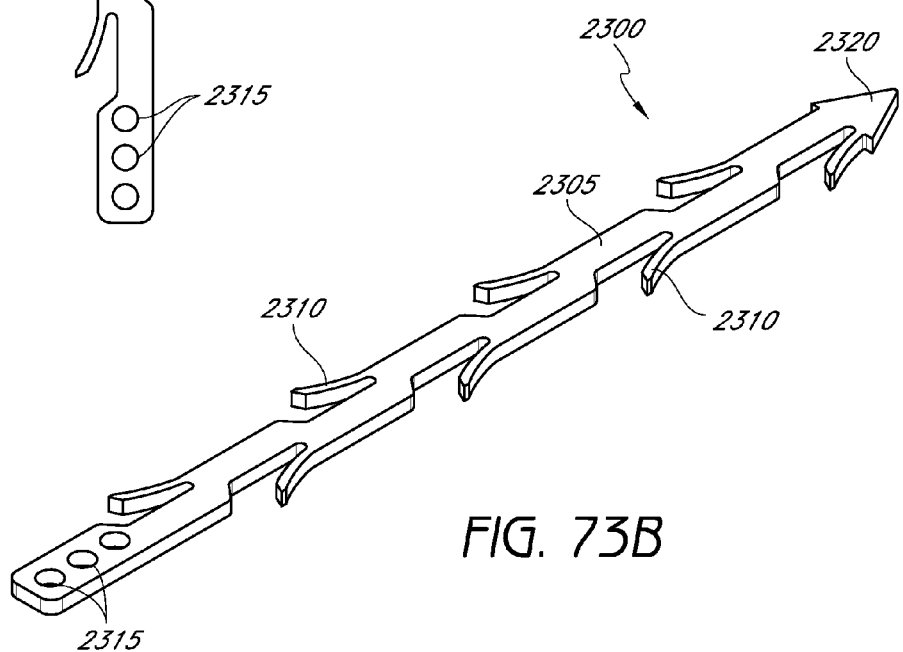
Figure 78A:
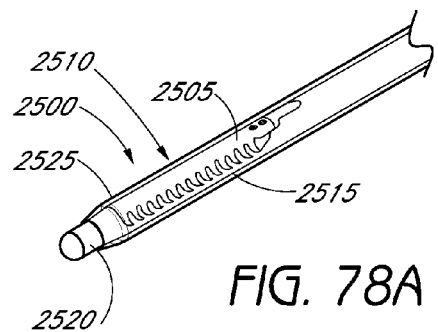
FIGS. 78A-78E depict embodiments of a staple anchor deployment device.
Figure 78B:
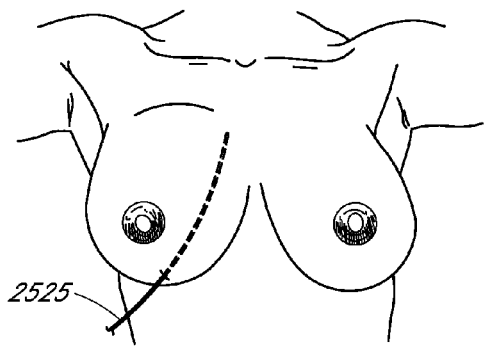
Figure 78C:
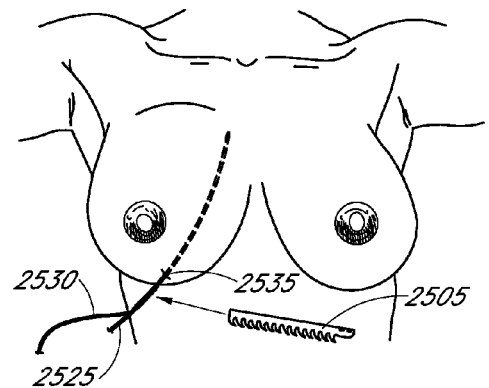
Figure 78D:
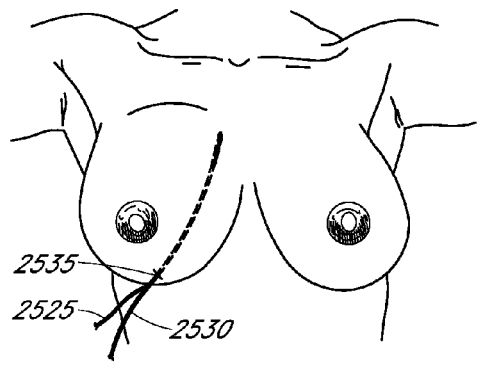
Figure 78E:
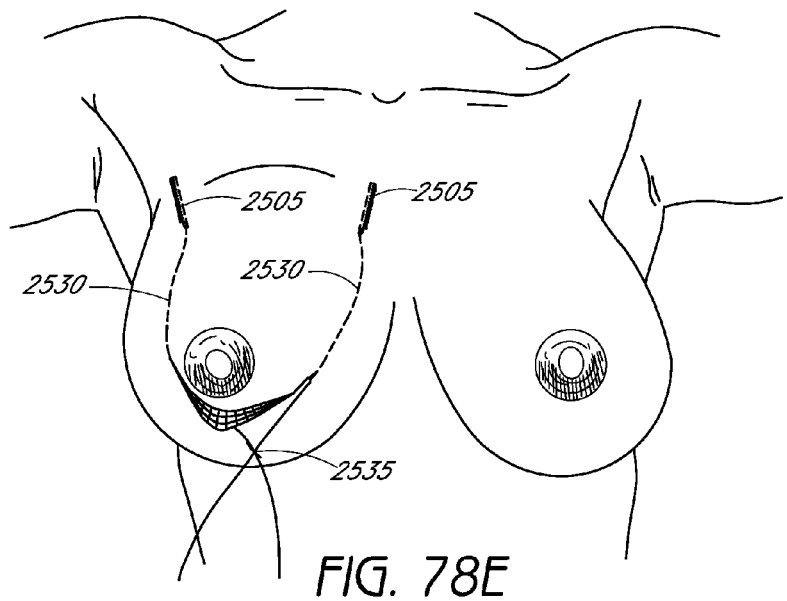

FIGS. 73A-73B depict embodiments of a bent barbed anchor 2300. The non-resorbable anchor is derived from a plate 2305, which has a series of barbs 2310 cut out either side with small holes throughout for tissue ingrowth. Each barb 2310 is curled outward in some embodiments. The anchor barbs 2310 may be pushed back toward the plate 2305 while the anchor 2300 is being advanced through tissue to a desired location. Once at the desired location, the barbs 2310 are released allowing them to secure into the tissue. In some embodiments, this design may be advantageous for adipose tissue securing. Also, an alternative version would be every other prong bent down, out of plane with the plate 2305, as shown in FIG. 73B, in order to obtain resistance in both the fat and fascia planes. In some embodiments, the anchor 2300 includes one or more holes 2315 at one end for securing to one or more sutures. In some embodiments, the plate 2305 includes a pointed head 2320 for separating tissue when the anchor 2300 is advanced through tissue.

The material of the anchor 2300 is preferably made of an implantable grade resorbable or non-resorbable polymer and/or metal material, including but not limited to, Polypropylene, Polyester, Nylon, PEEK, Polyurethane, Polycarbonate, Titanium, and Stainless Steel. The overall length of the anchor 2300 will be between about 0.125" and about 2" with a thickness of between about 1/32" and about 0.1875". The device will preferably be between about 0.0625" and about 0.75" wide. The diameter of the suture hole 2315 approximates the diameter of the suture used.

Barbed Plate

FIGS. 74A-74B and 75A-75B depict embodiments of a barbed plate anchor 2350. The non-resorbable barbed plate anchor 2350 consists of a plate 2355 with barbs 2360 stamped out of it with small holes throughout for tissue ingrowth. The barbs 2360 are then bent out of plane with the plate 2355 in order to grab fascia once installed in the tissue. This bending motion also allows the barbs 2360 to be substantially flat during delivery of the anchor. Embodiments depicted in FIGS. 74A-74B contain one or more holes 2365 at the bottom to create a friction fit with looped suture. Embodiments depicted in FIGS. 75A-75B contain reverse directing barbs 2370 in order to prevent movement upward. Once the anchor 2350 is at the desired location, it may be shifted up and down slightly to properly secure the fascia in both directions.

The material of the anchor is preferably made of an implantable grade resorbable or non-resorbable polymer and/or metal material, including but not limited to, Polypropylene, Polyester, Nylon, PEEK, Polyurethane, Polycarbonate, Titanium, and Stainless Steel. The overall length of the anchor will preferably be between about 0.125" and about 2" with a thickness between about 1/32" and about 0.1875". The device will preferably be between about 0.0625" and about 0.75" wide. The diameter of the suture hole approximates, in some embodiments, the diameter of the suture used.

Staple Anchor

FIGS. 76A-76B and 77A-77B depict embodiments of a staple anchor 2400. The non-resorbable anchor 2400 is derived from a partial (e.g., half) tube 2405 with a series of teeth 2410 cut out on the sides allowing for securing into the fascia. Due to the curvature of the partial tube 2405, the direction of the teeth 2410 will facilitate penetration into the fascia. The back end of the anchor will preferably contain a hole 2415 for suture securing and device deployment. FIGS. 76A-76B contain two holes at back end to allow the suture to loop secure anchor and feed into the center of the device. FIGS. 77A-77B show a series of holes 2420 to optimize ingrowth. In some embodiments, there is a divot created along the top of the anchor 2400 for the suture to lay flush on top. This can aid in condensing the delivery sheath diameter. In addition, the teeth 2410 may be bent outward in order to grab the fascia more easily. For some of these embodiments, every other tooth 2410 would be bent out slightly and twisted out to create a paddle effect against the tissue.

The material of the anchor is preferably made of an implantable grade resorbable or non-resorbable polymer and/or metal material, including but not limited to, Polypropylene, Polyester, Nylon, PEEK, Polyurethane, Polycarbonate, Titanium, and Stainless Steel. The overall length of the anchor will preferably be between about 0.125" and about 2" with a thickness between about 1/32" and about 0.1875". The device will preferably be between about 0.0625" and about 0.75" wide. The arc of the anchor used from the tube will preferably be between about 5° and about 320°. The diameter of the suture hole approximates, in some embodiments, the diameter of the suture used.

Staple Anchor Deployment Device

FIGS. 78A-78E depict embodiments of a staple anchor deployment device 2500. The anchor 2505 can be cut from a half tube 2510. The other half 2515 of the tube can be used to in deployment to secure the anchor 2505 while be directed to an anchor site. The tube can allow for a breast needle 2520 to fit inside. The needle 2520 can then create a path to the anchor site. There is preferably a tapered sheath 2525 over the device to cover the anchor 2505 until at desired location. Once at the desired location, the outer sheath 2525 will be pulled slightly, allowing the anchor 2505 to be exposed enough to grab into the tissue. The outer sheath 2525 and needle 2520 may then be removed leaving the anchoring device and remaining tube. The suture 2530 may then be pulled at the exit hole 2535 to disconnect the lower portion of the tube from the anchor itself. Once the anchor 2505 is disconnected from the tube, the tube may be removed. The anchor is then secured by pulling slightly to secure into the fascia.

The delivery system is preferably wide enough, in some embodiments, to encompass the anchor, and, in some instances, is between about 0.0625" and about 0.75". The length of the delivery system is preferably enough to obtain desired delivery location, which, in some embodiments, is equal to or greater than about 0.25".

Supraareolar Device

Figure 79:
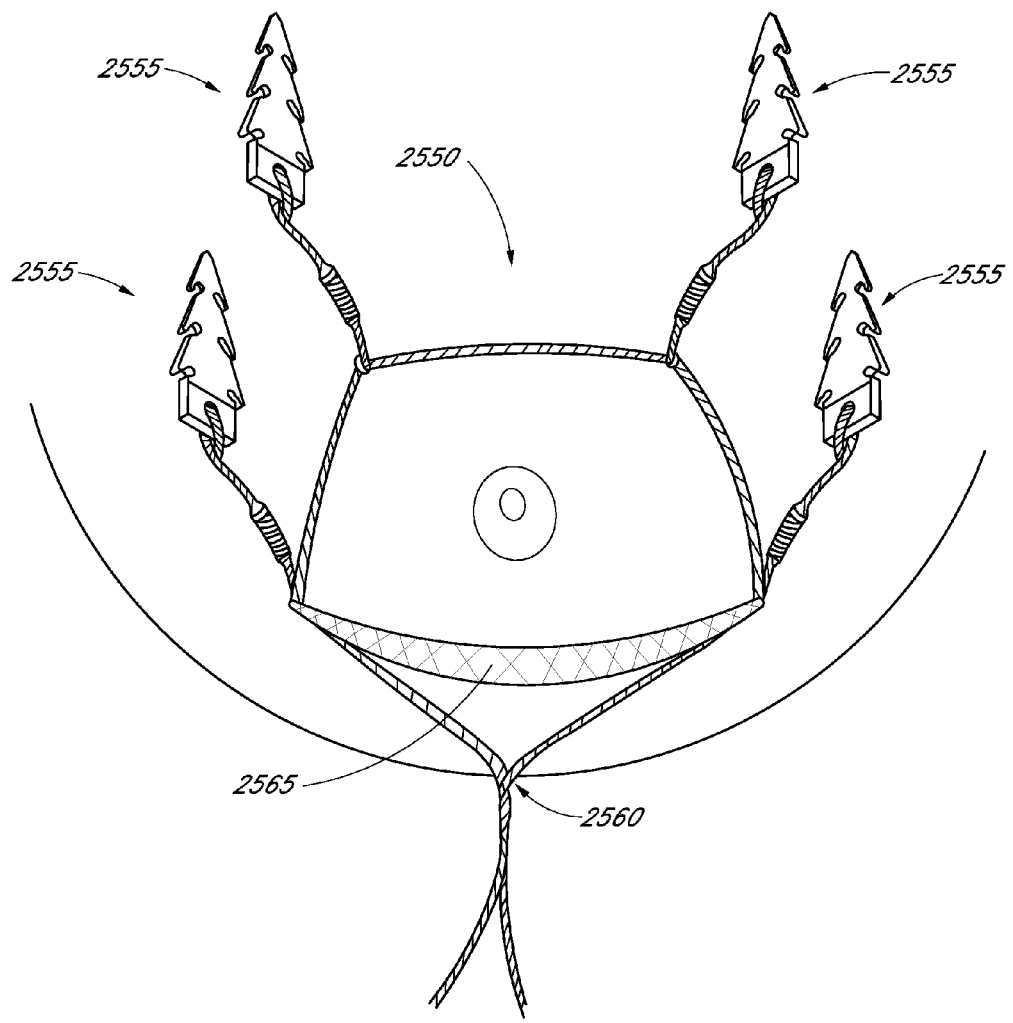
FIG. 79 depicts embodiments of a supraareolar device.

FIG. 79 depicts embodiments of a supraareolar device 2550. The device 2550 can include four anchor springs 2555. The breast needle will preferably be driven up into the breast from the bottom exit hole 2560. The needle will be directed up around and supraareolar. Then the needle will come around the other side of the breast, exiting out the entrance hole as if to create a circular path around the nipple. Each of the four anchors 2550 will be deployed through the circular path. In some embodiments, the top two anchors 2550 will carry supraareolar support, and in certain embodiments, the second two will support the sling 2565.

The length of the device 2550 is greater, in some embodiments, than the circumference of the areola and, in certain embodiments, is less than that of the breast.

Sling Positioning Procedure

Figure 80:
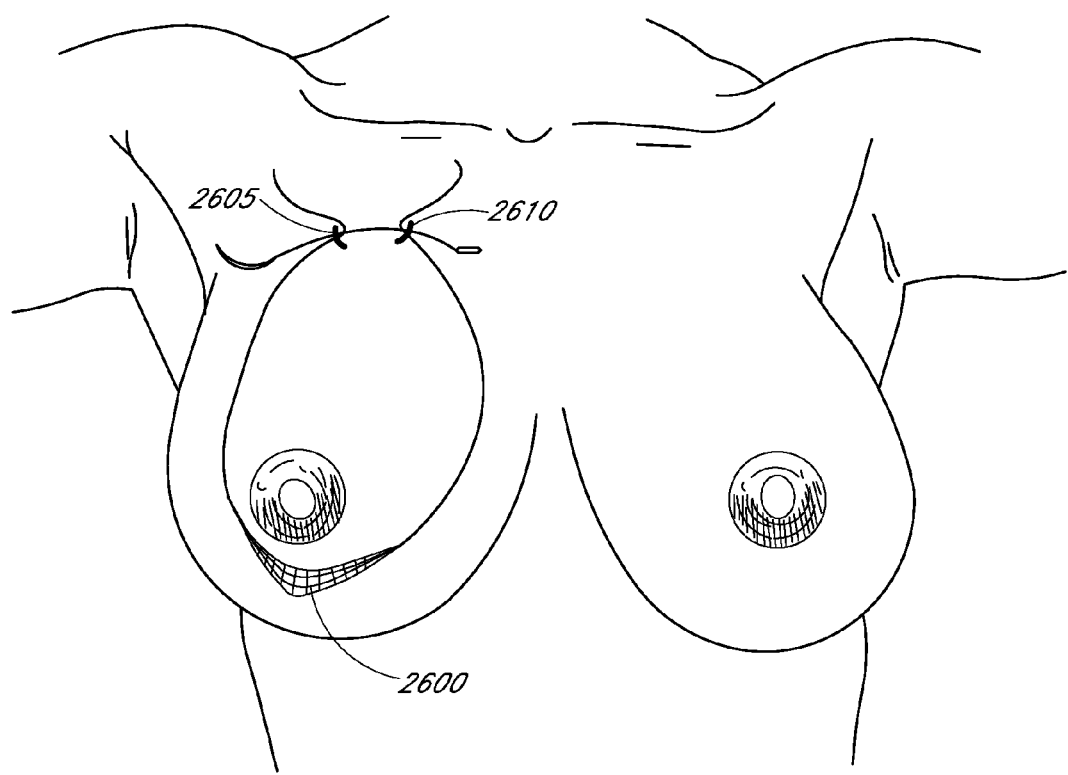
FIG. 80 depicts embodiments of a sling positioning procedure.

FIG. 80 depicts embodiments of a sling positioning procedure. This procedure will allow the sling 2600 to be repositioned without having to run a suture through the anchor loop. In some embodiments, control of the lateral part of the breast tissue is obtained through a lateral anchor hole 2605 and control of the medial part of the breast tissue through a medial anchor hole 2610. For modification, the 3-exit hole procedure will have the addition of a longer suture loop to the anchor needle. Instead of pulling the suture through the anchor, the anchor will leave an access suture that will run the anchor loop after positioning is deemed suitable.

Belt Buckle

Figure 81:
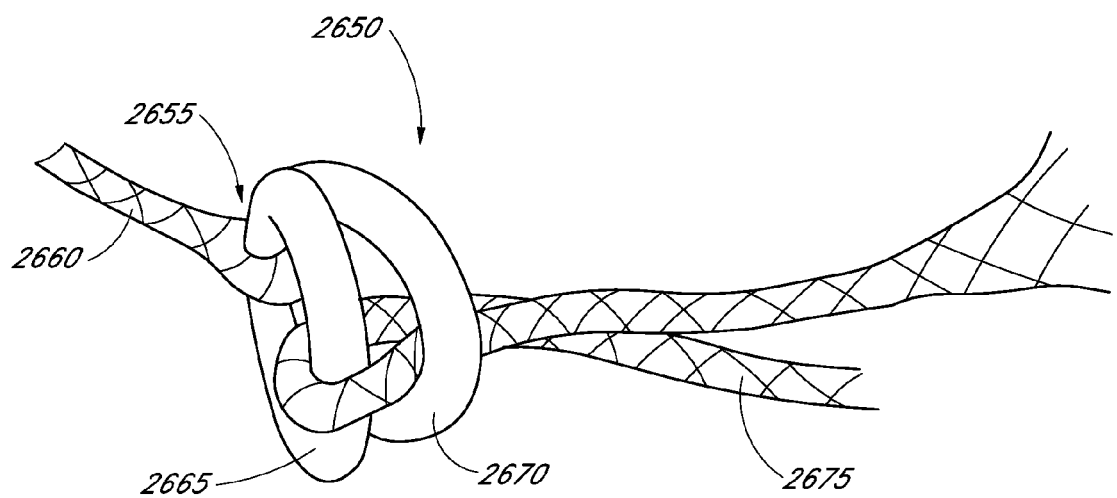
FIG. 81 depicts embodiments of a belt buckle securing device.

FIG. 81 depicts embodiments of a belt buckle securing device 2650. The belt buckle suture securing device 2650 is one that will allow movement of the implant within the breast tissue. One end 2655 of a suture 2660 is connected to two loops 2665, 2670. The end of a second suture 2675 is then wound though the two loops 2665, 2670. Once the device is in the appropriate location, the second suture 2675 can be pulled tight to obtain a friction fit connection. This can be done remotely from an exit point.

The material of the ring, or loop, is preferably made of an implantable grade resorbable or non-resorbable polymer and/or metal material, including but not limited to, Polypropylene, Polyester, Nylon, PEEK, Polyurethane, Polycarbonate, Titanium, and Stainless Steel. The ring or loop may have an ID of about 0.015" up to about 0.25" and a diameter from about 1/32" to about 0.0625".

Variable Durometer Spring

Incorporating a spring of variable durometers can allow a more secure range of movement. The lower durometers spring would allow for every day movement. Incorporating the higher durometers would ensure that there would be a buffer if high impact occurs. This would give relief to the anchor point and would allow that the suture not create a shock load. The durometers variations could include parallel variations or step variation, having one durometers next to another rather than along side.

The materials can include an implantable grade resorbable or non-resorbable polymer and/or metal material, including but not limited to, Polypropylene, Polyester, Nylon, PEEK, Polyurethane, Polycarbonate, Titanium, and Stainless Steel. In some embodiments, the two components may be any combination of the above said materials or the same material. In some embodiments, the durometers of the two components are dissimilar. The varying durometers may run, in some embodiments, concentric to each other, or on top of each other.

Recapturing Device

The recapturing device would allow the anchor to be relocated during a procedure if the anchor position was too superior. The recapturing device would be one that can be fed up through the exit point along the bottom of the anchor or where the anchor meets fascia. By being planar, parallel, and larger in diameter than the anchor, the component is able to be slid under the anchor and lifted to release the anchor from the fascia for repositioning.

The material of the recapturing device is preferably made of an implantable grade resorbable or non-resorbable polymer and/or metal material, including but not limited to, Polypropylene, Polyester, Nylon, PEEK, Polyurethane, Polycarbonate, Titanium, and Stainless Steel. The width and length of the device should be, at minimum, about 0.005" greater than the width and length of the anchor extracted, and greater than or equal to about 0.75", depending on the area of extraction and the size of implant. The thickness of the device should be, in some embodiments, between about 0.015" and about 0.25".

Angled Anchor Deployment

Figure 82:
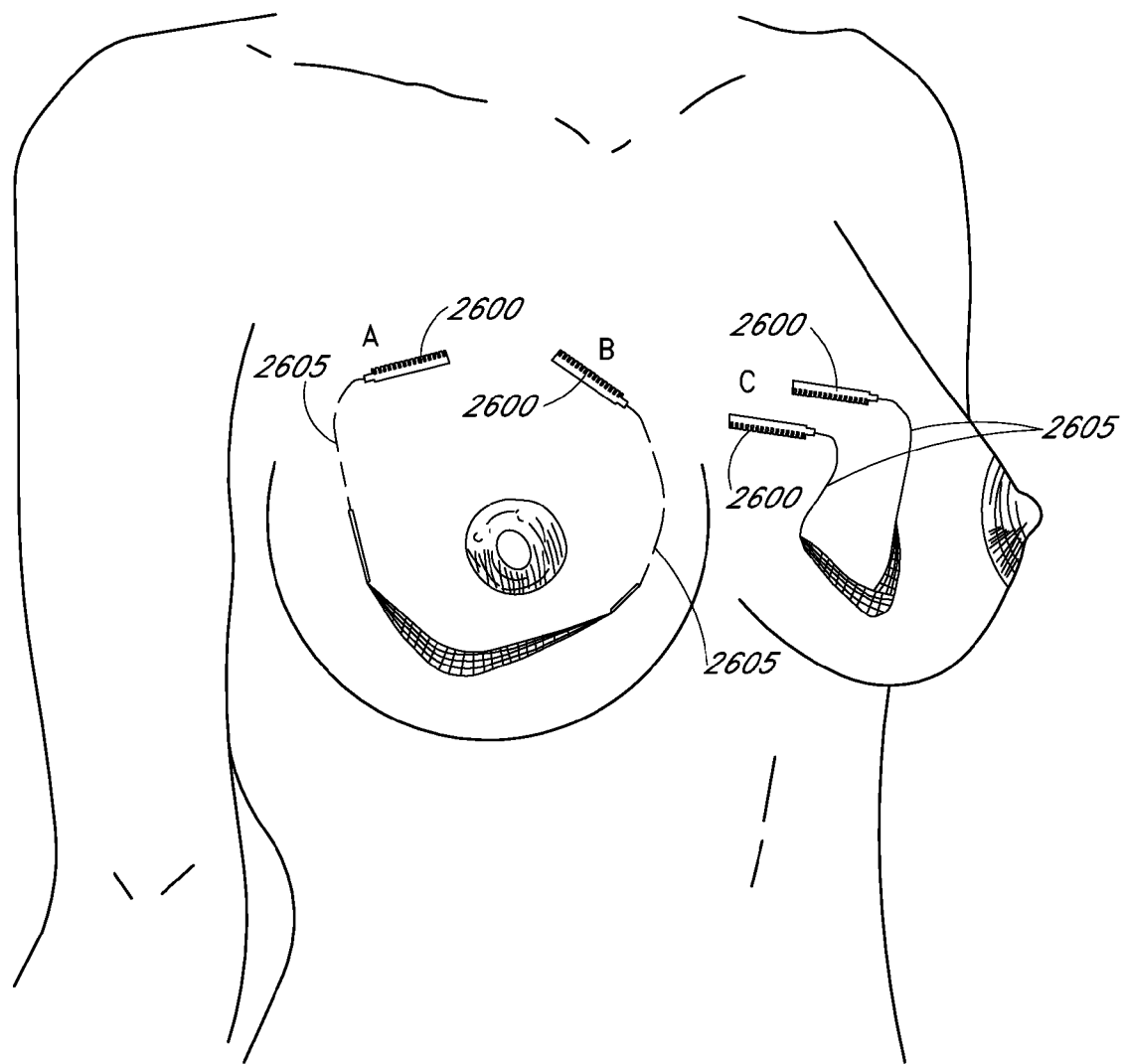
FIG. 82 depicts embodiments of an angled anchor deployment.
Figure 83A:
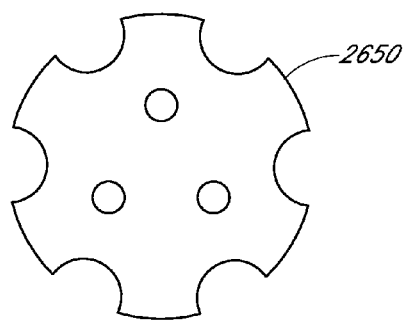
FIGS. 83A-83B depict embodiments of profiled springs.
Figure 83B:
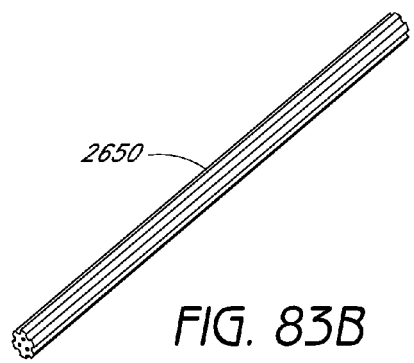
Figure 84A:
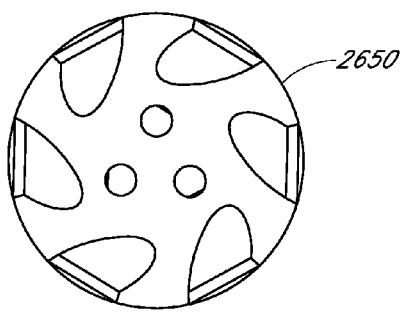
FIGS. 84A-84B depict embodiments of profiled springs.
Figure 84B:
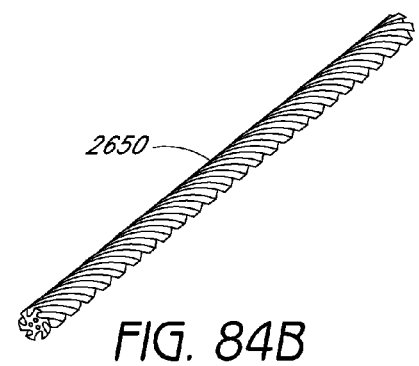
Figure 85A:
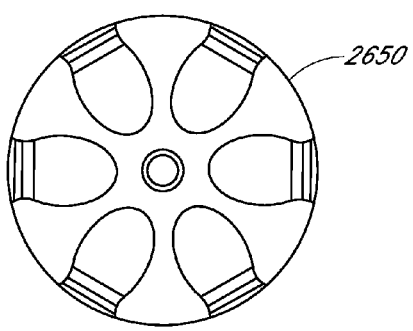
FIGS. 85A-85B depict embodiments of profiled springs.
Figure 85B:
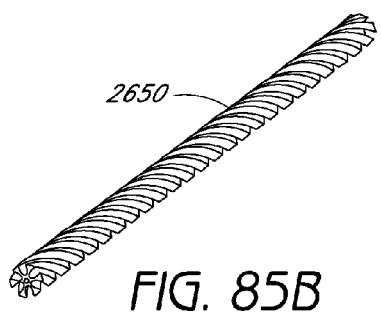

FIG. 82 depicts embodiments of an angled anchor deployment. While deploying the anchor within the fascia, orientation of the anchor 2600 becomes critical. The anchor 2600 may be deployed superiorly parallel to the fascia plane. This will allow the anchor 2600 to grasp the fascia or, depending on the anchor type, sit within the adipose flush to the fascia. It is also possible to orient the anchor 2600 so that it is not linear with the suture 2605, but rather angled to the suture 2605. While deploying the anchor 2600 into the anchor site, the anchor 2600 may then be turned approximately 90° or parallel or perpendicular to the muscle fibers depending on the anchor design. Depicted in FIG. 82, and designated as A is a perpendicular deployment of anchors. Designated as B is a parallel deployment of anchors, and designated as C is a posterior directed deployment of anchors.

In some embodiments, deployment of the anchors are dependent, in some embodiments, on the anchor used, and in certain embodiments, the angle will be any angle perpendicular and parallel to the angle of the chest wall up and down, or left to right.

Profiled Spring

FIGS. 83A-83B, 84A-84B, and 85A-85B depict embodiments of profiled springs. The profiled spring 2650 is one that is extruded and inserted into the braid for the suspension of the device. By profiling the spring it allows for less outer surface area in which the component may contract more allowing for greater extension. There are straight and helical extrusions allowing for varying deformation.

In some embodiments, the diameter (or cross-sectional dimension) of the spring will be between about 0.015" and about 0.325". The length of the spring will preferably be between about 1/16" and about 6". The helical component will preferably have between about 1 and about 60 revolutions per inch.

Progressive Knot Pusher

The progressive knot pusher would allow the device to be installed and properly fixed by deploying a series of previously tied knots at a specified distance within the breast. This would allow for securing of the sling on either side of the breast at the anchor points. This would ensure that the sling does not rotate, in addition, to the suture not cutting through the tissue. The knot pusher would be a polymer tube with interval slits for the knots. Once the device is as the desired location, the suture that is fed within the tube may be pulled, releasing the series of knots to secure the device.

The material of the pusher is preferably made of an implantable grade resorbable or non-resorbable polymer and/or metal material, including but not limited to, Polypropylene, Polyester, Nylon, PEEK, Polyurethane, Polycarbonate, Titanium, and Stainless Steel. The length of the pusher will preferably be sufficient to reach the final knot location from the outside of the body.

Interrupted Lumen

FIGS. 86A-86C depict embodiments of an interrupted lumen 2700. The interrupted lumen 2700 would allow for an anchor delivery system to run alongside the breast needle. A polymer lumen 2705 would be manufactured to slide over the breast needle 2710 and would contain the anchor at the tip 2715. Approximately halfway down the needle 2710 the lumen 2705 would be interrupted and the breast needle would exit, however, the lumen 2705 would continue alongside the breast needle 2710. At this point the anchor holding device 2720 would run down the middle of the lumen 2705. The top portion 2725 of the anchor holding device 2720 would sit on the outside of the lumen 2705 that is over the breast needle 2710 at the tip covering the anchor. The breast needle 2710 and device 2720 would be inserted into a desired location. Once there, the anchor covering device 2720 could be slid down, advancing or revealing the anchor to the tissue. Then the breast needle 2710 may be removed leaving the anchor in position.

The material of the sheath, slide, and other components is preferably made from a combination of an implantable grade resorbable or non-resorbable polymer and/or metal material, including but not limited to, Polypropylene, Polyester, Nylon, PEEK, Polyurethane, Polycarbonate, Titanium, and Stainless Steel. The length of the sheath should, in some embodiments, be sufficient to allow the tip to reach the desired anchor location but still have the interrupted portion of the lumen outside the body. This should be between about 0.5" and about 30". The Sheath length should preferably be long enough to cover at least a portion of, and preferably, the entirety of, the anchor, but preferably not to exceed it by more than about 2". The ID of the sheath should preferably be greater than the outer diameter of the needle used but not more than about 0.125" larger. The length of the lumen connection should be between about 0.125" and about 5".

Attached Lumen

FIGS. 87A-87C depict embodiments of an attached lumen delivery system 2750. The attached lumen delivery system 2750 is one that has added rigidity due to the addition of polymer loops 2755 at the distal end of the device. The loops 2755 are wrapped around the lumen and the breast needle to keep them together during deployment. The lumen contains the anchor at the tip. The anchor cover is controlled from the exit point. The breast needle is inserted into the breast up to the desired anchor position. Once at the right location, the anchor cover is pulled off using the controller that exits out of the breast. The breast needle is then pulled out, leaving the anchor in place. The lumen is attached to the breast needle using a series of loops 27555.

The material of the sheath, slide, and other components is preferably made from a combination of an implantable grade resorbable or non-resorbable polymer and/or metal material, including but not limited to, Polypropylene, Polyester, Nylon, PEEK, Polyurethane, Polycarbonate, Titanium, and Stainless Steel. The length of the sheath should preferably be sufficient to allow the tip to reach the desired anchor location but still have the interrupted portion of the lumen outside the body. This should preferably be between about 0.5" and about 30".

The Sheath length should preferably be long enough to cover then entirety of the anchor but, in some embodiments, not to exceed it more than about 2". The ID of the sheath should be greater than the OD of the needle used, but, in some embodiments, not more than about 0.125" larger. The length of the lumen connection should be between about 0.125" and about 5". The diameter of the loops should preferably be approximate to the diameter of the needle used. The length of the loop should preferably be between about 0.015" and about 1", depending on the scale of device used.

Tubular Spring

Figure 88:
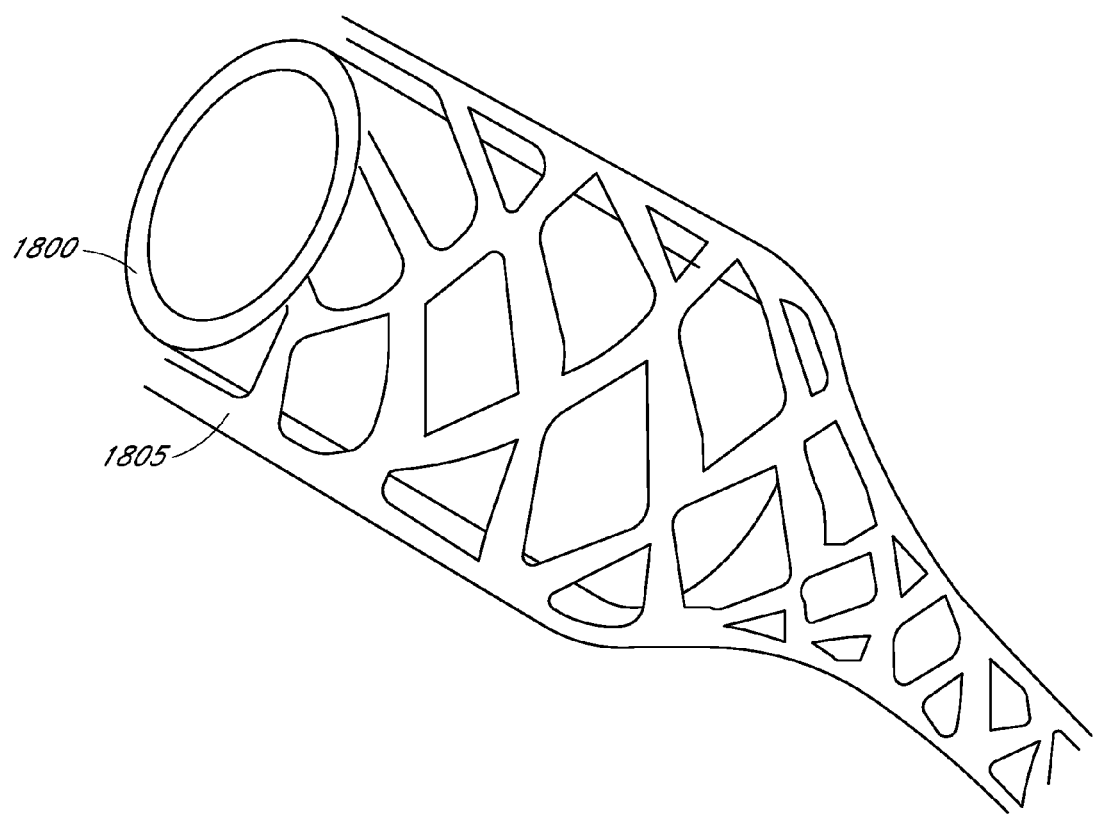
FIG. 88 depicts embodiments of a tubular spring.

FIG. 88 depicts embodiments of a tubular spring 2800. Rather than having a profiled spring, the tubular spring 2800 would be inserted into the suture 2805. The spring 2800 would be a tube that is hollow inside. Therefore when the spring 2800 is extended it will collapse into the center.

In some embodiments, the material of the suture components is preferably made from an implantable grade monofilament or multifilament resorbable or non-resorbable polymer and/or metal material, including but not limited to, Polypropylene, Polyester, Nylon, PEEK, Polyurethane, Polycarbonate, Titanium, and Stainless Steel. The spring component is preferably made from an implantable non-resorbable polymer including but not limited to a flexible silicone.

The outer diameter of the spring should preferably be able to fit within the spring center when fully expanded, but larger than the inner diameter of the suture when relaxed. The OD of the spring may be between about 0.002" and about 1" and the wall thickness between about 0.0001" and about 0.075". The length of the spring should be between about 0.01" and about 6".

Slide Sheath Deployment System

Figure 89:
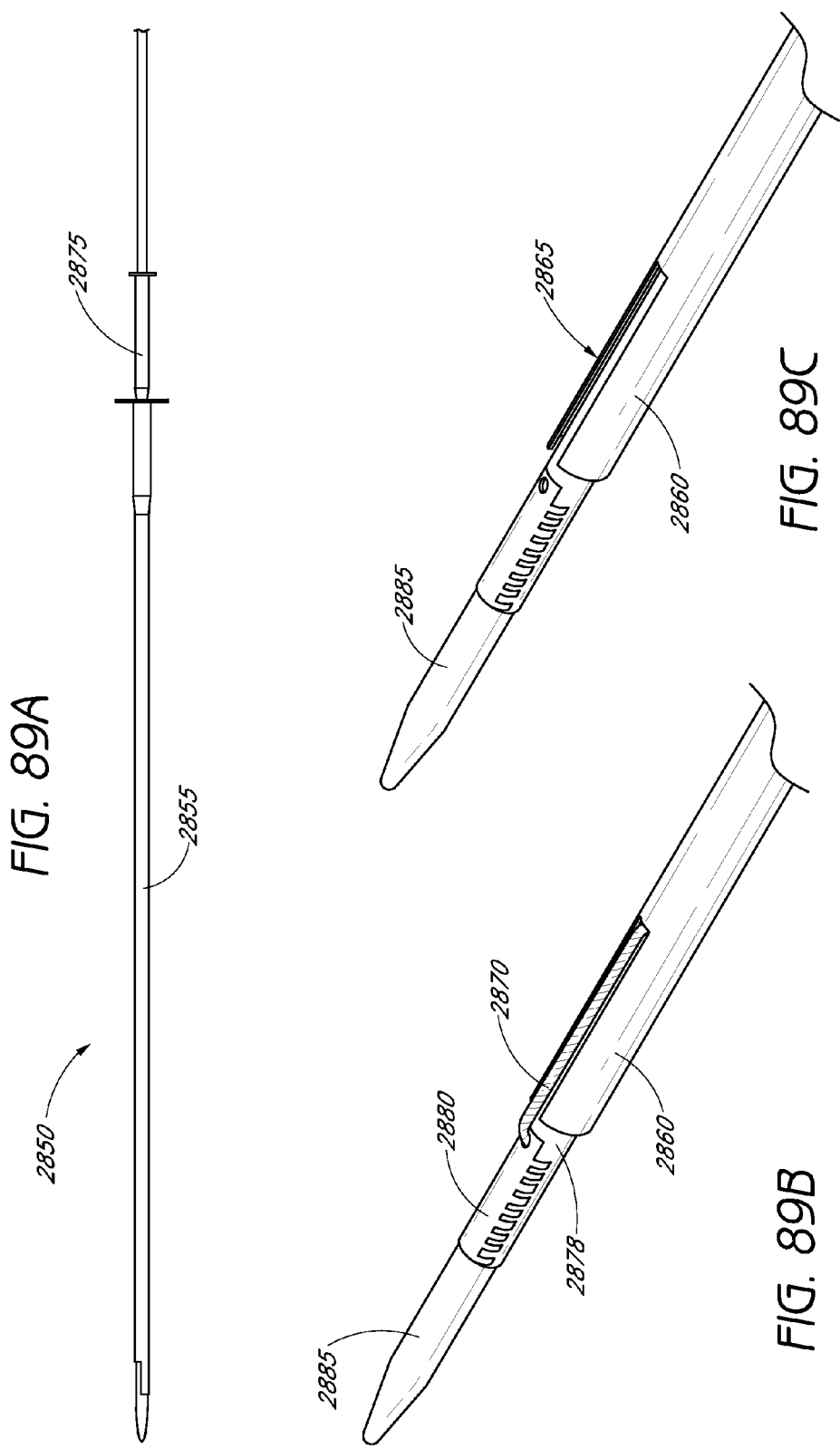
FIGS. 89A-89C depict embodiments of a slide sheath deployment system.

FIGS. 89A-89C depict embodiments of a slide sheath deployment system 2850. The slide sheath deployment system 2850 would be one that has a syringe-like base. The outer sheath 2855 of the syringe would be attached to a long lumen 2860. This lumen 2860 would have a slit 2865 at the end in which the suture 2870 that is attached to an anchor can slide. The inner sheath 2875 of the syringe like component would also be attached to an inner lumen 2878. This inner lumen would slide through the outer lumen and contain an anchor 2880 at the end. The anchor 2880 at the end would be connected to a piece of suture 2870 at the tip. This suture would be free to move due to the slit in the outer lumen. For deployment, the inner lumen would slide over the breast needle 2885. Once at a desired location within the tissue, the inner lumen would be pushed forward, therefore allowing the outer lumen to release the anchor 2880 and allow for the suture to easily slide through. Once the anchor 2880 is in place, the deployment portion of the device may be removed.

The material of the sheath, slide, and other components is preferably made from a combination of an implantable grade resorbable or non-resorbable polymer and/or metal material, including but not limited to, Polypropylene, Polyester, Nylon, PEEK, Polyurethane, Polycarbonate, Titanium, and Stainless Steel. The slit for the suture is preferably greater or equal to the diameter of the suture 2870, and is, in some embodiments, equal to or less than about 0.0125". The length of the slit will preferably be between about 0.015" and about 3". The overall length of the device will preferably be such that the syringe component is operative outside the body when the tip of the device is at the desired anchor location.

Corkscrew Deployment Device

Figure 90:
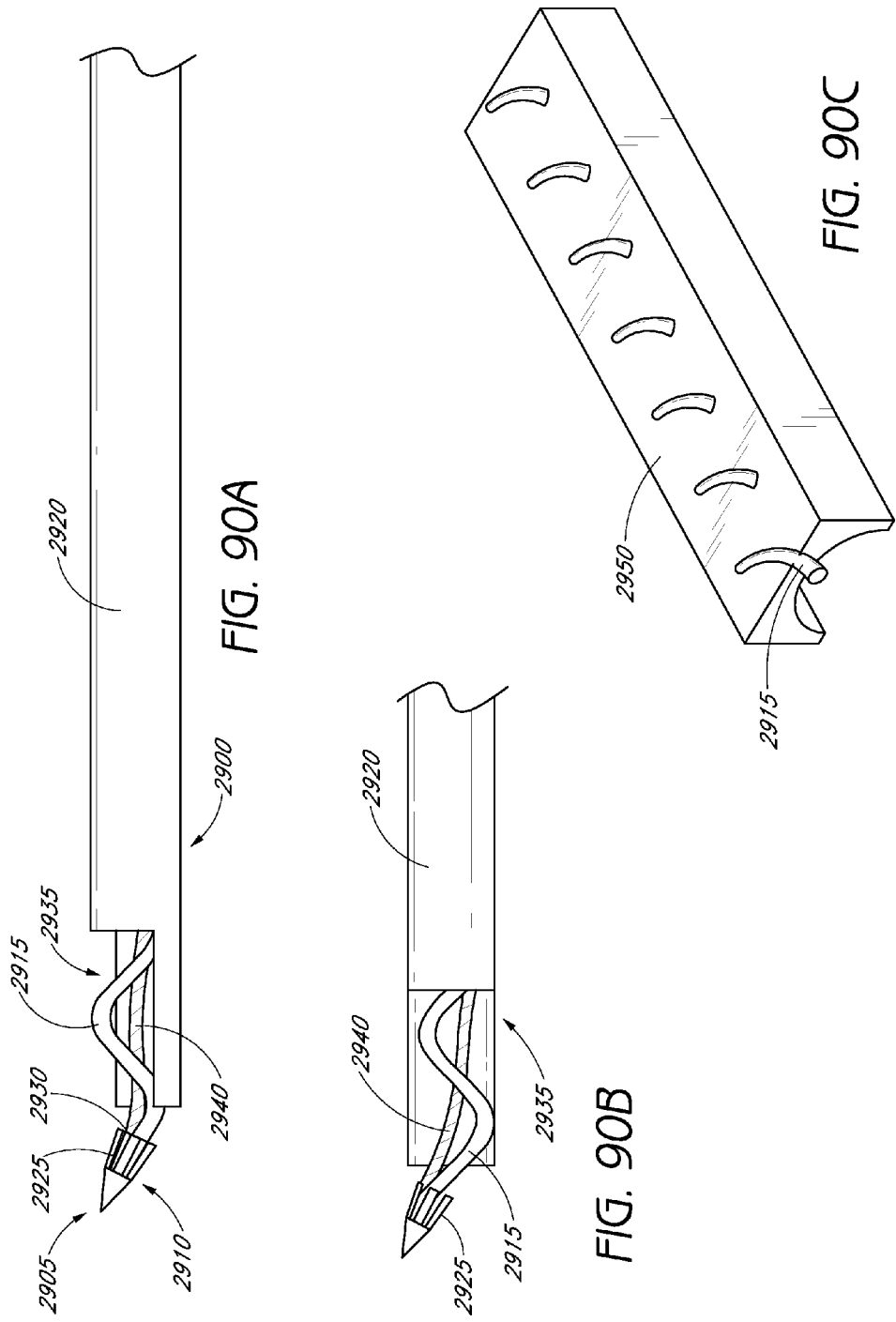
FIGS. 90A-90B depict embodiments of a corkscrew deployment device.
FIG. 90C depicts embodiments of a corkscrew plate.

FIGS. 90A-90B depict embodiments of a corkscrew deployment device 2900. The corkscrew deployment device 2900 is one in which the anchor 2905 is set at the 2910 tip of a corkscrew 2915. The corkscrew 2915 is set inside a deployment lumen 2920. The anchor 2905 at the tip would be one that is ring-like with an umbrella of barbs 2925. The anchor 2905 would also have a suture attachment 2930. The lumen 2920 would have an opening slit 2935 at the end exposing the corkscrew once at the desired location within the tissue. At that location, the corkscrew 2915 would be turned into the fascia. This turning motion would allow the suture 2940 to be sewed into the fascia for several throws. Once the corkscrew 2915 is fully deployed, turning of the corkscrew in the opposite direction would release the device. The barbs 2925 on the anchor 2905 would bite into the tissue and secure it place, leaving the suture loops in the fascia.

The material of the sheath, slide, and other components is preferably made from a combination of an implantable grade resorbable or non-resorbable polymer and/or metal material, including but not limited to, Polypropylene, Polyester, Nylon, PEEK, Polyurethane, Polycarbonate, Titanium, and Stainless Steel. The suture may be of the above materials in a monofilament or multifilament. The outer diameter of the corkscrew is preferably between about 0.015" and about 3", dependent on the location of deployment. The diameter of the corkscrew rod is less than one-third of the overall diameter. The corkscrew preferably has sufficient revolution, so as to thread the suture at a width of the suture diameter from each other. The anchor preferably has an inner diameter, so as to securely fit on the tip of the corkscrew rod. The length of the sheath cut is preferably sufficient to expose the tip of the anchor and deploy it. The overall length of the sheath is preferably sufficient to reach to the anchor site while maintaining control from out of the exit point. The inner diameter of the sheath is preferably greater than the diameter of the overall corkscrew, but is preferably small enough to maintain control of the corkscrew.

Corkscrew Plate

FIG. 90C depicts embodiments of a corkscrew plate 2950. The corkscrew plate 2950 is one that the corkscrew device 2900 sutures around. This plate 2950 would have a path for the corkscrew 2915 to cycle, leaving the suture 2940 behind and would allow a more solidified anchor to be placed in the body. The plate 2950 would be deployed above the fascia, allowing the suture loops to penetrate the fascia.

The material of the components is preferably made from a combination of an implantable grade resorbable or non-resorbable polymer and/or metal material, including but not limited to, Polypropylene, Polyester, Nylon, PEEK, Polyurethane, Polycarbonate, Titanium, and Stainless Steel. The width of the plate 2950 is preferably greater than the outer diameter of the corkscrew 2915. The length of the plate 2950 is preferably between about 0.015" and about 3" dependent on the location on implantation. The top and bottom portion of the plate may or may not be flat.

Barbed Multifilament Suture

Figure 91:
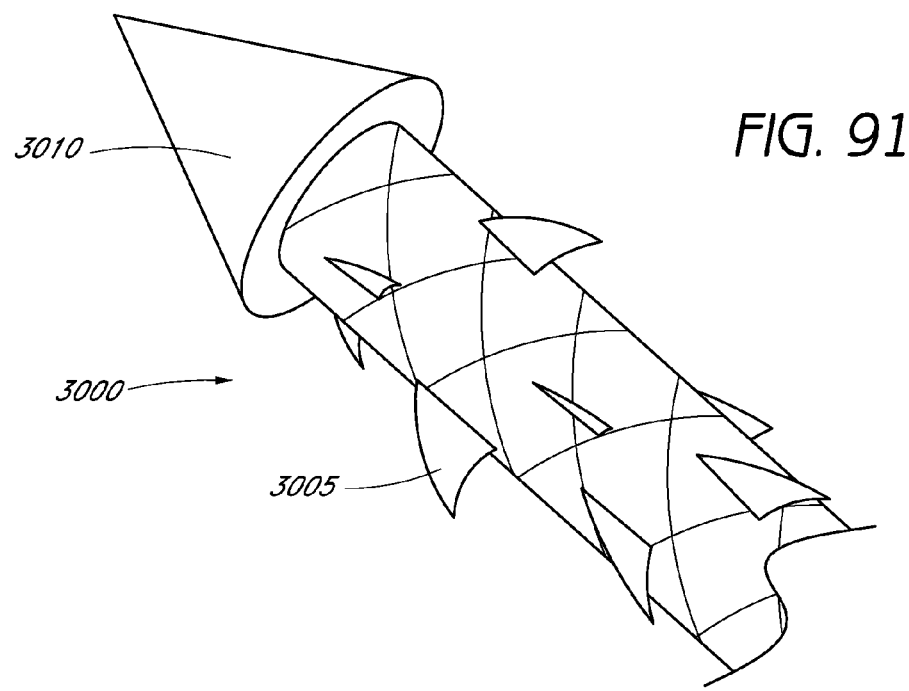
FIG. 91 depicts embodiments of a barbed multifilament suture.

FIG. 91 depicts embodiments of a barbed multifilament suture 3000. The barbed multifilament suture 3000 is one that has an insertion of barbs 3005 down the center of the braid and is capped by an anchor tip 3010. This allows the barbs 3005 to puncture through the side of the braid and catch the skin. This suture 3000 could be fed down the center of a deployment device, allowing the tip of the suture to direct the device and be deployed.

The material of the components is preferably made from a combination of an implantable grade resorbable or non-resorbable polymer and/or metal material, including but not limited to, Polypropylene, Polyester, Nylon, PEEK, Polyurethane, Polycarbonate, Titanium, and Stainless Steel.

Umbrella Suture

Figure 92:
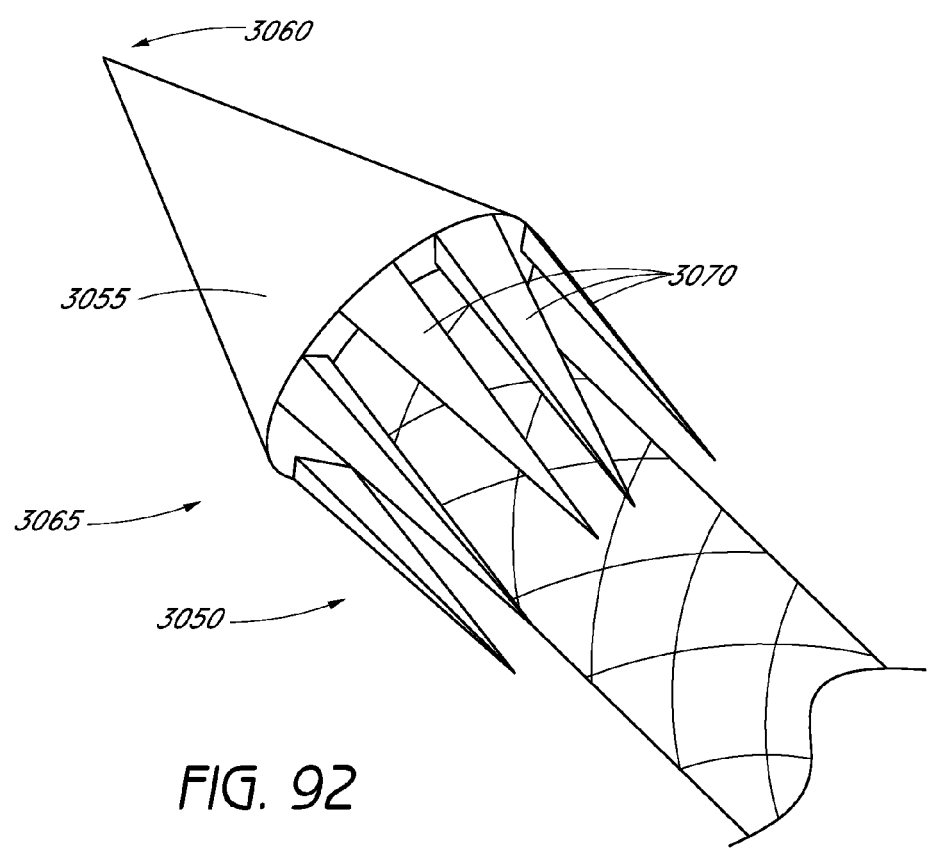
FIG. 92 depicts embodiments of an umbrella suture.

FIG. 92 depicts embodiments of an umbrella suture 3050. The umbrella suture 3050 is a suture that has a polymer tip 3055. The suture 3050 is bound to the polymer center. The polymer tip is pointed at the end 3060 for directing through tissue and separating tissue as it is advanced. At the base 3065 of the polymer tip 3055, there are barbs 3070 that extend out into the shape of an umbrella. The barbs 3070 are directed as to easily be inserted if suture is directed with the tip advancing first, however, if pulled in the opposite direction, the barbs catch the flesh and secure into the tissue.

The material of the components is preferably made from a combination of an implantable grade resorbable or non-resorbable polymer and/or metal material, including but not limited to, Polypropylene, Polyester, Nylon, PEEK, Polyurethane, Polycarbonate, Titanium, and Stainless Steel.

Umbrella Deployment Device

Some embodiments provide for an umbrella deployment device. The deployment device would utilize the umbrella suture. The suture preferably includes a sheath over the barbs. A sheath may be placed over the barbs and sit against the lip of the tip, allowing the suture to be pushed inside the breast. Once at the desired location within the tissue, the sheath may be removed, exposing the barbs so that they may be secured in the tissue.

The material of the components is preferably made from a combination of an implantable grade resorbable or non-resorbable polymer and/or metal material, including but not limited to, Polypropylene, Polyester, Nylon, PEEK, Polyurethane, Polycarbonate, Titanium, and Stainless Steel. The inner diameter of the deployment device preferably is larger than the largest diameter of the anchor but preferably equal to or less than about 0.5" than the largest diameter of the anchor. The suture and tip are preferably bonded by, but not limited to, material additive, heat set, friction or shrink fit, and plasma bonding.

Advancing Corkscrew

Figure 93:
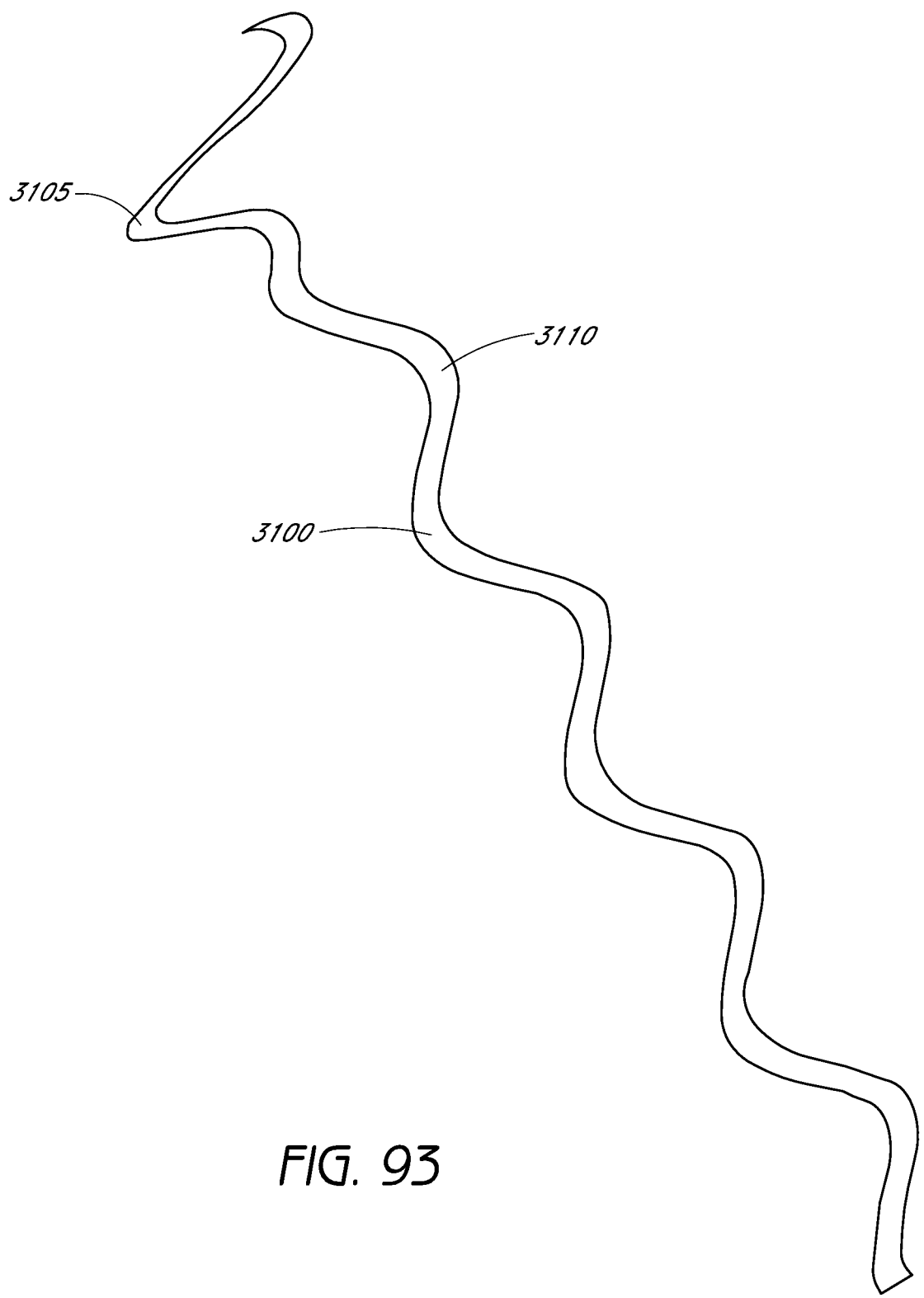
FIG. 93 depicts embodiments of an advancing corkscrew.

FIG. 93 depicts embodiments of an advancing corkscrew 3100. The advancing corkscrew 3100 would be one with two distinct varying pitch and angles springs that are either concentric or non-concentric in order to create an offset during installation. In some embodiments, for example, the corkscrew includes a larger diameter spring 3105 and a smaller diameter spring 3110. The larger diameter spring 3105 would preferably enter the tissue first in order to create a larger bite for tracking into the smaller diameter spring. This would allow for better feed into position.

Hanger

Figure 94A:
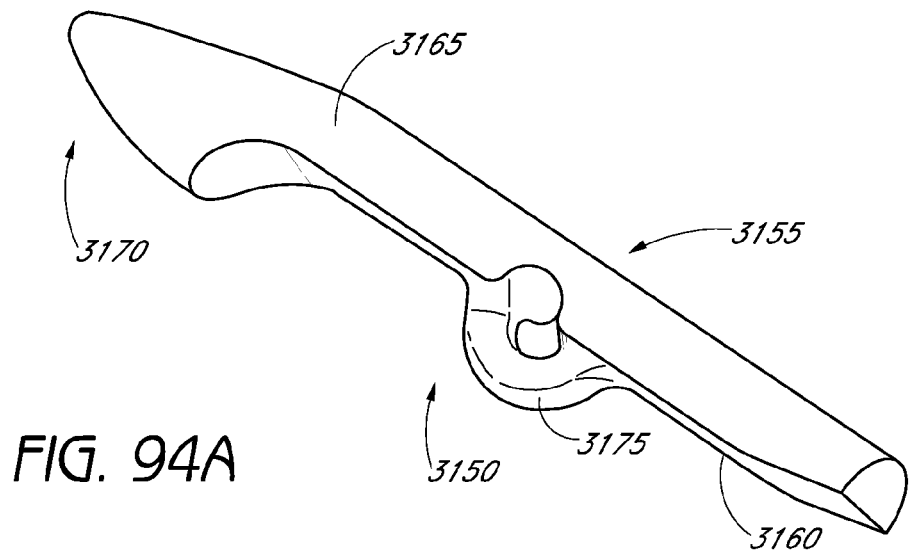
Figure 94B:
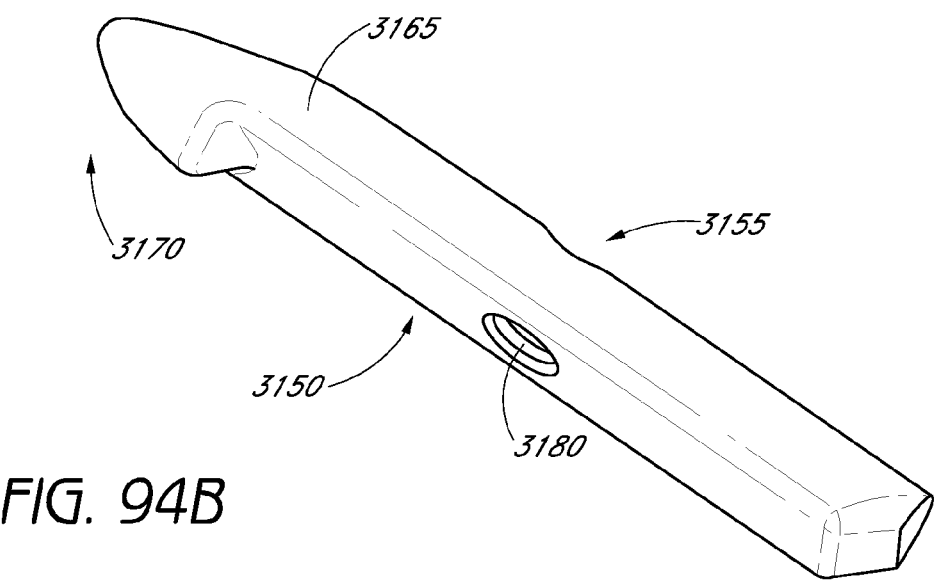
Figure 95:
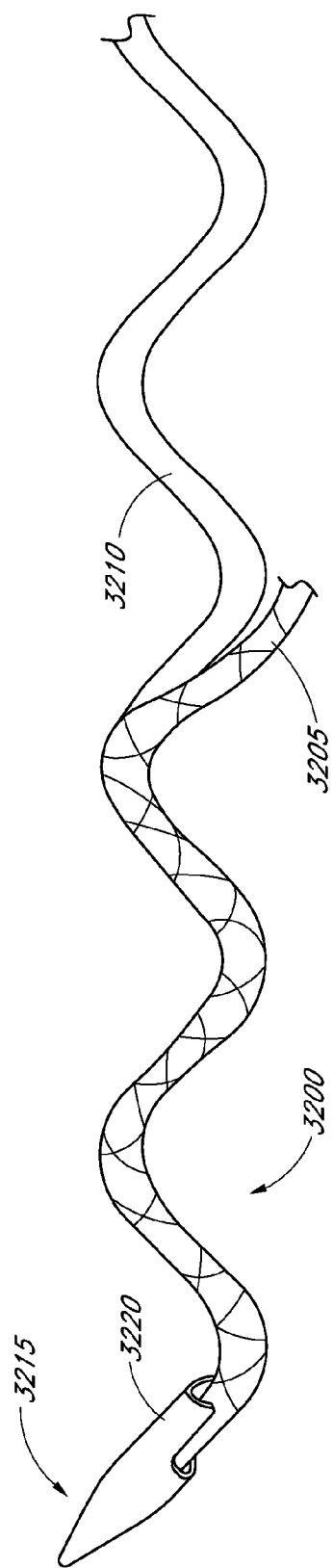

FIGS. 94A-94B depict embodiments of a hanger anchor 3150. The hanger 3150 is a resorbable or non-resorbable rod-like anchor that is attached perpendicularly to suture in the center 3155 of one side 3160 of a rod 3165. One end 3170 of the shaft is pointed to act as a guide in feeding up through the breast. Separated from the point, and shown approximately one-third down from the point, the cross-sectional shape of the shaft changes and is representative of a "D" encompassing less than, or half, the diameter of the original cross-section. Then, halfway down the shaft, the "D" shape has a ring 3175 attached to it for suture attachment.

The remaining portion of the shaft then resumes the "D"-shape. This "D" shape has multiple advantages. First, it allows the suture to lie alongside the anchoring device during insertion inside the breast, without increasing the overlying sheath diameter in order to accommodate the suture. Second, the flat portion of the "D" will lie perpendicularly to the force of pull within the fascia plane allowing for heightened support.

A second version (FIG. 94B) of the hanger 3150 does not contain an additional ring 3175. Rather, the "D" shape is still maintained for two-thirds of the device; however, less than half of the cross-sectional area is removed allowing for more mass to be maintained. Instead of having the ring 3175, there is a hole 3180 in the center of the hanger that runs parallel with the suture and perpendicular to the overall shape of the device. The hole 3180 is dual diameter with a larger diameter at the top of the device and a smaller one at the bottom. To secure the suture to the second version, a knot is tied in the suture. The larger diameter of the knot is to rest in the larger diameter portion of the hole, and the remainder of the suture is fed through the smaller hole. The suture can then be bonded in the larger diameter hole.

The material of the components is preferably made from a combination of an implantable grade resorbable or non-resorbable polymer and/or metal material, including but not limited to, Polypropylene, Polyester, Nylon, PEEK, Polyurethane, Polycarbonate, Titanium, and Stainless Steel. The length of the device is preferably greater than the width. The width is preferably greater than the diameter of the suture. For version 1 (FIG. 94A), the inner diameter of the hole preferably is greater or equal to the diameter of the suture. For version 2 (FIG. 94B), the smaller hole preferably is approximate to the diameter of the suture. The larger diameter hole preferably is great enough to hold the width of the suture tied in chosen knot.

Braid Overlay Corkscrew

The Braid Overlay corkscrew 3200 is a corkscrew-shaped device that may be inserted into the fascia to apply the suture in a stitched fashion. The suture 3205 is applied to the corkscrew 3210 prior to insertion. This is done by feeding the corkscrew 3210 down the center of the suture 3205. At the end of the suture 3205, the anchor 3215 will preferably be attached to the suture 3205, and the anchor 3215 will sit on the end of the corkscrew 3210. The anchor 3215 may or may not be used to drive into the tissue and fascia. Once the corkscrew 3210 is stitched into the tissue, the corkscrew 3210 is then removed by driving or rotating it in the opposite direction. By reversing the direction, the corkscrew 3210 will back out leaving the suture in place. This is aided by the fact that the anchor 3215 has a prong 3220 flange on the end that will secure into the tissue and allow the suture to stay in place and not back out with the corkscrew 3210.

The material of the components is preferably made from a combination of an implantable grade resorbable or non-resorbable polymer and/or metal material, including but not limited to, Polypropylene, Polyester, Nylon, PEEK, Polyurethane, Polycarbonate, Titanium, and Stainless Steel. The inner diameter of the suture is preferably large enough to easily slide over the corkscrew.

Leaf Anchor

Figure 96:
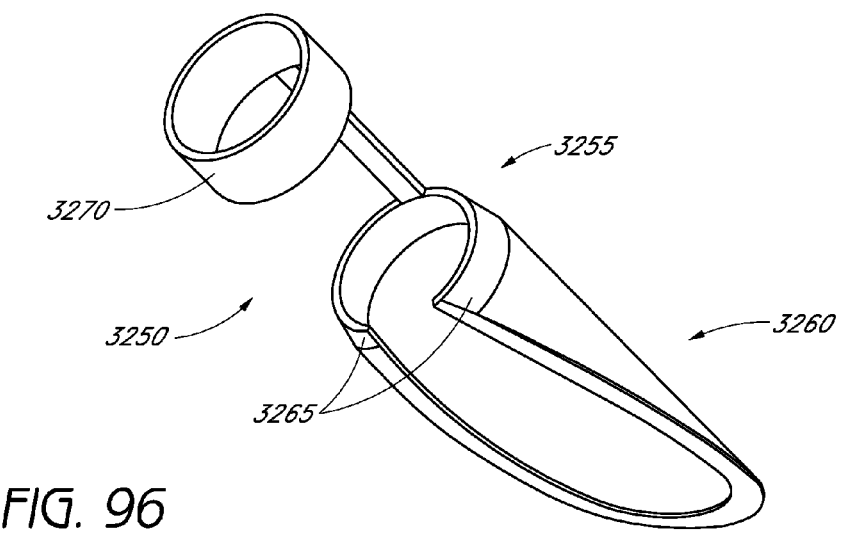

FIG. 96 depicts embodiments of a leaf anchor 3250. The leaf anchor 3250 is one that has one or more spear-shaped prongs 3255 around the tip 3260 of the anchor 3250. During deployment, leaves of the tip 3260 are wrapped around the suture that is attached to the anchor 3250. Once deployed, these spear-like prongs 3255 spring out and secure into the fascia perpendicularly to the pull. One or more of these may be applied around the anchor tip 3260. The prongs 3255 are attached via a slender attachment point that will allow deflection and perpendicular placement to the head of the anchoring system.

The material of the components is preferably made from a combination of an implantable grade resorbable or non-resorbable polymer and/or metal material, including but not limited to, Polypropylene, Polyester, Nylon, PEEK, Polyurethane, Polycarbonate, Titanium, and Stainless Steel. The inner diameter of a ring 3270, through which the suture may pass, on one end of the leaf anchor preferably is greater than that of the suture under radial compression.

Umbrella Anchor

Figure 97:
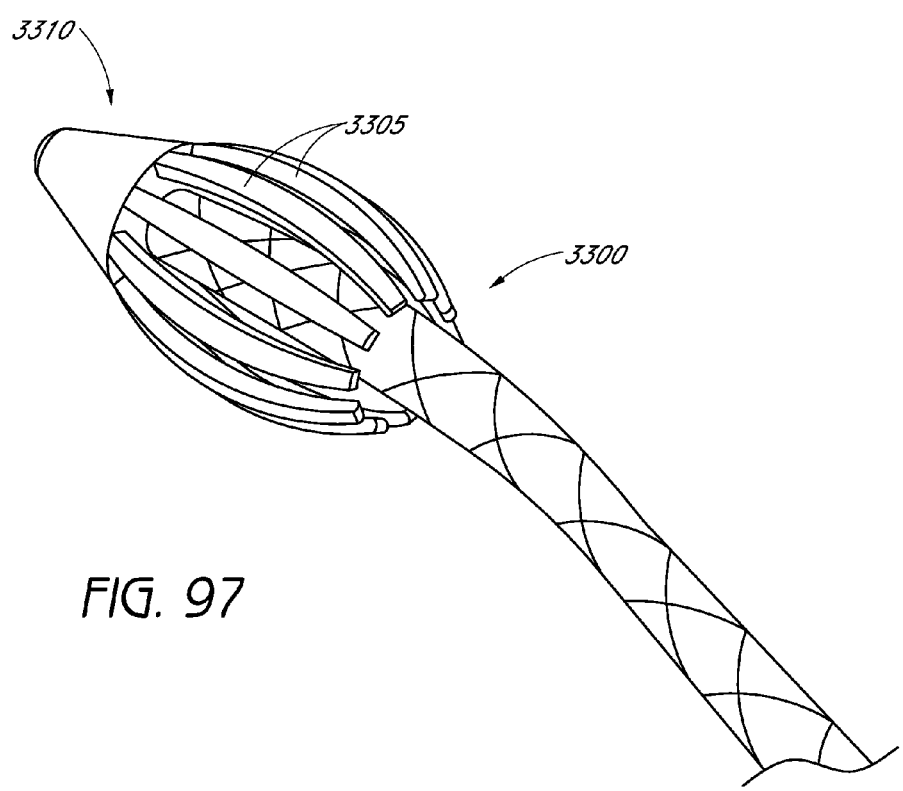

FIG. 97 depicts embodiments of an umbrella anchor 3300. The umbrella anchor 3300 is one that is shaped like an umbrella with prongs 3305 pointing in the a direction opposite than that of insertion. A tip 3310 of the anchor 3300 is used to drive and separate the tissue as the anchor 3300 is advanced therethrough. In some embodiments, a sheath is applied over the anchor tip. Once at a desired location within the tissue, the sheath is removed exposing the anchor. The anchor can then be pulled in the opposite direction of insertion. Once pulled, the prongs 3305 on the umbrella anchor 3300 then deploy outward grabbing onto the tissue.

The material of the components is preferably made from a combination of an implantable grade resorbable or non-resorbable polymer and/or metal material, including but not limited to, Polypropylene, Polyester, Nylon, PEEK, Polyurethane, Polycarbonate, Titanium, and Stainless Steel.

Washer Anchor

Figure 98A:
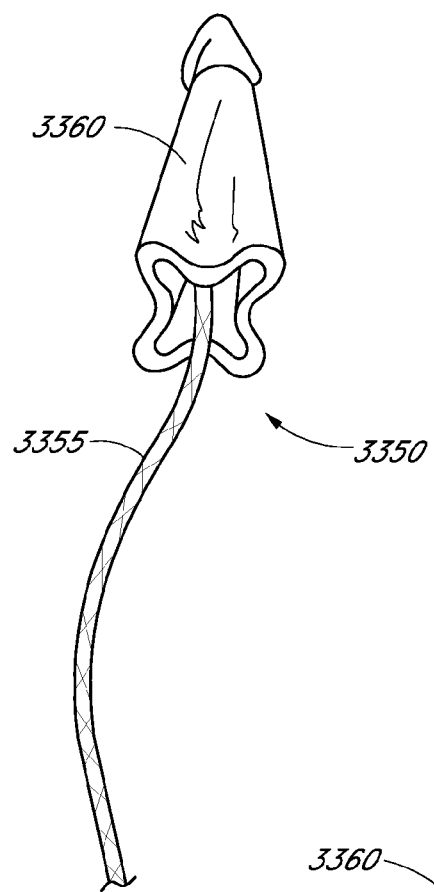
Figure 98B:
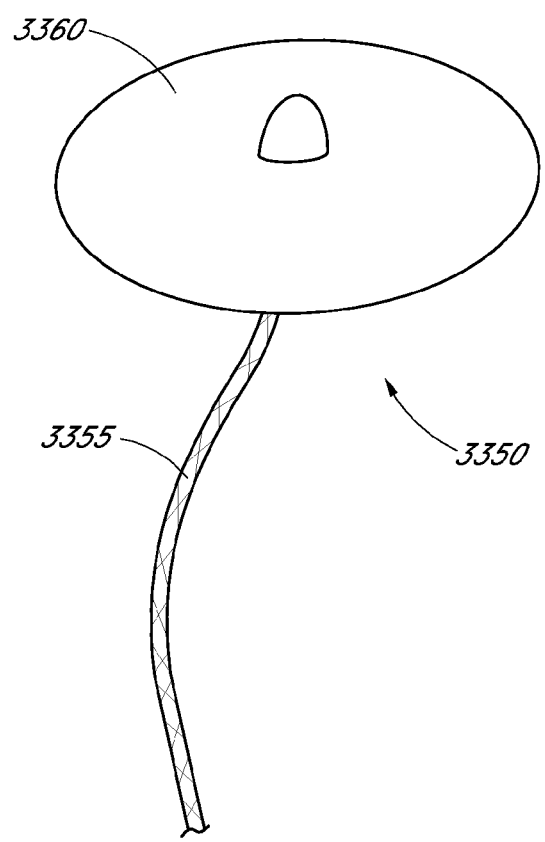

FIGS. 98A-98B depict embodiments of a washer anchor 3350. The washer anchor 3350 is an anchor created to adapt to the end of the corkscrew deployment system. The washer anchor 3350 is attached to the suture 3355. The anchor is a circular disk 3360 that is contractible, to have a first cross-sectional dimension in a compressed state (FIG. 98A), and is expandable, to have a second cross-sectional dimension (FIG. 98B), greater than the first cross-sectional dimension, in an expanded state. The washer is created to be deployed under the fascia. When pulled perpendicularly to the plane, the washer 3350 is expanded created a large surface area for pull through resistance. Prior to deployment, the washer wraps around the suture 3355 until it is deployed at the desired location.

The material of the components is preferably made from a combination of an implantable grade resorbable or non-resorbable polymer and/or metal material, including but not limited to, Polypropylene, Polyester, Nylon, PEEK, Polyurethane, Polycarbonate, Titanium, and Stainless Steel. The diameter of the disk is preferably greater than the diameter of the needle that is used to puncture the fascia. In some embodiments, the thickness is between about 0.00001" and about 0.3"

T-Bar Anchor Support

Figure 99:
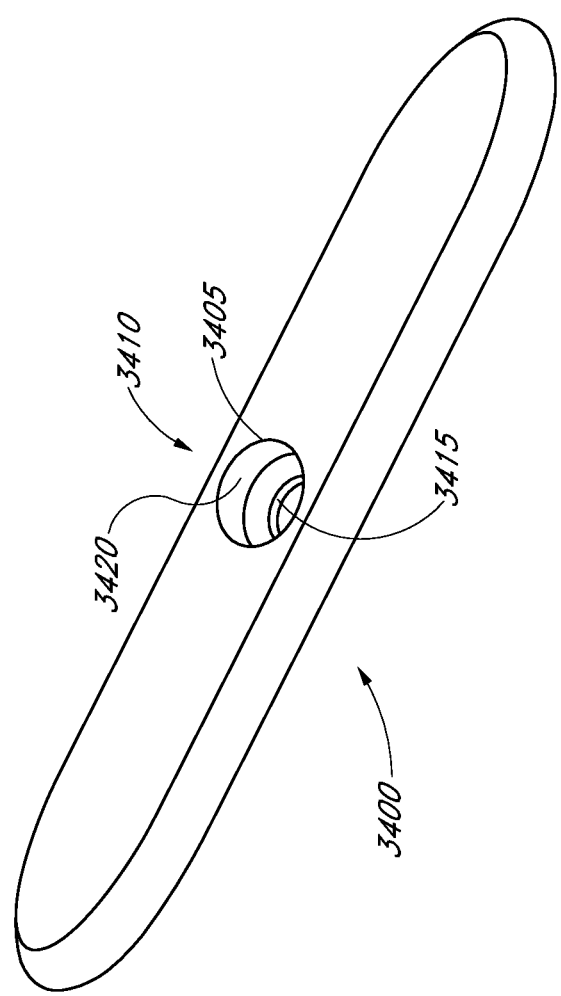

FIG. 99 depicts embodiments of a T-bar anchor support 3400. The T-Bar Anchor support 3400 is a rod-like component that runs perpendicular to the suture at varying distance from the anchor tip. The anchor support 3400 will have a suture attachment point 3405 (which, in FIG. 99, is depicted as a hole) at the center 3410. During deployment, the anchor support 3400 is turned parallel alongside the anchor. Once the distal anchor is deployed, the suture is pulled back in the opposite direction to engage the anchor support rods. The anchor supports 3400 then turn perpendicular to the suture and allow for additional support within the tissue. In some embodiments, the attachment point 3405 comprises a hole, and in certain embodiments, the hole can have a plurality of internal diameters. For example, as depicted in FIG. 99, the hole can include a smaller hole 3415, having a smaller diameter, and a larger hole 3420, having a larger diameter.

The material of the components is preferably made from a combination of an implantable grade resorbable or non-resorbable polymer and/or metal material, including but not limited to, Polypropylene, Polyester, Nylon, PEEK, Polyurethane, Polycarbonate, Titanium, and Stainless Steel. The length of the device is preferably greater than the width. The width is preferably greater than the diameter of the suture. The smaller hole is preferably approximate to the diameter of the suture. The larger diameter hole is preferably great enough to hold the width of the suture tied in chosen knot.

Fascia Puncture Deployment System

Figure 100:
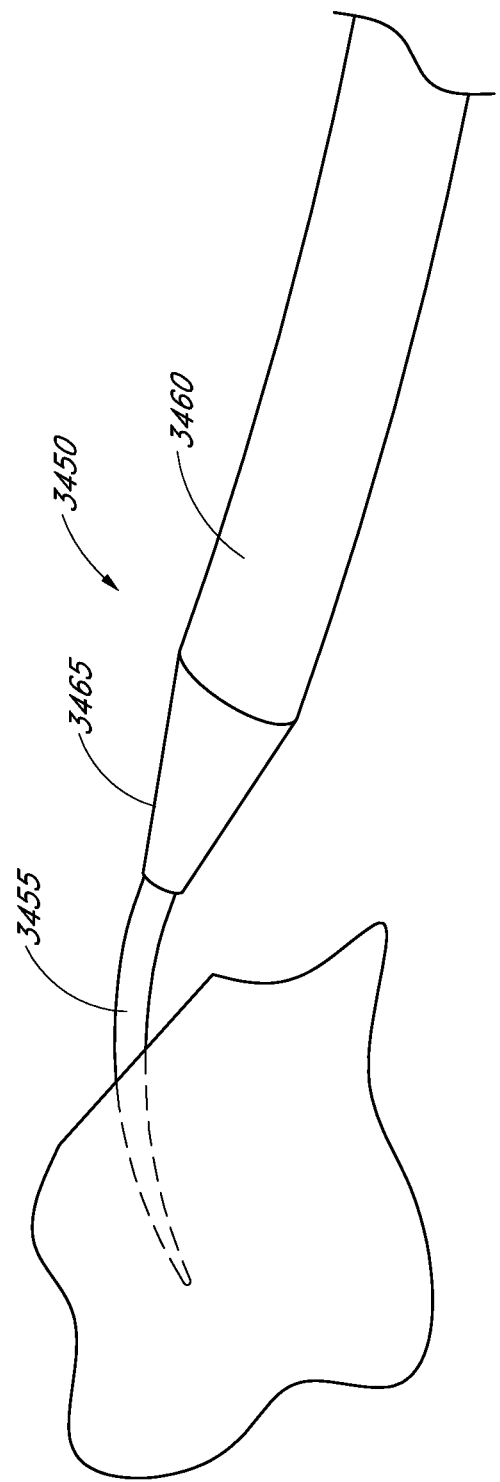

FIG. 100 depicts embodiments of a fascia puncture deployment system 3450. This deployment system 3450 is created specifically to locate and penetrate the fascia plane. The deployment system 3450 is inserted in the exit-hole consisting of a blunt needle with a sheath. The needle is slid up to the desired fascia plane location. The blunt needle is similar to a tipped hypotube in which a blunt tip shaped sheath is placed at the end. Therefore, once at the fascia plane, the blunt tip will not puncture through. Once the fascia plane is located, another sharper needle 3455 can be pushed through the hypotube 3460, out the blunt end 3465, and into the fascia. The sharp needle 3455 would have curvature as to allow angled deployment. Once punctured through the fascia, the sheath may then be slid through the fascia layer acting as a port. The needle 3455 may then be removed and the anchor may then be inserted under the fascia layer, leaving the suture exit through the fascia and into the tissue.

The material of the components is preferably made from a combination of an implantable grade resorbable or non-resorbable polymer and/or metal material, including but not limited to, Polypropylene, Polyester, Nylon, PEEK, Polyurethane, Polycarbonate, Titanium, and Stainless Steel. The length of the device is preferably greater than the width. The length of the device should preferably be sufficient to allow the inner needle to reach through the desired location on the fascia plane while allowing control out of the exit point.

Tree Branch

FIG. 101 depicts schematic representations of embodiments of a device 3500 that can be used alone or in combination with other embodiments described herein. The material of the components can be made from a combination of an implantable grade resorbable or non-resorbable polymer and/or metal material, including but not limited to, Polypropylene, Polyester, Nylon, PEEK, Polyurethane, Polycarbonate, Titanium, and Stainless Steel. The length of the device may be greater than the width. This shape will allow for the device 3500 to be inserted into the center of a braided suture and when pulled back, the branches 3505 will spread out away from a central portion 3510 and pierce the suture to form a barbed suture. This device 3500 can be made long and cut down to any appropriate size. The amount of barbs, or branches 3505, shown will dictate the amount of grip the device will have. The diameter of the main branch is preferably less than the inner diameter of the suture at full expansion.

Y-barb

Figure 102A:
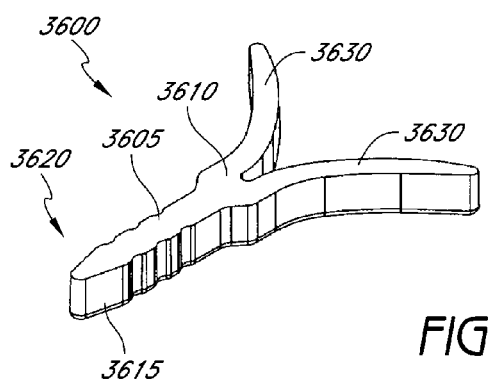
Figure 102B:
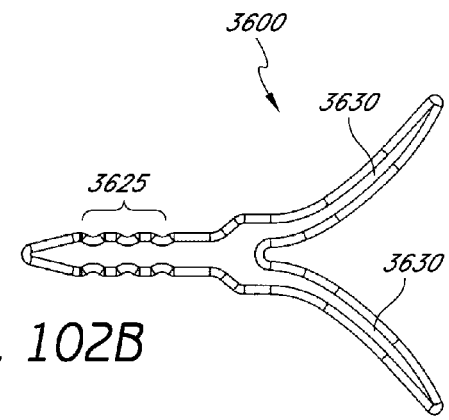
Figure 102C:
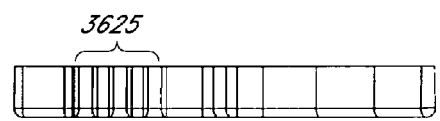

FIGS. 102A-102D depict embodiments of a y-barb anchor 3600 that can be used in connection with other embodiments and methods provided herein. FIG. 102A is a perspective view of the anchor 3600. The anchor 3600 has a neck 3605 that extends from a central portion 3610 of the anchor and that can include a slight taper 3615 at a distal end 3620 of the neck 3605. The slight taper 3615 can be used to facilitate advancement of the anchor 3600 through tissue by providing a decreased cross-sectional measurement, relative to a cross-sectional measurement of the neck 3605, that can separate tissue as the anchor moves through the tissue. The neck 3605 can include, as depicted shown in the bottom view of FIG. 102B and the top view of FIG. 102D, a plurality of ridges 3625 along one or more sides that can increase the gripping capabilities of the anchor 3600.

The anchor extends proximally from the center portion 3610, in some embodiments, with two laterally extending legs 3630. The legs 3630 are preferably constructed such that as the anchor 3600 is advanced distally through tissue, the distal end 3620 separates tissue, and the legs 3630 are slightly deflected towards each other. When the anchor 3600 is positioned in a desired location, the anchor 3600 is drawn slightly proximally, and the legs are directed apart from each other and function as a barb, or anchor, in the tissue, limiting proximal withdrawal. Although the anchor 3600 is depicted as having two legs 3630, in some embodiments, the anchor 3600 can have more or less than two legs 3630. For example, in some embodiments, the anchor 3600 can have three, four, five, or six legs 3630. In some embodiments, the anchor 3600 can have more than six legs 3630. In some embodiments, the portion of the anchor 3600 distal to the central portion 3610 can include legs for engaging tissue, and in some embodiments, these legs 3630 can be oriented in opposition to the proximally positioned legs 3630 such as those depicted in FIG. 102A-102D. FIG. 102A-102D depict the anchor as extending substantially along a plane, in which the legs 3630 also extend. In some embodiments, the legs 3630 can extend out of or through a plane that contains a remaining portion of the anchor, as described above in connection with other embodiments of anchors.

Figure 102D:
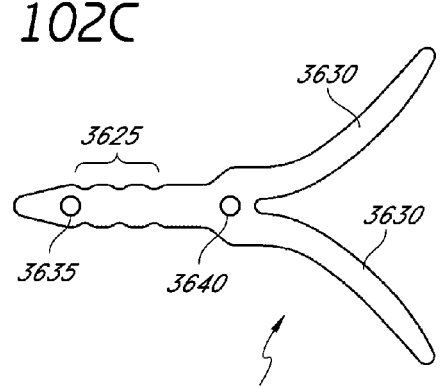

In some embodiments, the anchor 3600 includes at least one of a distal aperture 3635 and a proximal aperture 3640, as shown in FIG. 102D. These apertures 3635, 3640 can be used to attach the anchor to a suture. In some embodiments, a suture extending distal to the anchor 3600 is attached to, passes through, or coupled to distal aperture 3635, and in some embodiments, a suture extending proximal to the anchor 3600 is attached to, passes through, or coupled to proximal aperture 3640. In some embodiments, the suture can extend from proximal to the anchor through the proximal aperture 3640, along the anchor 3600, pass through the distal aperture 3635, and extend distal to the anchor 3600. The suture, can have securing devices along its length to limit movement or migration of the anchor 3600 along the suture. In some embodiments, a knot can be tied in the suture on either side of the apertures 3635, 3640 to limit or restrict movement of the anchor along suture. In some embodiments (not depicted), the anchor can have a central lumen extending, for example, with a proximal opening at the proximal end to a distal opening at the distal end. In some embodiments, the suture can extend through the central lumen, and the suture can have securing devices, knots, or the like, for limiting axial movement of the anchor along the suture.

In some embodiments, the suture, as a woven or braided element can be woven or braided over the anchor such that the anchor 3600 is, after manufacturing, effectively an integral part of the suture. In these embodiments, the suture can be provided with one or more anchors for insertion in the body.

Superior Entry

FIGS. 103A-103S depict embodiments of devices for and methods of elevating, or lifting, soft tissue through introduction of the devices through a superior entry. Depicted is an exemplary procedure for elevating breast tissue, but the same or similar devices and methods can be used to elevate other soft tissue. For example, the devices and methods relating to superior entry can also be used in connection with elevating tissue of the buttocks, face, etc.

As described herein, superior generally refers to a direction that is relatively cephalad or towards the head while inferior generally refers to a direction that is relatively caudal or toward the feet. A superior-inferior axis of an anchor support line may be inclined with respect to or substantially parallel with respect to the patient's longitudinal (cephalad-caudal) axis. Generally the superior-inferior axis will be within about 85 degrees, often within about 65 degrees, and in some applications within about 45 degrees of the longitudinal axis of the patient, measured in at least one of the anterior-posterior or medial-lateral planes, depending on the desired cosmetic result. In some implantations, the angle will be no more than about 25 degrees.

Similarly, medial generally refers to a direction closer to the midline of the body with respect to a lateral location; a medial-lateral axis could be transverse or substantially transverse with respect to the patient's longitudinal axis, or angularly deviated such as within about 85 degrees, 65 degrees, 45 degrees, 25 degrees, or less with respect to an axis transverse to the longitudinal axis of a patient.

Figure 103B:
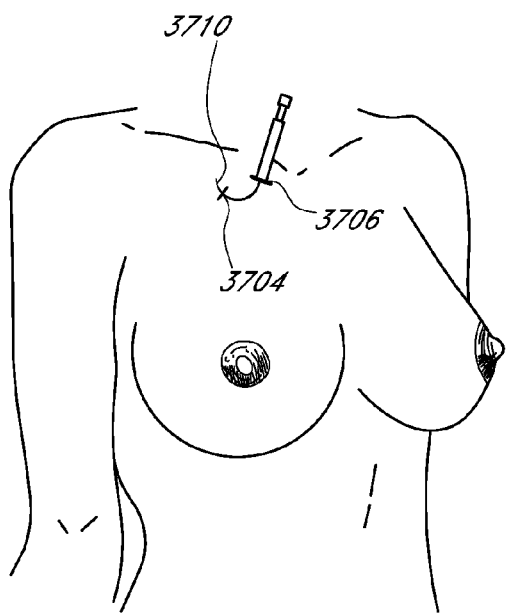

In some embodiments, as depicted in FIG. 103A, the patient is marked preoperatively with a superior entry point 3700 and medial 3702 and lateral 3704 exit points. At the superior entry point 3700, a superior port 3706 is inserted, for example, with a trocar and port dilator 3708. FIG. 103B depicts removal of the trocar and port dilator 3708, leaving the superior port 3706 extending transcutaneously into the patient. A suture or anchor needle 3710 is advanced through the superior port 3706, through the patient and exits at the lateral exit point 3704.

Figures 103C, 103D:
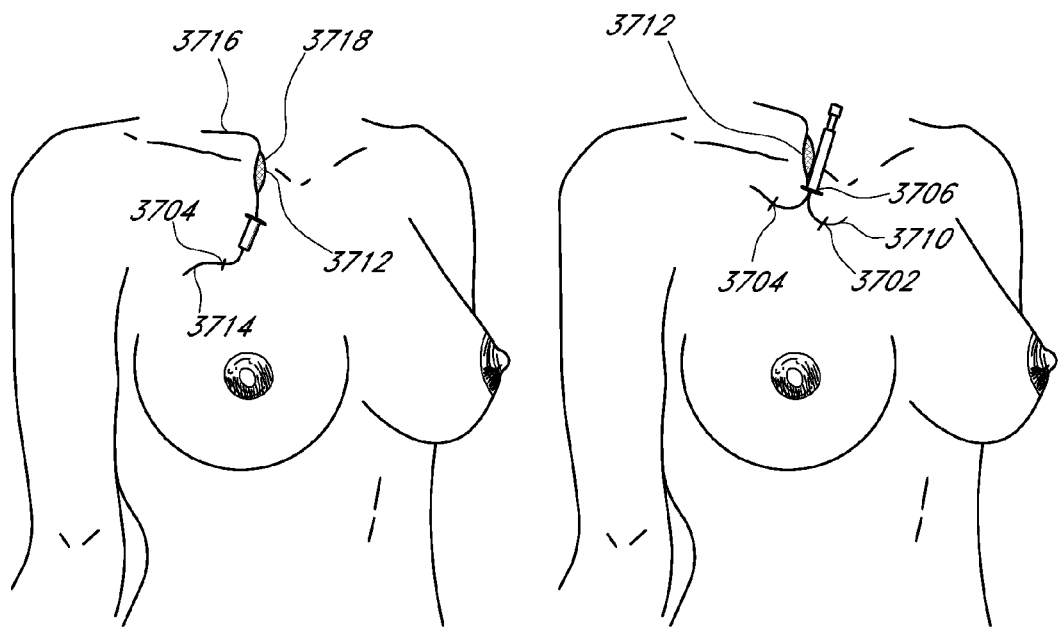

FIG. 103C illustrates a first end 3714 of a superior sling 3712 being advanced, by the needle 3710, through the superior port 3706, and out of the patient at the lateral exit point 3704. The first end 3714 of the superior sling 3712 is advanced while keeping, at this point, a sling portion 3718 of the superior sling 3712 from entering the superior port 3706.

Figures 103E, 103F:
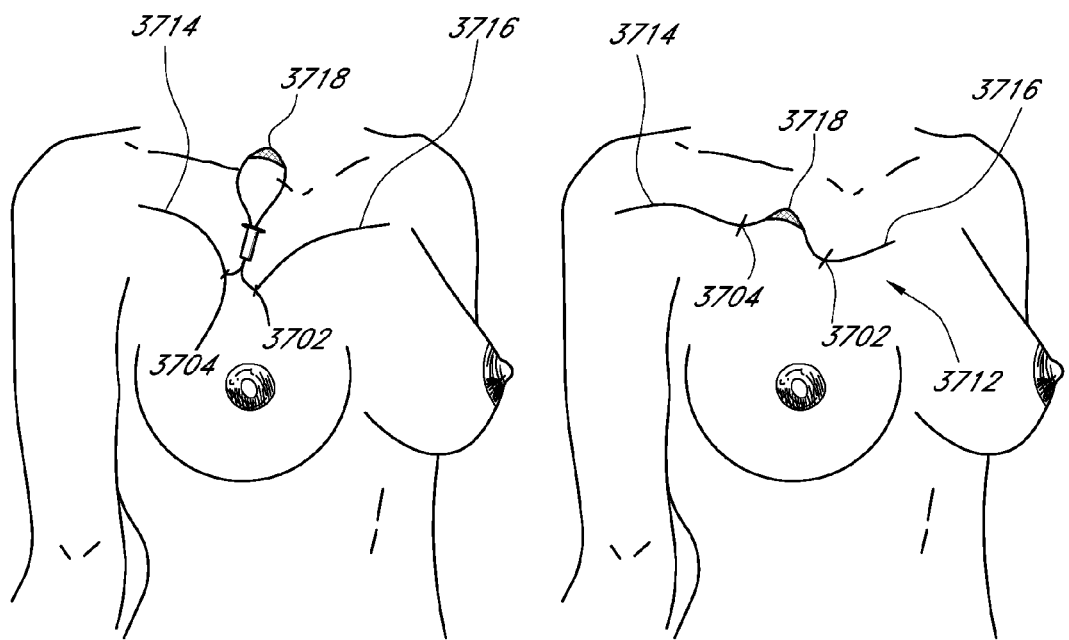

In FIG. 103D, the needle 3710 is advanced through the superior port 3706 and exits the patient at the medial exit point 3702. FIG. 103E illustrates that a second end 3716 of the superior sling 3712 has been advanced, by the needle 3710, through the superior port 3706 and out of the patient at the medial exit point 3702. The second end 3716 of the sling 3712 is advanced, in some embodiments, while keeping a sling portion 3718 of the superior sling 3712 from entering the superior port 3706.

With the sling portion 3718 extending out of the superior port 3706, and the first 3714 and second ends 3716 of the superior sling 3712 extending through the superior port 3706 and respectively out of the lateral 3704 and medial exit point 3702, the first 3714 and second ends 3716 of the superior sling 3712 can be pulled to advance the sling portion 3718 into the superior port 3706. As the first 3714 and second 3716 ends of the superior sling 3712 are pulled further, the sling portion 3718 advances through the superior port 3706 and emerges from a distal end of the port 3706, which is beneath the surface of the patient's skin. The first 3714 and second ends 3716 of the superior sling 3712 can be further pulled to spread out the sling portion 3718, as depicted in FIG. 103F, while keeping the sling 3712 in a centered position between the lateral 3704 and medial 3702 exit points. The superior port 3706 can then be removed.

The above steps provide introduction of a superior sling 3712, or supporting member, within a contoured pathway that leads from the lateral exit point 3704 to the medial exit point 3702 through three small entries in the patient's skin. The depth of the sling portion 3718 can be determined by the depth the superior port 3706 is advanced into the patient.

Figures 103G, 103H:
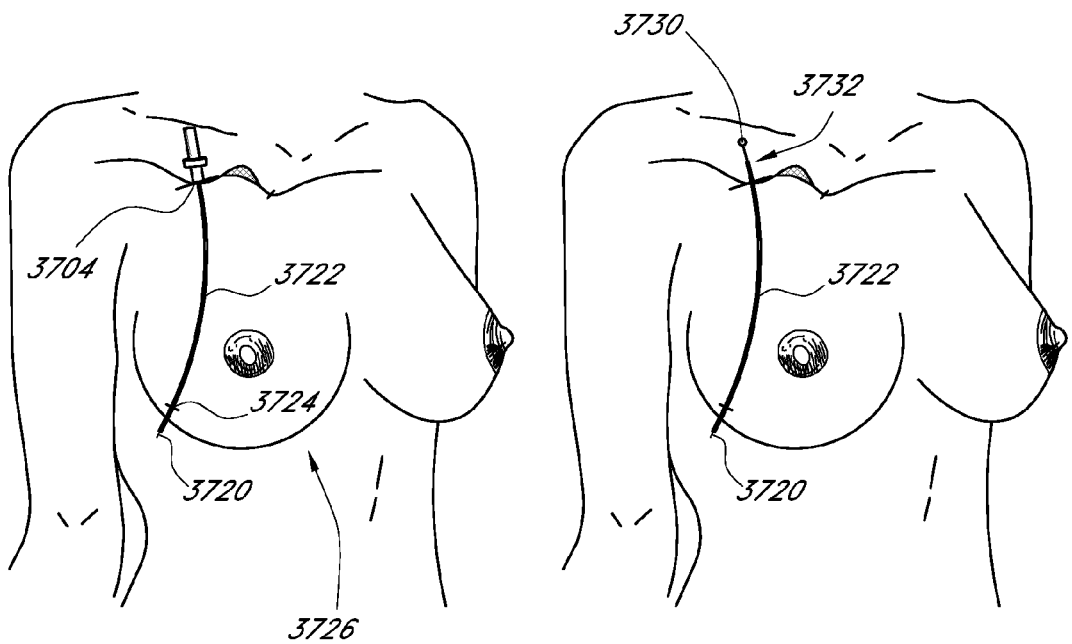
Figures 103I, 103J:
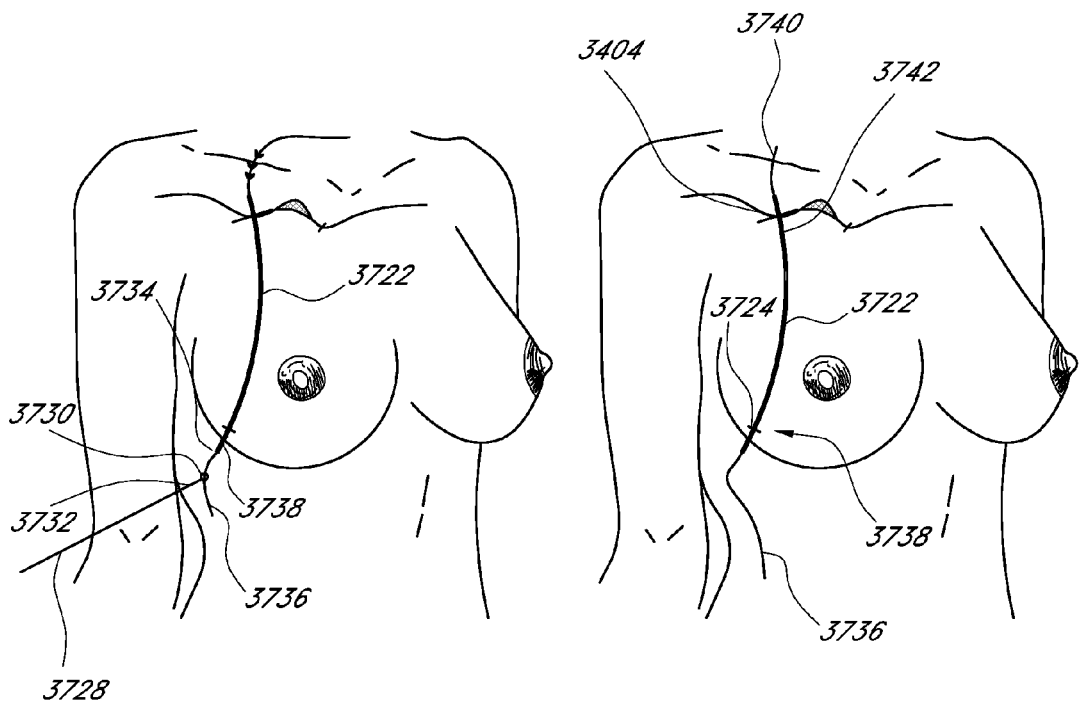

FIG. 103G depicts advancement inferiorly of a needle 3720 and cannula 3722 from the lateral exit point 3704 to an exit point 3724 at a base of the breast 3726. FIG. 103H illustrates removal of the needle 3720 from the cannula 3722 and advancement, through the cannula 3722, of a feeder rod 3728 having, for example, a loop 3730 at a proximal end 3732 of the rod 3728. A distal end 3736 of an anchor 3734 is coupled to the proximal end 3732 of the rod 3728, for example, through the loop 3730, and the rod 3728 is further advanced through the cannula 3722, drawing the distal end 3736 of the anchor suspension line 3734 through the cannula 3722, as shown in FIG. 103I. The anchor suspension line 3735 carrying one or more inferior anchors 3734 is advanced through the cannula 3722 until the distal end 3736 emerges from the distal end 3738 of the cannula 3722.

In the step depicted in FIG. 103J, the cannula 3722 is withdrawn proximally until the distal end 3738 of the cannula 3722 is adjacent the exit point 3724 at the base of the breast 3726. A desired location of the anchor suspension line 3735 including anchor 3734, within the cannula 3722, is determined, and the anchor 3734 is adjusted to the desired location by measuring a first length of the distal end 3736 of the anchor suspension line 3735 extending out of the distal end 3738 of the cannula 3722 or by measuring a second length of the proximal end 3740 of the anchor suspension line 3735 extending out of the proximal end of the cannula 3722.

Figures 103K, 103L:
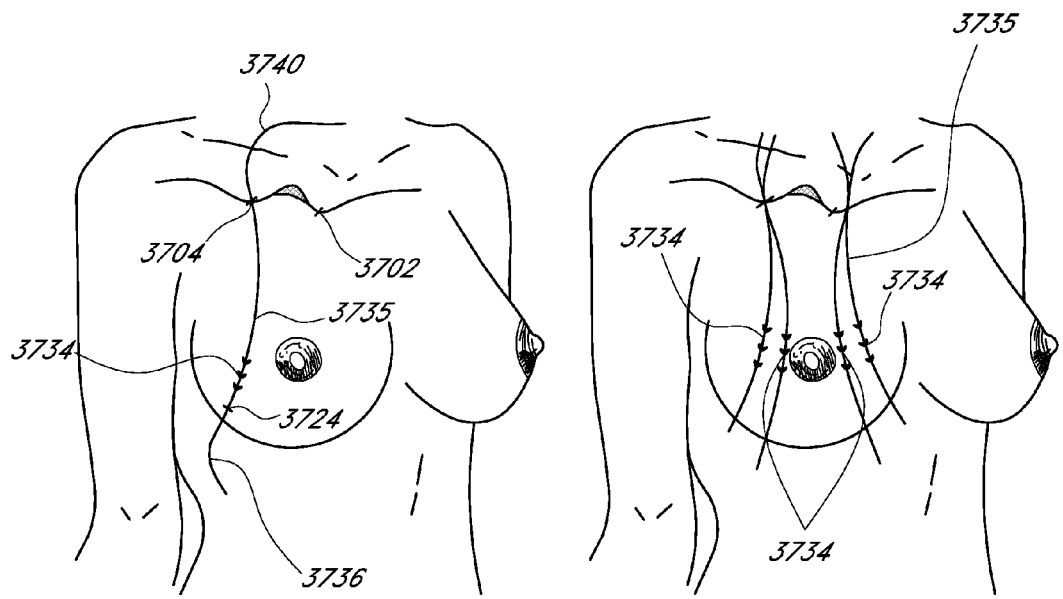

FIG. 103K depicts removal of the cannula 3722 while leaving the anchor suspension line 3735 in place. In this step, the anchor suspension line 3735 and anchor 3734 is held in a substantially stationary position, while the cannula 3722 is withdrawn proximally from the patient through the lateral exit point 3704. Once the cannula 3722 is withdrawn from the patient, the anchor 3734 can be drawn slightly proximally to ensure proper positioning and lift. If a problem exists with the positioning or placement of the anchor 3734, the distal end 3736 of the anchor suspension line 3735 can be pulled distally, and the anchor suspension line 3735 can be completely removed from the exit point 3724 at the base of the breast 3726. The procedure can then be repeated by advancing the cannula 3722 back into the patient for proper placement or positioning of the anchor suspension line 3735. A plurality of anchor suspension lines 3735 can be inserted through each of the lateral 3704 and medial 3702 exit points, and each can have a different path through the breast 3726 such that a plurality of anchor suspension lines 3735 are disposed radially across the breast 3726, as depicted in FIG. 103L.

Figures 103M, 103N:
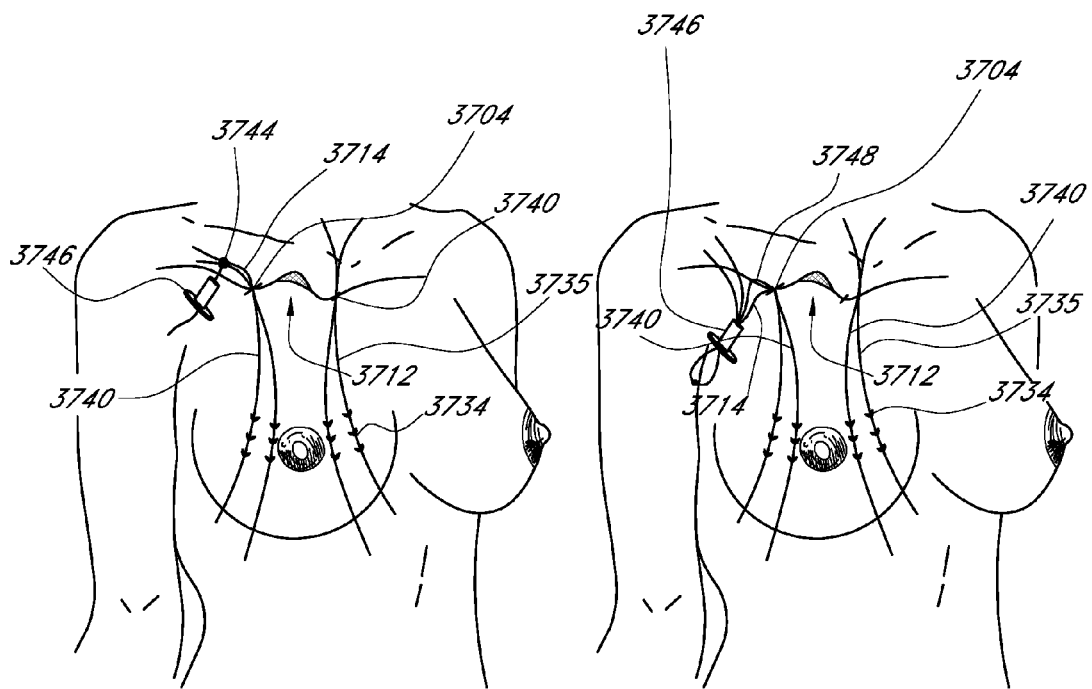
Figures 103O, 103P:
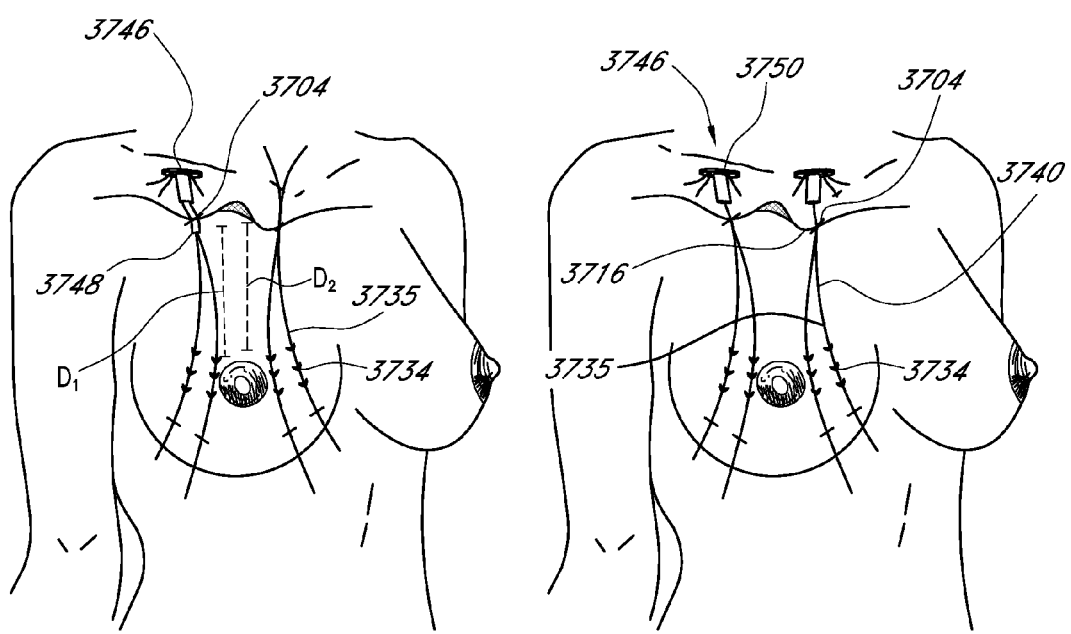

The next steps comprise coupling the anchor suspension line 3735 with the superior sling 3712. FIG. 103M illustrates, at the lateral exit point 3704, the first end 3714 of the superior sling 3712 and the proximal ends 3740 of the anchors suspension line 3735 advanced through the lateral exit point 3704 being advanced through a suture loop 3744 at a base of a knot tube 3746. FIG. 103N depicts the first end 3714 of the superior sling 3712 and the proximal ends 3740 of the anchor suspension line 3735 advanced through the lateral exit point 3704 being pulled through the knot tube 3746 by the suture loop 3744. Once they are pulled through the knot tube 3746, the suture loop 3744 is removed. The knot tube 3746 is then advanced over the first end 3714 of the superior sling 3712 and the proximal ends 3740 of the anchor suspension line 3735, and a distal end 3748 of the knot tube 3746 is advanced into opening of the lateral exit point 3704, as illustrated in FIG. 103O. The breast 3726 is then lifted, and a distance $D_1$ between the sling portion 3718 and an inferior anchor 3734 is decreased (compared with $D_2$). In some embodiments, the breast 3726 is manually distracted, and in some embodiments, the breast 3726 can be distracted by pulling on the proximal ends 3740 of the anchor suspension line 3735. The proximal ends 3740 of the anchor suspension lines 3735 are independently drawn at a hub 3750 of the knot tube 3746 and secured in position, for example, with a clamp. In some embodiments, the superior sling 3712 is clamped first. The same, or similar, steps are followed with the second end 3716 of the superior sling 3712 and the proximal ends 3740 of the anchor suspension line 3735 extending from the medial exit point 3702, as illustrated in FIG. 103P.

Figures 103Q, 103R:
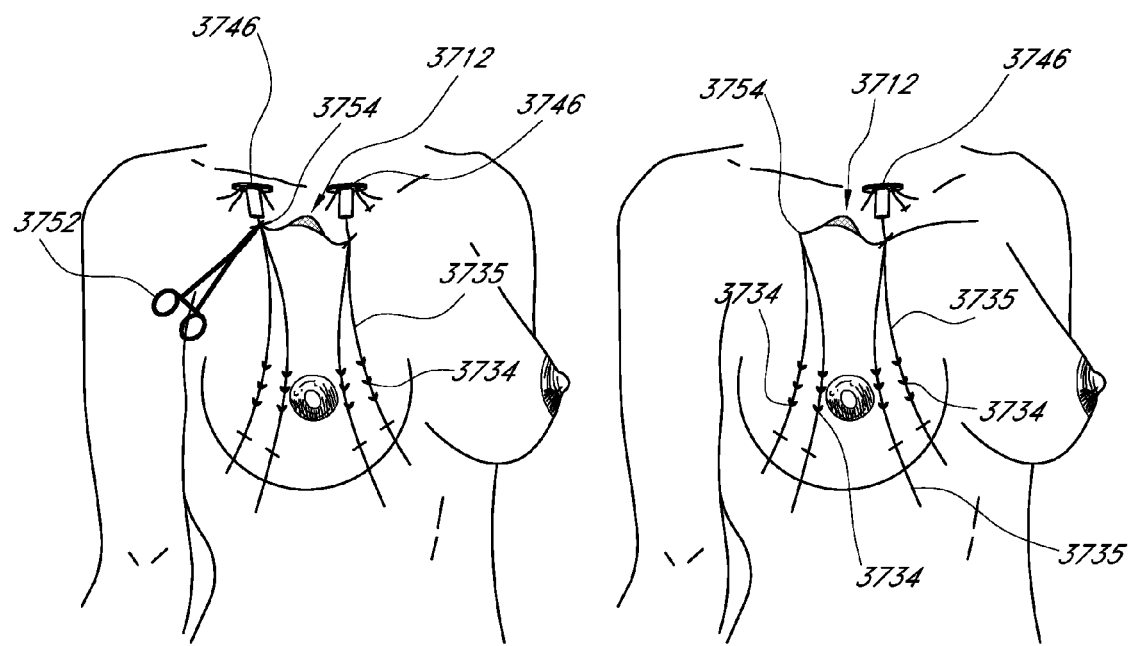

FIG. 103Q depicts the step of securing the superior sling 3712 with the proximal ends 3740 of the anchor suspension line 3735. The figure depicts lifting the knot tube 3746 until the sutures 3754, or first end 3714 of the superior sling 3712 and proximal ends 3740 of the anchor suspension line 3735, are visible at the base of the knot tube 3746. The sutures 3754 are clamped with, for example, hemostats 3752, and the knot tube 3746 is removed. The sutures 3754 are tied together using a standard surgeon's knot, and the clamp 3752 is released. The knotted sutures 3754 are then drawn back into the tissue, as illustrated in FIG. 103R. The same, or similar, procedure is followed with the other of the knot tubes 3746. The excess material from the superior sling 3712 and anchor suspension line 3735 is then trimmed and the openings at the exit points are closed, as illustrated in FIG. 103S.

The above-referenced methods and devices provide an inverted sling and anchor system that engages tissue in the lower portion of the breast where the tissue tends to be stronger and where the anchors will hold position better, in some embodiments, than with superior anchor placement. As described, multiple anchors may be attached to each end of an upper sling to adjust tissue into position relative to the pre-treatment ptosis. Upper breast fullness and lift is achieved in these techniques by moving the breast tissue toward the sterna notch. Additional movement of the nipple being repositioned is achieved by lifting the tissue associated and surrounded by the anchored tissue. In some embodiments, the procedure will both accomplish (1) adjusting a center of the tissue mass superiorly and (2) adjusting the nipple angle superiorly, and sometimes medially depending on the desired cosmetic result. This could be accomplished by implanting at least a first anchor support line (which could be 2, 3, 4, or more anchor support lines) to elevate the tissue, and then implanting at least a second anchor support line, along a different axis, to elevate or otherwise adjust the nipple trajectory.

The anchors as described above are made from bio-inert materials such as stainless steel, Nitinol or cobalt-chromium (NP35N) or polymers such as polypropylene, nylon, PEEK or Teflon. They may be integral to the suspension lines or mounted secondarily with single or multiple anchors attached to each suspension line. As they are single direction engagement, they may be repositioned or removed if desired during placement. Some embodiments utilize anchors, suspension lines, and/or sutures depicted and described above.

As discussed above, the anchor lines may be dispensed through a sheath to protect the surrounding tissue and can be engaged superior to the nipple for maximum adjustability. The anchors may also be used in conjunction with an elastomeric or spring suspension line for load absorption or the anchor can be designed to absorb the excess loading. Additionally, this technique can be modified to eliminate, limit, or reduce use of, the anchor portion and utilize a continuous length suture to create a loop at the top and bottom of the breast tissue where a gathering of tissue both top and bottom would provide a force vector similar to the discrete anchors described above. In some embodiments, the anchors can be attached to the suspension lines and about 2-4 anchors would be attached to each line. In some embodiments, a system could include at least 1, 2, 3, 4, 5, 6, or more suspension lines. For a B-cup sized breast, for example, two to four anchors could be in each breast depending upon how much lift is desired.

Figures 104A, 104B:
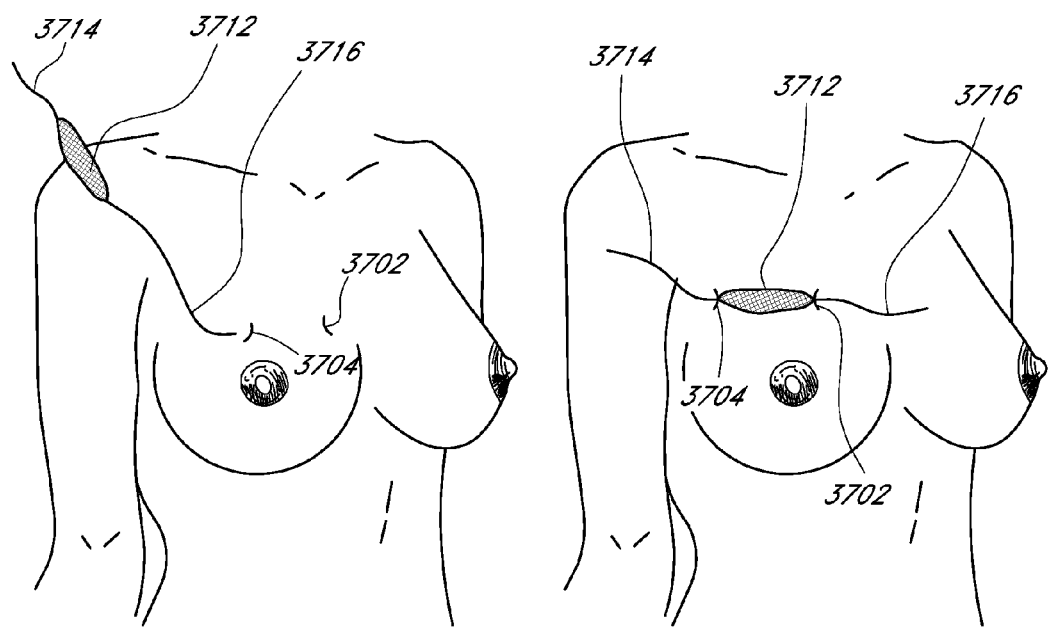
Figure 104C:
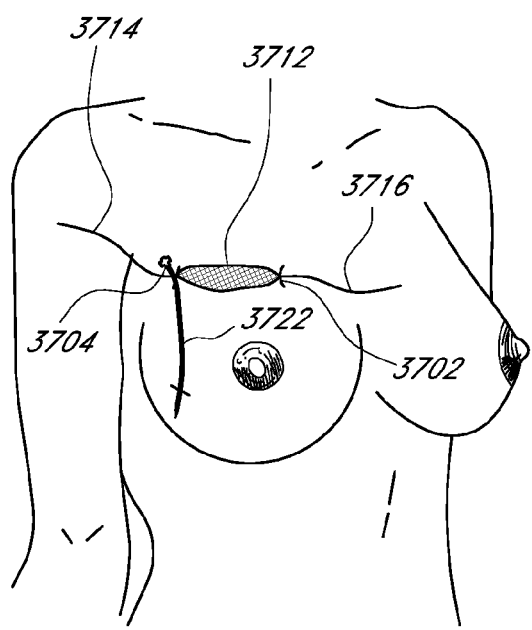
Figure 104D:
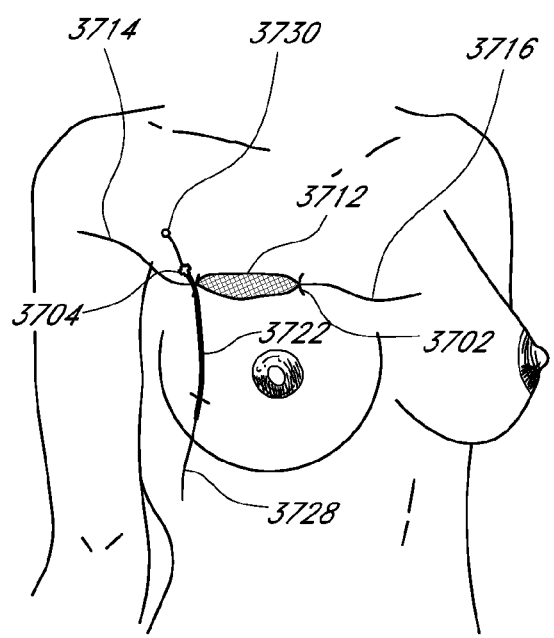
Figures 104E, 104F:
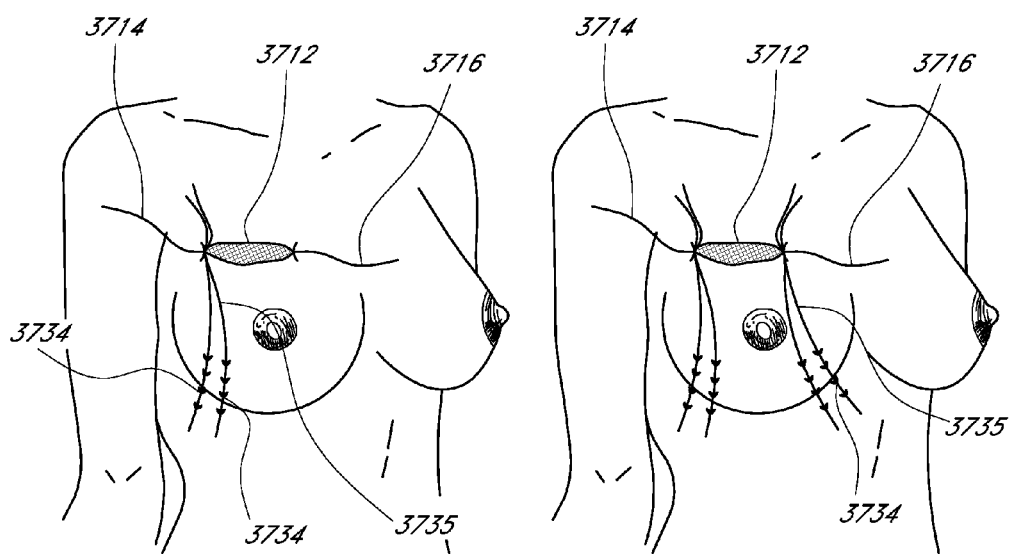

FIGS. 104A-104H depict embodiments of inserting the superior support suspension lines through two incisions. In FIGS. 104A-104B, a support element 3712 having one or more suspension lines 3714, 3716 is inserted into a first incision 3704. FIG. 104B depicts the support element 3712 inserted into the tissue and positioned between the first incision 3704 and a second incision 3702 with a suspension line 3714, 3716, or suture, extending out of the patient from two ends of the support element 3712 through the first 3704 and second 3702 incisions.

Figures 104G, 104H:
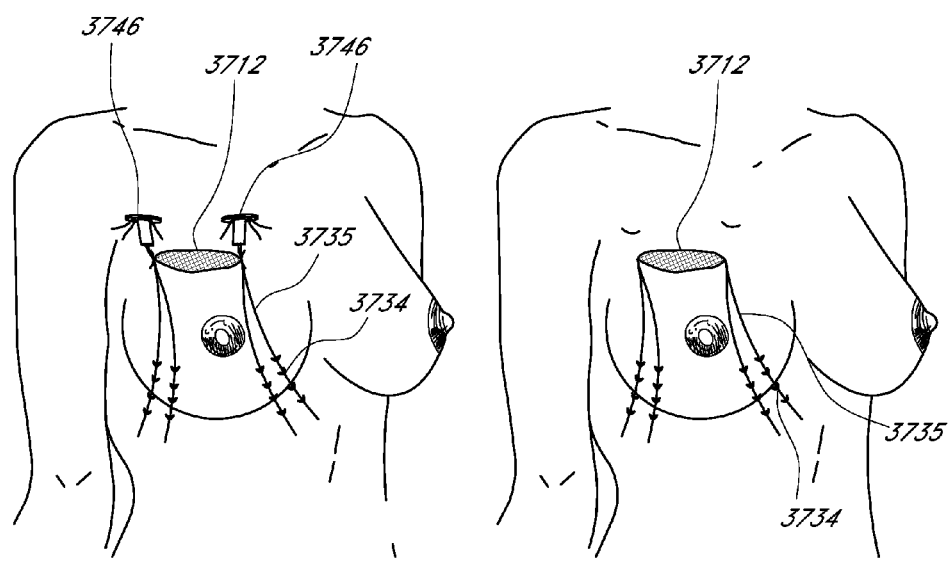

FIGS. 104C-104H depict a process similar to those described above with respect to FIGS. 103A-103S of inserting anchors 3734 inferiorly through the breast tissue, securing the superior connection of the anchor suspension line 3735 to the support element 3712, and trimming the excess line following positioning of the knots under the patient's skin. FIG. 104H depicts the support element 3712 connected to four anchor suspension lines 3735 that extend inferiorly into the breast tissue.

FIGS. 105A-105J depict embodiments of inserting the superior support suspension lines through a single incision 3756 which can be, for example, in between, such as at or near the midpoint between previously described medial and lateral incisions. These embodiments can be performed similar to those described previously with respect to an inferior approach. In some embodiments, introduction of the suspension lines follow similar processes as described above with respect to embodiments described in FIGS. 103A-103S and FIGS. 104A-104H.

Figures 105A, 105B:
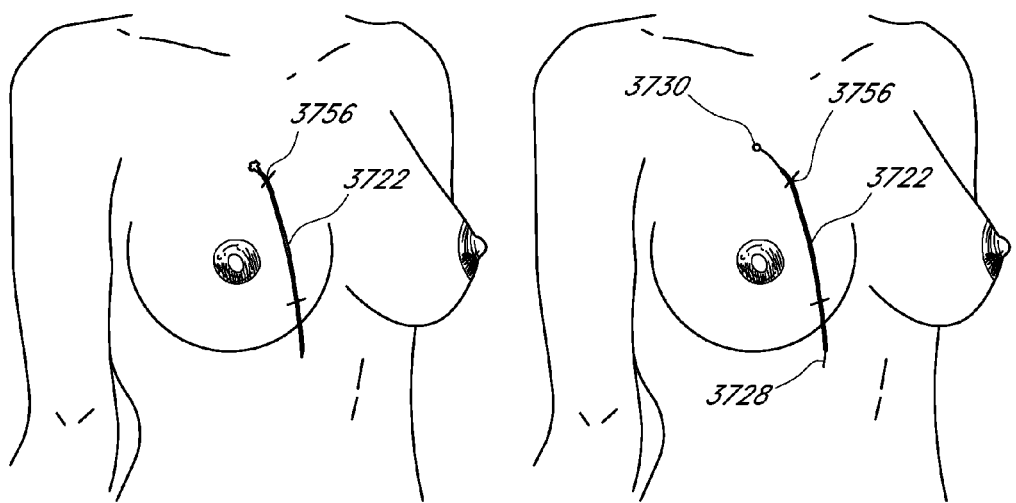
Figure 105C:
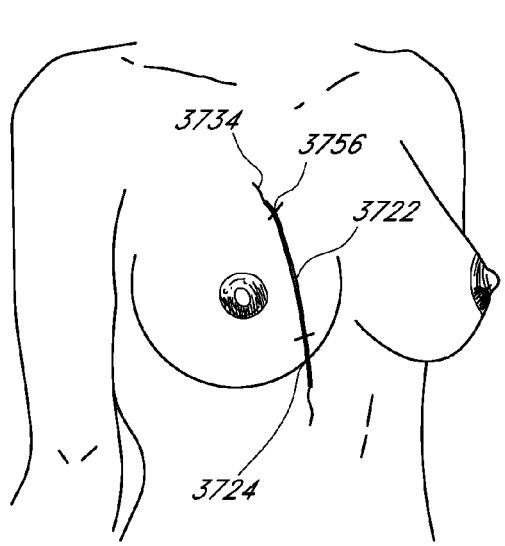
Figure 105D:
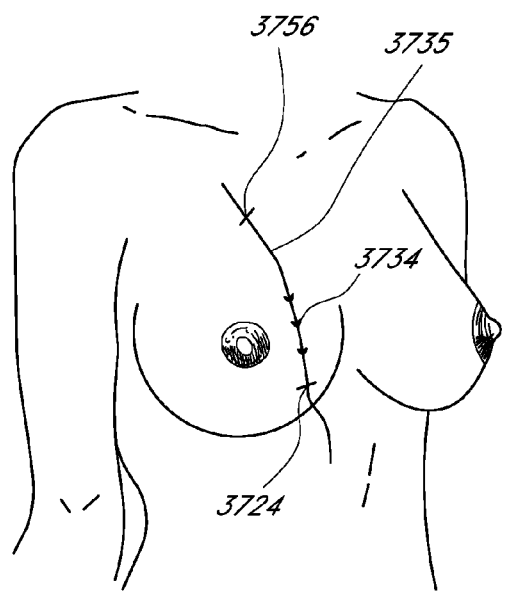
Figures 105E, 105F:
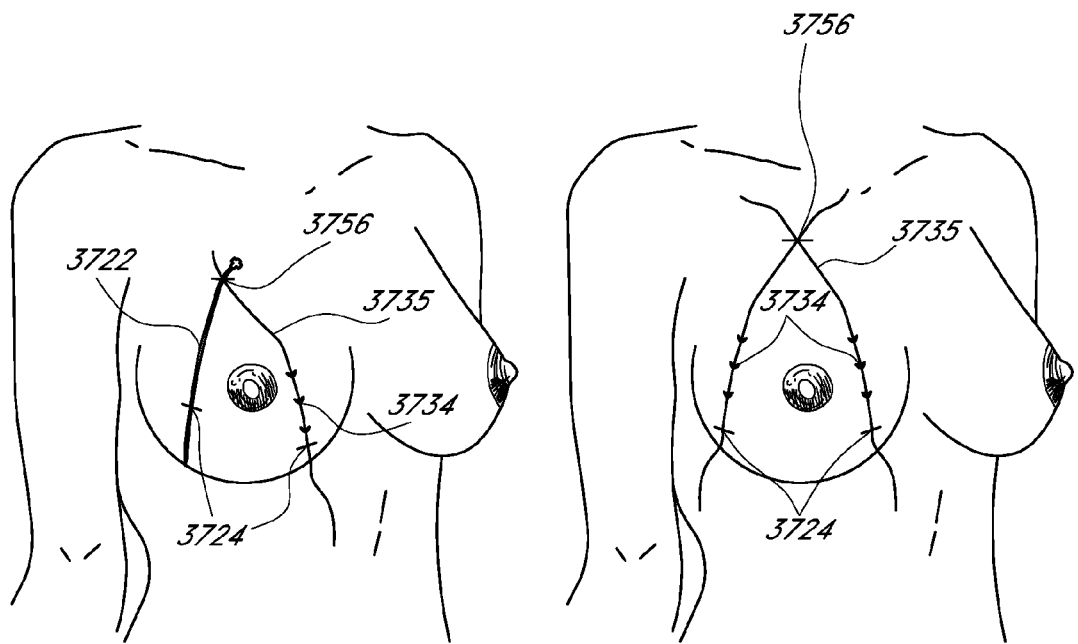
Figures 105G, 105H:
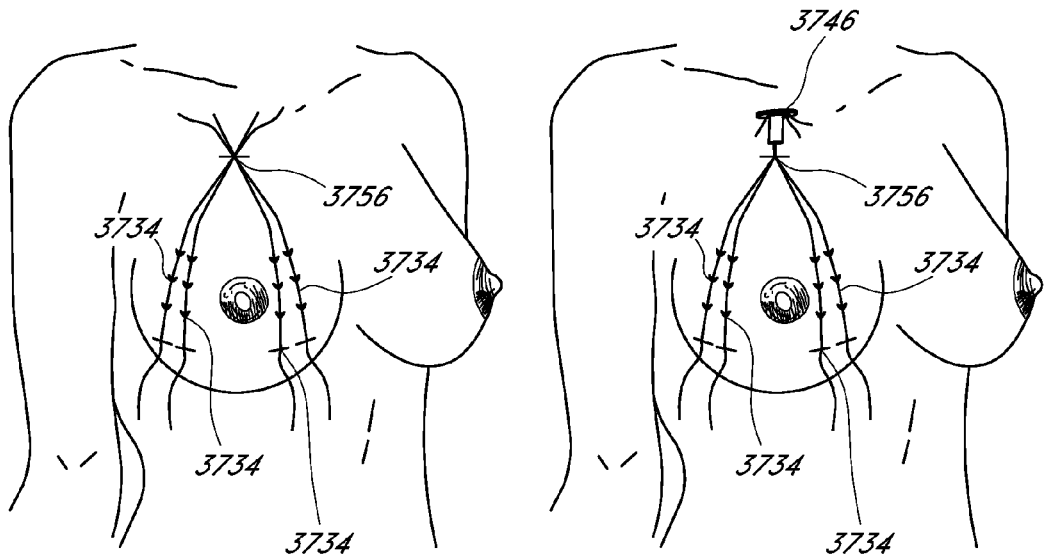
Figure 105I:
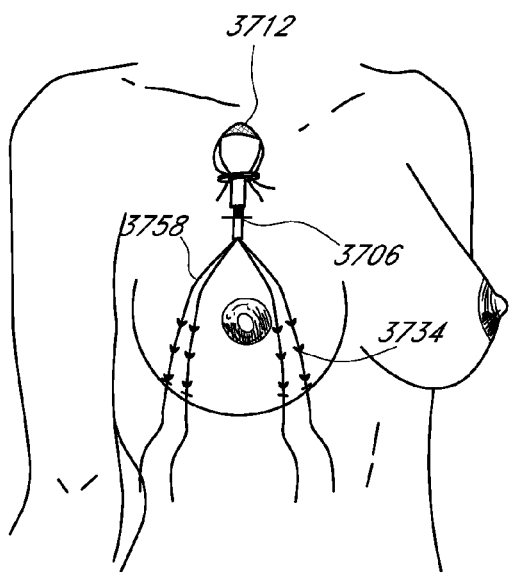
Figure 105J:
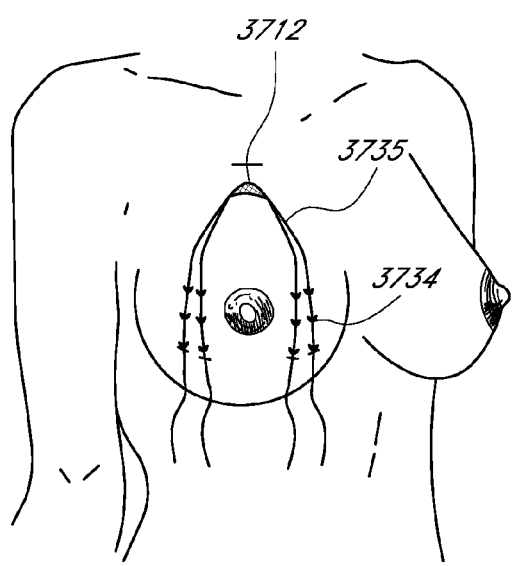

FIGS. 105A-105D depict introduction of a first anchor suspension line 3735 through the superior incision 3756 and advancement of the anchor 3734 through the breast tissue. As described with respect to embodiments above, the anchor suspension line 3735 can be advanced through an exit aperture 3724 toward the base of the breast. FIGS. 105E-105H depict that this procedure is repeated for a plurality of lines through additional inferior exit aperture 3724', and FIGS. 105I-105J depict securing of a proximal end 3758 of the plurality of lines 3735 to a support member 3712 and introduction of the support member 3712 into the tissue through a port 3706. In some embodiments, introduction of the plurality of lines 3734 can be performed through a port 3706, which can increase the depth of tissue into which the support member 3712 is ultimately placed. As explained above, in some embodiments, increasing the depth of the support member 3712 can limit or reduce the likelihood of a dimple or indentation created in the tissue after the procedure when the anchors 3734 pull on the support member 3712.

Pull-Out Force Resistance and Surface Area Properties of Superior and Inferior Anchors In some embodiments, the pull-out force of an anchor is generally greater near the top of the breast (superior) than at the bottom (inferior). Thus, in some embodiments, the force in an inferior direction required to pull out the superior anchor (e.g., the support element or sling) exceeds the force in the superior direction to pull out the inferior anchor by at least about 2×, at least about 3×, at least about 4×, at least about 6×, or even at least about 8× in certain implementations. Not to be limited by theory, but in some embodiments having anchors with dissimilar properties, such as with a more robust superior anchor with respect to the inferior anchor, can be advantageous to reduce the risk of anchor pull-out as the superior breast tissue tends to have a softer, fat-like consistency while the inferior breast tissue tends to have a tougher, fibrous-like consistency. Using the same anchors both superiorly and inferiorly that are configured to resist pull-out of the superior anchor could cause the inferior anchor to become visible, palpable, and/or cause dimpling.

The superior support element or anchor (e.g., the sling) has a first surface area that can be an inferiorly facing surface area. Each barb or other transverse aspect of the inferior anchors has a surface which has a component facing in the superior direction. The sum of all of the superior facing surface areas on all of the support lines can be considered to be a second surface area. In some embodiments, the first surface area exceeds the second surface area by at least about 2×, at least about 3×, sometimes at least about 5× and sometimes at least about 10×.

In some embodiments, the top support load of the superior anchor (e.g., the superior sling) will be distributed over a relatively large surface area, which can advantageously reduce potential shear forces as compared to an anchor with a smaller anchoring surface area. In certain embodiments, the top load will be distributed over an area that is at least about 1 cm$^2$, 2 cm$^2$, 3 cm$^2$, 4 cm$^2$, 6 cm$^2$, 8 cm$^2$, 10 cm$^2$ or more.

In some embodiments, the implanted system is free floating to some extent (e.g., not suspended to bone or cartilage) both superiorly and inferiorly to optimize natural motion of the tissue. The superior sling acts like a leaf spring under load, since the anchor support lines will bend the ends of the sling inferiorly (decrease the radius of curvature of the sling). However, the radius of the sling will resiliently rebound once the transient load is removed. In addition, the transverse elements of each anchor could act like a small lever under load. The net effect is to dampen the effects of intermittent loading cycles to advantageously preserve native tissue resiliency, look and feel, and could also help avoid anchor pull out under high loads.

Minimally Invasive System as an Adjunct to Surgical Mastopexy

While the systems and methods described herein can be used as part of a stand-alone minimally invasive tissue lift or mastopexy system, they can also be used as an adjunct to a surgical mastopexy (or lift procedure of any tissue other than breast tissue) to produce improved fullness, for example, in the superior medial quadrant. Surgical mastopexies elevate nipple trajectory but often leave a mild concavity or flatness in the superior medial quadrant. In some embodiments, a patient requiring mastopexy can be identified, and a surgical mastopexy can be performed along with implanting the minimally invasive system as described herein. The minimally invasive system implantation can occur concurrently (e.g., while the patient is still in the operating room, on the same day). In other embodiments, a patient that has previously had a surgical mastopexy with suboptimal results could have the minimally invasive system described herein implanted as a revision or "tune-up" procedure. In some embodiments, the revision procedure of implanting the minimally invasive mastopexy system can occur within 1 day, 1 week, 2 weeks, 1 month, 2 months, 3 months, 6 months, 1 year, 2 years, 3 years, 4 years, 5 years, or more of the surgical mastopexy procedure.

Materials & Construction

Elements of the support system can comprise a number of materials including, without limitation, biocompatible polymers (e.g., ePTFE), intestinal sub-mucosal mesh, tendon, Gore-Tex®, and polypropylene. Materials can be monofilament, or multifilament, and can be braided, woven, or knitted. In some embodiments materials are absorbable (i.e., biodegradable). In some embodiments, the materials comprise coatings or other agents that promote healing, reduce inflammation, or improve biocompatibility.

In some embodiments, the use of biological materials can improve tissue interaction with the device. Where a lack of tissue ingrowth or vascularization is a concern, the materials can be further modified by perforation, or by other treatments such as fixation with radiation, glutaraldehyde, heat or 1-ethyl-3-(3-dimethylaminopropyl)-carbodiimide (EDC), to improve porosity.

In some embodiments, the mesh material of the support member, for example a sling or hammock, comprises a flexible, polypropylene monofilament that resists weakening or degradation when implanted within a patient. One such material is Marlex. Other mesh and non-mesh materials, can comprise, but are not limited to, synthetic biomaterials, allografts, homografts, heterografts, autologous tissues, materials disclosed in U.S. provisional application Nos. 60/263,472; 60/281,350; and 60/295,068; the contents of all of which are herein incorporated by reference in their entireties, synthetic materials (such as metallics, polymerics, and plastics) and any combinations thereof.

In some embodiments, the support member material will result in minimal or no reaction with body tissues and fluids and indefinitely retain its particular material characteristics and mechanical properties. Further, portions or all of the support member can be configured or fabricated from a material to either promote or prevent tissue in-growth, or are resorbable.

In some embodiments, the support member, support member assembly or portions thereof, can have one or more substances associated therewith through processes such as coating, impregnation, or combinations of these processes. Examples of appropriate substances include, without limitation, drugs, hormones, antibiotics, antimicrobial substances, dyes, silicone elastomers, polyurethanes, radiopaque markers, filaments or substances, anti-bacterial substances, chemicals or agents, and any combinations thereof.

The substances can be used to enhance treatment effects, reduce potential rejection by the body, enhance visualization, indicate proper orientation, resist infection or other effects. For example, a substance such as a dye may be coated on one surface of a component of the support system. The dye can provide the practitioner/surgeon with a visual indicator to aid in orienting the support member or suspension members at the target site within the patient and to avoid undesirable twists along the length of the system. In some embodiments, one or more components can be configured to be visualized transcutaneously. As another example, the system may be coated by the process described in U.S. Pat. Nos. 5,624,704; 5,756,145; 5,853,745; 5,902,283 and 6,162,487; the entire contents of which are hereby incorporated by reference.

It will be apparent to those skilled in the art that varying geometries for the components of the device will be useful. For example, certain dimensions of thickness, width, or length will be recognized as being of particular advantage. In addition, components that are woven, braided, wide or narrow can also provide particular support functions.

For example, as described above, in some embodiments the support member comprises a "hammock" or "sling" shaped element. A sling or hammock can be especially useful for supporting glandular tissues, such as breast tissue. In some embodiments, a hammock with dimensions of about 7 cm to about 15 cm in length, and about 2 cm to about 5 cm in width, with a pocket of about 0.5 to about 3 cm, provides effective tissue support. In some embodiments, a hammock can have a length of about 10 cm, a width of 2.5 cm and a pocket depth of about 1 cm. In manufacturing a hammock, the particular shape can be formed by wrapping the material about a spherical or elliptical shaped mandrel, followed by heating and cooling the mandrel to induce the material to conform to the shape of the mandrel.

A sling (or hammock) can comprise first and second major surfaces, a pair of end portions, and a support portion for placement in a therapeutically effective position relative to a physiological environment intended to be supported (e.g. the glandular tissue of the breast). In some embodiments, the sling has a tension adjustment or control member associated with the sling, for transferring sling adjustment forces from one portion of the sling to other portions of the sling such as the ends of a support portion of the sling. The member affords effective repositioning of the sling while avoiding undesirable permanent deformation of the sling.

The support member can be substantially surrounded by a protective sheath. The support member, tension control element, and sheath can be made of biocompatible materials with sufficient strength and structural integrity to withstand the various forces exerted upon these components during an implant procedure, and/or following implantation within a patient. In some embodiments, the protective sheath is constructed of a material that affords visual examination of the implantable support member material and that affords convenient passage of the assembly through tissue of the patient.

In some embodiments, a woven mesh with a predetermined pore or opening size to permit tissue ingrowth can be used. The shape of the openings is not considered limiting to the scope of the present disclosure, and square, rectangular, and/or round openings are useful. In some embodiments the size of the openings can vary, for example and without limitation, from an area of at least about 0.1 mm2 to no more than about 30 mm2. The arrangement of pores can vary throughout the device in order to provide some areas with added porosity, or to provide more support. Some areas can comprise pores, while in other areas pores can be absent. The device can be produced from elastic materials, or alternatively can be fashioned from relatively rigid materials.

In some embodiments, the mesh-like support member is woven from a monofilament line. Some monofilament lines are finished with a smooth surface, while others are roughened during the manufacturing process. Roughening the surface increases surface area and thus increases opportunities for tissue ingrowth throughout the surface interstices.

Roughening can be accomplished during the extrusion process where the material is flowing through the extrusion die hot thus creating a dimpled surface. Other roughening methods include, without limitation, sanding, grinding, roll forming, laser etching, chemically etching, and spirally or radially scoring to a predefined depth with a cutting blade, laser, or other means. Examples of sanding may use a 5-100 grit sand paper pulled across the material. This drags portions of the material along the longitudinal axis and leaves behind whiskers or microscopic barbs that can also be effective to engage the tissue. A similar process could be used with a grinding wheel. Grinding can be performed in a radial pattern, a helical pattern, or a combination of patterns. Roll forming allows for a predetermined shape or pattern to be pressed into the monofilament, and can be performed either with a heated roll or at ambient temperatures.

Laser etching allows for an inline process to be added to the formation of the monofilament. The laser can be angled or focused directly perpendicular to the material. Chemical etching removes material at a predictable random pattern and a predefined depth based on chemical strength and length of contact with the material being etched. Other materials can be plasma etched to create a desired surface finish where a chamber is pumped to a preset base pressure and gas is introduced and a radio frequency field is applied to the electrodes of the chamber producing a glow-discharge plasma.

Knife scoring allows a partial cut to the material to a predetermined depth leaving behind a ribbed monofilament material that will be more flexible and allow tissue ingrowth to the cut sections. These cuts can also be in a spiral patterning to allow a continuous cut throughout the material length. This also allows for tissue ingrowth.

In some embodiments, partially or completely absorbable materials are used, such that a component(s) can be absorbed over a period ranging from about 6 weeks to about 2 years. This allows the skin and other tissues to retighten and remodel, while otherwise being supported in a desired position. Other methods are also useful in remodeling or tightening the skin around the breast including, without limitation, forced scarring, use of laser, heat, and the like.

In some embodiments, the overall dimensions of the support member assembly, including individual sheath, mesh element and tension control member, are effective to extend from the upper most connection point down partially encircling the lower portion of the breast and back up to the upper most portion of the connection point, with additional length to account for the imprecision associated with the range of human anatomy sizes. In some embodiments, the support member has a length, width, and thickness of within the ranges of length: 8 cm to 16 cm, width: 1.0 cm to 6.0 cm and thickness: 0.10 mm to 1.0 mm. In addition, the length of the tension control element can be approximately equivalent to or slightly longer than the length of the support member to tighten or loosen the sling after it is placed in the body. Alternative lengths, widths and thicknesses can also be used, depending on the particular anatomical features of the individual patient, and the tissue(s) being supported.

In addition, the size of the resultant openings or pores, in support members configured as a mesh, can be adapted to allow tissue in-growth and fixation within surrounding tissue. The quantity and type of fiber junctions, fiber weave, pattern, and material type influence various sling properties or characteristics. Non-mesh sling configurations are also included within the scope of the invention.

As an example, and not intended to be limiting, the mesh can be woven polypropylene monofilament, knitted with a warp tricot. The stitch count can be 10±1 courses per cm, and 5±1 wales per cm. In an exemplary mesh, the mesh thickness can be 0.6 mm.

The support system of the present disclosure is not limited by the need for additional sutures or other anchoring devices, although such sutures and devices can be used if desired. The frictional forces created between the system and patient tissue are effective to prevent movement and loss of tension once the system is properly located at the target site. As a result, the system remains securely in place, even when subjected to various forces imparted on the tissue as will in the patient during various activities.

The system is designed to remain within the body of a patient as an implant for a predetermined therapeutically effective amount of time. Implantation can be temporary or permanent. The system can be non-absorbable, absorbable or resorbable, including any combinations of these material properties, depending on the desired treatment. For example, portions of the system may be constructed of a bioabsorbable material designed to last for a predetermined period of time within the patient. The general characteristics of the materials and design used in the system will withstand the various forces exerted upon it during implantation (for example, frictional forces associated with tissue resistance) and after implantation (for example, normal activities, including walking, running, coughing, sneezing, and other "normal" activities).

The system as disclosed can be anchored to a variety of locations in the body, including, but not limited to fascia, muscle, bone, ligament, and the like. In addition, an anchor can further comprise an adjustment device that permits the surgeon to adjust the tension on the suspension members either at the time of implantation, or post-implantation. The adjustment device can be a simple screw-like mechanism, around which an end of the suspension line is wrapped. Turning the screw in one direction increases the tension on the line, while turning in the opposite direction decreases tension. In some embodiments, the tensioner is adjusted through a small incision using an endoscope or other like instrument, in combination with a tool designed to turn the tensioner.

In some embodiments the suspension members can be anchored to a single attachment point. In some embodiments multiple attachment points are used. The elements of the devices can be elastic, or non-elastic as desired. In some embodiments, a braided portion overlying an elastomeric portion is used. In some embodiments, the braided portion is also elastomeric.

Design/Fabrication of Anchor, Mesh Sling System

FIGS. 106-107 shows a schematic of some examples of tools and devices that can be involved in the implantation of the anchor and sling support system, of which details of further embodiments will be disclosed. In some embodiments, one, two, or more of the tools and devices described herein can be part of a system or packaged together as part of a kit. FIG. 106 schematically illustrates a needle 3802 that can be configured to create a subcutaneous tissue pathway for the support element or sling. The needle 3802 can have any desired shape depending on the desired clinical result. In some embodiments, the needle 3802 forms an arc of about 180 degrees. FIG. 107 illustrates an alternative needle 1803 that forms an arc of about 270 degrees. In some embodiments, the needle forms an arc of between about 120 and 330 degrees, between about 180 and 270 degrees, or at least about 150, 165, 180, 195, 210, 225, 240, 255, 270, 285, or 300 degrees in some embodiments, but less than 360 degrees.

Referring back to FIG. 106, also illustrated is a needle 3720 that can be disposed within a cannula 3722 to create a subcutaneous pathway 3800 (dashed line) for one or more inferior anchors (not shown). In some embodiments, the needle 3720 is curved and having a radius of curvature of between about 6" and 12", between about 8" and 10", or about 9" in some embodiments. In some embodiments, the needle 3720 has a total length of between about 6" and 12", between about 8" and 10", or about 9". Also illustrated is the a superior entry point 3704 and inferior exit point 3724 that can be as previously described.

In some embodiments, an example of a system or kit includes one, two, or more of the following items:

Trocar and port dilator for creating one or more superior ports

Superior port with one, two, or more lumens, to allow for insertion of other instruments such as a superior support element Superior support element insertion tool, such as a curved needle for creating a tissue pathway for a superior support element (e.g., a sling)

Inferior anchor insertion tool, such as an elongate needle that may be disposed within a cannula, for creating a tissue pathway for an anchor along a generally superior-inferior axis Elongate wire, such as a feeder rod, that can have a coupling element such as a loop on the proximal and/or distal end for releasable connection to the inferior anchor line Knot tube having a hub for releasably housing an end of the inferior anchor lines therethrough One, two, or more clamps, such as hemostats for releasably holding an end of the inferior anchor lines, such as when running through the knot tube Superior support element, such as a sling assembly, including an elongate, flexible sling that can be operably connected to a first suture for connection to a first inferior anchor line and a second suture for connection to a second inferior anchor line One, two, three, four, or more anchor lines, each having one, two, three, or more inferior anchors Connector to connect the sling assembly and anchor line, such as a retainer—wedge device configured to maintain a desired suture tension Adjustment element, such as a spool tensioner to allow for tensioning of the suture lines in situ as described further below Various combinations of the above elements as well as any of the other items mentioned elsewhere in the disclosure can also be made part of a system or kit.

Anchor Line Assembly

In some embodiments, the anchor could be injection molded, extruded, or created using other known techniques. The anchors could also be heat treated to increase the performance of the implanted material by increasing the strength and decreasing the potential water absorption during implantation time. The heat treatment could also be used to tailor the durability, or conversely the bioabsorbability of the anchor.

The heat set PET rod 4000 is cut at an angle, such as about 45 degrees to produce two anchors 4010, each about 15 mm in length with one rounded end 4004 and one cut end 4006. A small blade is used to pierce an aperture 4008 that is about 0.065"×0.013" through the center of the anchor 4010 as shown in FIG. 108. The aperture 4008 could be oriented lengthwise along the long axis of the anchor 4010 as shown, or transversely or at an angle in other embodiments.

Figure 109A:
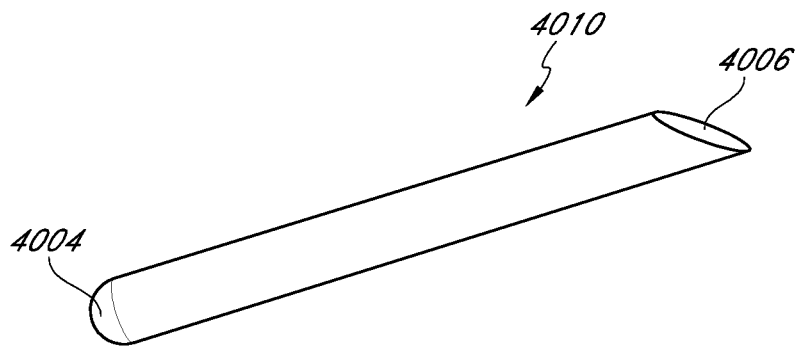
Figure 109B:
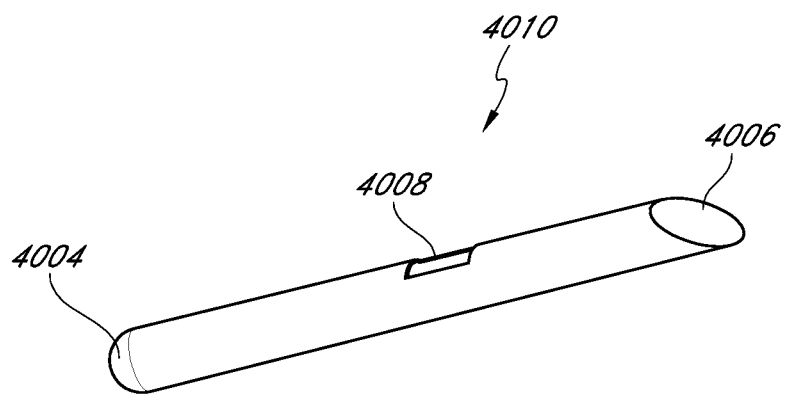
Figure 109C:
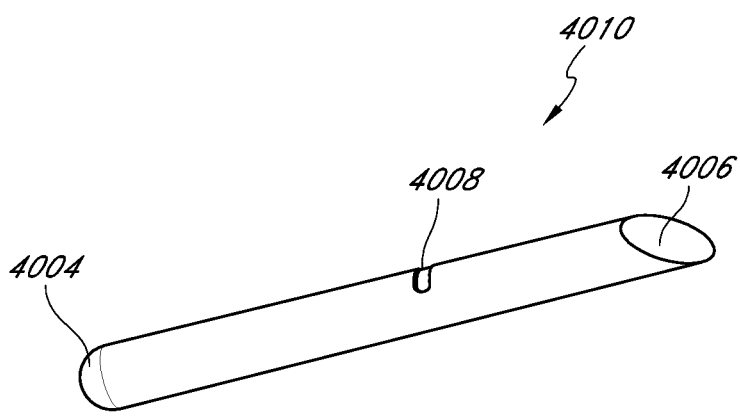
Figure 109D:
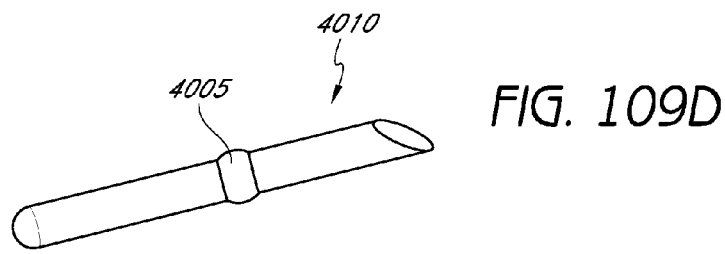

FIGS. 109A-109C depict various embodiments of an anchor 4010. FIG. 109A depicts an anchor 4010 prior to the hole 4008 being cut through the center. FIGS. 109B-C show the anchor 4010 with a hole 4008 through its center. FIG. 109B illustrates that the aperture 4008 is a slit oriented lengthwise parallel to the long axis of the anchor 4010. FIG. 109C illustrates an arcuate-shaped aperture 4008. The anchors may alternatively have a non-circular cross-section. For example, an anchor may have a tapered design, rectangular cross section, or contain a member that is hinged.

Figure 109E:
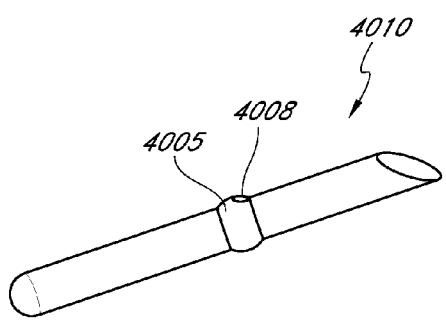
Figure 109F:
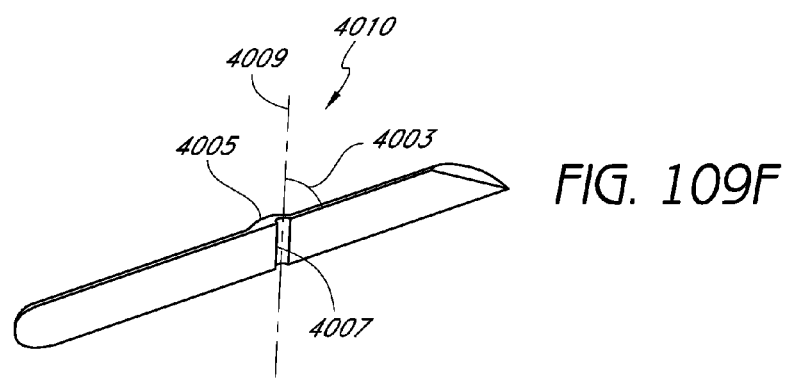
Figure 109G:
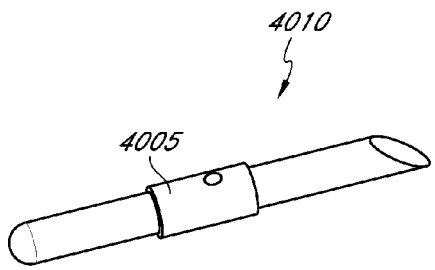

In some embodiments, anchors 4010 such as the ones shown in FIGS. 109D-G have a reinforcing component 4005 such as a band, or the anchor 4005 could be alternatively have an integrally formed or welded central portion made of a stronger material and/or larger outside diameter that could provide a larger cross-section that could aid in making the anchor 4010 stronger at the region of relatively greater stress in order to reduce the risk of fracturing of the anchor 4010. In certain embodiments, there is a benefit to keeping the anchor 4010 smaller on both ends as the suture (not shown) and anchor 4010 will lie side by side which increases the crossing profile. Additionally, having a noncircular cross section might optimize the anchor line profile. For example, the anchor could have a semi circular cross section allowing the suture to lay in the remaining space, for a smaller overall "round" crossing profile. In the designs shown in FIGS. 109D-G, the suture could actually be crimped or compressed down inside the hole 4008. If the anchor 4010 is essentially in-line with the suture, it may have the tendency to deploy in parallel with the suture. Placing an acute angled cut at the tip of the anchor, as illustrated in FIG. 109E and in cross-section in FIG. 109F, could assist in directing the anchor away from the suture pathway. The orientation of the suture exiting from the anchor is also an important feature in certain embodiments that may determine anchor placement. The anchors in FIGS. 109D-G show that the hole may be cut at different angles to aid in directing the angle that the suture exits and therefore the path at which the anchor travels into the tissue with respect to the suture pathway. In many cases, maintaining the anchor more perpendicular to the suture pathway will increase the load carrying ability. In some embodiments, the aperture 4008 has a central axis 4009 that forms an angle 4003 with the longitudinal axis of the anchor. The angle 4003, in some embodiments, can be about 90 degrees, or between about 10 and 90 degrees, such as between about 30 and 60 degrees, or about 45 degrees in some embodiments. FIG. 109G illustrates an embodiment of an anchor 4010 with a relatively longer reinforcing component 4005. In some embodiments, the reinforcing component 4005 has a length that is at least about 5%, 10%, 15%, 20%, 25%, 30%, or more of the total length of the anchor 4010.

In one embodiment, the suture component 4014 is comprised of braided PET material, wound into a 16 carrier braid with 28 picks per inch that can be cut into lengths. Alternatively, the suture component 4014 may also be comprised of any other appropriate materials, such as monofilament PTFE or polypropylene for example.

Figure 110A:
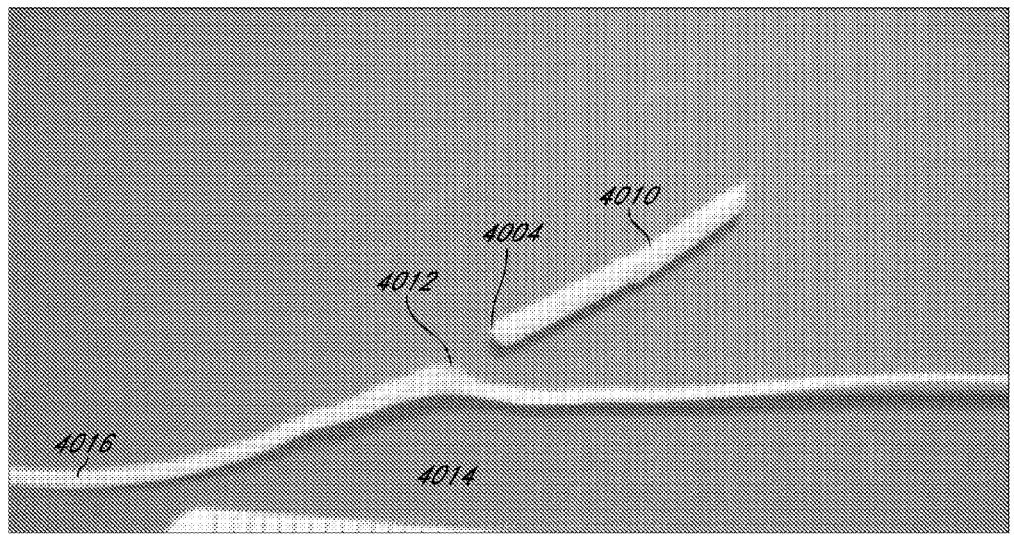
Figure 110B:
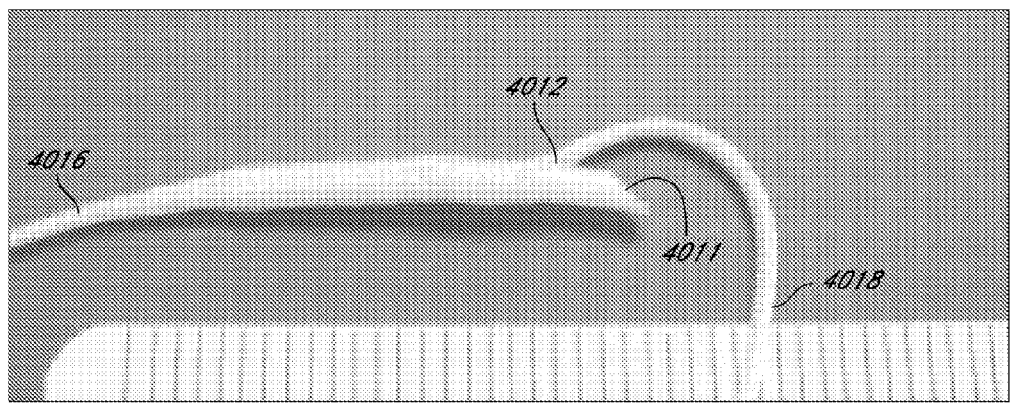
Figure 110C:
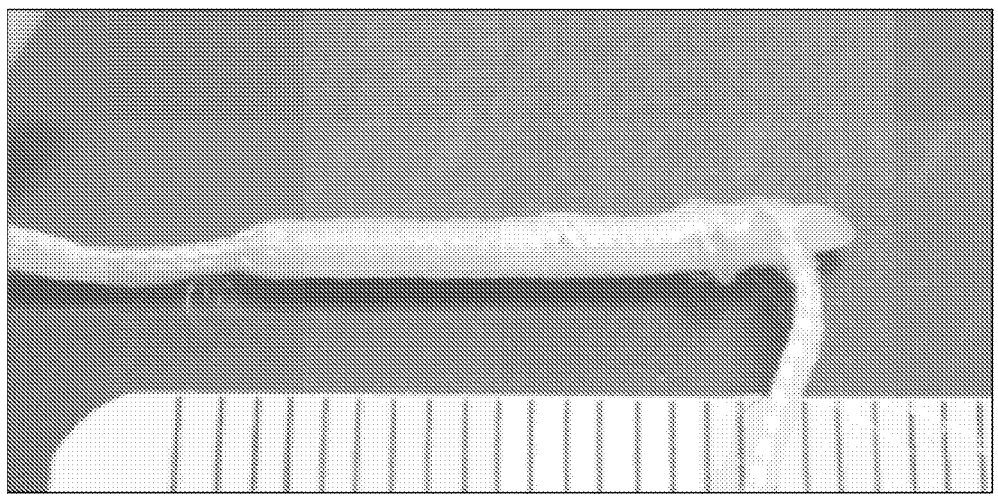
Figure 111:
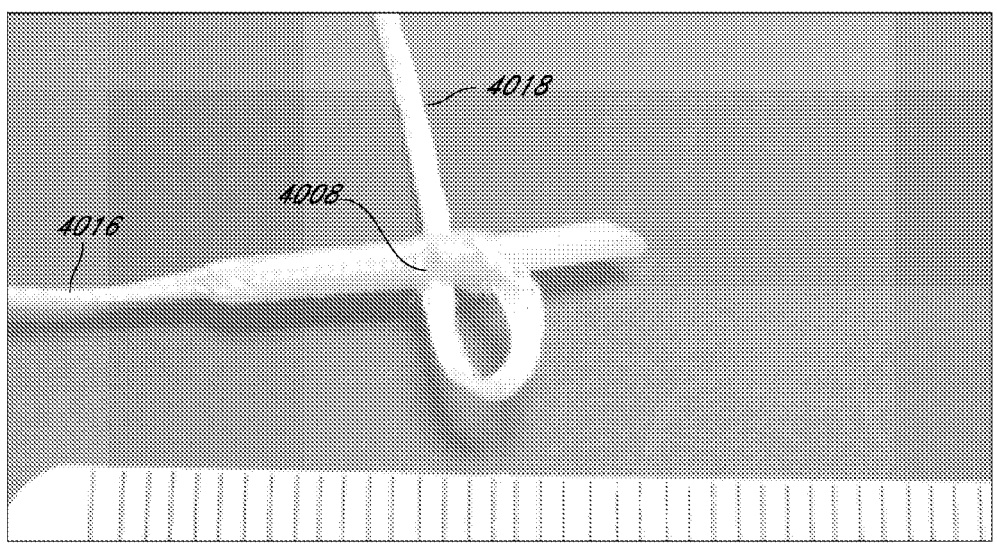

In one embodiment, the anchor 4010 is inserted into the suture component 4014. FIG. 110A illustrates the anchor 4010 prior to its insertion into the suture component 4014 at the insertion point 4012. The anchor 4010 is inserted into the insertion point 4012 rounded end 4004 towards the tail 4016 (lower suture) as shown in FIG. 110B. The anchor 4010 is inserted into the suture 4014 such that the exposed tip 4011 can be used to pierce through the braid 2 to 4 strands up from the insertion point 4012 as shown in FIG. 110C. Next, 1 to 3 strands are separated creating a gap over the anchor piercing 4008 such that the upper suture 4018 can be directly inserted as illustrated in FIG. 111. To maintain a small crossing profile, the upper suture 4018 is pulled tight through the anchor 4010. This process is used to prevent the anchor 4010 from sliding with relation to the suture line 4014.

In other embodiments, additional anchors may be placed following the same procedure from lowest anchor to highest. This forms a maximum crossing profile of the diameter of the anchor and 3 layers of the diameter of the suture line.

Sling Assembly

In one embodiment, the sling assembly is comprised of woven polypropylene tape 4020. In one embodiment, the polypropylene tape 4020 has a 0.006 inch warp and 0.004 inch weft and is cut into 35 mm lengths. A heat sealer is used to bond together the strands creating a sling 4032.

In one embodiment, a suture 4030 comprised of polyethylene terephthalate (PET), wound into a 16 carrier braid with 28 picks per inch is cut into 64 cm lengths. The suture 4030 is woven through the sling 4032 in a zig-zag pattern that will allow the sling to act as a strain relief under tension and maintain a flat or substantially flat configuration when implanted. Each end 4034 of the sling 4032 can be secured to the main suture with a USP 5.0 size 8 carrier braid, 60 picks per inch PET suture line. This smaller suture line is looped around the center portion of the sling and the main suture multiple times. It is then looped in a fan array from the end of the sling 4032 through the lower portion of the main suture 4016. This process is repeated again at the opposite end of the sling. FIG. 112 shows the position of the sling assembly between the tail lengths 4016 of the main suture line 4014.

Anchors may be supported from a generally superior location in a variety of ways. One embodiment uses a sling type mesh that will support anchor lines from each end of the sling. The sling is used to spread the load of the anchor lines over a large area of tissue preventing the line from cutting through tissue due to the weight of the tissue pulling on the anchor lines. In some embodiments, a range of mesh slings could be 4 mm wide by 15 mm long to 20 mm wide by 100 mm long, depending on the mass to be supported. The sling can be tapered at both ends to ease entry of the device through the skin. The sling is positioned in an arched configuration that can be convex or concave in some embodiments using a curved needle as described above to create the proper placement. The arch helps to prevent the sling from folding thus reducing its effective surface area. Suture line is woven through the sling from end to end in a sinusoidal path to give greater strength to the suture-sling connection and to further keep the sling from folding.

Anchors can also be supported superiorly by other anchors inserted upward. This situation creates tension between the two sets of anchors each keeping tension on the other.

Variations on Anchor Design

Further reduction in crossing profile is possible through use of a two piece anchor 4040 in which the suture (not shown) is inserted into a hole 4042 in the leading end 4044 and held in place with pins 4046 pressed from the first length 4048 through the suture 4012 and into holes 4050 in the second length 4052 as shown in FIGS. 113A-C from both a lateral and an axial perspective. FIG. 113A shows the whole two piece anchor 4040 and the locations of the split line and the hole 4042 in the rounded, leading end 4044. FIG. 113B shows the first half 4048 of the anchor with the pins 4046 pushed through it. FIG. 113C shows the second half of the anchor with the holes 4046 for receiving the pins.

The suture may also be held in place by creating a dovetail or square wave type path between the anchor parts. This reduces the crossing profile by moving the suture 4014 from the outside to the inside of each anchor. FIG. 114A illustrates one piece of a 2 piece anchor with a channel 4056 for the suture to sit in and protrusions 4058 on the inside of the channel 4056 to lock in the suture 4012. The mating half of the anchor would be complementary to the half shown in FIG. 114A. The anchor may also be over-molded onto a line or wire for a secure hold and reduction in profile in other embodiments.

FIGS. 114B-C depict other embodiments of 2 piece anchors. FIG. 114B shows a first half of a 2 piece anchor with a trough 4043 that the suture could be placed into with pins 4045 that will lock the anchor into the suture. Pins 4045 are added to help align the tip side 4049 of the anchor. Another ridge 4047 may be added to the entire length of the anchor which would aid in strength and cohesion of the anchor. FIG. 114C shows the mating part that is connected to the anchor half shown in FIG. 114B to lock in the suture. The two pieces may be connected in a variety of ways including the mechanical snaps shown in FIGS. 114B-C, or alternatively, for example, press fits, heat, adhesive, ultrasonic welds, or solvent. FIG. 114D shows the two halves of a 2 piece anchor ready to be mated together. FIG. 114E shows a complete 2 piece anchor with the two pieces mated together.

A benefit of this design is added strength for increased clinical durability. The parts may simply be attached, such as by snapping on, and additionally adhered if necessary. The design may not, in some embodiments, have a need for piercing, threading, suturing, or knot tying, all of which might degrade the strength of the components. Parts may be put together manually or in an automated fashion. For example, two feeder bowls that contain the left and right parts, respectively, may be used. The parts may then be aligned and fastened to the suture in a conveyor type system. This may add to increased quality while also improving manufacturing efficiency.

In another embodiment, a 2 part anchor may utilize a suture that has a knot in it. This would add to the mechanical holding ability without relying as much on the protrusions or tabs to pierce through the suture.

A multiple piece anchor may also "scissor" out from the insertion line, or in other words expand radially outwardly, such as via a shape memory setting or radially outward bias to create a double barb to hold tissue as shown in FIG. 115. In some embodiments, an anchor could have at least 2, 3, 4, 5, 6, 7, 8, or more barbs extending radially off a single point off the insertion line.

In one embodiment, the anchor is made from a polyester, more specifically polyethylene terephthalate or PET. Other materials that could be used include, among others, polyetheretherketone (PEEK), polyester, nylon or other polymers, metals, and ceramics. Materials, including the anchors, insertion lines, and the sling may be permanently implantable for a long effective life or alternatively biodegradable/bio-absorbable such that the implant is effectively removed from the tissue in a given amount of time. Materials may be coated to prevent tissue ingrowth onto the anchor or coated with a tissue ingrowth material such that tissue will grow into the anchors. In some embodiments, one or more of the anchors, insertion lines, or sling could be coated with a drug, for example, an antibiotic.

The surface finish of the anchor may be smooth for ease of delivery or textured for greater contact area and hold on the tissue. The exposed tip of the anchor may skew out at an angle to assist it in the transition from 0 to 90° when applying tension. The tip may be forked to gain a hold on the tissue and to prevent it from sliding longitudinally.

In one embodiment, screw-type threaded anchors are used. Screw type anchors may be drilled directly through the skin or delivered to a preferable site via a cannula. In one embodiment, threaded devices may range in length from 1 cm to 10 cm, and in diameter from 2 mm to 10 mm. Thread pitch may range from 2 to 20 threads per inch. Longer screw devices 4064 may be broken into several sections 4066 for flexibility with or without linkages to prevent independent rotation as shown in FIG. 116. Anchors may be relatively straight, or curved as shown.

In another embodiment, corkscrew anchors as shown in FIG. 117 are used. A corkscrew anchor having the same dimensional range as the screw type may result in greater tissue support with less implanted material. Screw/corkscrew anchors can be driven using a tubular driver such that the suture line will travel through the driver avoiding windup. The connection between the screw head and the driver can be of any format desired, such as slotted, Philips, hex, star, or square headed for example.

A tether line, such as a suture line, connects the various parts of the system, for example, connecting a sling to an anchor. Suture material can be elastic or inelastic. A non-elastic suture may provide greater strength to the support system while an elastic suture may be able to give a more natural elasticity depending on the desired clinical result.

Device Technique

Some embodiments of the system insertion technique are described below. One embodiment is shown in FIGS. 118-119 in which the leading end 4004 of each anchor 4010 is contained within the suture line 4014. This feature forces the anchor 4010 to be in the same orientation as the suture 4014. In this position, the device has its minimum crossing profile and is able to move smoothly through a cannula and/or tissue in the direction of insertion as shown in FIG. 118. When tension is applied to the suture as shown in FIG. 119, the crossing profile increases and the anchors become embedded within the tissue.

In one embodiment, the device is delivered through a cannula, such as a 9.5 French diameter cannula. A long, curved needle sheathed inside a cannula is inserted superiorly into the top of the breast tissue and exits inferiorly at the bottom of the breast just below the areola. The needle is then removed, leaving the cannula in place creating a pathway for the anchor system to be delivered. A flexible feeder rod with a needle eye at one end is used to pull the lower (inferior) suture line through the cannula. Once the lower suture line has exited the lower end of the cannula the feeder rod is removed. At this time the upper (superior) suture line is extending out of the cannula leer and the lower suture line is extending out of the tip of the cannula. By pulling each line, the anchors can be optimally positioned within the breast tissue. Once the optimal position is obtained, the physician can hold the lower suture line in place and remove the cannula, thus exposing the anchors to the tissue. The device can be positioned before removing the cannula through the insertion site.

In another embodiment, the device is delivered by threading the anchor lift component directly into the tissue using a sheathless needle. In this case, the suture line is fed through the eye of a rigid needle which will pull the lower suture line into the upper breast tissue and exit the lower breast. The anchors are pulled into the tissue to the desired position by pulling on the lower suture line. The device is positioned using external reference points on the suture line. If initial placement is too high, the device will easily move through tissue by applying tension to the lower suture line. If initial placement is too low, the top and bottom suture lines are tied together using the upper line to pull the lower line through the tissue in a full circle. Lower suture lines are not a functional requirement of the system, although they could be advantageous in some circumstances to provide ease of placement and facilitate retrieval in the event of misplacement. Lift is created when tension is applied to the anchor via the sling, thus raising the soft tissue.

When securing the device in place, tension is applied to the upper suture line which causes pressure to be applied to the angled surface on the exposed tips of the anchors which causes the anchors to rotate out and engage the tissue.

Small Profile Device

In one embodiment, a small profile device such as illustrated in FIG. 120 is provided. By reducing the profile 4013 of the device, smaller openings are required in the tissue. Smaller openings reduce the amount of scarring, pain, and trauma while increasing ease of delivery. In one embodiment, the anchor diameter measures about 0.02 to 0.09 inches, such as about 0.07 inches. The anchor length could range from about 0.5 to 2.0 cm, such as about 1.5 cm in length in some embodiments. The relatively small diameter of the anchor with respect to the suture is an advantageous aspect in this device as a large insertion hole created to place this device below the skin surface could cause scarring due to the entry hole. Reducing the crossing profile of the device would also help reduce the amount of pain and tissue trauma, while increasing ease and efficiency of delivery.

Another advantageous feature of the embodiment is the ratio of the length of the anchor to the diameter and exposed portion of the suture. This aspect ratio, which can be defined as the surface area of the transverse anchor with respect to the combined cross-sectional diameter of the anchor and the suture, would be rather small if the suture measured about 0.03 inches and the anchor measured about 0.06 inches where the ratio would be 2:1. In this embodiment, the aspect ratio could be between about 6:1 and 10:1, such as between about 7:1 or 9:1, or about 8.5:1 in some embodiments as the anchor is allowed to tilt outward from the central axis allowing additional tissue engagement. This feature could have additional benefits given the plurality of tissue anchors attached to each suture, such as at least 2, 3, 4, 5, 6, 7, 8, 9, 10, 11, 12, 13, 14, 15 anchors, or more in some embodiments.

When securing the device in place, tension is applied to the upper suture line 4018, applying pressure to the angled surface 4017 on the exposed tips of the anchors as shown in FIG. 121. This pressure causes the anchors to rotate from the line pathway) (0°) to a maximum angle perpendicular to the suture line 4018 to a maximum of 90 degrees as shown in FIG. 122. The large aspect ratio creates more surface area to disperse the load onto more tissue.

Anchor design that allows for direct insertion (without a cannula or sheath) would also aid in decreasing the system profile. For direct insertion, the device should, in some embodiments, not only have a small delivery profile, but also have a smooth finish and gradual transitions. This embodiment of the device and attachment method allows for both. A system size of 9.6 F can be reduced down to 7 F or less without the use of a cannula or sheath.

Optimal Tissue Pathway

In inserting the upper portion of the device, it can be desirable to create a pathway with great holding and tissue supporting ability. One way to create this pathway is to use the upper needle design that creates a path beneath the skin that has a high arch aspect ratio in relationship to the distance between the entry points 4070. For example, if the entry points are 7.5 cm apart, the arch pathway could be 1 to 2 cm higher in a 270 degree needle, versus a 180 degree needle. In this example, the 270 degree needle would have a curvature radius of 7.5 cm, while the 180 degree needle would have a curvature radius of about 10 cm. Since of the needle needs to be exposed for the user to push and pull, the 270 degree allows for the optimal semi-circular path under the skin, while having needle exposed to hold. This higher tissue path arch 4072, such as an arch of greater than about 180 degrees, or about 270 degrees helps hold more tissue and begins to create a more vertical component to the sling rather than a flatter arc 4074 that will migrate into a smaller radius curve under loading. In some embodiments, as noted above the arc formed could be between about 120 and 330 degrees, between about 180 and 270 degrees, or at least about 150, 165, 180, 195, 210, 225, 240, 255, 270, 285, or 300 degrees in some embodiments. A vertical path 4076 at the endpoints helps prevent a sharp angle from the sling to anchor lines which could result in cheese wire cut (more focal stress). This extra distance 4078 as shown in FIG. 123 will help maintain the initial position of the lifted or suspended tissue. It has been demonstrated clinically that the tissue tends to pull the upper sling from a flat implanted position to a more arched shape under loading. In some embodiments, the sling forms an arc of, for example, of between about 120 and 330 degrees, between about 180 and 270 degrees, or at least about 150, 165, 180, 195, 210, 225, 240, 255, 270, 285, or 300 degrees in some embodiments, but less than about 360 degrees.

Minimize Acute Lift Loss

To minimize acute lift loss, a mechanism for quickly securing and preventing slippage of the suture material is desired rather than conventional surgeons' knots for attachment of the suture. It is difficult to tie knots external to the skin surface and push them below the skin surface without losing some tension or lift due to the extension of the sling outside the skin. The disclosure here discusses a mechanism for placing the two suture lines under the skin during tensioning so there is very limited loss of tension during the suture connection.

Another embodiment of the support device is a method to tension and secure the components without the use of knots. Knots have been known to slip and are difficult to throw under the skin surface, depending on the suture material and the type of knot used. Knots with suture sometimes require several throws and can be time consuming. Also, if a knot is tied outside the skin, some tension may be lost as the knot is pushed down into the tissue. For these reasons, a device to secure the sutures with respect to each other at the site of implantation is beneficial.

The device placement of the mesh sling line and the anchor lines can be performed using the same percutaneous approach as described earlier. The components described here allow for quick adjustment at initial implantation and could also be readjusted at a later date.

Figure 124D:
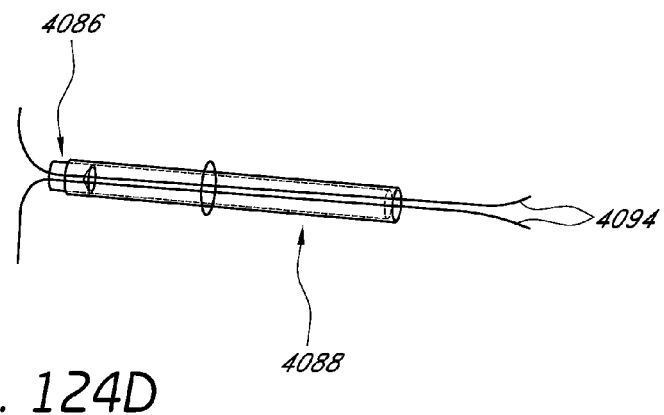
Figure 124E:
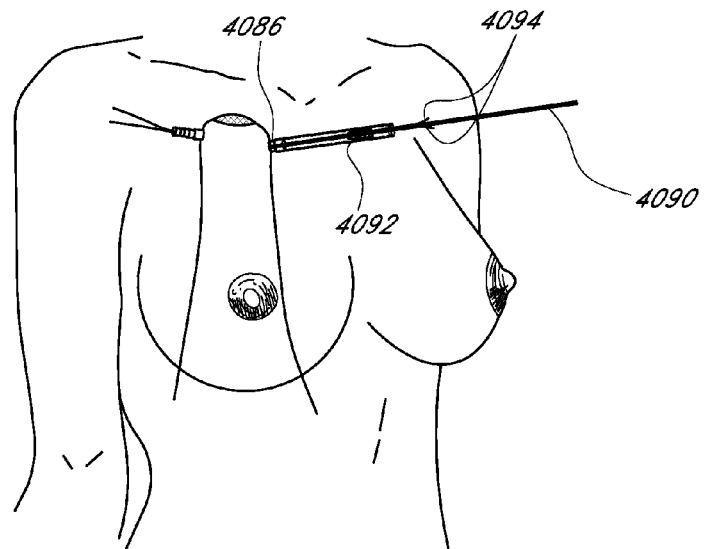
Figure 124F:
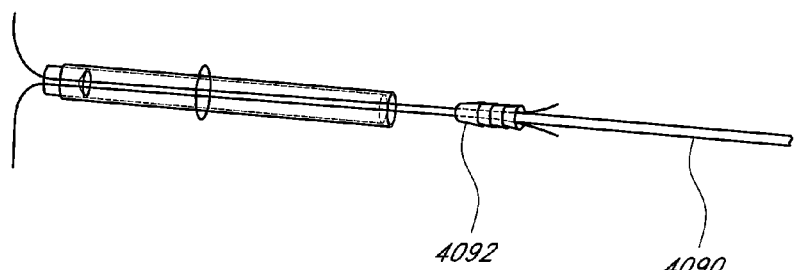
Figure 124G:
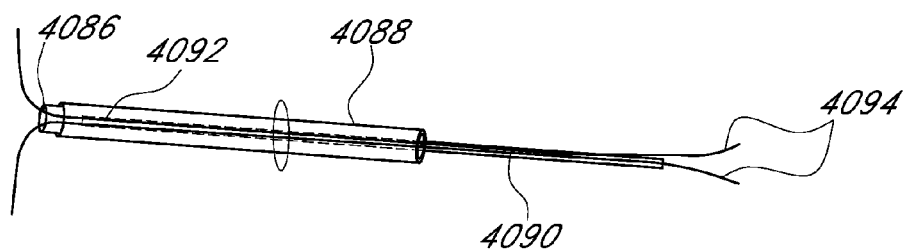
Figure 124H:
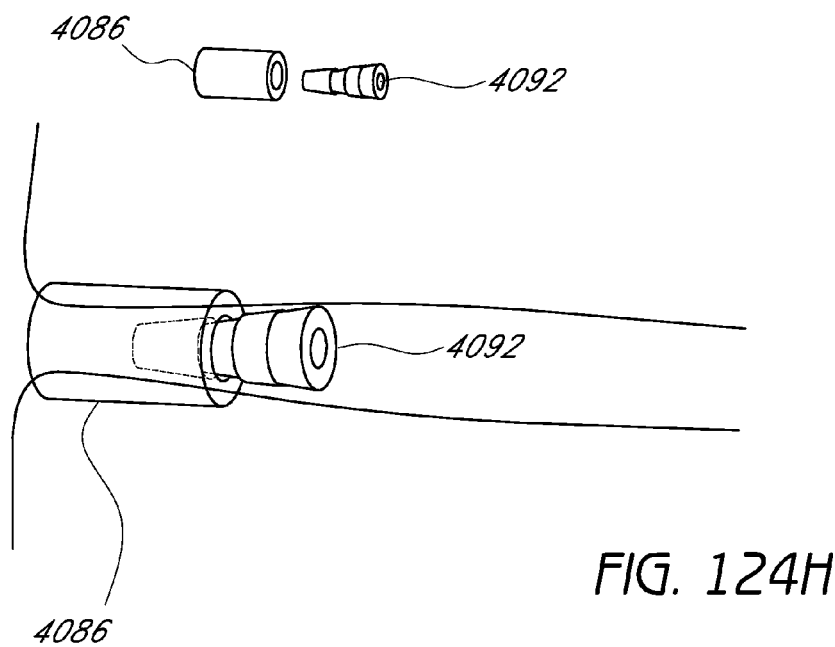
Figure 124I:
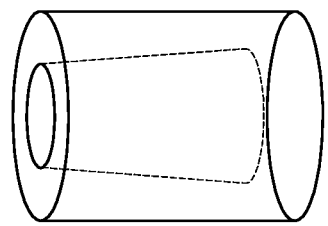

The sling 4032 and anchor lines 4082 are first inserted using a percutaneous approach to the desired locations as shown in FIG. 124A. The upper suture tails 4094 are then lifted and the medial and lateral suture ends secured using releasable clamps 4084 as shown schematically in FIG. 124B. The retainer 4086 is then placed over suture lines 4094 and pushed down into the tissue using the retainer push tube 4088 as shown in FIGS. 124C-D. While the suture lines 4094 are being tensioned, the wedge push rod 4090 is used to deliver the wedge 4092 down through the retainer push tube 4088 and into the retainer 4086 to lock the sutures into place as shown in FIGS. 124E-G. The wedge push rod 4090 and retainer push tube 4088 are then removed, leaving the wedge 4092 locked into the retainer 4086 as shown in FIG. 124H.

In one embodiment, the retainer is made of an implantable polymer such as polyethylene terephthalate or PET. Alternatively, the retainer could be made from other materials including, among others, polyetheretherketone (PEEK), polyester, nylon or other polymers, metals, and ceramics. The dimensions of the retainer may range from about 1 to about 10 mm in outer diameter and a length of about 1 to about 10 mm. Preferably, the retainer has an outer diameter of about 3 mm, a length of about 5 mm, and an inner diameter of about 1.75 mm. The retainer may be a straight tube, or of noncircular design, or of a tapered shape. The retainer shown in FIG. 124I has a tapered inner diameter. This will mate with the wedge shown in FIG. 124J and have increased locking ability with increased tension.

The retainer push tube (RPT) mates with the retainer to push down over the suture lines. The RPT may be made of polymers providing a relatively rigid sheath material such as nylon, pebax, Teflon, PEEK, or polyimide. It may also be made of a metal. The dimensions of the RPT could be around 1.5 mm to about 12 mm in outer diameter and about 1 to about 20 cm in length. In some embodiments, the RPT would have an outer diameter of about 3.5 mm, a length of about 50 mm, and an inner diameter of about 2.5 mm. The distal end could have an inset shelf or counter bore with a diameter of about 3.1 mm and a length of at least 1 mm to hold the retainer. The RPT could be press fit with the retainer. Alternatively, the RPT could have an active means of locking, unlocking, and relocking if necessary for future adjustment. The tip of the RPT should have a tapered transition to allow for less traumatic delivery. The back end of the RPT could have a handle, luer connecter, or other feature to help hold, push, torque, or steer the retainer to the desired location. If the RPT has an active lock/engagement, this could be located as a tab/knob activation on this back end handle.

The wedge is designed to fit inside the retainer and capture the sutures in place between the wedge and retainer. The wedge may be made of an implantable polymer such as polyethylene terephthalate (PET). Alternatively, the wedge could be made from other materials including, among others, polyetheretherketone (PEEK), polyester, nylon or other polymers, metals, and ceramics. The back end of the wedge has a connection feature to lock into the wedge push rod. The wedge may be tapered, barbed, grooved, or have some other locking feature to provide additional locking ability. In one embodiment, the wedge has barbs that lock in the suture and increase their hold when the wedge is pushed farther into the retainer.

The dimensions of the wedge may comprise an outer diameter of about 1 to 10 mm and a length of about 1 to 10 mm. Preferably, the dimensions comprise a diameter of about 1.5 mm at the tip to 2.4 mm over a 5 mm length.

Figure 124J:
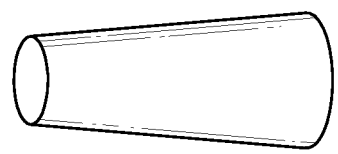

An embodiment of a round, tapered wedge is shown in FIG. 124J. The wedge may come in a variety of geometries such as, e.g., straight, tapered, round, rectangular, oval, or tubular.

The wedge push rod (WPR) is designed to deliver the wedge. It may be made of a relatively rigid material such as steel or certain polymers. In one embodiment, the WPR is made of solid stainless steel with a first enlarged diameter and a second reduced diameter at the tip to mate with the wedge. The rod could have a diameter of about 0.5 to 5 mm, but more preferably around 1 mm. The mating tip of the rod could then be reduced from the rod diameter to about 0.75 mm in this example. The length of the reduced diameter could be around 0.1 mm to 10 mm, but more preferably about 1.5 mm in some embodiments. The device has a releasable mating feature to deliver the wedge, but then releases once the wedge is in place. The WPR could be press fit with the wedge. Alternatively, the WPR may have active means of locking, unlocking, and relocking if necessary for future adjustment. The back end of the WPR could have a handle, luer connector, or other feature to help hold, push, torque, or steer the wedge to the desired location. If the WPR has an active lock or engagement, it could be located as a tab or knob activation on the back end handle.

Spool Tensioner

The spool tensioner is another component that allows for tensioning of the suture lines in situ. This system may be used during the implantation procedure of the sling and anchor system. This system may also be used post-procedurally at any time after the initial procedure to create additional tension, and lift. This system may also be used in other applications involving tensioning of sutures, wires, strands, and other flexible components.

Figure 125A:
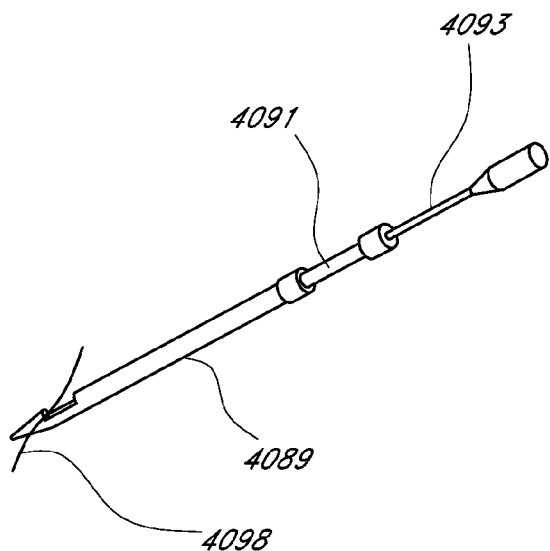

FIG. 125A shows one example of a delivery system including: the delivery shaft 4089, the cap delivery tube 4091, and the tensioning driver 4093. A suture line 4095 is also shown in this figure. The spool 4097 and spool cap 4087 are shown embedded in the delivery shaft 4089, as shown in the more detailed cut-away view of FIG. 125B. The delivery shaft 4089, cap delivery tube 4091, and the tension driver 4093 can all be coaxial as shown in the FIG. 125A, but other embodiments may be configured non-coaxially. In non-coaxial embodiments, the delivery tools may be hollow or solid.

In one embodiment, the delivery shaft is made of a small diameter tube made of a rigid polymer or metal. The distal tip may have a pointed or cone shaped end to help pierce and deliver through skin and tissue. The back end may have an enlarged or textured region that creates a handle to help steer, torque, and push the system. The diameter of the shaft is in the range of about 1 to 10 mm in diameter, but more preferably 3 mm and about 2 to 20 cm in length, but more preferably 5 cm.

In one embodiment, the cap delivery tube is made of a small diameter tube made of a rigid polymer or metal. The distal tip may have a locking mechanism to deliver the cap. Pins that extend past the distal tip of the cap delivery tube can also be present that will mate with 2 holes in the cap. This allows for torque and push, but will release when retracted with enough force. The back end may have an enlarged or textured region that creates a handle to help steer, torque and push the system. The diameter of the shaft could in some embodiments be in the range of about 1 mm to about 10 mm, such as about 2.8 mm. The shaft length could be in the range of about 2 to about 25 cm, such as about 7 cm.

Figure 125B:
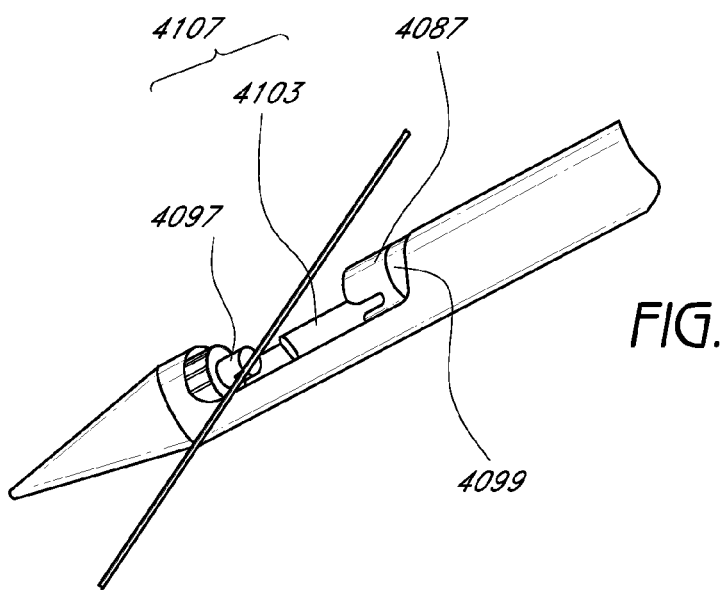

In one embodiment, the tension driver is made of a small diameter tube made of a rigid polymer or metal. The distal tip may have a twisting mechanism like that of a screw driver or Allen wrench. FIG. 125B shows the head of a flat screwdriver 4103 on the distal end that extends to mate with the slot of the spool 4097. This allows the ability to torque or twist the spool 4097 to wind up the suture, but will release when retracted. The back end may have an enlarged or textured region that creates a handle to help steer, torque and push the system. The diameter of the shaft is in the range of about 0.1 to 5 mm, such as about 1 mm, and in the embodiment shown fits through the cap and cap delivery tube. The shaft length could in some embodiments be in the range of about 2 cm to about 30 cm, but more preferably about 9 cm. FIG. 125B also shows the spool 4097 and cap 4099 seated inside the delivery shaft window 4107.

Figure 125C:
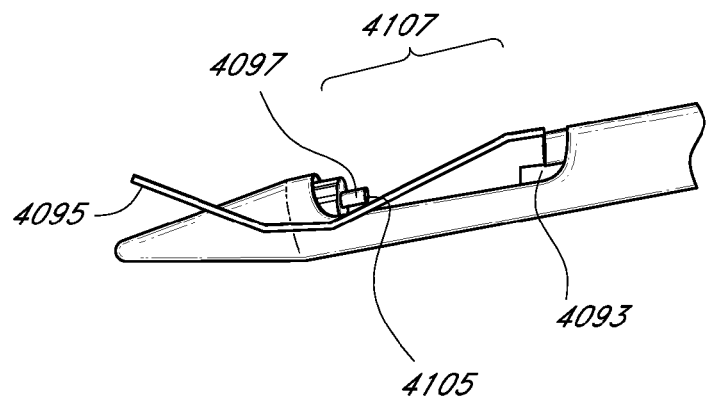

FIG. 125C depicts how the delivery shaft and the spool function as a hook. The suture 4095 falls into the window 4107 of the delivery shaft and rides along the edge of the window until it catches in the slot 4105 of the spool 4097. The spool 4097 is then wound by extending the tension driver 4093 forward and twisting until the desired amount of suture is wound, therefore shortening and tensioning the suture 4095.

Figure 125D:
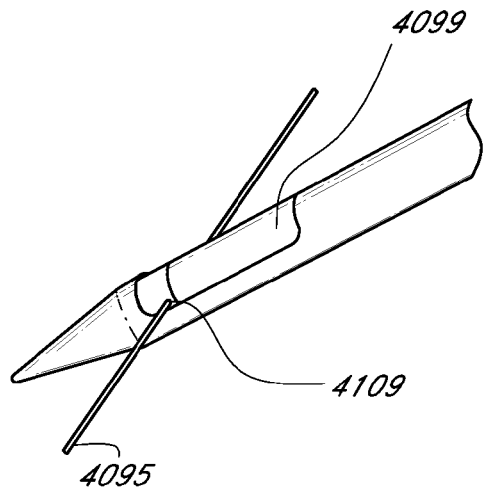

After the spool 4097 is wound the desired amount, the cap 4099 is advanced forward to lock the suture 4095 wound around the spool as shown in FIG. 125D. The cap 4099 is pushed forward using the cap delivery tube. In one embodiment, there are keys in the cap that lock into the keyways in the spool to prevent them from spinning in relation to each other. In the embodiment shown, the cap 4099 has a through slot 4109 that allows the suture to pass through. Other embodiments may have multiple slots, such as at least 2, 3, 4, or more slots, a single slot, or no slot at all.

Figure 125E:
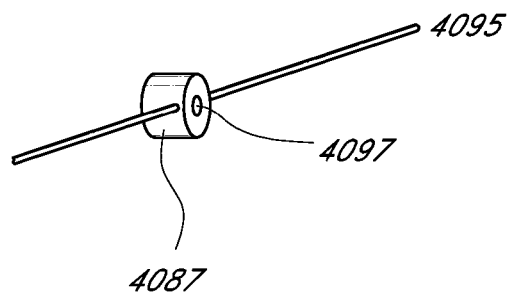
Figure 126A:
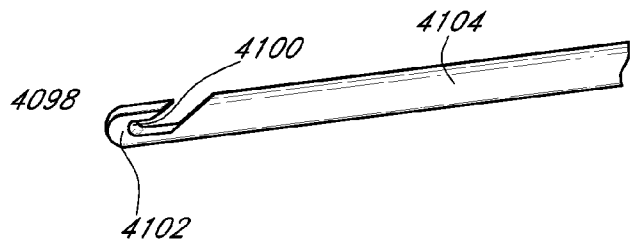
Figure 126B:
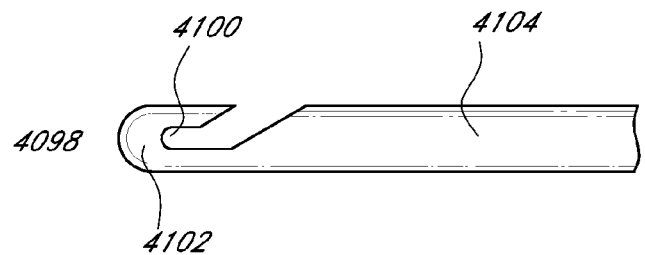
Figure 126C:
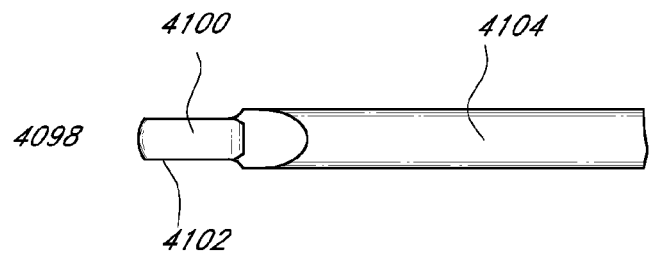
Figure 126D:
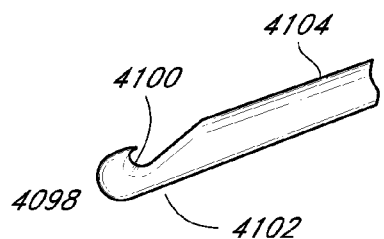
Figure 127A:
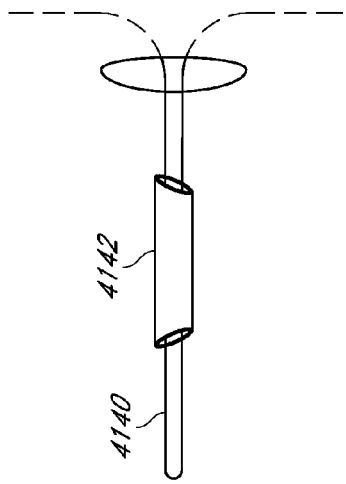
Figure 127B:
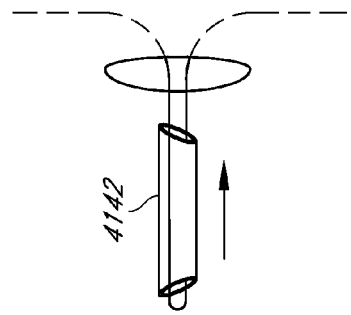
Figure 127C:
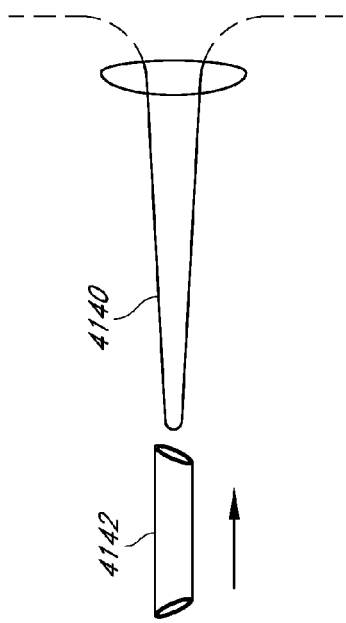
Figure 127D:
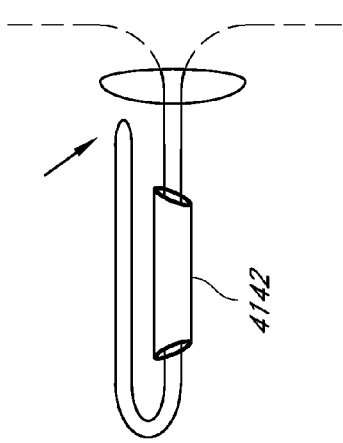
Figure 128A:
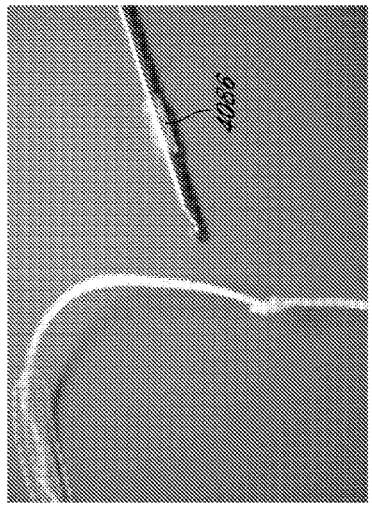
Figure 128B:
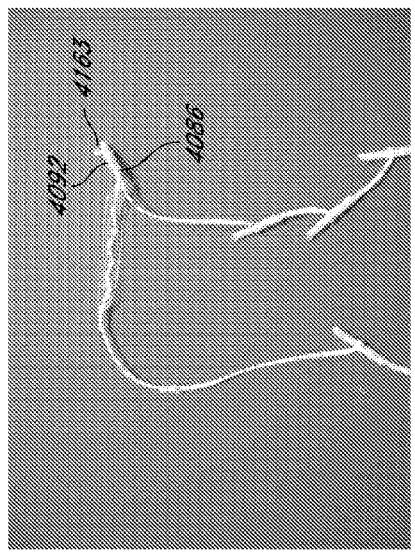
Figure 128C:
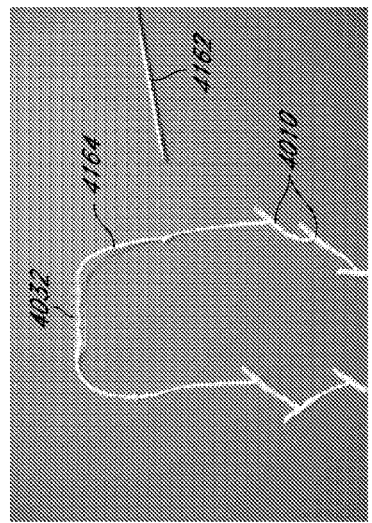
Figure 128D:
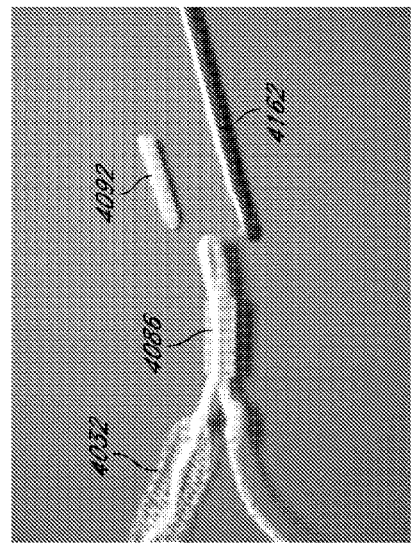

The tension driver and cap tube are then retracted. The spool, cap and suture are then disengaged from the delivery shaft window. The remaining implant device is the spool 4097, the spool cap, 4087, and the suture 4095 as shown in FIG. 125E.

Post-Procedural Adjustment

The purpose of post-procedural adjustment is to adjust a previously implanted system which would entail locating the point of attachment, adjusting the tension and re-securing the suture. The capability for adjustment after the procedure has been completed would also allow for an adjustment to correct any irregularities during the initial installation. Furthermore, after the initial tissue has settled due to gravity, an additional lift or adjustment may be desired.

Tools to locate an existing device can be used begin the process of retensioning. A simple tool to capture the suture or implant could include a small hook to be placed under the skin and maneuvered to locate the suture material for tension and knotting or securing. One embodiment of the hook is shown in FIGS. 126A-D. It could be made of a metal such as stainless steel, with a diameter of about 1 mm and a hook 4098 that could be J-shaped formed into the end in some embodiments. The J-shaped hook could be configured such that it has a radius of curvature 4100 and flat sides 4102 such that the diameter of the hook is less than the diameter of the round shaft of the hook body 4104. This allows suture to be located on both sides of the hook and still give the hook portion 4098 a smaller cross-section than the round shaft of the hook body 4104. This allows the hook 4098 and suture to pass through a small diameter securement component.

Location of these sutures may be difficult, so additional tools may be needed to locate the lines externally, from above the skin. Radiopaque markers may be placed on the implant to allow imaging modalities such as X-ray, fluoroscopy or ultrasound to be used. CT or MRI imaging could also be used, but would delay the physician due to processing times associated with those technologies. The simplest technique may be a combination of internal hooks or tools in combination with the physician's tactile feel for the device on the surface of the skin during the suture exploration. In some embodiments, the markers may be magnetic to facilitate locating the implant.

Beads or other radially enlarged elements may also be attached to the suture ends to help locate them. Additionally, visual tools such as endoscopes or integrated fiber optics may help locate the suture through small port access in the skin. Polymer, metal, or ceramic beads could be added onto the suture by methods including mechanically tying, crimping, adhesive bonds, and over-molding. The beads may be located by methods such as fluoroscopy or tactile feel.

The adjustment may be accomplished by tensioning the suspension lines farther or shortening the length between the anchors. In one embodiment of the device, anchors are suspended from the sling where the sling is superior to the anchors and the anchors are engaged in soft tissue. The distance from the superior sling to the anchors may be shortened, thus increasing the tension and lifting the soft tissue further. This shortening technique may be accomplished by a simple knotting where excess suture is taken up through the knot and the section between the sling and anchors is reduced in length.

Additional techniques in suture shortening include winding, looping, coiling, or other means to reduce the length and add tension or lift the associated tissue. In some embodiments, an adjustment element such as a lockable spool could be present along an anchoring line that could be adjusted without the need for detaching and reattaching a portion of the anchor line. One additional method to shorten the suture would be to loop 4140 the suture material through a tubular member 4142 and traverse the loop 4140 back around the tube, securing it upon itself and locking it into position as shown in FIGS. 127A-D. For this technique, a tapered edge would be advantageous to keep the suture from slipping off the end and disengaging from the tubular portion. The tubular portion may be constructed from an elastic material to accommodate variations in loading conditions acting as an energy absorption component. This translates a linear tension force into a compression force and allows for better fatigue resistance. The tubular material may be of a soft durometer material such as silicone or any biocompatible urethane material. The tubular portion has dimensions to allow passage of the suture material through the inner diameter and a wall thickness to maintain structural integrity throughout the life of the implant. In some embodiments, dimensions could include an inner diameter of about 0.05 inches and an outer diameter of about 0.090 inches and a length ranging from about 0.2 inches to about 0.5 inches depending upon the lift or shortening desired.

An alternative adjustment technique is accomplished by using a hook type device 4162 to find the suture line 4164. Once the suture line 4164 is found, the method for the acute lift loss previously described may be used to secure the device as shown in FIGS. 128A-D. The Retainer 4086 would first be placed over the suture lines and pushed down into the tissue using the retainer push tube. While tensioning the suture lines 4164, the wedge push rod is used to deliver the wedge 4092 down through the retainer push tube and into the retainer 4086 to lock the sutures in place. The retainer push tube and wedge push rod are then removed. The material 4163 that is captured by the wedge-retainer creates tension and shortening between the sling 4032 and anchors 4010. One or both sides may be adjusted.

Variable Product Life Span

Sling materials may include, for example, flat, oval, or round polypropylene materials woven or braided into an open architecture for tissue in-growth. ePTFE or another porous material may be used in some embodiments. Other materials that may be used include cross-linked tissue such as bovine, equine or porcine tissues, xenografts, or allografts that the surrounding tissue would recognize as inert. Other biological tissues such as collagen or small intestinal submucosa could also be used. These and other materials could be fixed or designed to maintain their inert properties or promote ingrowth. They may also be designed to erode, allowing the surrounding tissue to absorb the implant over a defined period. The advantage of arcuate such as round construction is that there is no preferential axis to cut into the tissue under loading. Flat materials would be the smallest construction and allow the smallest entry hole through the skin. Folding for installation and flattening after installation would allow the material to be installed with a small profile and perform open, displaying the largest surface area possible. This function of small entry is helpful in reducing the scars the patient may receive from the device installation.

Device materials and procedures for implanting the device may be varied according to the life span goals of the device. Durable materials could be used for a device to remain implanted in the body for at least 1, 2, 3, 4, 5, 6, 7, 8, 9, 10, or more years. In some cases, a shorter device life span, such as 5 years, 1 year, or even less may be desirable for the patient who wants short term benefits. This may be due to the patient's anatomy, additional sagging, life activities, and body structure among other things that cause the patient to no longer want the device effective or even present. This phenomenon is observed as many gel/saline implants are removed as a patient's desire or age changes.

Durable materials may be metals, polymers, or ceramics. More specific examples are PEEK, PET, Nylon, stainless steel, nitinol, and cobalt chromium among others.

Absorbable materials include poly(alpha-hydroxy acid) such as poly-L-lactide (PLLA); poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino-acids), or related copolymers materials, PET, ceramic, and hydroxyapatite among others. Many polymers can be processed to change mechanical integrity or absorbability. Materials and designs of components may be selected to result in devices with a predetermined life span or including a certain safety value, like containing a shear pin.

Mechanical characteristics may be created for more complex materials by having a composite or reinforced part to add rigidity and strength where needed and flexible and soft materials in other places. For example, greater strength could be achieved with metal ribs placed in the attachment area, such as at the hole location, with the rest of the device made from a polymer. The product may be insert molded. Short term fastening features like barbs or hooks may be made from bioabsorbable material.

Anchor to Anchor Suture Lines

One embodiment of the device includes a sling portion made entirely of suture, without any mesh. This device may then be implanted through a single pathway and at any location. Varying lengths, diameters, materials and number of barbs may be used.

Enhanced Suspension Elements

With enhanced suspension elements in the system, the device may achieve better compliance and a better look and feel. In one embodiment, enhanced suspension is achieved by adding springs along the suture line. The springs may be made of metal. A variety of springs may be used including coil springs, leaf springs, torque springs, and wave springs. In another embodiment, pressurized air cylinders may be used in line with the sutures to achieve enhanced suspension. Alternatively, an elastomeric material may be inserted inside the suture braid to enhance suspension. The elastomeric material may also be inserted in a cylinder type design so that it is in compression, increasing its suspension capabilities.

Device Used to Suspend or Position Gel or Saline Implants in Tissue

Figure 129A:
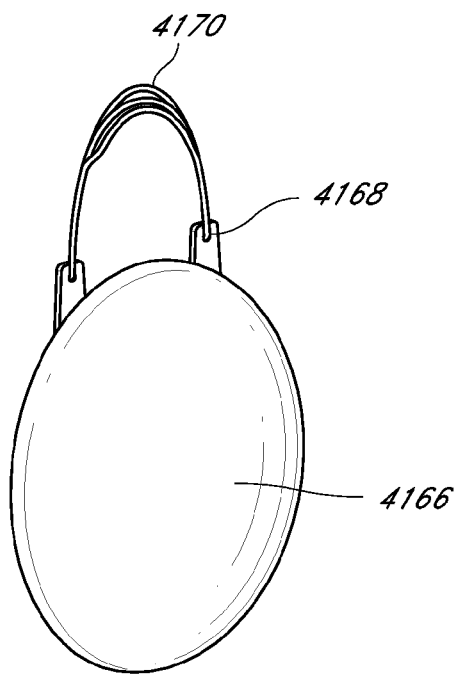
Figure 129B:
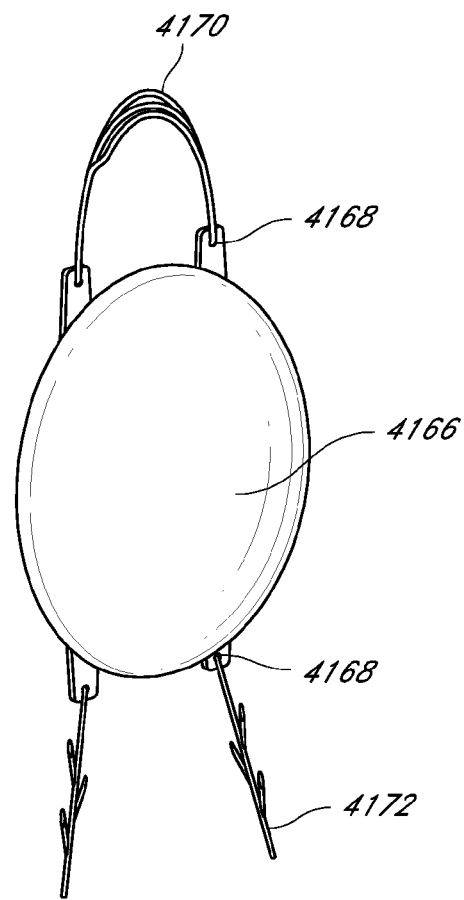
Figure 129C:
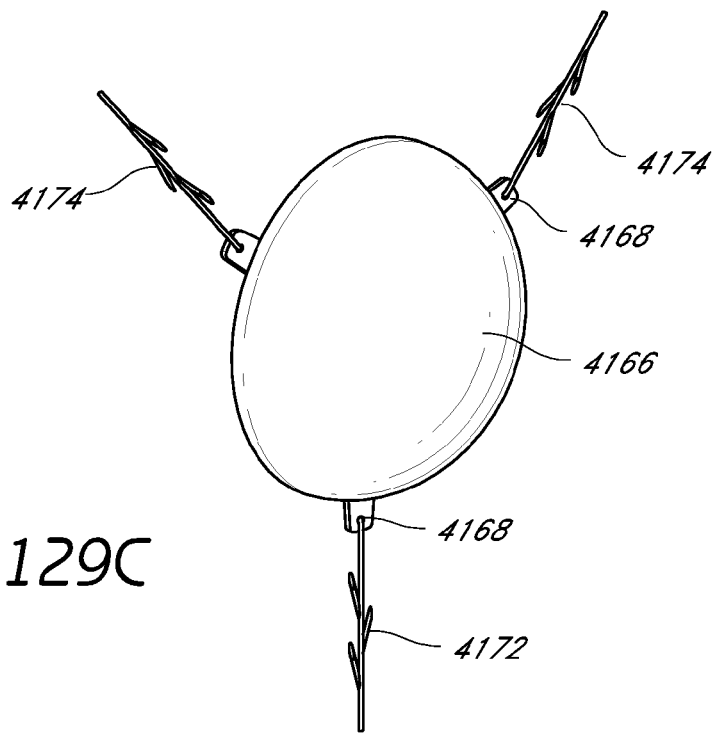
Figure 129D:
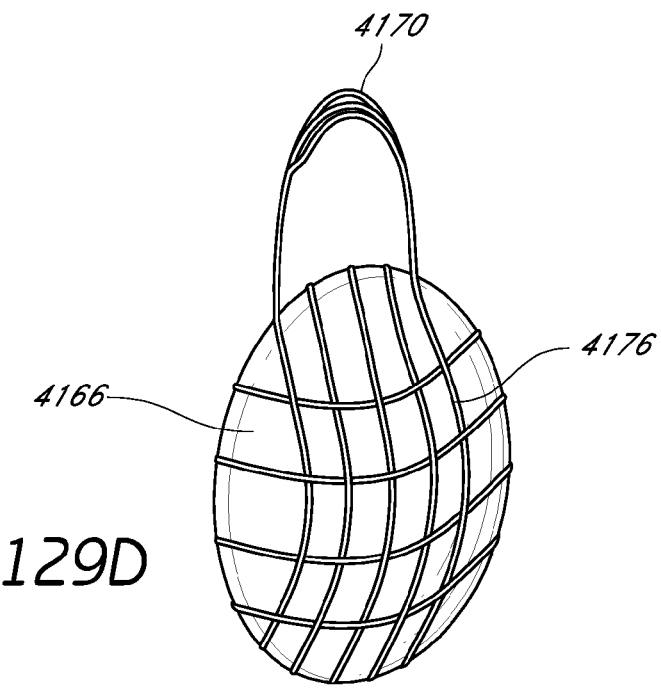

Common breast implants are placed beneath or above the pectoral muscle. Pockets are often created to house or locate the implant in a defined position, but due to activity, the implants often shift or move from their desired location. This movement may also be caused by gravitational forces over time. If an additional component such as one of the suspension devices disclosed above were attached to the implant, the implant may have a lower tendency to droop or bottom out. The suture lines may be attached to the implant by means of tabs or attachment points to the implant where a plurality of sutures hold the relative position of the implant with respect to the upper sling. In one embodiment, the implants are manufactured so that the tabs or other connection devices are integrated into current implants. Alternatively, tabs may be attached to pockets, retainers, meshes, bags, harnesses or the like to aid us using the system with off the shelf items. Each implant may be attached using one, two, or more tabs. The tabs may be connected at the bottom or top of the implant or both. The tabs may be of various lengths. Additionally, the tabs may be rigid or elastic to absorb any shock loading of the suture lines attached. The tabs may be attached to sling type anchors or barbed type anchors, several of which are described elsewhere in the application, or sutured directly to or around tissue or bone. Other soft tissue implants other than breast implants, such as gluteal, lip, nasolabial fold, cheek, etc. implants can also be suspended as disclosed herein. FIGS. 129A-D depict various implants 4166. FIG. 129A illustrates an embodiment of an implant 4166 with superior tabs 4168 with apertures or other attachment means for connection to a superior support sling 4170 that can be as previously described. FIG. 129B illustrates an implant 4166 with both superior and inferior tabs 4168 suspended superiorly using sling 4170 as noted above. The implant 4166 is attached via the inferior tabs 4168 to suspension lines 4172, which may include anchors that may be in the form of barbs as shown. In some embodiments, the implant 4166 could be suspended by at least 1, 2, 3, 4, 5, or more superior and/or inferior anchor suspension lines. FIG. 129C illustrates an implant 4166 suspended by multiple superior 4174 and inferior anchor suspension lines 4168 spaced about 120 degrees apart. The anchor suspension lines could be spaced unequally apart in other embodiments. FIG. 129D illustrates an implant 4166 inside of an enclosure 4176 which could be an open structure such as a weave as shown or a closed structure more akin to a handbag. Implant 4166 can be supported superiorly by a sling 4170 as previously described. Any combination of other elements described to support an implant such as tabs, an enclosure, etc. can be used with any of the described above embodiments to fix the implant to tissue or bone, for example with sutures. The implants shown may be filled with saline, silicone, or other substances depending on the desired clinical result. In some embodiments, the implants can be as described, for example, in U.S. Pat. No. 3,852,832 or 6,913,626 to McGhan or U.S. Pat. No. 5,525,275 or 5,964,803 to Iversen et al., which are all incorporated by reference in their entireties. In some embodiments, another element may suspend from beneath the implant with additional sling(s) to hold the relative position with respect to the upper sling.

Removal Tools

After implantation, the device may be removed by means of locating and coring tools to release the device from the surrounding tissue. Once located, the suture or implant could be held relative to a coring tool to cut the surrounding tissue by advancement around the suture material. This allows a section of tissue and the implant to be separated from the patient with little trauma or bleeding. By separating the device into multiple components, it aids in the removal process due to the reduction in component length and complexity of the implant pathway. The coring tool may be a simple hypo tube made from stainless steel or Nitinol where the distal tip is sharpened to provide a cutting means. The tube may also be constructed of a flexible proximal section and a more rigid distal section where flexibility allows articulation about the device. Additional means for removal include a rotational tool to twist the implant from the surrounding tissue and release any tissue attachment. The device may then be pulled from the patient with little force and trauma. This method requires a locational tool to find the suture and an attachment of the tool to the suture for rotational forces to twist the implant from the surrounding tissue.

Additional Areas where Soft Tissue Lift and Suspension would be Desired

Additional areas possibly requiring soft tissue lift and suspension include the buttocks, thighs, abdomen, and facial areas, such as, for example, eyelids, eyebrows, forehead wrinkles, nasolabial folds, chin, facial droop caused by temporary or permanent paralysis such as Bell's palsy or a stroke, or other locations where the scale of the device needs to be adjusted for the associated anatomy and surrounding attachment points. An example is a device used in the buttocks that is scaled up in size and has an increased anchoring area or is fixed to a bone structure. Another example is a device in the facial where the size is culled down for less support and a thinner tissue and fat layer to be supported.

Although preferred embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above.

What is claimed is:

1. A method of lifting a target tissue, comprising the steps of:

providing a tissue lift system comprising a superior soft tissue anchor, and a plurality of inferior soft tissue anchors, the superior soft tissue anchor comprising an elongate flexible mesh;

introducing the superior soft tissue anchor into a patient, the superior anchor having an inferiorly facing total surface area, the mesh positioned in the patient superior to the target tissue and not directly contacting the target tissue, the mesh comprising a superior-most part of the tissue lift system; and introducing the plurality of inferior soft tissue anchors into the patient, such that the inferior soft tissue anchors are suspended from and are supported by the superior soft tissue anchor, the sum of all of the plurality of inferior soft tissue anchors having a superiorly facing total surface area, wherein the inferiorly facing total surface area of the superior anchor is at least two times greater than the superiorly facing total surface area of the plurality of inferior anchors.

2. The method of claim 1, wherein the superior soft tissue anchor is anchored to soft tissue.

3. The method of claim 2, wherein the plurality of inferior soft tissue anchors are anchored to soft tissue.

4. The method of claim 1, wherein the target tissue comprises breast tissue.

5. The method of claim 1, wherein the target tissue comprises facial tissue.

6. The method of claim 1, wherein the target tissue comprises abdominal wall tissue.

7. The method of claim 1, wherein the target tissue comprises gluteal tissue.

8. The method of claim 1, wherein the inferiorly facing total surface area of the superior anchor is at least three times greater than the superiorly facing total surface area of the plurality of inferior anchors.

9. The method of claim 8, wherein the inferiorly facing total surface area of the superior anchor is at least four times greater than the superiorly facing total surface area of the plurality of inferior anchors.

10. The method of claim 9, wherein the inferiorly facing total surface area of the superior anchor is at least five times greater than the superiorly facing total surface area of the plurality of inferior anchors.

11. The method of claim 10, wherein the inferiorly facing total surface area of the superior anchor is at least ten times greater than the superiorly facing total surface area of the plurality of inferior anchors.

12. The method of claim 1, comprising introducing at least three inferior soft tissue anchors into the patient.

13. The method of claim 12, comprising introducing at least four inferior soft tissue anchors into the patient.

14. The method of claim 1, wherein the inferiorly facing surface area of the superior anchor is at least about 1 cm$^2$.

15. The method of claim 14, wherein the inferiorly facing surface area of the superior anchor is at least about 2 cm$^2$.

* * * * *